(12) United States Patent
Zhong et al.

(10) Patent No.: US 7,667,004 B2
(45) Date of Patent: Feb. 23, 2010

(54) HUMANIZED ANTIBODIES AGAINST VASCULAR ENDOTHELIAL GROWTH FACTOR

(75) Inventors: Pingyu Zhong, Mountain View, CA (US); Peizhi Luo, Sunnyvale, CA (US); Kevin C. Wang, San Francisco, CA (US); Mark Hsieh, San Francisco, CA (US); Yan Li, San Jose, CA (US)

(73) Assignee: Abmaxis, Inc., Mountain View, CA (US)

( * ) Notice: Subject to any disclaimer, the term of this patent is extended or adjusted under 35 U.S.C. 154(b) by 220 days.

(21) Appl. No.: 10/723,434

(22) Filed: Nov. 26, 2003

(65) Prior Publication Data
US 2004/0133357 A1  Jul. 8, 2004

Related U.S. Application Data

(63) Continuation-in-part of application No. 10/443,134, filed on May 20, 2003, now abandoned, which is a continuation-in-part of application No. 10/153,159, filed on May 20, 2002, now Pat. No. 7,117,096, and a continuation-in-part of application No. 10/153,176, filed on May 20, 2002, which is a continuation-in-part of application No. 10/125,687, filed on Apr. 17, 2002, now abandoned.

(60) Provisional application No. 60/284,407, filed on Apr. 17, 2001.

(51) Int. Cl.
C12P 21/08 (2006.01)
(52) U.S. Cl. .................. 530/388.1; 530/350; 530/387.3
(58) Field of Classification Search ............. 530/350, 530/387.3, 388.1
See application file for complete search history.

(56) References Cited

U.S. PATENT DOCUMENTS 6,682,736 B1 * 1/2004 Hanson et al. ........... 424/144.1
2002/0032315 A1   3/2002 Baca et al.

FOREIGN PATENT DOCUMENTS

WO  WO 96/06625       3/1996
WO  WO 98/45331 A2   10/1998

OTHER PUBLICATIONS

Rudikoff et al (Proc. Natl. Acad. Sci. USA 1982 vol. 79 p. 1979).*
Colman et al (Research in Immunology 1994, 145:33-36).*
Schier et al (J. Mol Biol. 1996, 263:551-567).*
Paul, Fundamental Immunology, 3rd Edition, 1993, pp. 292-295.*
Colman. Research in Immunology, 145:33-36, 1994.*
Bendig M. M. Methods: A Companion to Methods in Enzymology, 1995; 8:83-93.*
MacCallum et al. J. Mol. Biol., 262, 732-745, 1996.*
Casset et al. Biochemical and Biophysical Research Communications, 307:198-205, 2003.*
Chothia et al., Structural Determinants in the Sequences of Immunoglobulin Variable Domain, J. Mol. Biol., vol. 278, pp. 457-459, 1998.
Iba et al., Changes in the Specificity of Antibodies Against Steroid Antigens by Introduction of Mutations into Complementarity-Determining Regions of the $V_H$ Domain, Protein Engineering, vol. 11, No. 5, pp. 361-370, 1998.
Knappik et al., Fully Synthetic Human Combinatorial Antibody Libraries (HuCAL) Based on Modular Consensus Frameworks and CDRs Randomized with Trinucleotides, J. Mol. Biol., vol. 296, pp. 57-86, 2000.
Mandal, C. et al., "ABGEN A Knowledge-Based Automated Approach for Antibody Structure Modeling", *Nature Biotechnology*, vol. 14, Mar. 1996, pp. 323-328.
Borrebaeck, C. et al., "Antibody evolution beyond Nature", *Nature Biotechnology*, vol. 20, Dec. 2002, pp. 1189-1190.
Bowie, J. et al., "A Method to Identify Protein Sequences That Fold into a Known Three-Dimensional Structure", *Science*, vol. 253, Jul. 1991, pp. 164-170.
Voigt, C. et al., "Computational method to reduce the search space for directed protein evolution", *Proc. Natl. Acad. Sci. USA*, vol. 98, No. 7, Mar. 2001, pp. 3778-3783.
Moore, G. et al., "Computational Challenges in Combinatorial Library Design for Protein Engineering", *AIChE Journal*, vol. 50, No. 2, Feb. 2004, pp. 262-272.
Kono, H. et al., "Statistical Theory for Protein Combinatorial Libraries. Packing Interactions, Backbone Flexibility, and the Sequence Variability of a Main-chain Structure", *J. Mol. Biol.*, vol. 306 (2001), pp. 607-628.
Wu, H. et al., "Stepwise in vitro affinity maturation of Vitaxin, an $\alpha v \beta_3$-specific humanized mAb", *Proc. Natl. Acad. Sci. USA*, vol. 95, May 1998, pp. 6037-6042.
Janway, et al. Structure of the antibody molecule and the immunoglobulin genes. In: Immunobiology. 1994; 3:1-3:3.

* cited by examiner

*Primary Examiner*—Stephen L Rawlings
*Assistant Examiner*—Brad Duffy
(74) *Attorney, Agent, or Firm*—Vineet Kohli; David A. Muthard

(57) ABSTRACT

Methods are provided for designing and selecting antibodies against human antigens with high affinity and specificity in silico and in vitro. In some particular embodiments, methods are provided for designing and selecting humanized or fully human antibodies against vascular endothelial growth factor (VEGF) with high affinity and specificity. In another aspect of the invention, monoclonal antibodies against VEGF are provided. In particular, humanized or human anti-VEGF monoclonal antibodies are provided with ability to bind to human VEGF with high affinity, inhibit VEGF-induced proliferation of endothelial cells in vitro and inhibit VEGF-induced angiogenesis in vivo. These antibodies and their derivative can be used in a wide variety of applications such as diagnosis, prevention, and treatment of diseases such as cancer, AMD, diabetic retinopathy, and other diseases derived from pathological angiogenesis.

9 Claims, 34 Drawing Sheets

Figure 1A

Figure 3:
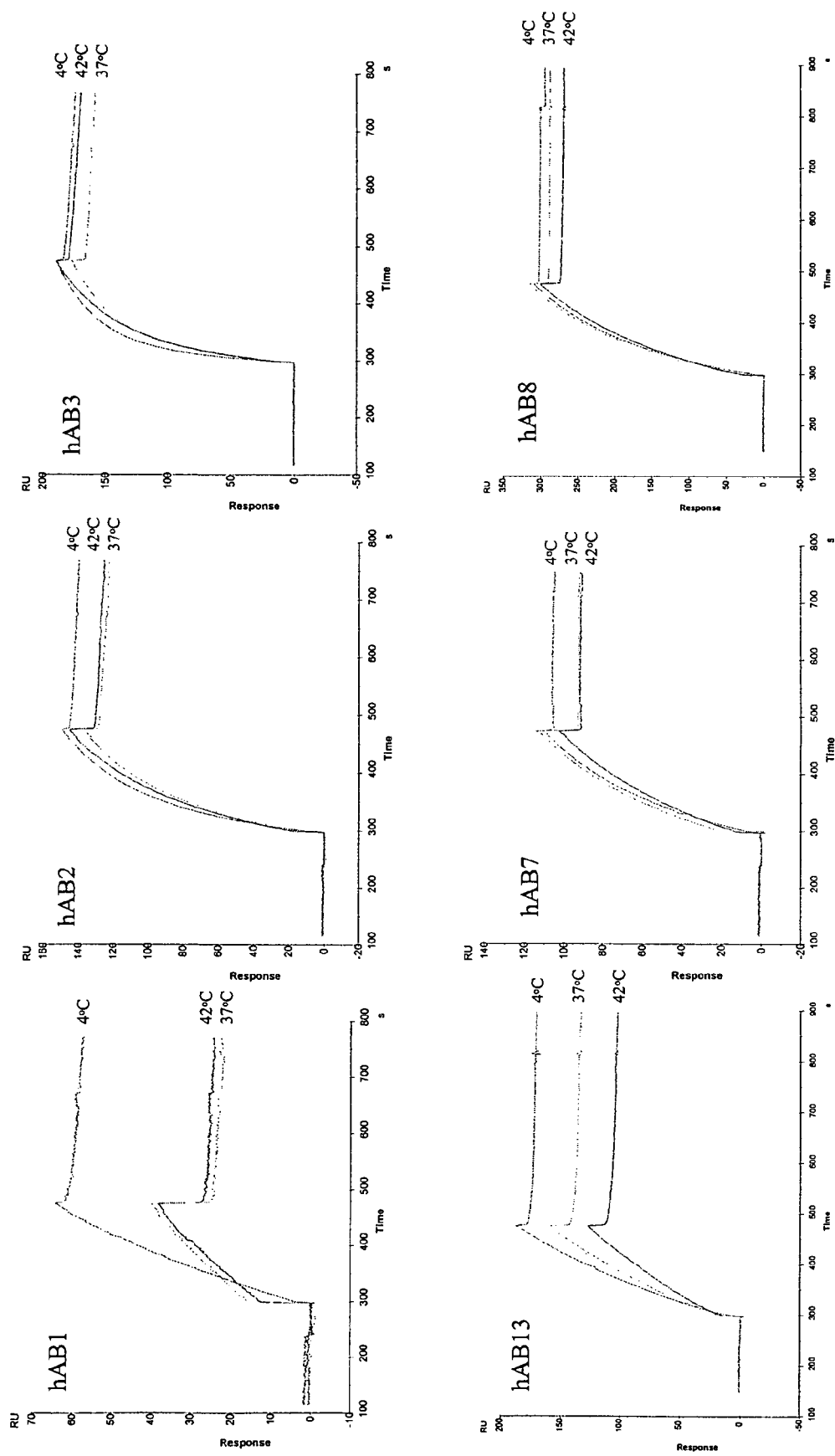

```
          1234567890123456789012345678901234567890123456789012345678901234567
          diqmtqspsslsasvgdrvtitcsasqdisnylnwyqqkpgkapkvliyftsslhsgvpsrfsgsgsgtdftltisslqpedfatyycqqystvpwt
          ---------------------------------------------------------------------------------------------------
          ..v...hk........s.s......v........s.rl..aa..y....d....n.....ys......ea..l.v........
          el tt.tm tta e ai . r    .gsava      dhtvh.  . fr.t . t .r   . .f  rv.. .a    hc s c
          l        v l      h      t           q .     c     a  g      y  i  .        n a f
                   p        k                  n       d     g  s      n  .  v         y g l
                            n                  q       g     y                          t q
                            q                  s       s     n                          c y
                                               y                                        d
                                                                                        e
                                                                                        k
                                                                                        n
                                                                                        q
                                                                                        r
                                                                                        w
                                                                                        y
```

Summary of amino acid sequences of $V_L$ hit variants listed above:

$DIX_1X_2TQX_3X_4X_5X_6X_7SX_8X_9X_{10}GX_{11}RX_{12}X_{13}IX_{14}CX_{15}ASQDX_{16}X_{17}X_{18}X_{19}X_{20}X_{21}WYQQKPX_{22}X_{23}X_{24}X_{25}X_{26}X_{27}LIY$
$X_{28}X_{29}SX_{30}X_{31}X_{32}X_{33}GVPX_{34}RFX_{35}GX_{36}X_{37}SGTDX_{38}X_{39}X_{40}TISX_{41}X_{42}X_{43}X_{44}EDX_{45}AX_{46}YYCQQX_{47}X_{48}TX_{49}PX_{50}T$

Figure 1B

```
          1234567890123456789012345678901234567890123456789012345678901234
          evqlvesggglvqpggslrlscaasgytftnygmnwvrqapgkglewvgwintytgeptyaadfkrrftfsldtskstaylqmnslraedtavyycakyphygsshwyfdvwg
----|-----------------------------------------------------------------------------------------------------------------
....q....v..........i............................................v............l....................s..c..c......
q           t  t  v   falahfal   .       p    v  nn  s   vpe t  .irn  n  nkl    .          rasyv.stn.c  y
                      d dr sv    a                t   d        l         pp                 h.rcdd atng    l
                      n ns

Figure 1C

Amino Acid Sequences of V_L of Selected Anti-VEGF Antibodies

SEQ ID NO:1
DIQMTQSPSSLSASVGDRVTITCSASQDISNYLNWYQQKPGKAPKVLIYFTSSLHSGVPSRFSGSGSGTDFTLTISSLQPEDFATYYCQQYSTVPWTFGQGTKVEIK

SEQ ID NO:2
DIELTQSPSPSSLSVSAGDRVTISCSASQDISNYLNWYQQKPGKAPRVLIYFTSSLHSGVPYRFSGSGSGTDFTLTISSLQPEDVAVYYCQQYSTVPWTFGQGTKVEIK

SEQ ID NO:3
DIELTQSPSSLSVTPGERATITCSASQDISNYLNWYQQKPGKAPQVLIYFTSSLHSGVPDRFSGSGSGTDFTLTISSLQAEDFAIYYCQQYSTVPWTFGQGTKVEIK

SEQ ID NO:4
DIELTQSPSSLSVTPGERATITCSASQDISNYLNWYQQKPGQAPQLLIYFTSSLHSGVPDRFSGSGSGTDFTLTISRLQAEDVAVYYCQQYSTVPWTFGQGTKVEIK

SEQ ID NO:5
DIEMTQSPSSLSASLGERVTISCSASQDISNYLNWYQQKPGKAPHLLIYFTSSLHSGVPYRFSGSGSGTDFTLTISSLQAEDFAAYYCQQYSTVPWTFGQGTKVEIK

SEQ ID NO:6
DIVMTQSPSSLSATPGERVTITCSASQDISNYLNWYQQKPGQAPRVLIYFTSSLHSGVPDRFSGSGSGTDFTLTISSLQPEDVAVYYCQQYSTVPWTFGQGTKVEIK

SEQ ID NO:7
DIVMTQSPSSLSATPGERVTISCSASQDISNYLNWYQQKPGKAPSLLVYFTSSLHSGVPSRFSGSGSGTDFTLTISRLQAEDFAIYYCQQYSTVPWTFGQGTKVEIK

SEQ ID NO:8
DIVLTQSPSSLSATPGDRVTISCSASQDISNYLNWYQQKPGQAPQLLIYFTSSLHSGVPSRFSGSGSGTDFTLTISSLQAEDVATYYCQQYSTVPWTFGQGTKVEIK

SEQ ID NO:9
DIVLTQSPSSLSATPGERATITCSASQDISNYLNWYQQKPGKAPHLLIYFTSSLHSGVPYRFSGSGSGTDFTLTISSLQAEDFAIYYCQQYSTVPWTFGQGTKVEIK

SEQ ID NO:10
DIEMTQSPSSLSATPGDRVTITCSASQDISNYLNWYQQKPGKAPRVLIYFTSSLHSGVPDRFSGSGSGTDFTLTISRLQPEDVATYYCQQYSTVPWTFGQGTKVEIK

SEQ ID NO:11
DIEMTQSPSSLSVTPGDRVTITCSASQDISNYLNWYQQKPGKAPHLLIYFTSSLHSGVPDRFSGSGSGTDFTLTISRLQPEDFATYYCQQYSTVPWTFGQGTKVEIK

SEQ ID NO:12
QIELTQSPSSLSATLGERVTISCSASQDISNYLNWYQQKPGKAPHVLIYFTSSLHSGVPSRFSGSGSGTDFTLTISRLQAEDVATYYCQQYSTVPWTFGQGTKVEIK

Figure 1C-cont.

```
SEQ ID NO:13
DIEMTQSPSSLSASVGDRVTITCSASQDISNYLNWYQQKPGQAPRVLIYFTSSLHSGVPDRFSGSGSGTDFTLTISSLQAEDFAVYYCQQYSTVPWTFGQGTKVEIK

SEQ ID NO:14
DIQLTQSPSSLSASAGDRVTISCSASQDISNYLNWYQQKPGKAPQLLIYFTSSLHSGVPSRFSGSGSGTDFTLTISSLQPEDFATYYCQQYSTVPWTFGQGTKVEIK

SEQ ID NO:15
DIVMTQSPSSLSASPGERATISCNASQSIGTYLAWYQQKPGQAPQVLIYGASNLASGVPGRFSGSGSGTDFTLTISSLQPEDFAVYYCQQYNSKPWTFGGGTKVEIK

SEQ ID NO:16
DIVMTQSPSSLSASPGERATISCRASQSISSYLAWYQQKPGQAPQVLIYGASNLASGVPNRFSGSGSGTDFTLTISSLQPEDFAVYYCQQYSSSPWTFGGGTKVEIK

SEQ ID NO:17
DIVMTQSPSSLSASPGERATITCHASQSISTYLAWYQQKPGQAPHVLIYGASNLASGVPGRFSGSGSGTDFTLTISSLQPDDFAVYYCQQYNSAPWTFGGGTKVEIK

SEQ ID NO:18
DIVMTQSPSSLSASPGERATITCHASQSISTYLAWYQQKPGQAPQVLIYDASNLASGVPNRFSGSRSGTDFTLTISSLQPEDFAVYYCQQYNSAPWTFGGGTKVEIK

SEQ ID NO:19
DIVMTQSPSSLSASPGERATITCKASQSISTYLAWYQQKPGQAPRVLIYDASNLASGVPNRFSGSRSGTDFTLTISSLQPEDFAVYYCQQYSTPYTFGGGTKVEIK

SEQ ID NO:20
DIKMTQSPSSLSASPGERATISCKASQSIGSYLAWYQQKPGQAPSVLIYAASNLASGVPNRFSGSRSGTDFTLTISSLQPEDFAVYYCQQYYSGPWTFGGGTKVEIK

SEQ ID NO:21
DIKMTQSPSSLSASPGERATICNASQSISTYLAWYQQKPGQAPKVLIYGASNLASGVPNRFSGSGSGTDFTLTISSLQPEDFAVYYCQQYNSAPWTFGGGTKVEIK

SEQ ID NO:22
DIVMTQSPSTLSASPGERATISCKASQSIGSYLAWYQQKPGQAPRVLIYSASNLASGVPSRFSGSRSGTDFTLTISSLQPEDFAVYYCQQYNSTPWTFGGGTKVEIK

SEQ ID NO:23
DIVMTQSPSTLSASPGERATISCKASQSIGTYLAWYQQKPGQAPRVLIYDASNLASGVPNRFSGSRSGTDFTLTISSLQPEDFAVYYCQQYYSTPWTFGGGTKVAIK

SEQ ID NO:24
DIVMTQSPSTLSASPGERATISCKASQSIGTYLAWYQQKPGQAPRVLIYSASNLASGVPNRFSGSGSGTDFTLTISSLQPEDFAVYYCQQYSSTPWTFGGGTKVEIK
```

Figure 1C-cont.

SEQ ID NO:25
DIVMTQSPSTLSASPGERATITCHASQSISSYLAWYQQKPGQAPNVLIYGASNLASGVPDRFSGSRSGTDFTLTISSLQPEDFAVYYCQQYNSTPWTFGGGTKVEIK

SEQ ID NO:26
DIVMTQSPSTLSASPGERATITCHASQSISTYLAWYQQKPGQAPRVLIYGASNLASGVPNRFSGSGSGTDFTLTISSLQPEDFAVYYCQQYNSAPWTFGGGTKVEIK

SEQ ID NO:27
DIVMTQSPSTLSASPGERATITCKASQSISTYLAWYQQKPGQAPQVLIYDASNLASGVPNRFSGSGSGTDFTLTISSLQPEDFAVYYCQQYNSAPWTFGGGTKVEIK

SEQ ID NO:28
DIVMTQSPSTLSASPGERATITCNASQSIGSYLAWYQQKPGQAPKVLIYGASNLASGVPSRFSGSRSGTDFTLTISSLQPEDFAVYYCQQYNSTPWTFGGGTKLEIK

SEQ ID NO:29
DIVMTQSPSTLSASPGERATITCNASQSIGTYLAWYQQKPGQAPNLLIYDASNLASGVPGRFSGSRSGTDFTLTISSLQPEDFAVYYCQQYSSTPWTFGGGTKVEIK

SEQ ID NO:30
DIVMTQSPSTLSASPGERATITCNASQSIGTYLAWYQQKPGQAPNVLIYDASNLASGVPSRFSGSRSGTDFTLTISSLQPEDFAVYYCQQYYSAPWTFGGGTKVEIK

SEQ ID NO:31
DIVMTQSPSTLSASPGERATITCNASQSISTYLAWYQQKPGQAPRVLIYGASNLASGVPSRFSGSGSGTDFTLTISSLQPEDFAVYYCQQYNSTPWTFGGGTKVEIK

SEQ ID NO:32
DIVMTQSPSTLSASPGERATITCQASQSISTYLAWYQQKPGQAPKVLIYDASNLASGVPGRFSGSGSGTDFTLTISSLQPEDFAVYYCQQYNSTPWTFGGGTKVEIK

SEQ ID NO:33
DIVMTQSPSTLSASPGERATITCRASQSISTYLAWYQQKPGQAPRLLIYSASNLASGVPNRFSGSGSGTDFTLTISSLQPEDFAVYYCQQYYSTPWTFGGGTKVEIK

SEQ ID NO:34
DIVMTQSPSTLSASPGERATITCSASQSIGTYLAWYQQKPGQAPSVLIYGASNLASGVPGRFSGSGSGTDFTLTISSLQAEDFAVYYCQQYNSAPWTFGGGTKVEIK

SEQ ID NO:35
DIVMTQSPSTLSASPGERATITCSASQSISTYLAWYQQKPGQAPQVLIYAASNLASGVPNRFSGSGSGTDFTLTISSLQPEDFAVYYCQQYSTPWTFGGGTKVEIK

SEQ ID NO:36
AIRMTQSPSSVSASVGDTVTIACRASQAIRNDLTWYQQKPGTAPKLLIYGATTLQSVPSRFSGSGSGTDFTLTISSLQPEDFATYYCQQSSTTPWTFGQGTKVDIK

SEQ ID NO:37
DIVMTQTPSSLSASVGDTVTITCRASRDIRNDLAWYQQKPGKAPELLIYAASSLQSGVPSRFSGSGSGTDFTLTISSLQPEDFATYYCQQSYSTPWTFGQGTKVDIK

Figure 1C-cont.

SEQ ID NO:38
EIVLTQSPSSLSASIGDRVAITCRASRDITTDLAWYQQIPGKAPKLLIYAASRLQSGVPSRFSGSGSGTDFTLTISSLQPEDFAAYYCQQSYSTPWTFGQGTKVDIK

SEQ ID NO:39
EIVLTQSPSSLSASVGDRITITCRASRDIRDDLAWYQQKPGKAPKVLIYAASSLQSGVPSRFSGSGSGTDFTLTISSLQPEDFATYYCQQSYSTPWTFGQGTKLEIK

SEQ ID NO:40
EIVLTQSPSSLSASVGDRVTITCRASQSISTYINWYQQKPGKAPKLLIYAASSLQSGVTSRFSGSGSGTDFTLTIRSLQPEDFATYYCQQSYSTPWTFGQGTKVEIK

SEQ ID NO:41
EIVLTQSPSSLSASVGDRVTITCRASQAIYDYLAWYQQKPGKAPNLLIYAASRLQSGVPSRFSGSGSGTDFTLTISSLQPEDFATYYCQQSYSTPWTFGQGTKVDIK

SEQ ID NO:42
EIVMTQSPSSLSASVGDRVTITCRASQDIRKDLAWYQQKPGIAPKVLIYAASTLQSGVPSRFSGSGSGTDFTLTISSLQPEDFATYYCQQSYSPPWTFGQGTKLEIK

SEQ ID NO:43
EIVMTQSPSSLSASVGDRVTITCRASQSISTYINWYQQKPGKAPKLLIYAASSLQSGVTSRFSGSGSGTDFTLTIRSLQPEDFATYYCQQSYSTPWTFGQGTKVEIK

SEQ ID NO:44
EIVMTQSPSSLSASVGDTVTIACRASRDIRNDLAWYQQKPGKAPKLLIYAASRLQSGVPSRFSGTGSGTDFALTISSLQPEDSASYYCQQSYTIPWTFGQGTKLEIK

SEQ ID NO:45
ETTLTQSPSSLSASVGDTITISCRSSQPITNDLAWYQQKPGKAPNLLIYAASRLQGGVPSRFSGSGSGTDFTLTISSLQPEDFATYYCQQSYSTPWTFGQGTKVEIK

SEQ ID NO:46
LPVLTQPPSASGTPGQRVTISCSGSTSNIGSNPVNWYQQLPGTAPKLLIYSNNQRPSGVPDRLSGSKSGTSASLAISGLLSEDEADYYCASWDDSLTGYVFGTGTQL
TVL

SEQ ID NO:47
LPVLTQPPSASGTPGQRVTISCSGSGSYSNIGSNAVNWYQQLPGAAPKVLMYTNNQRPSGVPDRFSGSKSGTSASLAISGLRSEDEADYYCAAWDDSLNGYVFGTGTKL
TVL

SEQ ID NO:48
NFMLTQPPSTSGTPGQRVTISCSGSTSNIGSNSVTWYQQLPGTAPKVLMYTNNQRPSGVPERFSGSKSGTSASLAISGLQSEDEADYYCAAWDDSLNGYVFGTGTKL
TVL

SEQ ID NO:49
QAVLTQPPSASGTPGQSVTISCSGTTSNIGSNSVNWYQQLPGTAPKVLIYGNDQRPSGVPDRFSGSRSATSASLAISGLQSEDEADYYCAAWDDSLSGYVFGAGTQL
TVL

Figure 1C-cont.

```
SEQ ID NO:50
QPVLTQPPSASATPGQRVTISCSGSGSSSNIGSNPVNWYQQLPGTAPKVLIYSNNQRPSGVPDRFSGSKSGTSASLAISGLQSEDEADYYCAAWDDSLSGYVFGTGTKL
TVL

SEQ ID NO:51
QPVLTQPPSASGTPGQRVTISCSGSGSSSNVGRNTVNWYQQFPGTAPKFLMYGNDERPSGVPDRFSGSKSGTSASLAISGLQSEDEADYYCATWDDSLNGYVFGTGTQL
TVL

SEQ ID NO:52
QPVLTQPPSTSGTPGQRVTISCSGSGSSNIGSNSVTWYQQLPGTAPKVLMYTNNQRPSGVPERFSGSKSGTSASLAISGLQSEDEADYYCAAWDDSLSGYVFGTGTKL
TVL

SEQ ID NO:53
QSVLTQPPSASGTPGQRVTISCSGSGSNSNIGSNNVYWYQQFPGTAPKVLIYGNNQRPSGVPDRFSGSKSGTSASLAISGLQSEDEADYYCGAWDDSLNGYVFGTGTKL
TVL

SEQ ID NO:54
QSALTQPPSVSGAPGQRVTISCTGRSSNIGAGHDVHWYQQLPGTAPKLLIYANDQRPSGVPDRFSDSKSGTSASLGISGLRSEDEADYFCATWDDSLHGYVFGTGTK
VTVL

SEQ ID NO:284
DIQMTQTTSSLSASLGDRVIISCSASQDISNYLNWYQQKPDGTVKVLIYFTSSLHSGVPSRFSGSGSGTDYSLTISNLEPEDIATYYCQQYSTVPWTFGGGTKLEIK
```

Figure 1C-cont.

Amino Acid Sequences of V_L/CDR1 of Selected Anti-VEGF Antibodies

| | |
|---|---|
| SEQ ID NO:164 | NASQSIGTYLA |
| SEQ ID NO:165 | KASQSIGTYLA |
| SEQ ID NO:166 | HASQSISSYLA |
| SEQ ID NO:167 | SASQSISTYLA |
| SEQ ID NO:168 | RASQSISTYLA |
| SEQ ID NO:169 | KASQSIGSYLA |
| SEQ ID NO:170 | HASQSISTYLA |
| SEQ ID NO:171 | RASQSISSYLA |
| SEQ ID NO:172 | NASQSIGSYLA |
| SEQ ID NO:173 | SASQSIGTYLA |
| SEQ ID NO:174 | KASQSISTYLA |
| SEQ ID NO:175 | NASQSISTYLA |
| SEQ ID NO:176 | HASQSIGTYLA |
| SEQ ID NO:177 | QASQSISTYLA |
| SEQ ID NO:178 | RASQSISTYIN |
| SEQ ID NO:179 | RASRDIRNDLA |
| SEQ ID NO:180 | RASRDITTDLA |
| SEQ ID NO:181 | RASQDIRKDLA |
| SEQ ID NO:182 | RASQAIRNDLT |
| SEQ ID NO:183 | RASQAIYDYLA |
| SEQ ID NO:184 | RSSQPITNDLA |
| SEQ ID NO:185 | RASRDIRDDLA |
| SEQ ID NO:186 | SGSSSNVGRNTVN |
| SEQ ID NO:187 | SGSTSNIGSNPVN |
| SEQ ID NO:188 | TGRSSNIGAGHDVH |
| SEQ ID NO:189 | SGSNSNIGSNNVY |
| SEQ ID NO:190 | SGSYSNIGSNAVN |
| SEQ ID NO:191 | SGTTSNIGSNSVN |
| SEQ ID NO:192 | SGSSSNIGSNSVT |
| SEQ ID NO:193 | SGSTSNIGSNSVT |
| SEQ ID NO:194 | SGSSSNIGSNPVN |

Figure 1C-cont.

Amino Acid Sequences of V$_L$/CDR2 of Selected Anti-VEGF Antibodies

| | |
|---|---|
| SEQ ID NO:195 | GASNLAS |
| SEQ ID NO:196 | DASNLAS |
| SEQ ID NO:197 | SASNLAS |
| SEQ ID NO:204 | AASNLAS |
| SEQ ID NO:198 | AASSLQS |
| SEQ ID NO:199 | AASRLQS |
| SEQ ID NO:200 | AASTLQS |
| SEQ ID NO:201 | GATTLQS |
| SEQ ID NO:202 | AASRLQG |
| SEQ ID NO:203 | GNDERPS |
| SEQ ID NO:205 | ANDQRPS |
| SEQ ID NO:206 | GNNQRPS |
| SEQ ID NO:207 | TNNQRPS |
| SEQ ID NO:208 | GNDQRPS |
| SEQ ID NO:209 | SNNQRPS |

Amino Acid Sequences of V$_L$/CDR3 of Selected Anti-VEGF Antibodies

| | |
|---|---|
| SEQ ID NO:210 | QQYNSKPWT |
| SEQ ID NO:211 | QQYSSTPYT |
| SEQ ID NO:212 | QQYNSTPWT |
| SEQ ID NO:213 | QQYYSTPWT |
| SEQ ID NO:214 | QQYNSAPWT |
| SEQ ID NO:215 | QQYSSSPWT |
| SEQ ID NO:216 | QQYYSGPWT |
| SEQ ID NO:217 | QQYSSTPWT |
| SEQ ID NO:218 | QQYYSAPWT |
| SEQ ID NO:219 | QQSYSTPWT |
| SEQ ID NO:220 | QQSYSPPWT |
| SEQ ID NO:221 | QQSYTIPWT |
| SEQ ID NO:222 | QQSSTTPWT |
| SEQ ID NO:223 | ATWDDSLNGYV |
| SEQ ID NO:224 | ASWDDSLTGYV |
| SEQ ID NO:225 | ATWDDSLHGYV |
| SEQ ID NO:226 | GAWDDSLNGYV |
| SEQ ID NO:227 | AAWDDSLNGYV |
| SEQ ID NO:228 | AAWDDSLSGYV |

Figure 1C-cont.

Amino Acid Sequences of V$_L$/FRs of Selected Anti-VEGF Antibodies

SEQ ID NOS 229 and 351-353
DIVMTQSPSSLSASPGERATISC/CDR1/WYQQKPGQAPQVLIY/CDR2/GVPGRFSGSGSGTDFTLTISSLQPEDFAVYYC/CDR3/FGGGTKVEIK SEQ ID NOS 230, 354-355 and 353
DIVMTQSPSTLSASPGERATITC/CDR1/WYQQKPGQAPRVLIY/CDR2/GVPNRFSGSRSGTDFTLTISSLQPEDFAVYYC/CDR3/FGGGTKVEIK SEQ ID NOS 231, 356-357 and 353
DIVMTQSPSTLSASPGERATITC/CDR1/WYQQKPGQAPNVLIY/CDR2/GVPDRFSGSRSGTDFTLTISSLQPEDFAVYYC/CDR3/FGGGTKVEIK SEQ ID NOS 232, 351, 355 and 353
DIVMTQSPSTLSASPGERATITC/CDR1/WYQQKPGQAPQVLIY/CDR2/GVPNRFSGSRSGTDFTLTISSLQPEDFAVYYC/CDR3/FGGGTKVEIK SEQ ID NOS 233, 358, 355 and 353
DIVMTQSPSTLSASPGERATITC/CDR1/WYQQKPGQAPRLLIY/CDR2/GVPNRFSGSRSGTDFTLTISSLQPEDFAVYYC/CDR3/FGGGTKVEIK SEQ ID NOS 234, 354, 359 and 353
DIVMTQSPSTLSASPGERATITC/CDR1/WYQQKPGQAPRVLIY/CDR2/GVPSRFSGSRSGTDFTLTISSLQPEDFAVYYC/CDR3/FGGGTKVEIK SEQ ID NOS 235, 354, 360 and 353
DIVMTQSPSTLSASPGERATITC/CDR1/WYQQKPGQAPRVLIY/CDR2/GVPNRFSGSGSGTDFTLTISSLQPEDFAVYYC/CDR3/FGGGTKVEIK SEQ ID NOS 236, 351, 360 and 353
DIVMTQSPSSLSASPGERATISC/CDR1/WYQQKPGQAPQVLIY/CDR2/GVPNRFSGSGSGTDFTLTISSLQPEDFAVYYC/CDR3/FGGGTKVEIK SEQ ID NOS 237, 361, 359 and 362
DIVMTQSPSTLSASPGERATITC/CDR1/WYQQKPGQAPKVLIY/CDR2/GVPSRFSGSRSGTDFTLTISSLQPEDFAVYYC/CDR3/FGGGTKLEIK SEQ ID NOS 238, 363, 355 and 353
DIKMTQSPSSLSASPGERATISC/CDR1/WYQQKPGQAPSVLIY/CDR2/GVPNRFSGSRSGTDFTLTISSLQPEDFAVYYC/CDR3/FGGGTKVEIK SEQ ID NOS 239, 363-364 and 353
DIVMTQSPSTLSASPGERATITC/CDR1/WYQQKPGQAPSVLIY/CDR2/GVPGRFSGSGSGTDFTLTISSLQAEDFAVYYC/CDR3/FGGGTKVEIK SEQ ID NOS 240 and 351-353
DIVMTQSPSSLSASPGERATITC/CDR1/WYQQKPGQAPQVLIY/CDR2/GVPGRFSGSGSGTDFTLTISSLQPEDFAVYYC/CDR3/FGGGTKVEIK

Figure 1C-cont.

SEQ ID NOS 241, 351, 360 and 353
DIVMTQSPSTLSASPGERATITC/CDR1/WYQQKPGQAPQVLIY/CDR2/GVPNRFSGSGSGTDFTLTISSLQPEDFAVYYC/CDR3/FGGGTKVEIK SEQ ID NOS 242, 354, 360 and 353
DIVMTQSPSTLSASPGERATISC/CDR1/WYQQKPGQAPRVLIY/CDR2/GVPNRFSGSGSGTDFTLTISSLQPEDFAVYYC/CDR3/FGGGTKVEIK SEQ ID NOS 243, 354, 365 and 353
DIVMTQSPSTLSASPGERATITC/CDR1/WYQQKPGQAPRVLIY/CDR2/GVPSRFSGSGSGTDFTLTISSLQPEDFAVYYC/CDR3/FGGGTKVEIK SEQ ID NOS 244, 366-367 and 353
DIVMTQSPSTLSASPGERATITC/CDR1/WYQQKPGQAPNLLIY/CDR2/GVPGRFSGSRSGTDFTLTISSLQPEDFAVYYC/CDR3/FGGGTKVEIK SEQ ID NOS 245, 368-369 and 353
DIVMTQSPSSLSASPGERATITC/CDR1/WYQQKPGQAPHVLIY/CDR2/GVPNRFSGSRSGTDFTLTISSLQPDDFAVYYC/CDR3/FGGGTKVEIK SEQ ID NOS 246, 354-355 and 370
DIVMTQSPSTLSASPGERATISC/CDR1/WYQQKPGQAPRVLIY/CDR2/GVPNRFSGSGSGTDFTLTISSLQPEDFAVYYC/CDR3/FGGGTKVAIK SEQ ID NOS 247, 361 and 352-353
DIVMTQSPSTLSASPGERATITC/CDR1/WYQQKPGQAPKVLIY/CDR2/GVPGRFSGSGSGTDFTLTISSLQPEDFAVYYC/CDR3/FGGGTKVEIK SEQ ID NOS 248, 356, 359 and 353
DIVMTQSPSTLSASPGERATITC/CDR1/WYQQKPGQAPNVLIY/CDR2/GVPSRFSGSRSGTDFTLTISSLQPEDFAVYYC/CDR3/FGGGTKVEIK SEQ ID NOS 249, 361, 360 and 353
DIKMTQSPSSLSASPGERATITC/CDR1/WYQQKPGQAPKVLIY/CDR2/GVPNRFSGSGSGTDFTLTISSLQPEDFAVYYC/CDR3/FGGGTKVEIK SEQ ID NOS 250 and 371-373
EIVMTQSPSSLSASVGDRVTITC/CDR1/WYQQKPGKAPKLLIY/CDR2/GVTSRFSGSGSGTDFTLTISSLQPEDFATYYC/CDR3/FGQGTKVEIK SEQ ID NOS 251 and 374-376
DIVMTQTPSSLSASVGDTVTITC/CDR1/WYQQKPGKAPELLIY/CDR2/GVPSRFSGSGSGTDFTLTISSLQPEDFATYYC/CDR3/FGQGTKVDIK SEQ ID NOS 252, 377-378 and 376
EIVLTQSPSSLSASIGDRVAITC/CDR1/WYQQIPGKAPKLLIY/CDR2/GVPSRFSGSGSGTDFTLTISSLQPEDFAAYYC/CDR3/FGQGTKVDIK SEQ ID NOS 253 and 371-373
EIVLTQSPSSLSASVGDRVTITC/CDR1/WYQQKPGKAPKLLIY/CDR2/GVTSRFSGSGSGTDFTLTIRSLQPEDFATYYC/CDR3/FGQGTKVEIK

Figure 1C-cont.

SEQ ID NOS 254, 379, 375 and 380
EIVMTQSPSSLSASVGDRVTITC/CDR1/WYQQKPGIAPKVLIY/CDR2/GVPSRFSGSGSGTDFTLTISSLQPEDFATYYC/CDR3/FGQGTKLEIK SEQ ID NOS 255, 371, 381 and 380
EIVMTQSPSSLSASVGDTVTIAC/CDR1/WYQQKPGKAPKLLIY/CDR2/GVPSRFSGTGSGTDFALTISSLQPEDSASYYC/CDR3/FGQGTKLEIK SEQ ID NOS 256, 382 and 375-376
AIRMTQSPSSVSASVGDTVTIAC/CDR1/WYQQKPGTAPKLLIY/CDR2/GVPSRFSGSGSGTDFTLTISSLQPEDFATYYC/CDR3/FGQGTKVDIK SEQ ID NOS 257, 383 and 375-376
EIVMTQSPSSLSASVGDRVTITC/CDR1/WYQQKPGKAPNLLIY/CDR2/GVPSRFSGSGSGTDFTLTISSLQPEDFATYYC/CDR3/FGQGTKVDIK SEQ ID NOS 258, 383, 375 and 373
ETTLTQSPSSLSASVGDTITISC/CDR1/WYQQKPGKAPNLLIY/CDR2/GVPSRFSGSGSGTDFTLTISSLQPEDFATYYC/CDR3/FGQGTKVEIK SEQ ID NOS 259, 384, 375 and 380
EIVLTQSPSSLSASVGDRITITC/CDR1/WYQQKPGKAPKVLIY/CDR2/GVPSRFSGSGSGTDFTLTISSLQPEDFATYYC/CDR3/FGQGTKLEIK SEQ ID NOS 260, 385, 375 and 373
DIQLTQSPSSLSASAGDRVTISC/CDR1/WYQQKPGKAPQLLIY/CDR2/GVPSRFSGSGSGTDFTLTISSLQPEDFATYYC/CDR3/FGQGTKVEIK SEQ ID NOS 261 and 386-388
QPVLTQPPSASGTPGQRVTISC/CDR1/WYQQFPGTAPKFLMY/CDR2/GVPDRFSGSKSGTSASLAISGLQSEDEADYYC/CDR3/FGTGTQLTVL SEQ ID NOS 262, 389-390 and 388
LPVLTQPPSASGTPGQRVTISC/CDR1/WYQQLPGTAPKLLIY/CDR2/GVPDRLSGSKSGTSASLAISGLLSEDEADYYC/CDR3/FGTGTQLTVL SEQ ID NOS 263, 389 and 391-392
QSALTQPPSVSGAPGQRVTISC/CDR1/WYQQLPGTAPKLLIY/CDR2/GVPDRFSDSKSGTSASLGISGLRSEDEADYFC/CDR3/FGTGTKVTVL SEQ ID NOS 264, 393, 387 and 394
QSVLTQPPSASGTPGQRVTISC/CDR1/WYQQFPGTAPKVLIY/CDR2/GVPDRFSGSKSGTSASLAISGLQSEDEADYYC/CDR3/FGTGTKLTVL SEQ ID NOS 265, 395-396 and 394
LPVLTQPPSASGTPGQRVTISC/CDR1/WYQQLPGAAPKVLMY/CDR2/GVPDRFSGSKSGTSASLAISGLRSEDEADYYC/CDR3/FGTGTKLTVL SEQ ID NOS 266 and 397-399
QAVLTQPPSASGTPGQSVTISC/CDR1/WYQQLPGTAPKVLIY/CDR2/GVPDRFSGSRSATSASLAISGLQSEDEADYYC/CDR3/FGAGTQLTVL

Figure 1C-cont.

SEQ ID NOS 267, 400-401 and 394
QPVLTQPPSTSGTPGQRVTISC/CDR1/WYQQLPGTAPKVLMY/CDR2/GVPERFSGSKSGTSASLAISGLQSEDEADYYC/CDR3/FGTGTKLTVL SEQ ID NOS 268, 400-401 and 394
NFMLTQPPSTSGTPGQRVTISC/CDR1/WYQQLPGTAPKVLMY/CDR2/GVPERFSGSKSGTSASLAISGLQSEDEADYYC/CDR3/FGTGTKLTVL SEQ ID NOS 269, 397, 387 and 394
QPVLTQPPSASATPGQRVTISC/CDR1/WYQQLPGTAPKVLIY/CDR2/GVPDRFSGSKSGTSASLAISGLQSEDEADYYC/CDR3/FGTGTKLTVL

Figure 1D

Amino Acid Sequences of V_H of Selected Anti-VEGF Antibodies

SEQ ID NO:55
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGSSH
WYFDVWGQGTLVTVSS

SEQ ID NO:56
EVQLVESGGGLVQPGGSLRLSCAASGYDFTHYGMNWVRQAPGKGLEWVGWINTYTGEPTYAADFKRRFTFSLDTSKSTAYLQMNSLRAEDTAVYYCAKYPYYYGTSH
WYFDVWGQGTLVTVSS

SEQ ID NO:57
EGQLVQSGGGVVQPGGSLRLSCAASGYTFTNYGMNWIRQAPGKGLEWVGWINTYTGEPTYAADFKRRFTFSLDTSKSTAYLQLNSLRAEDTAVYYCAKYPYYYGTSH
WYFDVWGQGTLVTVSS

SEQ ID NO:58
EVQLVESGGGVVQPGGSLRLSCAASGYTFTNYGMNWIRQAPGKGLEWVGWINTYTGEPTYAADFKRRFTISLDNSKSQAYLQMNSLRAEDTAVYYCAKYPHYGSSH
WYFDVWAQGTLVTVSS

SEQ ID NO:59
EVQLVQSGGGLVQPGGTLRLSCAASGYTFTNYGMNWIRQAPGKGLEWVGWINTYTGEPTYAADFKRRFTFSLDTSKNTAYLQMNSLRAEDTAVYYCAKYPHYGSSH
WYFDVWGQGTLVTVSS

SEQ ID NO:60
EVQLVQSGGGVVQPGGSLRLRCAASGYTFTNYGMNWIRQAPGKGLEWVGWINTYTGEPTYAADFKRRVTFSLDTSKSTAYLQLNSLRAEDTAVYYCAKYPHYGSSH
WYFDVWGQGTLVTVSS

SEQ ID NO:61
EVQLVQSGGGVVQPGGSLRLSCAASGFDFTNYGMNWIRQAPGKGLEWVGWINTYTGEPTYAADFKRRVTFSLDTSKSTAYLQLNSLRAEDTAVYYCAKYPHYGSSH
WYFDVWGQGTLVTVSS

SEQ ID NO:62
EVQLVQSGGGVVQPGGSLRLSCAASGYALDHFGLNWIRQAPGKGLEWVGWINTYTGEPTYAADFKRRVTFSLDTSKSTAYLQLNSLRAEDTAVYYCAKYPHYGSSH
WYFDVWGQGTLVTVSS

SEQ ID NO:63
EVQLVQSGGGVVQPGGSLRLSCAASGYDFYNYGINWVRQAPGKGLEWVGWINTYTGEPTYAHEFTRRVTFSLDTSKSTAYLQLNSLRAEDTAVYYCAKYPHYGSSH
WYFDVWGQGTLVTVSS

Figure 1D-cont.

SEQ ID NO:64
EVQLVQSGGGVVQPGGSLRLSCAASGYSLDHYGMNWVRQAPGKGLEWVGWINTYTGEPTYAADFKRRVTFSLDTSKSTAYLQLNSLRAEDTAVYYCAKYPHYYGSSH
WYFDVWGQGTLVTVSS

SEQ ID NO:65
EVQLVQSGGGVVQPGGSLRLSCAASGYTFTNYGMNWIRQAPGKGLEWVGWINTYTGEPTYAADFKRRFTFSLDTSKNTAYLQLNSLRAEDTAVYYCAKYPHYYGSSH
WYFDVWGQGTLVTVSS

SEQ ID NO:66
EVQLVQSGGGVVQPGGSLRLSCAASGYTFTNYGMNWIRQAPGKGLEWVGWINTYTGEPTYAADFKRRFTISLDNSKSTVYLQMNSLRAEDTAVYYCAKYPHYYGSSH
WYFDVWGQGTLVTVSS

SEQ ID NO:67
EVQLVQSGGGVVQPGGSLRLSCAASGYTFTNYGMNWIRQAPGKGLEWVGWINTYTGEPTYAADFKRRVTFSLDTSKSTAYLQLNSLRAEDTAVYYCAKYPHYYGSSH
WYFDVWGQGTLVTVSS

SEQ ID NO:68
EVQLVQSGGGVVQPGGSLRLSCAASGYTFTNYGMNWIRQAPGKGLEWVGWINTYTGEPTYAADFKRRVTFSLNTSKSTAYLQLNSLRAEDTAVYYCAKYPHYYGSSH
WYFDVWGQGTLVTVSS

SEQ ID NO:69
EVQLVQSGGGVVQPGGSLRLSCAASGYTFTNYGMNWIRQAPGKGLEWVGWINTYTGEPTYAADFKRRFTFSLDTSKNTAYLQLNSLRAEDTAVYYCAKYPHYYGSSH
WYFDVWGQGTLVTVSS

SEQ ID NO:70
EVQLVQSGGGVVQPGGSLRLSCAASGYTFTNYGMNWIRQAPGKGLEWVGWINTYTGEPTYAADFKRRFTFSLDTSKSTAYLQMNSLRAEDTAVYYCAKYPHYYGSSH
WYFDVWGQGTLVTVSS

SEQ ID NO:71
EVQLVQSGGGVVQPGGSLRLTCAASGYTFTNYGMNWIRQAPGKGLEWVGWINTYTGEPTYAADFKRRFTFSLDNSKSTAYLQLNSLRAEDTAVYYCARYPHYYGSSH
WYFDVWGQGTLVTVSS

SEQ ID NO:72
EVQLVQSGGGVVQPGGSLRLTCAVSGYTFTNYGMNWIRQAPGKGLEWVGWINTYTGEPTYAADFKRRFTISRDTSKNQAYLQMNSLRAEDTAVYYCAKYPHYGSSH
WYFDVWGQGTLVTVSS

Figure 1D-cont.

SEQ ID NO:73
EVQLVQSGGGVVQPGGTLRLSCAASGYTFTNYGMNWIRQAPGKGLEWVGWINTYTGEPTYAADFKRRVTFSLDTSKSTAYLQLNSLRAEDTAVYYCAKYPHYYGSSH
WYFDVWGQGTLVTVSS

SEQ ID NO:74
EVQLVQSGGGVVQPGGTLRLTCAASGYTFTNYGMNWIRQAPGKGLEWVGWINTYTGEPTYAADFKRRVTFSLDTSKSTAYLQMNSLRAEDTAVYYCAKYPHYYGSSH
WYFDVWGQGTLVTVSS

SEQ ID NO:75
EVQLVQSGGGVVQPGGTLRLTCAASGYTFTNYGMNWVRQAPGKGLEWVGWINTYTGEPTYAADFKRRVTFSLDTSKSTAYLQMNSLRAEDTAVYYCAKYPHYYGSSH
WYFDVWGQGTLVTVSS

SEQ ID NO:76
EVQLVQSGGGVVQPGGTLRLTCAASGYTFTNYGMNWVRQAPGKGLEWVGWINTYTGEPTYAADFKRRVTISLDTSKSTVYLQMNSLRAEDTAVYYCAKYPHYYGSSH
WYFDVWGQGTLVTVSS

SEQ ID NO:77
QVQLVESGGGLVQPGGSLRLTCAASGYTFTNYGMNWIRQAPGKGLEWVGWINTYTGEPTYAADFKRRFTFSLDTSKSKAYLQLNSLRAEDTAVYYCARYPHYYGSSH
WYFDVWGQGTLVTVSS

SEQ ID NO:78
QVQLVQSGGGLVQPGGTLRLTCAVSGYTFTNYGMNWIRQAPGKGLEWVGWINTYTGAPTYAADFKRRLTFSLDNSKNPPYLQMNSLRAEDTAVYYCAKYPHYYGSSH
WYFDVWGQGTLVTVSS

SEQ ID NO:79
QVQLVQSGGGVVQPGGSLRLSCAASGYTFTNYGMNWIRQAPGKGLEWVGWINTYTGEPTYAADFKRRVTFSLDNSKSTVYLQMNSLRAEDTAVYYCAKYPHYYGSSH
WYFDVWGQGTLVTVSS

SEQ ID NO:80
QVQLVQSGGGVVQPGGSLRLSCAASGYTFTNYGMNWVRQAPGKGLEWVGWINTYTGEPTYAADFKRRFTISLDTSKNTAYLQLNSLRAEDTAVYYCAKYPHYYGSSH
WYFDVWGQGTLVTVSS

SEQ ID NO:81
QVQLVQSGGGVVQPGGSLRLTCAASGYTFTNYGMNWIRQAPGKGLEWVGWINTYTGEPTYAADFKRRVTISLDTSKSQAYLQMNSLRAEDTAVYYCAKYPHYYGSSH
WYFDVWGQGTLVTVSS

SEQ ID NO:82
QVQLVQSGGGVVQPGGSLRLTCAASGYTFTNYGMNWIRQAPGKGLEWVGWINTYTGEPTYAADFKRRVTISLDTSKSTAYLQLNSLRAEDTAVYYCAKYPHYYGSSH
WYFDVWGQGTLVTVSS

Figure 1D-cont.

SEQ ID NO:83
QVQLVQSGGGVVQPGGSLRLTCAASGYTFTNYGMNWVRQAPGKGLEWVGWINTYTGEPTYAADFKRRETISLDTSKSQAYLQMNSLRAEDTAVYYCAKYPHYYGSSH
WYFDVWGQGTLVTVSS

SEQ ID NO:84
QVQLVQSGGGVVQPGGTLRLTCAASGYTFTNYGMNWIRQAPGKGLEWVGWINTYTGEPTYAADFKRRETFSLDTSKNTAYLQMNSLRAEDTAVYYCAKYPHYYGSSH
WYFDVWGQGTLVTVSS

SEQ ID NO:85
EVQLVQSGGGVVQPGGSLRLSCAASGYTFTHYGLNWLRQAPGKGPEWVGWVNTYTGETTYADEFKRRVTFSLDTSKSTAYLQLNSLRAEDTAVYYCAKYPYYGRSHW
YFDVWGQGTLVTVSS

SEQ ID NO:86
EVQLVQSGGGVVQPGGSLRLSCAASGFNFTHYGINWIRQAPGKGPEWVGWINTNNGEPTYAQDFKRRVTFSLDTSKSTAYLQLNSLRAEDTAVYYCAKYPYYGRSH
WYFDVWGQGTLVTVSS

SEQ ID NO:87
EVQLVQSGGGVVQPGGSLRLSCAASGYDFAHYGLNWIRQAPGKGLEWVGWVNTYTGESTYVPEFKRRVTFSLDTSKSTAYLQLNSLRAEDTAVYYCAKYPYYGRSH
WYFDVWGQGTLVTVSS

SEQ ID NO:88
EVQLVQSGGGVVQPGGSLRLSCAASGYDFAHYGVNWLRQAPGKGLEWVGWINTYTGETTYAHDFKRRVTFSLDTSKSTAYLQLNSLRAEDTAVYYCAKYPYYGRSH
WYFDVWGQGTLVTVSS

SEQ ID NO:89
EVQLVQSGGGVVQPGGSLRLSCAASGYDFASFGINWIRQAPGKGLEWVGWINTYTGESTYAQDFKRRVTFSLDTSKSTAYLQLNSLRAEDTAVYYCAKYPYYGRSH
WYFDVWGQGTLVTVSS

SEQ ID NO:90
EVQLVQSGGGVVQPGGSLRLSCAASGYDFDHFGINWIRQAPGKGPEWVGWINTYTGEPTYVDEFKRRVTFSLDTSKSTAYLQLNSLRAEDTAVYYCAKYPYYGRSH
WYFDVWGQGTLVTVSS

SEQ ID NO:91
EVQLVQSGGGVVQPGGSLRLSCAASGYDFNNYGMNWIRQAPGKGPEWVGWINTYNGEPTYAPDFKRRVTFSLDTSKSTAYLQLNSLRAEDTAVYYCAKYPYYGRSH
WYFDVWGQGTLVTVSS

Figure 1D-cont.

SEQ ID NO:92
EVQLVQSGGGVVQPGGSLRLSCAASGYDFSHFGINWIRQAPGKGLEWVGWINTYTGETTYAHDFKRRVTFSLDTSKSTAYLQLNSLRAEDTAVYYCAKYPYYYGRSH
WYFDVWGQGTLVTVSS

SEQ ID NO:93
EVQLVQSGGGVVQPGGSLRLSCAASGYDFSHFGINWVRQAPGKGPEWVGWINTYTGETTYVPEFKRRVTFSLDTSKSTAYLQLNSLRAEDTAVYYCAKYPYYYGRSH
WYFDVWGQGTLVTVSS

SEQ ID NO:94
EVQLVQSGGGVVQPGGSLRLSCAASGYDFSNYGLNWVRQAPGKGPEWVGWINTYTGEPTYAEEFTRRVTFSLDTSKSTAYLQLNSLRAEDTAVYYCAKYPYYYGRSH
WYFDVWGQGTLVTVSS

SEQ ID NO:95
EVQLVQSGGGVVQPGGSLRLSCAASGYDFETHYGLNWIRQAPGKGPEWVGWINTYTGETTYAHEFTRRVTFSLDTSKSTAYLQLNSLRAEDTAVYYCAKYPYYYGRSH
WYFDVWGQGTLVTVSS

SEQ ID NO:96
EVQLVQSGGGVVQPGGSLRLSCAASGYNFYHYGVNWVRQAPGKGPEWVGWVNTYTGETTYAQEFKRRVTFSLDTSKSTAYLQLNSLRAEDTAVYYCAKYPYYYGRSH
WYFDVWGQGTLVTVSS

SEQ ID NO:97
EVQLVQSGGGVVQPGGSLRLSCAASGYNFYSYGLNWVRQAPGKGPEWVGWINTYTGEPTYAQEFKRRVTFSLDTSKSTAYLQLNSLRAEDTAVYYCAKYPYYYGRSH
WYFDVWGQGTLVTVSS

SEQ ID NO:98
EVQLVQSGGGVVQPGGSLRLSCAASGYSFDHYGLNWVRQAPGKGLEWVGWINTYTGEPTYADEFTRRVTFSLDTSKSTAYLQLNSLRAEDTAVYYCAKYPYYYGRSH
WYFDVWGQGTLVTVSS

SEQ ID NO:99
EVQLVQSGGGVVQPGGSLRLSCAASGYTFTNYGMNWIRQAPGKGLEWVGWINTYTGEPTYAADFTRRVTFSLDTSKSTAYLQLNSLRAEDTAVYYCAKYPYYYGRSH
WYFDVWGQGTLVTVSS

SEQ ID NO:100
EVQLVQSGGGVVQPGGSLRLSCAASGYTFTNYGMNWIRQAPGKGLEWVGWINTYTGEPTYAADFKRRVTFSLDTSKSTAYLQLNSLRAEDTAVYYCAKYPYYYGRSH
WYFDVWGQGTLVTVSS

SEQ ID NO:101
EVQLVQSGGGVVQPGGSLRLSCAASGYTFTNYGMNWVRQAPGKGLEWVGWINTYTGEPTYAADFKRRFTFSLDTSKSTAYLQMNSLRAEDTAVYYCAKYPYYYGRSH
WYFDVWGQGTLVTVSS

Figure 1D-cont.

SEQ ID NO:102
EVQLVQSGGGVVQPGGSLRLSCAASGYTFTNYGMNWVRQAPGKGLEWVGWINTYTGEPTYAADFKRRFTFSLDTSKSTAYLQMNSLRAEDTAVYYCAKYPYYGTSH
WYFDVWGQGTLVTVSS

SEQ ID NO:103
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPYYYGTSH
WYFDVWGQGTLVTVSS

SEQ ID NO:104
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYGRSH
WYFDVWGQGTLVTVSS

SEQ ID NO:105
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPYYYGRSH
WYFDVWGQGTLVTVSS

SEQ ID NO:106
EVQLVQSGGGVVQPGGSLRLSCAASGYDFTHFGLNWIRQAPGKGPEWVGWINTYTGEPTYAQDFKRRVTFSLDTSKSTAYLQLNSLRAEDTAVYYCAKYPYYYGRSH
WYFDVWGQGTLVTVSS

SEQ ID NO:107
EVQLVQSGGGVVQPGGSLRLSCAASGYDLSHYGLNWIRQAPGKGPEWVGWINTYTGEPTYAPDFTRRVTFSLDTSKSTAYLQLNSLRAEDTAVYYCAKYPYYYGRSH
WYFDVWGQGTLVTVSS

SEQ ID NO:108
EVQLVQSGGGVVQPGGSLRLSCAASGYNFSHFGLNWLRQAPGKGLEWVGWINTYNGETTYAPDFKRRVTFSLDTSKSTAYLQLNSLRAEDTAVYYCAKYPYYYGRSH
WYFDVWGQGTLVTVSS

SEQ ID NO:109
EVQLVQSGGGVVQPGGSLRLSCAASGYNFSHFGLNWLRQAPGKGPEWVGWINTYTGEPTYAPEFKRRVTFSLDTSKSTAYLQLNSLRAEDTAVYYCAKYPYYYGRSH
WYFDVWGQGTLVTVSS

SEQ ID NO:110
EVQLVQSGGGVVQPGGSLRLSCAASGYDFTHFGLNWVRQAPGKGLEWVGWVNTYTGETTYAHEFKRRVTFSLDTSKSTAYLQLNSLRAEDTAVYYCAKYPYYYGRSH
WYFDVWGQGTLVTVSS

Figure 1D-cont.

SEQ ID NO:283
EIQLVQSGPELKQPGETVRISCKASGYTFTNYGMNWVKQAPGKGLKWMGWINTYTGEPTYAADFKRRFTFSLETSASTAYLQISNLKNDDTATYFCAKYPHYYGSSH
WYFDVWGAGTTVTVSS

SEQ ID NO:285
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAHSRHYGSSP
QYFDV WGQGTLVTVSS

SEQ ID NO:286
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYGYYYGSSH
WYFDVWGQGTLVTVSS

SEQ ID NO:287
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGASH
WYFDVWGQGTLVTVSS

SEQ ID NO:288
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYGGCH
WYFDVWGQGTLVTVSS

SEQ ID NO:289
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYGGSH
WYFDVWGQGTLVTVSS

SEQ ID NO:290
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYGGYN
QYFDVWGQGTLVTVSS

SEQ ID NO:291
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYGRSH
WYFDVWGQGTLVTVSS

SEQ ID NO:293
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYGRSQ
WYLDVWGQGTLVTVSS

Figure 1D-cont.

SEQ ID NO:294
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYSRTC
QYFDVWGQGTLVTVSS

SEQ ID NO:295
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYSSSH
WYFDVWGQGTLVTVSS

SEQ ID NO:296
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYSSSH
WYFDVWGQGTLVTVSS

SEQ ID NO:297
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPYYHGSSH
WYFDVWGQGTLVTVSS

SEQ ID NO:298
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPYYNGSSH
WYFDVWGQGTLVTVSS

SEQ ID NO:299
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPYYNSTSH
WYFDVWGQGTLVTVSS

SEQ ID NO:300
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPYSGTSH
WYFDVWGQGTLVTVSS

SEQ ID NO:301
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPYYSGTSH
WYFDVWGQGTLVTVSS

SEQ ID NO:302
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPYYGRSH
WYFDVWGQGTLVTVSS

SEQ ID NO:303
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPYYGSSH
WYFDVWGQGTLVTVSS

Figure 1D-cont.

SEQ ID NO:304
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPYYYGSSS
WYFDVWGQGTLVTVSS

SEQ ID NO:305
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPYYSTSH
WYFDVWGQGTLVTVSS

SEQ ID NO:306
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYRDFNGSSH
WYFDVWGQGTLVTVSS

SEQ ID NO:307
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYSYYGSSH
WYFDVWGQGTLVTVSS

SEQ ID NO:308
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCARARHYYGSSH
CYFDLWGQGTLVTVSS

SEQ ID NO:309
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCARDSHYYGSSH
QYFDLWGQGTLVTVSS

SEQ ID NO:310
EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYGTSH
WYFDVWGQGTLVTVSS

Figure 1D-cont.

Amino Acid Sequences of V$_H$/CDR1 of Selected Anti-VEGF Antibodies

| | |
|---|---|
| SEQ ID NO:111 | GFDFTNYGMN |
| SEQ ID NO:112 | GYTFTNYGMN |
| SEQ ID NO:113 | GYSLDHYGMN |
| SEQ ID NO:114 | GYALDHFGLN |
| SEQ ID NO:115 | GYDFYNYGIN |
| SEQ ID NO:116 | GYTFTNYGMN |
| SEQ ID NO:117 | GYSFDHYGLN |
| SEQ ID NO:118 | GYDFSNYGLN |
| SEQ ID NO:119 | GYDFSHFGIN |
| SEQ ID NO:120 | GYDFAHYGVN |
| SEQ ID NO:121 | GYDFDHFGIN |
| SEQ ID NO:122 | GYDFNNYGMN |
| SEQ ID NO:123 | GYDFASFGIN |
| SEQ ID NO:124 | GFNFTHYGIN |
| SEQ ID NO:125 | GYDFAHYGLN |
| SEQ ID NO:126 | GYNFYHYGVN |
| SEQ ID NO:127 | GYDFTHYGLN |
| SEQ ID NO:128 | GYNFYSYGLN |
| SEQ ID NO:129 | GYDFSHFGIN |
| SEQ ID NO:130 | GYTFTHYGLN |
| SEQ ID NO:131 | GYDFTHFGLN |
| SEQ ID NO:132 | GYDLSHYGLN |
| SEQ ID NO:133 | GYNFSHFGLN |
| SEQ ID NO:134 | GYNFSHFGLN |
| SEQ ID NO:135 | GYDFTHFGLN |

Figure 1D-cont.

Amino Acid Sequences of V$_H$/CDR2 of Selected Anti-VEGF Antibodies

| | |
|---|---|
| SEQ ID NO:136 | WINTYTGEPTYAHEFTR |
| SEQ ID NO:137 | WINTYTGEPTYAADFTR |
| SEQ ID NO:138 | WINTYTGEPTYADEFTR |
| SEQ ID NO:139 | WINTYTGEPTYAEEFTR |
| SEQ ID NO:140 | WINTYTGETTYVPEFKR |
| SEQ ID NO:141 | WINTYTGETTYAHDFKR |
| SEQ ID NO:142 | WINTYTGEPTYVDEFKR |
| SEQ ID NO:143 | WINTYNGEPTYAPDFKR |
| SEQ ID NO:144 | WINTYTGESTYAQDFKR |
| SEQ ID NO:145 | WINTNNGEPTYAQDFKR |
| SEQ ID NO:146 | WVNTYTGESTYVPEFKR |
| SEQ ID NO:147 | WVNTYTGETTYAQEFKR |
| SEQ ID NO:148 | WINTYTGETTYAHEFTR |
| SEQ ID NO:149 | WINTYTGEPTYAQEFKR |
| SEQ ID NO:150 | WINTYTGETTYAHDFKR |
| SEQ ID NO:151 | WVNTYTGETTYADEFKR |
| SEQ ID NO:152 | WINTYTGEPTYAQDFKR |
| SEQ ID NO:153 | WINTYTGEPTYAPDFTR |
| SEQ ID NO:154 | WINTYNGETTYAPDFKR |
| SEQ ID NO:155 | WINTYTGEPTYAPEFKR |
| SEQ ID NO:156 | WVNTYTGETTYAHEFKR |

Figure 1D-cont.

Amino Acid Sequences of V_H/CDR3 of Selected Anti-VEGF Antibodies

SEQ ID NO:311    CAHSRHYYGSSPQYFDV
SEQ ID NO:312    CAKYGYYYGSSHWYFDV
SEQ ID NO:313    CAKYPHYYGASHWYFDV
SEQ ID NO:314    CAKYPHYYGGCHWYFDV
SEQ ID NO:315    CAKYPHYYGGSHWYFDV
SEQ ID NO:316    CAKYPHYYGGYNQYFDV
SEQ ID NO:317    CAKYPHYYGRSHWYFDV
SEQ ID NO:318    CAKYPHYYGRSQWYLDV
SEQ ID NO:319    CAKYPHYYSRTCQYFDV
SEQ ID NO:320    CAKYPHYYSSSHWYFDV
SEQ ID NO:321    CAKYPYFYGSSHWYFDV
SEQ ID NO:322    CAKYPYYHGSSHWYFDV
SEQ ID NO:323    CAKYPYYNGSSHWYFDV
SEQ ID NO:324    CAKYPYYNSTSHWYFDV
SEQ ID NO:325    CAKYPYYSGTSHWYFDV
SEQ ID NO:326    CAKYPYYSGTSHWYFDY
SEQ ID NO:327    CAKYPYYYGRSHWYFDV
SEQ ID NO:328    CAKYPYYYGSSHWYFDV
SEQ ID NO:329    CAKYPYYYGSSSWYFDV
SEQ ID NO:330    CAKYPYYYSTSHWYFDV
SEQ ID NO:331    CAKYRDFNGSSHWYFDV
SEQ ID NO:332    CAKYSYYYGSSHWYFDV
SEQ ID NO:333    CARARHYYGSSHCYFDL
SEQ ID NO:334    CARDSHYYGSSHQYFDL
SEQ ID NO:335    CAKYPHYYGTSHWYFDV
SEQ ID NO:336    CAKYPHYYGSSHWYFDV
SEQ ID NO:337    CAKYPYYYGTSHWYFDV

Figure 1D-cont.

Amino Acid Sequences of V_H/FRs of Selected Anti-VEGF Antibodies

SEQ ID NOS 157 and 402-404
EVQLVQSGGGVVQPGGSLRLSCAAS/CDR1/WVRQAPGKGLEWVG/CDR2/RFTFSLDTSKSTAYLQMNSLRAEDTAVYYCA/CDR3/WGQGTLVTVSS SEQ ID NOS 158, 402, 405 and 404
EVQLVQSGGGVVQPGGSLRLSCAAS/CDR1/WVRQAPGKGLEWVG/CDR2/RFTFSLDTSKNTAYLQLNSLRAEDTAVYYCA/CDR3/WGQGTLVTVSS SEQ ID NOS 159, 406-407 and 404
EVQLVQSGGGVVQPGGSLRLSCAAS/CDR1/WIRQAPGKGLEWVG/CDR2/RFTISLDNSKSTVYLQMNSLRAEDTAVYYCA/CDR3/WGQGTLVTVSS SEQ ID NOS 160, 406, 408 and 404
EVQLVQSGGGVVQPGGSLRLTCAVS/CDR1/WIRQAPGKGLEWVG/CDR2/RFTISRDTSKNQAYLQMNSLRAEDTAVYYCA/CDR3/WGQGTLVTVSS SEQ ID NOS 161, 406, 409 and 404
EVQLVQSGGGVVQPGGSLRLSCAAS/CDR1/WIRQAPGKGLEWVG/CDR2/RVTFSLDTSKSTAYLQLNSLRAEDTAVYYCA/CDR3/WGQGTLVTVSS SEQ ID NOS 162, 402, 410 and 404
QVQLVQSGGGVVQPGGSLRLTCAAS/CDR1/WVRQAPGKGLEWVG/CDR2/RFTISLDTSKSQAYLQMNSLRAEDTAVYYCA/CDR3/WGQGTLVTVSS SEQ ID NOS 163, 402, 411 and 404
EVQLVQSGGGVVQPGGTLRLTCAAS/CDR1/WVRQAPGKGLEWVG/CDR2/RVTFSLDTSKSTAYLQMNSLRAEDTAVYYCA/CDR3/WGQGTLVTVSS SEQ ID NOS 270, 406 and 412-413
EVLVESGGGVVQPGGSLRLSCAAS/CDR1/WIRQAPGKGLEWVG/CDR2/RFTISLDNSKSQAYLQMNSLRAEDTAVYYCA/CDR3/WAQGTLVTVSS SEQ ID NOS 271, 406, 414 and 404
EVQLVQSGGGLVQPGGTLRLSCAAS/CDR1/WIRQAPGKGLEWVG/CDR2/RFTFSLDTSKNTAYLQMNSLRAEDTAVYYCA/CDR3/WGQGTLVTVSS SEQ ID NOS 272, 406, 409 and 404
EVQLVQSGGGVVQPGGSLRLRCAAS/CDR1/WIRQAPGKGLEWVG/CDR2/RVTFSLDTSKSTAYLQLNSLRAEDTAVYYCA/CDR3/WGQGTLVTVSS SEQ ID NOS 273, 406, 405 and 404
EVQLVQSGGGVVQPGGSLRLSCAAS/CDR1/WIRQAPGKGLEWVG/CDR2/RFTFSLDTSKNTAYLQLNSLRAEDTAVYYCA/CDR3/WGQGTLVTVSS SEQ ID NOS 274, 406, 409 and 404
EVQLVQSGGGVVQPGTLRLSCAAS/CDR1/WIRQAPGKGLEWVG/CDR2/RVTFSLDTSKSTAYLQLNSLRAEDTAVYYCA/CDR3/WGQGTLVTVSS

Figure 1D-cont.

SEQ ID NOS 275, 406, 411 and 404
EVQLVQSGGGVVQPGGTLRLTCAAS/CDR1/WIRQAPGKGLEWVG/CDR2/RVTFSLDTSKSTAYLQMNSLRAEDTAVYYCA/CDR3/WGQGTLVTVSS SEQ ID NOS 276, 402, 415 and 404
EVQLVQSGGGVVQPGGTLRLTCAAS/CDR1/WVRQAPGKGLEWVG/CDR2/RVTISLDTSKSTVYLQMNSLRAEDTAVYYCA/CDR3/WGQGTLVTVSS SEQ ID NOS 277, 406, 416 and 404
QVQLVESGGGLVQPGGSLRLTCAAS/CDR1/WIRQAPGKGLEWVG/CDR2/RFTFSLDTSKSKAYLQLNSLRAEDTAVYYCA/CDR3/WGQGTLVTVSS SEQ ID NOS 278, 406, 417 and 404
QVQLVQSGGGVVQPGGSLRLSCAAS/CDR1/WIRQAPGKGLEWVG/CDR2/RVTFSLDNSKSTVYLQMNSLRAEDTAVYYCA/CDR3/WGQGTLVTVSS SEQ ID NOS 279, 402, 418 and 404
QVQLVQSGGGVVQPGGSLRLSCAAS/CDR1/WVRQAPGKGLEWVG/CDR2/RFTISLDTSKNTAYLQLNSLRAEDTAVYYCA/CDR3/WGQGTLVTVSS SEQ ID NOS 280, 406, 419 and 404
QVQLVQSGGGVVQPGGSLRLTCAAS/CDR1/WIRQAPGKGLEWVG/CDR2/RVTISLDTSKSQAYLQMNSLRAEDTAVYYCA/CDR3/WGQGTLVTVSS SEQ ID NOS 281, 406, 420 and 404
QVQLVQSGGGVVQPGGSLRLTCAAS/CDR1/WIRQAPGKGLEWVG/CDR2/RVTISLDTSKSTAYLQLNSLRAEDTAVYYCA/CDR3/WGQGTLVTVSS SEQ ID NOS 282, 406, 414 and 404
QVQLVQSGGGVVQPGGTLRLTCAAS/CDR1/WIRQAPGKGLEWVG/CDR2/RFTFSLDTSKNTAYLQMNSLRAEDTAVYYCA/CDR3/WGQGTLVTVSS

Figure 2A

| Variants | $K_{on}$ ($10^4$ $M^{-1}s^{-1}$) | $K_{off}$ ($10^{-4}$ $s^{-1}$) | $K_d$ (nM) | hAB1 $K_d$/Variant $K_d$ |
|---|---|---|---|---|
| hAB1 | 0.85 | 1.10 | 13.0 | 1 |
| hAB2 | 1.79 | 0.69 | 3.9 | 3.4 |
| hAB3 | 3.74 | 1.15 | 3.1 | 4.2 |
| hAb4 | 0.40 | 1.04 | 26.0 | 0.5 |
| hAb5 | 1.22 | 0.72 | 5.9 | 2.2 |
| hAB9 | 0.29 | 0.14 | 4.9 | 2.7 |

Figure 2B

| Variants | $K_{on}$ ($10^4$ $M^{-1}s^{-1}$) | $K_{off}$ ($10^{-4}$ $s^{-1}$) | $K_d$ (nM) | hAB1 $K_d$/Variant $K_d$ |
|---|---|---|---|---|
| hAB1 | 0.61 | 0.85 | 13.8 | 1 |
| hAB10 | 0.11 | 0.03 | 2.2 | 6.3 |
| hAB11 | 1.59 | 0.87 | 5.4 | 2.6 |
| hAB12 | 0.23 | 0.03 | 1.5 | 9.2 |

Figure 2C

| Variants | $K_{on}$ ($10^4$ $M^{-1}s^{-1}$) | $K_{off}$ ($10^{-4}$ $s^{-1}$) | $K_d$ (nM) | hAB1 $K_d$/Variant $K_d$ |
|---|---|---|---|---|
| hAB1 | 1.02 | 4.20 | 41.4 | 1 |
| hAB7 | 0.85 | 0.09 | 1.1 | 37.6 |
| hAB8 | 1.58 | 0.17 | 1.1 | 37.6 |
| hAB13 | 1.52 | 0.56 | 3.7 | 11.2 |
| hAB14 | 1.71 | 0.62 | 3.6 | 11.5 |
| hAB15 | 2.34 | 0.86 | 3.7 | 11.2 |
| hAB16 | 2.93 | 0.47 | 1.6 | 25.9 |
| hAB17 | 1.86 | 2.13 | 11.5 | 3.7 |
| hAB18 | 0.71 | 2.59 | 36.3 | 1.1 |
| hAb19 | 1.27 | 9.82 | 77.1 | 0.5 |
| hAB20 | 2.18 | 3.08 | 14.2 | 3.0 |
| hAB35 | 8.28 | 0.62 | 0.7 | 59.1 |
| hAB36 | 4.75 | 0.37 | 0.7 | 59.1 |
| hAB37 | 5.73 | 0.44 | 0.8 | 51.8 |
| hAB38 | 5.00 | 0.48 | 0.9 | 46.0 |
| hAB39 | 2.84 | 0.48 | 1.8 | 23.0 |

HUMANIZED ANTIBODIES AGAINST VASCULAR ENDOTHELIAL GROWTH FACTOR

CROSS REFERENCE TO RELATED APPLICATIONS

This application is a continuation-in-part of U.S. application Ser. No. 10/443,134, filed May 20, 2003, now abandoned entitled "Generation and Selection of Protein Library in Silico" which is a continuation-in-part of U.S. application Ser. No. 10/153,159, filed May 20, 2002, now U.S. Pat. No. 7,117,096 entitled "Structure-Based Selection And Affinity Maturation of Antibody Library, and also a continuation-in-part of application Ser. No. 10/153,176, filed May 20, 2002, entitled "Generation Affinity Maturation of Antibody Library in Silico", both of which are a continuation-in-part of U.S. patent application Ser. No. 10/125,687 entitled "Structure-based construction of human antibody library" filed Apr. 17, 2002, now abandoned which claims the benefit of U.S. Provisional Application Serial No. 60/284,407 entitled "Structure-based construction of human antibody library" filed Apr. 17, 2001. These applications are incorporated herein by reference.

BACKGROUND OF THE INVENTION

The present invention provides antibodies against human antigens and methods for generating high affinity antibodies against these targets. More particularly, the invention provides humanized or human antibodies against vascular endothelial growth factor (VEGF) and methods for generating such anti-VEGF antibodies. In addition, the invention provides compositions, kits and methods of using these antibodies and derivatives thereof to inhibit angiogenesis in vitro, and for diagnosing or treating diseases associated with abnormal angiogenesis such as cancer, rheumatoid arthritis, ischemic-reperfusion related brain edema and injury, cortical ischemia, ovarian hyperplasia and hypervascularity, endometriosis, psoriasis, diabetic retinopaphy, and other ocular angiogenic diseases.

Angiogenesis has been involved in many physiological and pathological processes. Angiogenesis consists of multiple steps that ultimately resulting in proliferation and differentiation of endothelial cells, and formation of tubes and cavities (angiogenesis). Factors that promote angiogenesis include VEGF, aFGF, bFGF, TGF-α, TGF-β, HGF, TNF-α, angiogenin, IL-8, etc., whereas factors that inhibit angiogenesis include thrombospondin (Good et al. *Proc. Natl. Acad. Sci. USA*. 87:6624-6628 (1990)), the N-terminal fragment of prolactin (Clapp et al. *Endocrinology*, 133:1292-1299 (1993)), kringle 5 domain of plasminogen (Cao et al., *J. Biol. Chem.*, 271:29461-29467 (1996), angiostatin (O'Reilly et al. *Cell*, 79:315-328 (1994)) and endostatin (O'Reilly et al. *Cell*, 88:277-285 (1996)).

Vascular endothelial cell growth factor (VEGF) is a growth factor acting specifically with its receptors on vascular endothelial cells to promote their angiogenesis. It is known that angiogenesis plays an important role in the development of new vasculature from preexisting blood vessels and/or circulating endothelial stem cells (Asahara et al., *Science*, 275 (5302):964-967, 1997; Springer et al., *Mol. Cell*, 2(5):549-558, 1998; Folkman and Shing, *J. Biol. Chem.*, 267:10931-10934,1992). Angiogenesis also plays a vital role in many physiological processes, such as embryogenesis, wound healing and menstruation. More importantly, angiogenesis is further involved in pathological conditions such as tumor formation, metastasis, diabetic retinopathy, etc. It is known that the growth of a solid tumor requires tumor vascularization for supplying oxygen and nutrients and the metastasis of tumor cells occurs through blood vessels resulting from the tumor vascularization. VEGF is believed to be a pivotal angiogenic factor in this vascularization for tumors. Therefore, it is expected that the growth and metastasis of tumor can be inhibited by certain substances neutralizing the vascularization activity of VEGF. Recent studies (Burrows and Thorpe, Pharmacol. Ther., 64:155-174, 1994; Proc. Natl. Acad. Sci. USA, 90:8996-9000, 1994) have used such a strategy to target the vasculature of solid tumors. Targeting the blood vessels of the tumors, rather than the tumor cells themselves, has certain advantages in that it is not likely to lead to the development of resistant tumor cells, and that the targeted cells are readily accessible. Moreover, destruction of the blood vessels leads to an amplification of the anti-tumor effect, as many tumor cells rely on a single vessel for their oxygen and nutrients In nearly half of diabetics diabetic retinopathy occurs as one of complications of diabetes. It is believed that the formation of microcapillaries is promoted in diabetic retinopathy by oxygen deficiency. These microcapillaries will sooner or later be ruptured to bleed to form scar tissue, leading to detached retinas. Age-related macular degeneration is another eye disease that has been demonstrated to be involved in pathological vascularization in the retina. Hence, it is expected that inhibition of vascularization can prevent retinopathy from developing. Based on experiments using monkey, Miller et al. reported that VEGF is related very closely to the development of vegetative retinopathy (Miller et al.: Am. J. Pathol. 145, 574-584 (1994)). For this reason, a substance neutralizing the vascularization activity of VEGF is considered useful for preventing or treating diabetic retinopathy and AMD (Lopez et al. Invest. Ophtalmo. Vis. Sci. 37:855-868 (1996)).

The recognition of VEGF as a primary stimulus of angiogenesis in pathological conditions has led to various attempts to block VEGF activity. Inhibitory anti-VEGF receptor antibodies, soluble receptor constructs, antisense strategies, RNA aptamers against VEGF and low molecular weight VEGF receptor tyrosine kinase (RTK) inhibitors have all been proposed for use in interfering with VEGF signaling (Siemeister et al., Cancer Metastasis Rev., 17(2):241-248., 1998). In fact, monoclonal antibodies against VEGF have been shown to inhibit human tumor xenograft growth and ascites formation in mice (Kim et al., Growth Factors 7:53 (1992); Nature 362:841-844 (1993); Asano et al., Hybridoma, 17:185-90, (1998); Mesiano et al., Am. J. Pathol., 153(4):1249-1256, (1998); Luo et al., Cancer Res., 58(12):2594-2600, (1998); Cancer Res., 58(12):2652-2660, (1998); Borgstrom et al. Cancer Res. 56:4032-4039 (1996); Borgstrom et al., Prostate, 35(1): 1-10, (1998)). Furthermore, the same strategy using anti-angiogenic molecules, anti-VEGF antibody, and VEGF antagonists have been utilized in experimental treatment of AMD and diabetic retinopathy (Adamis et al. Arch. Ophthalmol. 114:66-71 (1996)). For the therapeutic applications, antibodies are generally engineered to reduce their toxicities in repeated dosage by humanization, if they are derived originally from mouse and to improve other attributes such as binding affinity with the target molecules by affinity maturation (Winter and Milstein, Nature, 349:293-299, (1991); Baca et al, J. Biol. Chem., 272(16):10678-84, (1997); Presta, et al., Cancer Res., 57:4593-4599, (1997); Chen et al. (1999) J. Mol. Biol. 293:865-881; and Ryan et al. (1999) Toxicologic Pathology, 27(1):78-86).

Although the foregoing studies underscore the importance of VEGF in solid tumor growth, and its potential as a target for tumor therapy, the identification of additional agents that inhibit VEGF-induced angiogenesis would be of benefit in expanding the number of therapeutic options. The development of therapeutic agents that specifically inhibit VEGF to bind with its receptor represents important alternatives to target angiogenesis more effective with potentially improved therapeutic benefits.

SUMMARY OF THE INVENTION

The present invention provides an innovative methodology for engineering proteins with desired structures and functions, especially for engineering antibodies with desirable properties from a therapeutic perspective, including high binding affinity for the target antigen, ability to effectively inhibit abnormal cell proliferation in vitro and in vivo, and minimal toxicity or side effects.

In one aspect of the invention, methods are provided for designing and selecting antibodies against human antigens with high affinity and specificity in silico and in vitro. In some particular embodiments, methods are provided for designing and selecting humanized or fully human antibodies against vascular endothelial growth factor (VEGF) with high affinity and specificity.

In another aspect of the invention, monoclonal antibodies against VEGF are provided. In particular, humanized or human anti-VEGF monoclonal antibodies are provided that can bind to human VEGF with high affinity. Preferably, these antibodies can inhibit VEGF-induced proliferation of endothelial cells in vitro and inhibit VEGF-induced angiogenesis in vivo. These antibodies and their derivative can be used in a wide variety of applications such as diagnosis, prevention, and treatment of diseases such as cancer, AMD, diabetic retinopathy, and other diseases derived from pathological angiogenesis.

In one embodiment, a monoclonal antibody is provided that specifically binds to a human VEGF with dissociation constant $K_d$ equal to or lower than 0.2 nM, optionally lower than 0.1 nM, optionally lower than 0.08 nM, optionally lower than 0.05 nM, optionally lower than 0.01 nM, or optionally lower than 0.005 nM, in the form of scFv, Fab, or other form of antibody measured at a temperature of about 4° C., 25° C., 37° C. or 42° C.

Preferably, $K_d$ of the anti-VEGF antibody, if in the form of scFv and measured at a temperature of 35-37° C., is lower than 1 nM, optionally lower than 0.8 nM, optionally lower than 0.5 nM, optionally lower than 0.2 nM, optionally lower than 0.11 nM, optionally lower than 0.08 nM, optionally lower than 0.05 nM, optionally lower than 0.01 nM, or optionally lower than 0.005 nM.

Also preferably, $K_d$ of the anti-VEGF antibody, if in the form of Fab and measured at a temperature of 35-37° C., is lower than 0.5 nM, optionally lower than 0.2 nM, optionally lower than 0.1 nM, optionally lower than 0.08 nM, optionally lower than 0.05 nM, optionally lower than 0.01 nM, or optionally lower than 0.005 nM.

In inhibition of VEGF-induced proliferation of endothelial cells in vitro, the anti-VEGF antibody preferably has an effective dose for inhibition of 50% cell proliferation $ED_{50}$ equal to or lower than 10 nM, optionally lower than 5 nM, optionally lower than 1 nM, optionally lower than 0.5 nM, optionally lower than 0.1 nM, optionally lower than 0.05 nM, or optionally lower than 0.01 nM in the form of scFv, Fab or other form of antibody.

In a preferred embodiment, a monoclonal antibody is provided that specifically binds to a human VEGF and has $V_L$ comprising the amino acid sequence of $X_1X_2$ $X_3X_4TQX_5PSX_6X_7SX_8X_9X_{10}GX_{11}X_{12}X_{13}X_{14}IX_{15}C\underline{X_{16}}$ $\underline{X_{17}SX_{18}X_{19}IX_{20}X_{21}X_{22}X_{23}X_{24}}WYQQX_{25}PGX_{26}APX_{27}$ $X_{28}LX_{29}Y\underline{X_{30}X_{31}X_{32}X_{33}LX_{34}X_{35}}GVX_{36}X_{37}RFSGX_{38}$ $X_{39}SGTDFX_{40}LTIX_{41}X_{42}LQX_{43}X_{44}DX_{45}AX_{46}YYC$ $QQ\underline{X_{47}X_{48}X_{49}X_{50}P\underline{X_{51}}}TFGX_{52}GTKX_{53}X_{54}IK$ (SEQ ID NO: 338), wherein the underlined regions are designated as $V_L$/CDR1, $V_L$/CDR2, and $V_L$/CDR3, respectively, whereas the rest of the region is designated as framework, and wherein $X_1$ is D, E or A; $X_2$ is I, or T; $X_3$ is V, E, K, R, Q, or T; $X_4$ is M, or L; $X_5$ is S, or T; $X_6$ is S, or T; $X_7$ is L, or V; $X_8$ is A, or V; $X_9$ is S, or T; $X_{10}$ is P, V, L, A, or I; $X_{11}$ is E, or D; $X_{12}$ is R, or T; $X_{13}$ is A, or V I; $X_{14}$ is T, or A; $X_{15}$ is T, S, or A; $X_{16}$ is S, R, N, K, H, or Q; $X_{17}$ is A, or S; $X_{18}$ is Q, or R; $X_{19}$ is S, D, A, or P; $X_{20}$ is S, G, R, T, or Y; $X_{21}$ is T, N, S, D, or K; $X_{22}$ is Y, or D; $X_{23}$ is L, or I; $X_{24}$ is A, N, or T; $X_{25}$ is K, or I; $X_{26}$ is Q, K, T, or I; $X_{27}$ is R, K, Q, N, H, S, or E; $X_{28}$ is V, or L; $X_{29}$ is I, or V; $X_{30}$ is F, A, G, D, or S; $X_{31}$ is A, or T; $X_{32}$ is S, or T; $X_{33}$ is N, S, R, or T; $X_{34}$ is A, H, or Q; $X_{35}$ is S, or G; $X_{36}$ is P, T; $X_{37}$ is S, N, D, G, or Y; $X_{38}$ is S, or T; $X_{39}$ is G, or R; $X_{40}$ is T, or A; $X_{41}$ is S, or R; $X_{42}$ is S, or R; $X_{43}$ is P, or A; $X_{44}$ is E, or D; $X_{45}$ is F, V, or S; $X_{46}$ is V, T, I, A, or S; $X_{47}$ is Y, or S; $X_{48}$ is S, Y, or N; $X_{49}$ is S, or T; $X_{50}$ is T, V, A, P, K, G, S, or I; $X_{51}$ is W or Y; $X_{52}$ is Q, or G; $X_{53}$ is V, or L; and $X_{54}$ is E, D, or A.

Such preferred $V_L$ sequences may be combined with the preferred $V_H$ sequences or $V_H$ of other antibodies, provided that the antibody so produced binds to the human VEGF with a desired affinity.

In another preferred embodiment, a monoclonal antibody is provided that specifically binds to a human VEGF and has $V_L$ comprising the amino acid sequence of $X_1X_2X_3$ $LTQPPSX_4SX_5TPGQX_6VTISCSG\underline{X_7X_8SNX_9GX_{10}NX_{11}}$ $V\underline{X_{12}}WYQQ\underline{X_{13}}PGX_{14}APKX_{15}LX_{16}YX_{17}NX_{18}X_{19}RPS$ $GVPX_{20}RX_{21}SGSX_{22}SX_{23}TSASLAISGLX_{24}SEDEADYY$ $C\underline{X_{25}X_{26}WDDSLX_{27}GYVFGX_{28}GTX_{29}LTVL}$ (SEQ ID NO: 339), wherein the underlined regions are designated as $V_L$/CDR1, $V_L$/CDR2, and $V_L$/CDR3, respectively, whereas the rest of the region is designated as framework, and wherein $X_1$ is Q L, or N; $X_2$ is P A F, or S; $X_3$ is V, or M; $X_4$ is A, or T; $X_5$ is G, or A; $X_6$ is R, or S; $X_7$ is S, or T; $X_8$ is S, TY, or N; $X_9$ is I, or V; $X_{10}$ is S, or R; $X_{11}$ is S, P, N, A, or T; $X_{12}$ is N, T, or Y; $X_{13}$ is L, or F; $X_{14}$ is T, or A; $X_{15}$ is V, L, or F; $X_{16}$ is M, or I; $X_{17}$ is G, T, or S; $X_{18}$ is N, or D; $X_{19}$ is Q, or E; $X_{20}$ is D, or E; $X_{21}$ is F, or L; $X_{22}$ is K, or R; $X_{23}$ is G, or A; $X_{24}$ is Q, L, or R; $X_{25}$ is A, or G; $X_{26}$ is A, S, or T; $X_{27}$ is N, S, or T; $X_{28}$ is T, or A; and $X_{29}$ is K, or Q.

Such preferred $V_L$ sequences may be combined with the preferred $V_H$ sequences or $V_H$ of other antibodies, provided that the antibody so produced binds to the human VEGF with a desired affinity.

In yet another preferred embodiment, a monoclonal antibody is provided that specifically binds to a human VEGF and has $V_L$ comprising the amino acid sequence of QSALTQP PSVSGAPGQRVTISCTGRSSNIGAGHDVHWYQQLPG TAPKLLIYANDQRPSGVPDRFSDSKSGTSASLGISGLR SEDEADYFCATWDDSLHGYVFGTGTKVTVL (SEQ ID No: 54). This $V_L$ sequence may be combined with the preferred $V_H$ sequences or $V_H$ of other antibodies, provided that the antibody so produced binds to the human VEGF with a desired affinity.

In yet another preferred embodiment, a monoclonal antibody is provided that specifically binds to a human VEGF and has $V_H$ comprising the amino acid sequence of $X_1X_2QLVX_3SGGGX_4VQPGGX_5LRLX_6CAX_7SGX_8X_9$ $\underline{X_{11}X_{12}X_{13}GX_{14}}NWX_{15}RQAPGKGX_{16}EWVG\underline{WX_{17}}$ $\underline{NTX_{18}X_{19}GX_{20}X_{21}TYX_{22}X_{23}X_{24}FX_{25}RRX_{26}TX_{27}SX_{28}}$ $X_{29}X_{30}SKX_{31}X_{32}X_{33}YLQX_{34}NSLRAEDTAVYYCA\underline{X_{35}}$ $\underline{YPX_{36}YYGX_{37}SHWYFDVW}X_{38}QGTLVTVSS$ (SEQ ID NO: 340), wherein the underlined regions are designated as CDR1, CDR2, and CDR3, respectively, whereas the rest of the region is designated as framework according to Kabat nomenclature, and wherein $X_1$ is E, or Q; $X_2$ is V, or G; $X_3$ is Q, or E; $X_4$ is V, or L; $X_5$ is S, or T; $X_6$ is S or T, or R; $X_7$ is A, or V; $X_8$ is Y, or F; $X_9$ is T, D, N, S, or A; $X_{10}$ is F, or L; $X_{11}$ is T, D, Y, A, S, or N; $X_{12}$ is N, H, or S; $X_{13}$ is Y, or F; $X_{14}$ is M, L, I, or V; $X_{15}$ is I, V, or L; $X_{16}$ is L, or P; $X_{17}$ is I, or V; $X_{18}$ is Y, or N; $X_{19}$ is T, or N; $X_{20}$ is E, or A; $X_{21}$ is P, T, or S; $X_{22}$ is A, or V; $X_{23}$ is A, H, Q, P, D, or E; $X_{24}$ is D, or E; $X_{25}$ is K, or T; $X_{26}$ is V, F, or L; $X_{27}$ is F, or I; $X_{28}$ is L, or R; $X_{29}$ is D, or N; $X_{30}$ is T, or N; $X_{31}$ is S, or N; $X_{32}$ is T, Q, P, or K; $X_{33}$ is A, V, or P; $X_{34}$ is L, or M; $X_{35}$ is K, or R; $X_{36}$ is H, or Y; $X_{37}$ is S, R, or T; and $X_{38}$ is G, or A.

Such preferred $V_H$ sequences may be combined with the preferred $V_L$ sequences or $V_L$ of other antibodies, provided that the antibody so produced binds to the human VEGF with a desired affinity.

In one embodiment, a monoclonal antibody is provided that specifically binds to a human VEGF and has $V_L$ comprising the amino acid sequence selected from the group consisting of SEQ ID NOs:2-54, more preferably comprising the amino acid sequence selected from the group consisting of SEQ ID NO:14, SEQ ID NO:26, SEQ ID NO:28, SEQ ID NO:36, SEQ ID NO:37, SEQ ID NO:44, SEQ ID NO:47, and SEQ ID NO:54.

Such preferred $V_L$ sequences may be combined with the preferred $V_H$ sequences or $V_H$ of other antibodies, provided that the antibody so produced binds to the human VEGF with a desired affinity.

In one embodiment, a monoclonal antibody is provided that specifically binds to a human VEGF and has $V_H$ comprising the amino acid sequence selected from the group consisting of SEQ ID NOs:57-110 and SEQ ID NOs:285-310, and preferably comprising the amino acid sequence selected from the group consisting of SEQ ID NOs:61-64, SEQ ID NO:67, 68, 70, 75, 83, 88, 89, 90, 91, 92, 93, 94, and 96-110.

Such preferred $V_H$ sequences may be combined with the preferred $V_L$ sequences or $V_L$ of other antibodies, provided that the antibody so produced binds to the human VEGF with a desired affinity.

In yet another embodiment, a monoclonal antibody is provided that specifically binds to a human VEGF and has CDR1 in the $V_L$ region ($V_L$/CDR1) comprising the amino acid sequence selected from the group consisting of SEQ ID NOs: 164-194.

Such preferred $V_L$/CDR1 may be combined with other regions of preferred light chain, or of other light chain, and the preferred heavy chain variable region sequence or with other heavy chain variable region sequences, provided that the antibody so produced binds to human VEGF with desired affinity.

In yet another embodiment, a monoclonal antibody is provided that specifically binds to a human VEGF and has CDR2 in the $V_L$ region ($V_L$/CDR2) comprising the amino acid sequence selected from the group consisting of SEQ ID NOs: 195-209.

Such preferred $V_L$/CDR2 may be combined with other regions of preferred light chain, or of other light chain, and the preferred heavy chain variable region sequence or with other heavy chain variable region sequence, provided that the antibody so produced binds human VEGF.

In yet another embodiment, a monoclonal antibody is provided that specifically binds to a human VEGF and has CDR3 in the $V_L$ region ($V_L$/CDR3) comprising the amino acid sequence selected from the group consisting of SEQ ID NOs: 210-228.

Such preferred $V_L$/CDR3 may be combined with other regions of preferred light chain, or of other light chain, and the preferred heavy chain variable region sequence or with other heavy chain variable region sequence, provided that the antibody so produced binds to human VEGF with desired affinity.

In yet another embodiment, a monoclonal antibody is provided that specifically binds to a human VEGF and has a framework region (FR) CDR3 in the $V_L$ region ($V_L$/FR) comprising the amino acid sequence selected from the group consisting of: SEQ ID NO:229-269 and 351-401, and preferably comprising the amino acid sequence selected from the group consisting of SEQ ID NO:232, 351, 355 and 353; 235, 354, 360 and 353; 237, 361, 359 and 362; 251 and 374-376; 255, 371, 381 and 380; 263, 389 and 391-392; and 265, 395-396 and 394.

Such preferred $V_L$/FR may be combined with CDR regions of preferred light chain, or of other light chain, and the preferred heavy chain variable region sequence or with other heavy chain variable region sequence, provided that the antibody so produced binds to human VEGF with desired affinity.

In one embodiment, a monoclonal antibody is provided that specifically binds to a human VEGF and has CDR1 in the $V_H$ region ($V_H$/CDR1) comprising the amino acid sequence of $GX_1X_2X_3X_4X_5X_6GX_7N$, wherein $X_1$ is Y, or F; $X_2$ is D, N, T, S, or A; $X_3$ is F, or L; $X_4$ is T, D, S, Y, A, or N; $X_5$ is H, N, or S; $X_6$ is Y, or F; $X_7$ is M, L, I, or V.

Further preferably $V_H$/CDR1 of the monoclonal antibody comprises the amino acid sequence selected from the group consisting of: SEQ ID NOs:111-135.

Such preferred $V_H$/CDR1 may be combined with other regions of preferred heavy chain or of other heavy chain, and the preferred light chain variable region sequence or with other light chain variable region sequence, provided that the antibody so produced binds human VEGF.

In one embodiment, a monoclonal antibody is provided that specifically binds to a human VEGF and has CDR2 in the $V_H$ region ($V_H$/CDR2) comprising the amino acid sequence of $WX_1NTX_2X_3GEX_4TYX_5X_6X_7FX_8R$, (SEQ ID NO: 341), wherein $X_1$ is I, or V; $X_2$ is Y, or N; $X_3$ is T, or N; $X_4$ is P, T, or S; $X_5$ is A, or V; $X_6$ is A, Q, P, H, D, or E; $X_7$ is D, or E; and $X_8$ is K, or T Preferably $V_H$/CDR2 of the monoclonal antibody comprises the amino acid sequence selected from the group consisting of: SEQ ID NOs:136-156.

Such preferred $V_H$/CDR2 may be combined with other regions of preferred heavy chain or of other heavy chain, and the preferred light chain variable region sequence or with other light chain variable region sequence, provided that the antibody so produced binds to human VEGF with desired affinity.

In one embodiment, a monoclonal antibody is provided that specifically binds to a human VEGF and has CDR3 in the $V_H$ region ($V_H$/CDR3) comprising the amino acid sequence of $KYPX_1YYGX_2SHWYFDV$ (SEQ ID NO: 342), wherein $X_1$ is Y, or H, and $X_2$ is R.

Preferably, the anti-VEGF antibody $V_H$/CDR3 has the amino acid sequence selected from the group consisting of SEQ ID NOs:311-337.

Such preferred $V_H$/CDR3 may be combined with other regions of preferred heavy chain or of other heavy chain, and the preferred light chain variable region sequences or with other light chain variable domain sequences, provided that the antibody so produced binds to human VEGF with desired affinity.

In one embodiment, a monoclonal antibody is provided that specifically binds to a human VEGF and has FR in the $V_H$ region ($V_H$/FR) comprising the amino acid sequence of $X_1VQLVX_2SGGGX_3VQPGGX_4LRLX_5CAX_6S$ (SEQ ID NO: 343) /CDR1/$WX_7RQAPGKGLEWVG$ (SEQ ID NO: 344)/CDR2/$RX_8TX_9SX_{10}DX_{11}SKX_{12}X_{13}X_{14}YLQX_{15}NS$ LRAEDTAVYYCA (SEQ ID NO: 345) /CDR3/ $WX_{16}QGTLVTVSS$(SEQ ID NO: 346), wherein $X_1$ is E, or Q; $X_2$ is Q, or E; $X_3$ is V, or L; $X_4$ is S, or T; $X_5$ is S, T, or R; $X_6$ is A, or V; $X_7$ is I, or V; $X_8$ is F, or V; $X_9$ is F, or I; $X_{10}$ is L, or R is $X_{11}$ is T, or N; $X_{12}$ is S, or N; $X_{13}$ is T, Q, or K; $X_{14}$ is A, or V; $X_{15}$ is M, or L; and $X_{16}$ is G, or A.

In one embodiment, a monoclonal antibody is provided that specifically binds to a human VEGF and has a $V_L$ and $V_H$ pair selected from the group consisting of: SEQ ID NO:1 and 70; SEQ ID NO:1 and 67; SEQ ID NO:1 and 75; SEQ ID NO:1 and 83; SEQ ID NO:14 and 55; SEQ ID NO:1 and 101; SEQ ID NO:1 and 100; SEQ ID NO:14 and 102; SEQ ID NO:1 and 103; SEQ ID NO:1 and:104; SEQ ID NO:1 and 105; SEQ ID NO:36 and 100; SEQ ID NO:26 and 100; SEQ ID NO:28 and 100; SEQ ID NO:37 and 100; SEQ ID NO:44 and 100; SEQ ID NO:54 and 100; and SEQ ID NO:47 and 100, preferably selected from the group consisting of SEQ ID NO:28 and 61; SEQ ID NO:28 and 62; SEQ ID NO:28 and 63; SEQ ID NO:28 and 64; SEQ ID NO:28 and 68; SEQ ID NO:28 and 85; SEQ ID NO:28 and 86; SEQ ID NO:28 and 87; SEQ ID NO:28 and 88; SEQ ID NO:28 and 89; SEQ ID NO:28 and 90; SEQ ID NO:28 and 91; SEQ ID NO:28 and 92; SEQ ID NO:28 and 93; SEQ ID NO:28 and 94; SEQ ID NO:28 and 95; SEQ ID NO:28 and 96; SEQ ID NO:28 and 97; SEQ ID NO:28 and 98; SEQ ID NO:28 and 99; SEQ ID NO:28 and 106; SEQ ID NO:28 and 107; SEQ ID NO:28 and 108; SEQ ID NO:28 and 109; and SEQ ID NO:28 and 110.

The binding affinity of the above-described antibody to a human VEGF, represented by dissociation constant $K_d$, is optionally lower than 100 nM, optionally lower than 10 nM, optionally lower than 8 nM, optionally lower than 5 nM, optionally lower than 1 nM, optionally lower than 0.8 nM, optionally lower than 0.5 nM, optionally lower than 0.2 nM, optionally lower than 0.1 nM, optionally lower than 0.08 nM, optionally lower than 0.05 nM, optionally lower than 0.01 nM, or optionally lower than 0.005 nM, in the form of scFv, Fab, or other form of antibody measured at a temperature of about 4° C., 25° C., 37° C. or 42° C.

The antibodies resulted from combination of the full-length $V_H$ and $V_L$, $V_H$/CDR, $V_H$/FR, $V_L$/CDR, $V_L$/FR (e.g., the hit variants provided in FIGS. 1A and 1B and amino acid sequences shown in FIGS. 1C and 1D) disclosed in the present invention are within the scope of the present invention; and such combination does not include the anti-VEGF antibodies disclosed in U.S. patent application Ser. No. 09/056,160, publication No: 2002/0032315.

BRIEF DESCRIPTION OF THE DRAWINGS

FIG. 1A shows an AA-PVP profile of $V_L$ hit variants designed by using the inventive methodology in silico. The AA-PVP of the VL chain uses the humanized VL (SEQ ID NO:1) by Baca et al. (1997) J Biol Chem 272: 10678-10684 as a reference sequence. The dot indicates the same amino acid as reference. CDRs are indicated in bold letters underlined. FIG. 1A discloses residues 1-97 of SEQ ID NO: 1 and SEQ ID NO: 349.

FIG. 1B shows an AA-PVP profile of $V_H$ hit variants designed by using the inventive methodology in silico. The AA-PVP of the VH chain uses the humanized VH (SEQ ID NO:55) by Baca et al. (1997), supra as a reference sequence. The dot indicates the same amino acid as reference. CDRs are indicated in bold letters underlined. FIG. 1B discloses residues 1-114 of SEQ ID NO: 55 and SEQ ID NO: 350.

FIG. 1C shows amino acid sequences of full-length VL (SEQ ID NOS:1-54 and SEQ ID NO: 284), VL/CDRs (CDR1 SEQ ID NOS: 164-194; CDR2 SEQ ID NOS: 195-209; CDR3 SEQ ID NOS: 210-228), and VL/FR sequences of certain embodiments of the antibodies according to the present invention. The VL/FR sequences are set forth as consecutive framework segments (i.e., FR1, FR2, FR3 and FR4) and CDR (ie., CDR1, CDR2 and CDR3) region placeholders. For example, the first VL/FR sequence set forth in FIG. 1C comprises a FR1 sequence (SEQ ID NO: 229) a placeholder for a CDR1 sequence, a FR2 sequence (SEQ ID NO: 351), a placeholder for CDR2, a FR3 sequence (SEQ ID NO: 352), a placeholder for CDR3, and a FR4 sequence (SEQ ID NO: 353).

FIG. 1D shows amino acid sequences of full-length VH (SEQ ID NOS: 55-110, SEQ ID NO: 283 and SEQ ID NOS: 285-310), VH/CDRs (CDR1 SEQ ID NOS: 111-135; CDR2 SEQ ID NOS: 136-156; CDR3 SEQ ID NOS: 311-337), and VH/FR sequences of certain embodiments of the antibodies according to the present invention. The VH/FR sequences are set forth as consecutive framework segments (ie., FR1, FR2, FR3 and FR4) and CDR (i.e.. CDR1, CDR2 and CDR3) placeholders, according to the same format described above for the VL/FR sequences set forth in FIG. 1C.

FIGS. 2A and 2B show the affinity analysis of a panel of variants of humanized anti-VEGF antibody using BioCore biosensor at 25° C. Antibody fragments in the format of single chain were expressed as described below and purified. The measurement was done by measuring the change of SPR units (y-axis) vs time (x-axis) when a purified antibody binds its antigen (VEGF) immobilized on the CM5 biochip at 25° C. $K_d$ values were calculated by the ratio of $K_{on}$ to $K_{off}$. A ratio of a variant $K_d$ to that of hAB1 for each variant antibody was also calculated. $K_{on}$ is defined as association rate constant expressed as the reciprocal of the multiple of concentration of the antibody fragment (in molar) and time (in second); whereas $K_{off}$ is defined as dissociation rate constant expressed as the reciprocal of time (in second); $K_d$ is defined as dissociation constant, which is the ratio of $K_{off}$ to $K_{on}$ expressed in molar concentration. hAB1 contains SEQ 1 and SEQ55 (which, if in the form of Fab, would be essentially Fab-12 as described in Chen et al. (1999) J. Mol. Biol. 293:865-881); hAB2 contains SEQ1 and SEQ70; hAB3 contains SEQ1 and SEQ67; hAB4 contains SEQ1 and SEQ83; hAB5 SEQ1 and SEQ75; hAB9 contains SEQ14 and SEQ102; hAB10 contains SEQ1 and SEQ103; hAB11 contains SEQ1 and SEQ104; hAB12 contains SEQ1 and SEQ105, as $V_L$ and $V_H$, respectively.

FIG. 2C shows the affinity analysis of a panel of variants of humanized anti-VEGF antibody using BioCore biosensor at 35° C. Antibody fragments in the format of single chain were expressed as described below and purified. The measurement was done by measuring the change of SPR units (y-axis) vs time (x-axis) when a purified antibody binds its antigen (VEGF) immobilized on the CM5 biochip at 35° C. $K_d$ values were calculated by the ratio of $K_{on}$ to $K_{off}$. A ratio of a variant $K_d$ to that of hAB1 for each variant antibody was also calculated. hAB1 contains SEQ1 and SEQ55 (which, if in the form of Fab, would be essentially Fab-12 as described in Chen et al. (1999) J. Mol. Biol. 293:865-881); hAB7 contains SEQ1 and SEQ101; hAB8 contains SEQ1 and SEQ100; hAB13 contains SEQ1 and SEQ56 (which, if in the form of Fab, would be Y0317 as described in Chen et al. (1999) J. Mol. Biol. 293: 865-881); hAB14 contains SEQ36 and SEQ100; hAB15 contains SEQ26 and SEQ100; hAB16 contains SEQ28 and SEQ100; hAB35 contains SEQ28 and SEQ106; hAB36 contains SEQ28 and SEQ107; hAB37 contains SEQ28 and SEQ108; hAB38 contains SEQ28 and SEQ109; hAB39 contains SEQ28 and SEQ110, as $V_L$ and $V_H$, respectively.

FIG. 3 shows the affinity analysis of six humanized anti-VEGF antibodies using BIAcore biosensor. The antibodies were incubated in 1×PBS buffer at 4° C., 37° C., or 42° C. for 16 hours before the assay. The measurement was done by measuring the change of SPR units (y-axis) vs time (x-axis) when a purified antibody binds its antigen (VEGF) immobilized on the CM5 biochip at 25° C. Both the on-rate and off-rate changes were determined from the data fitting using 1:1 Langmuir binding model, whereas $K_d$s were determined by the ratio of $K_{off}$ to $K_{on}$. Composition of the $V_L$ and $V_H$, respectively, is listed as following: hAB1 contains SEQ1 and SEQ55; hAB2 contains SEQ1 and SEQ70; hAB3 contains SEQ1 and SEQ67; hAB7 contains SEQ1 and SEQ101; hAB8 contains SEQ1 and SEQ100; hAB13 contains SEQ1 and SEQ56, as $V_L$ and $V_H$, respectively.

Figure 4:
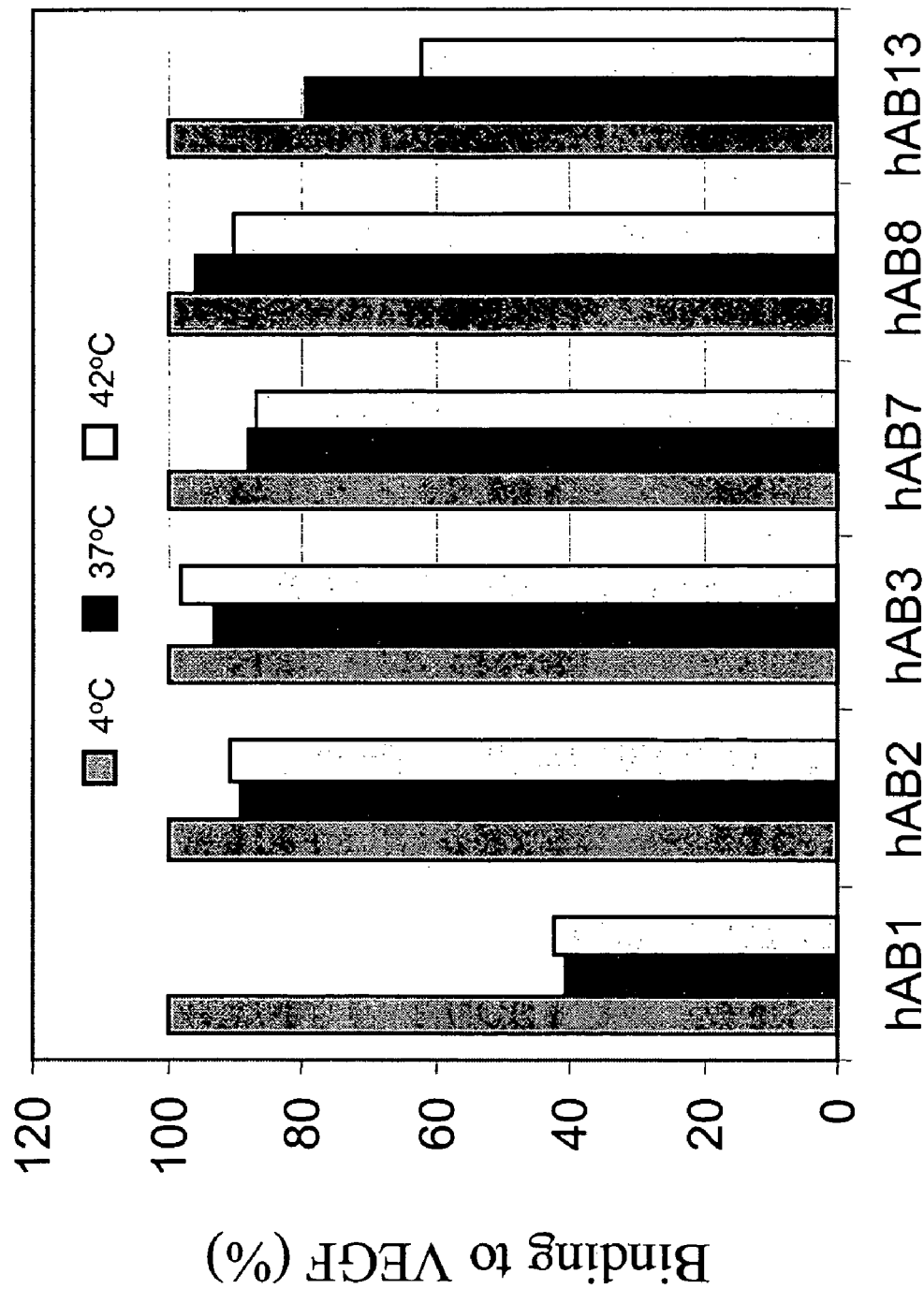

FIG. 4 summarized the data of the stability of the humanized anti-VEGF antibodies shown in FIG. 3. The y-axis shows the percentage of the antibody remain active in binding to the immobilized VEGF antigen using BIAcore at 25° C. after the purified antibody is incubated at 4° C., 37° C. and 42° C. for 16 hours as described in FIG. 3. The maximal binding of each antibody at different conditions was expressed as percentile of that of 4° C.

Figure 5:
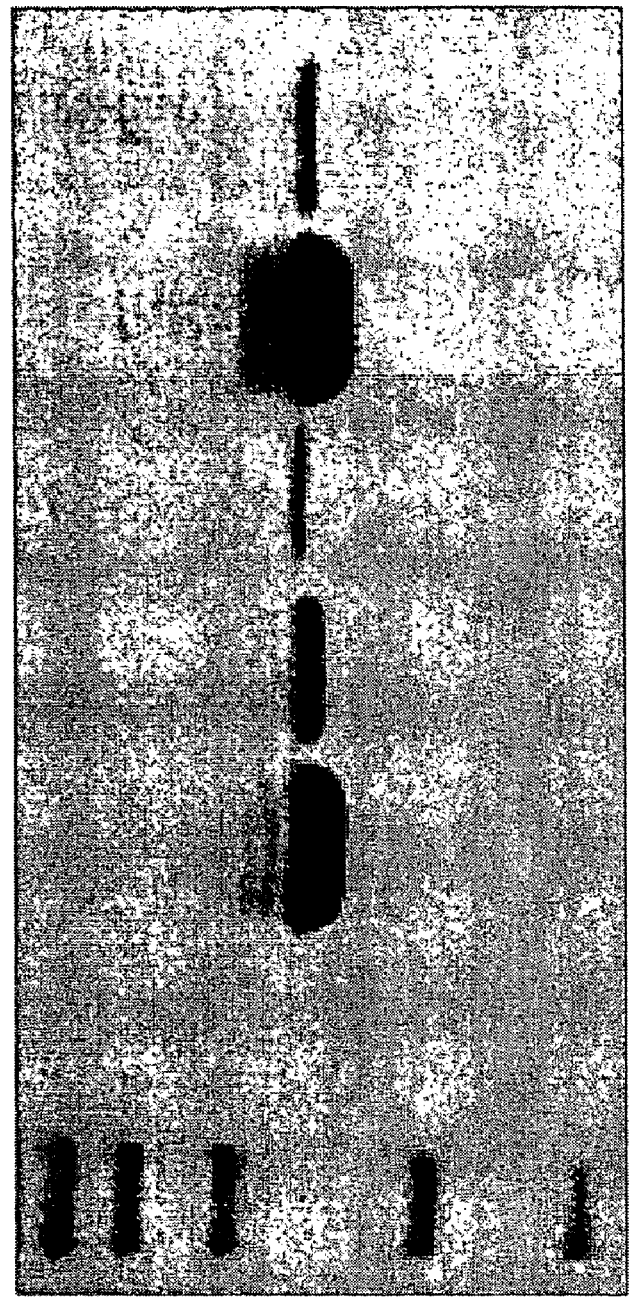

FIG. 5 shows the expression of the humanized anti-VEGF antibodies using *E. coli* expression system as described below. The expression level of each antibody fragment was evaluated by applying the same volume of the purified material from the same fraction as shown detected by SDS-PAGE/Coomassie blue staining. Composition of the $V_L$ and $V_H$, respectively, is listed as following: hAB1 contains SEQ1 and SEQ55; hAB35 contains SEQ28 and SEQ106; hAB36 contains SEQ28 and SEQ107; hAB37 contains SEQ28 and SEQ108; hAB38 contains SEQ28 and SEQ109; hAB39 contains SEQ28 and SEQ110, as $V_L$ and $V_H$, respectively.

Figure 6:
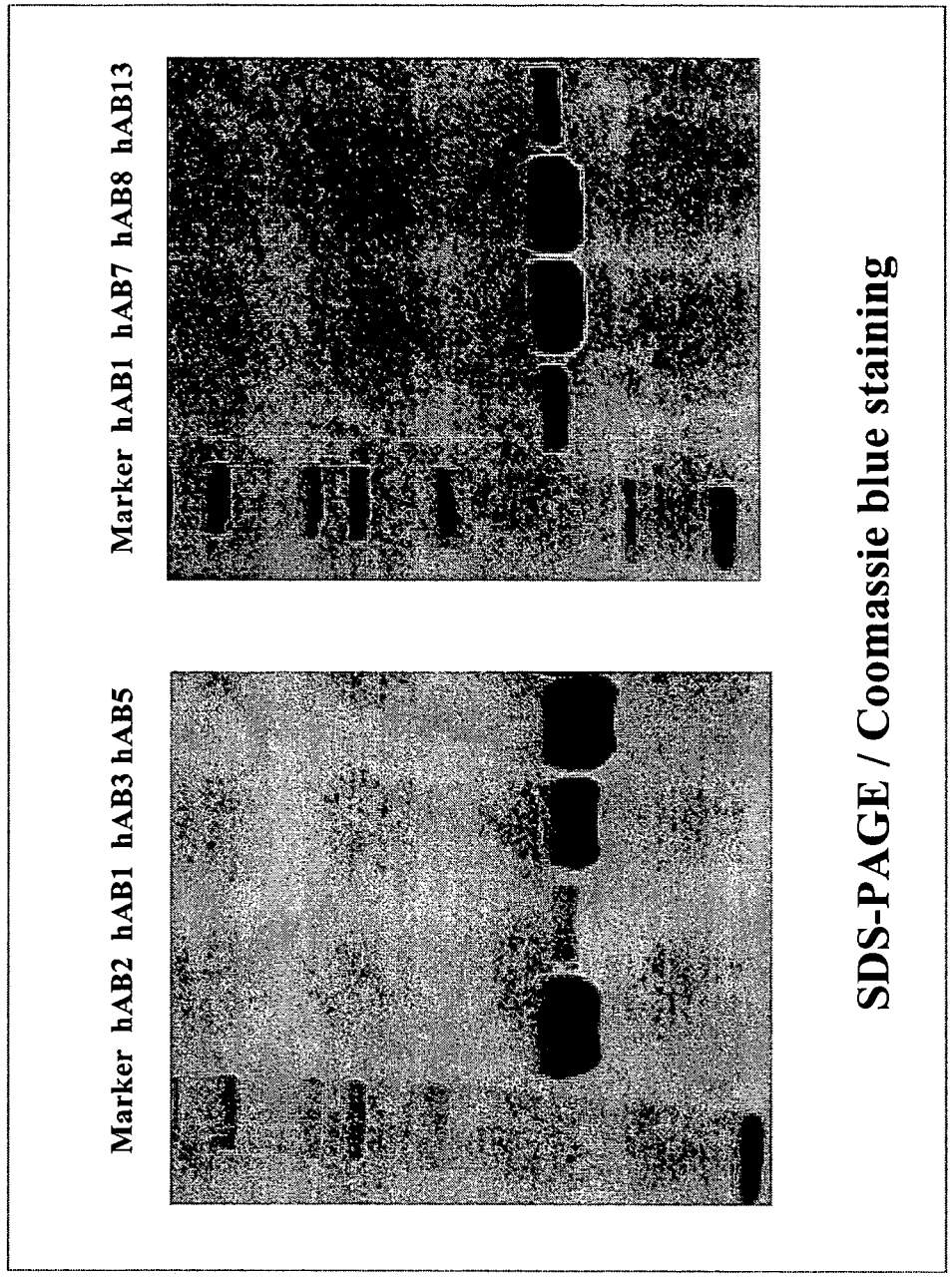

FIG. 6 shows expression of humanized anti-VEGF antibody in a eukaryotic system as described below. The expression level of each antibody fragment was evaluated by applying the same volume of the purified material from the same fraction as shown detected by SDS-PAGE/Coomassie blue staining. Composition of the $V_L$ and $V_H$, respectively, is listed as following: hAB1 contains SEQ1 and SEQ55; hAB2 contains SEQ1 and SEQ70; hAB3 contains SEQ1 and SEQ67; hAB5 contains SEQ1 and SEQ75; hAB7 contains SEQ1 and SEQ101; hAB8 contains SEQ1 and SEQ100; hAB13 contains SEQ1 and SEQ56, as $V_L$ and $V_H$, respectively.

Figure 7:
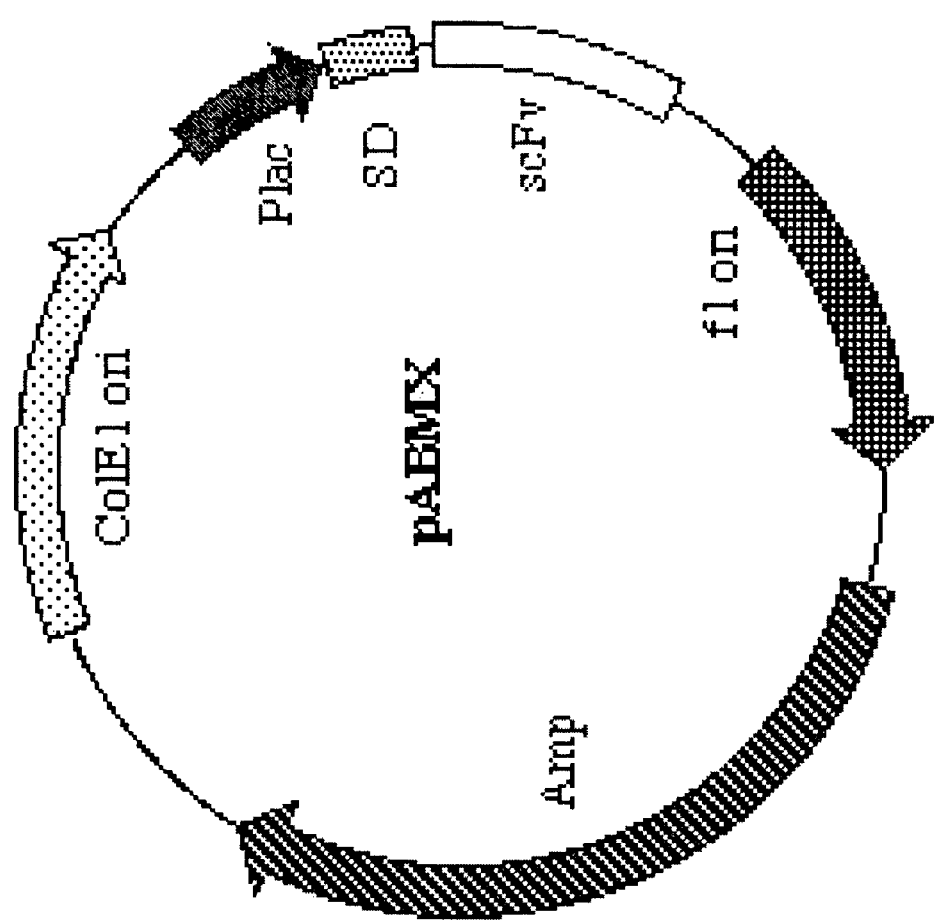

FIG. 7 illustrates a map of the vector used for expression of soluble antibody fragments in *E. coli*.

DETAILED DESCRIPTION OF THE INVENTION

The present invention provides an innovative methodology for engineering proteins, in particular antibodies, with desired structures and functions. In one aspect, methods are provided for designing and selecting antibodies against human antigens with high affinity and specificity. In some particular embodiments, methods are provided for designing and selecting humanized or fully human antibodies against vascular endothelial growth factor (VEGF) with high affinity and specificity. In another aspect, compositions, kits and methods are provided for using these antibodies and their derivatives to inhibit angiogenesis in vitro, and for diagnosing or treating diseases associated with abnormal angiogenesis such as cancer, rheumatoid arthritis, ischemic-reperfusion related brain edema and injury, cortical ischemia, ovarian hyperplasia and hypervascularity, endometriosis, psoriasis, diabetic retinopathy, and other ocular angiogenic diseases.

1. VEGF and Antibodies Against VEGF

VEGF is a key angiogenic factor in development and is involved in the growth of solid tumor by stimulating endothelial cells. A murine monoclonal antibody was found to block VEGF-dependent cell proliferation and slow the tumor growth in vivo (Kim K J, Li B, Winer J, Armanini M, Gillett N, Phillips H S, Ferrara N (1993) Nature 362, 841-844). This murine antibody was humanized (Presta L G, Chen H, O'Connor S J, Chisholm V, Meng Y G, Krummen L, Winkler M, Ferrara N (1997) Cancer Res. 57, 4593-4599; Baca M, Presta L G, O'Connor S J, Wells J A (1997) J Biol Chem 272, 10678-10684) and affinity-matured by using phage-display and off-rate selection (Chen Y, Wiesmann C, Fuh G, Li B, Christinger H W, McKay P, de Vos A M (1999) J Mol Biol 293, 865-881). X-ray structure for the complex formed between VEGF and the parental antibody was reported (Muller Y A, Chen Y, Christinger H W, Li B, Cunningham, B C, Lowman H B, de Vos A M (1998) Structure 6, 1153-1167.), as well as the one formed between VEGF and the matured antibody (Chen Y, Wiesmann C, Fuh G, Li B, Christinger H W, McKay P, de Vos A M, Lowman H B (1999) J. Mol Biol 293, 865-881). In addition, U.S. patent application Ser. No. 09/056,160, publication No: 2002/0032315, discloses certain anti-VEGF antibodies. These publications on VEGF and anti-VEGF antibodies are herein incorporated by reference in their entirety.

The present invention provides novel anti-VEGF antibodies that bind to human VEGF with high affinity and specificity. These anti-VEGF antibodies are humanized and optimized with some important attributes in binding affinity, stability, expression efficiency which are desirable for research, diagnostic and therapeutic applications.

The binding affinity of the selected anti-VEGF antibodies of the present invention to a human VEGF, represented by dissociation constant $K_d$, is optionally lower than 100 nM, optionally lower than 10 nM, optionally lower than 8 nM, optionally lower than 8 nM, optionally lower than 5 nM, optionally lower than 1 nM, optionally lower than 0.8 nM, optionally lower than 0.5 nM, optionally lower than 0.2 nM, optionally lower than 0.11 nM, optionally lower than 0.08 nM, optionally lower than 0.05 nM, optionally lower than 0.01 nM, or optionally lower than 0.005 nM, in the form of scFv, Fab, or other form of antibody measured at a temperature of about 4° C., 25° C., 37° C. or 42° C.

Preferably, $K_d$ of the selected anti-VEGF antibodies of the present invention, if in the form of scFv and measured at a temperature of 35-37° C., is lower than 11 nM, optionally lower than 0.8 nM, optionally lower than 0.5 nM, optionally lower than 0.2 nM, optionally lower than 0.11 nM, optionally lower than 0.08 nM, optionally lower than 0.05 nM, optionally lower than 0.01 nM, or optionally lower than 0.005 nM.

Also preferably, $K_d$ of the selected anti-VEGF antibodies of the present invention, if in the form of Fab and measured at a temperature of 35-37° C., is lower than 0.5 nM, optionally lower than 0.2 nM, optionally lower than 0.11 nM, optionally lower than 0.08 nM, optionally lower than 0.05 nM, optionally lower than 0.01 nM, or optionally lower than 0.005 nM.

In inhibition of VEGF-induced proliferation of endothelial cells in vitro the selected anti-VEGF antibodies of the present invention preferably has an $ED_{50}$ (effective dose for inhibition of 50% cell proliferation) equal to or lower than 10 nM, optionally lower than 5 nM, optionally lower than 1 nM, optionally lower than 0.5 nM, optionally lower than 0.1 nM, optionally lower than 0.05 nM, or optionally lower than 0.011 nM in the form of scFv, Fab or other form of antibody.

In a preferred embodiment, an anti-VEGF antibody is provided that has a light chain variable region comprising the amino acid sequence of: $X_1X_2X_3X_4TQX_5PSX_6X_7SX_8X_9X_{10}GX_{11}X_{12}X_{13}X_{14}IX_{15}C\underline{X_{16}X_{17}SX_{18}X_{19}IX_{20}X_{21}X_{22}X_{23}X_{24}}WYQQX_{25}PGX_{26}APX_{27}X_{28}LX_{29}Y\underline{X_{30}X_{31}X_{32}X_{33}LX_{34}X_{35}}GVX_{36}X_{37}RFSGX_{38}X_{39}SGTDFX_{40}LTIX_{41}X_{42}LQX_{43}X_{44}DX_{45}AX_{46}YYCQQ\underline{X_{47}X_{48}X_{49}X_{50}PX_{51}}TFGX_{52}GTKX_{53}X_{54}IK$ (SEQ ID NO: 338), wherein the underlined regions are designated as $V_L$/CDR1, $V_L$/CDR2, and $V_L$/CDR3, respectively, whereas the rest of the region is designated as framework, and wherein the position designated as "X" could be amino acids listed below:

$X_1$: D, E or A
$X_2$: I, or T
$X_3$: V, E, K, R, Q, or T
$X_4$: M, or L
$X_5$: S, or T
$X_6$: S, or T
$X_7$: L, or V
$X_8$: A, or V
$X_9$: S, or T
$X_{10}$: P, V, L, A, or I
$X_{11}$: E, or D
$X_{12}$: R, or T
$X_{13}$: A, or V I
$X_{14}$: T, or A
$X_{15}$: T, S, or A
$X_{16}$: S, R, N, K, H, or Q
$X_{17}$: A, or S
$X_{18}$: Q, or R
$X_{19}$: S, D, A, or P
$X_{20}$: S, G, R, T, or Y
$X_{21}$: T, N, S, D, or K
$X_{22}$: Y, or D
$X_{23}$: L, or I
$X_{24}$: A, N, or T
$X_{25}$: K, or I
$X_{26}$: Q, K, T, or I
$X_{27}$: R, K, Q, N, H, S, or E
$X_{28}$: V, or L
$X_{29}$: I, or V
$X_{30}$: F, A, G, D, or S
$X_{31}$: A, or T
$X_{32}$: S, or T
$X_{33}$: N, S, R, or T
$X_{34}$: A, H, or Q
$X_{35}$: S, or G
$X_{36}$: P, T
$X_{37}$: S, N, D, G, or Y
$X_{38}$: S, or T
$X_{39}$: G, or R
$X_{40}$: T, or A
$X_{41}$: S, or R
$X_{42}$: S, or R
$X_{43}$: P, or A
$X_{44}$: E, or D
$X_{45}$: F, V, or S
$X_{46}$: V, T, I, A, or S
$X_{47}$: Y, or S
$X_{48}$: S, Y, or N
$X_{49}$: S, or T
$X_{50}$: T, V, A, P, K, G, S, or I
$X_{51}$: W, or Y
$X_{52}$: Q, or G
$X_{53}$: V, or L
$X_{54}$: E, D, or A.

Such preferred light chain variable domain sequences may be combined with the preferred heavy chain variable domain sequences, or with other heavy chain variable domain sequences, provided that the antibody so produced binds to human VEGF with a desired affinity.

In another preferred embodiment, an anti-VEGF antibody is provided that has a light chain variable region comprising the amino acid sequence of: $X_1X_2X_3LTQPPSX_4SX_5TPGQX_6VTISCS\underline{GX_7X_8SNX_9GX_{10}NX_{11}VX_{12}}WYQQX_{13}PGX_{14}APKX_{15}LX_{16}Y\underline{X_{17}NX_{18}X_{19}RPS}GVPX_{20}RX_{21}SGSX_{22}SX_{23}TSASLAISGLX_{24}SEDEADYYC\underline{X_{25}X_{26}WDDSLX_{27}GYVFGX_{28}GTX_{29}}LTVL$ (SEQ ID NO: 339), wherein the underlined regions are designated as $V_L$/CDR1, $V_L$/CDR2, and $V_L$/CDR3, respectively, whereas the rest of the region is designated as framework, and wherein the position designated as "X" could be amino acids listed below:

$X_1$: Q L, or N
$X_2$: P A F, or S
$X_3$: V, or M
$X_4$: A, or T
$X_5$: G, or A
$X_6$: R, or S
$X_7$: S, or T
$X_8$: S, T Y, or N
$X_9$: I, or V
$X_{10}$: S, or R
$X_{11}$: S, P, N, A, or T
$X_{12}$: N, T, or Y
$X_{13}$: L, or F
$X_{14}$: T, or A
$X_{15}$: V, L, or F
$X_{16}$: M, or I
$X_{17}$: G, T, or S
$X_{18}$: N, or D
$X_{19}$: Q, or E
$X_{20}$: D, or E
$X_{21}$: F, or L
$X_{22}$: K, or R
$X_{23}$: G, or A
$X_{24}$: Q, L, or R
$X_{25}$: A, or G
$X_{26}$: A, S, or T
$X_{27}$: N, S, or T
$X_{28}$: T, or A
$X_{29}$: K, or Q.

Such preferred light chain variable domain sequences may be combined with the preferred heavy chain variable domain sequences, or with other heavy chain variable domain sequences, provided that the antibody so produced binds to human VEGF with desired affinity.

In yet another preferred embodiment, an anti-VEGF antibody is provided that has a light chain variable region comprising the amino acid sequence of: QSALTQPPSVSGAPGQRVTISCTGRSSNIGAGHDVHWYQQLPGTAPKLLIYANDQRPSGVPDRFSDSKSGTSASLGISGLRSEDEADYFCATWDDSLHGYVFGTGTKVTVL (SEQ ID NO:54), such preferred light chain variable domain sequences may be combined with the heavy chain variable domain sequences, or with other heavy chain variable domain sequences, provided that the antibody so produced binds to human VEGF with desired affinity.

In yet another preferred embodiment, an anti-VEGF antibody is provided that has a heavy chain variable region comprising the amino acid sequence of: $X_1X_2QLVX_3SGGGX_4VQPGGX_5LRLX_6CAX_7S\underline{GX_8X_9X_{10}X_{11}X_{12}X_{13}}$ G$X_{14}$NW$X_{15}$RQAP GKG$X_{16}$EWVGW$X_{17}$NT$X_{18}$$X_{19}$G$X_{20}$ $X_{21}$TY$X_{22}$$X_{23}$$X_{24}$F$X_{25}$RR$X_{26}$T$X_{27}$S$X_{28}$$X_{29}$$X_{30}$SK$X_{31}$$X_{32}$ $X_{33}$YLQ$X_{34}$NSLRAEDTAVYYCA$X_{35}$YP$X_{36}$YYG$X_{37}$ SHWYFDVW$X_{38}$QGTLVTVSS (SEQ ID NO: 340), wherein the underlined regions are designated as CDR1, CDR2, and CDR3, respectively, whereas the rest of the region is designated as framework according to Kabat nomenclature, and wherein the position designated as "X" could be amino acids listed below:

$X_1$: E, or Q
$X_2$: V, or G
$X_3$: Q, or E
$X_4$: V, or L
$X_5$: S, or T
$X_6$: S T, or R
$X_7$: A, or V
$X_8$: Y, or F
$X_9$: T, D, N, S, or A
$X_{10}$: F, or L
$X_{11}$: T, D, Y, A, S, or N
$X_{12}$: N, H, or S
$X_{13}$: Y, or F
$X_{14}$: M, L, I, or V
$X_{15}$: I, V, or L
$X_{16}$: L, or P
$X_{17}$: I, or V
$X_{18}$: Y, or N
$X_{19}$: T, or N
$X_{20}$: E, or A
$X_{21}$: P, T, or S
$X_{22}$: A, or V
$X_{23}$: A, H, Q, P, D, or E
$X_{24}$: D, or E
$X_{25}$: K, or T
$X_{26}$: V, F, or L
$X_{27}$: F, or I
$X_{28}$: L, or R
$X_{29}$: D, or N
$X_{30}$: T, or N
$X_{31}$: S, or N
$X_{32}$: T, Q, P, or K
$X_{33}$: A, V, or P
$X_{34}$: L, or M
$X_{35}$: K, or R
$X_{36}$: H, or Y
$X_{37}$: S, R, or T
$X_{38}$: G, or A.

In yet another preferred embodiment, an anti-VEGF antibody is provided that has a heavy chain variable region comprising the amino acid sequence of: $X_1$$X_2$QLV $X_3$SGGGX$_4$VQPGG$X_5$LRL$X_6$CA$X_7$S G$X_8$$X_9$$X_{10}$$X_{11}$$X_{12}$ $X_{13}$G$X_{14}$NW$X_{15}$RQAPGKG$X_{16}$EWVGW$X_{17}$NT$X_{18}$$X_{19}$ G$X_{20}$$X_{21}$TY$X_{22}$$X_{23}$$X_{24}$F$X_{25}$RR$X_{26}$T$X_{27}$S$X_{28}$$X_{29}$$X_{30}$SK $X_{31}$$X_{32}$$X_{33}$YLQ$X_{34}$NSLRAEDTAVYYCA$X_{35}$$X_{36}$$X_{37}$$X_{38}$ $X_{39}$$X_{40}$$X_{41}$$X_{42}$$X_{43}$$X_{44}$$X_{45}$Y$X_{46}$D$X_{47}$W$X_{48}$QGTLVTV, wherein the underlined regions are designated as CDR1, CDR2, and CDR3, respectively, whereas the rest of the region is designated as framework according to Kabat nomenclature, and wherein the position designated as "X" could be amino acids listed below:

$X_1$: E, or Q
$X_2$: V, or G
$X_3$: Q, or E
$X_4$: V, or L
$X_5$: S, or T
$X_6$: S T, or R
$X_7$: A, or V
$X_8$: Y, or F
$X_9$: T, D, N, S, or A
$X_{10}$: F, or L
$X_{11}$: T, D, Y, A, S, or N
$X_{12}$: N, H, or S
$X_{13}$: Y, or F
$X_{14}$: M, L, I, or V
$X_{15}$: I, V, or L
$X_{16}$: L, or P
$X_{17}$: I, or V
$X_{18}$: Y, or N
$X_{19}$: T, or N
$X_{20}$: E, or A
$X_{21}$: P, T, or S
$X_{22}$: A, or V
$X_{23}$: A, H, Q, P, D, or E
$X_{24}$: D, or E
$X_{25}$: K, or T
$X_{26}$: V, F, or L
$X_{27}$: F, or I
$X_{28}$: L, or R
$X_{29}$: D, or N
$X_{30}$: T, or N
$X_{31}$: S, or N
$X_{32}$: T, Q, P, or K
$X_{33}$: A, V, or P
$X_{34}$: L, or M
$X_{35}$: K R, or H
$X_{36}$: Y A D, or S
$X_{37}$: P R S, or G
$X_{38}$: Y H, or D
$X_{39}$: Y, or F
$X_{40}$: Y N S, or H
$X_{41}$: G, or S
$X_{42}$: S, T, R, G, or A
$X_{43}$: S, Y, C, or T
$X_{44}$: H, P, C, N, Q, or S
$X_{45}$: W, Q, or C
$X_{46}$: F, or L
$X_{47}$: V, L, or Y
$X_{48}$: G, or A.

Such preferred heavy chain variable domain sequences may be combined with the preferred light chain variable domain sequences or with other light chain variable domain sequences, provided that the antibody so produced binds to human VEGF with desired affinity.

In one embodiment, the invention provides an anti-VEGF antibody that preferably contains a light chain variable domain comprising the amino acid sequences of one of the following: SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:29, SEQ ID NO:30, SEQ ID NO:31, SEQ ID NO:32, SEQ ID NO:33, SEQ ID NO:34, SEQ ID NO:35, SEQ ID NO:38, SEQ ID NO:39, SEQ ID NO:40, SEQ ID NO:41, SEQ ID NO:42, SEQ ID NO:43, SEQ ID NO:45, SEQ ID NO:46, SEQ ID NO:48, SEQ ID NO:49, SEQ ID NO:50, SEQ ID NO:51, SEQ ID NO:52, and SEQ ID NO:53, further preferably SEQ ID NO:14, SEQ ID NO:26, SEQ ID NO:28, SEQ ID NO:36, SEQ ID NO:37, SEQ ID NO:44, SEQ ID NO:47, or SEQ ID NO:54. Such preferred light chain variable domain sequences may be combined with the preferred heavy chain variable domain sequences or with other heavy chain variable domain sequences, provided that the antibody so produced binds to human VEGF with desired affinity.

In another embodiment, the invention provides an anti-VEGF antibody that preferably contains a heavy chain variable domain comprising the amino acid sequence of one of the following: SEQ ID NO: ID NO:57, SEQ ID NO: ID NO:58, SEQ ID NO: ID NO:59, SEQ ID NO: ID NO:60, SEQ ID NO: ID NO:65, SEQ ID NO: ID NO:66, SEQ ID NO: ID NO:69, SEQ ID NO: ID NO:71, SEQ ID NO: ID NO:72, SEQ ID NO: ID NO:73, SEQ ID NO: ID NO:74, SEQ ID NO:76, SEQ ID NO:77, SEQ ID NO:78, SEQ ID NO:79, SEQ ID NO:80, SEQ ID NO:81, SEQ ID NO:82, SEQ ID NO:84, SEQ ID NO:85, SEQ ID NO:86, SEQ ID NO:87, further preferably SEQ ID NO:61, or SEQ ID NO:62, or SEQ ID NO:63, or SEQ ID NO:64, or SEQ ID NO:67, or SEQ ID NO:68, or SEQ ID NO:70, or SEQ ID NO:75, or SEQ ID NO:83, SEQ ID NO:88, or SEQ ID NO:89, or SEQ ID NO:90, or SEQ ID NO:91, or SEQ ID NO:92, or SEQ ID NO:93, or SEQ ID NO:94, or SEQ ID NO:95, SEQ ID NO:96, SEQ ID NO:97, SEQ ID NO:98, or SEQ ID NO:99, SEQ ID NO:100, or SEQ ID NO:101, or SEQ ID NO:102, or SEQ ID NO:103, or SEQ ID NO:104, or SEQ ID NO:105, or SEQ ID NO:106, SEQ ID NO:107, or SEQ ID NO:108, or SEQ ID NO:109, SEQ ID NO:110; or one of SEQ ID NOs: 285-310. Such preferred heavy chain variable region sequence may be combined with the preferred light chain variable region sequence or with other light chain variable region sequence, provided that the antibody so produced binds to human VEGF with desired affinity.

In yet another embodiment, the invention provides an anti-VEGF antibody that preferably contains the CDR1 regions of the light chain variable domain comprising the amino acid sequence of one of the following: SEQ ID NO:164, SEQ ID NO:165, SEQ ID NO:166, SEQ ID NO:167, SEQ ID NO:168, SEQ ID NO:169, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, and SEQ ID NO:194. Such preferred CDR1 sequence of light chain variable domain may be combined with other regions of preferred light chain, or of other light chain, and the preferred heavy chain variable region sequence or with other heavy chain variable region sequence, provided that the antibody so produced binds to human VEGF with desired affinity.

In yet another embodiment, the invention provides an anti-VEGF antibody that preferably contains the CDR2 regions of the light chain variable domain comprising the amino acid sequence of one of the following: SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, and SEQ ID NO:209. Such preferred sequence of light chain variable domain may be combined with other regions of preferred light chain, or of other light chain, and the preferred heavy chain variable region sequence or with other heavy chain variable region sequence, provided that the antibody so produced binds human VEGF.

In yet another embodiment, the invention provides an anti-VEGF antibody that preferably contains the CDR3 regions of the light chain variable domain comprising the amino acid sequence of one of the following: SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:226, SEQ ID NO:227, and SEQ ID NO:228. Such preferred CDR3 sequence of light chain variable domain may be combined with other regions of preferred light chain, or of other light chain, and the preferred heavy chain variable region sequence or with other heavy chain variable region sequence, provided that the antibody so produced binds to human VEGF with desired affinity.

In yet another embodiment, the invention provides an anti-VEGF antibody that preferably contains the framework regions of the light chain variable domain comprising the amino acid sequence of one of the following: SEQ ID NO:229 and 351-353, SEQ ID NO:230, 354-355 and 353 SEQ ID NO:231, 356-357 and 353, SEQ ID NO:233, 358, 355 and 353, SEQ ID NO:234, 354, 359 and 353, SEQ ID NO:236, 351, 360 and 353, SEQ ID NO:238, 363, 355 and 353, SEQ ID NO:239, 363-364 and 353, SEQ ID NQ:240 and 351-353, SEQ ID NO:241, 351, 360 and 353, SEQ ID NO:242, 354, 360 and 353, SEQ ID NO:243, 354, 365 and 353, SEQ ID NO:244, 366-367 and 353, SEQ ID NO:245, 368-369 and 353, SEQ ID NO:246, 354-355 and 370, SEQ ID NO:247, 361 and 352-353, SEQ ID NO:248, 356, 359 and 353, SEQ ID NO:249, 361, 360 and 353 SEQ ID NO:250 and 371 -373, SEQ ID NO:252, 377-378 and 376, SEQ ID NO:253 and 371 -373, SEQ ID NO:254, 379, 375 and 380, SEQ ID NO:256, 382 and 375-376, SEQ ID NO:257, 383 and 375-376, SEQ ID NO:258, 383, 375 and 373, SEQ ID NO:259, 384, 375 and 380 SEQ ID NO:260, 385, 375 and 373, SEQ ID NO:261 and 386-388, SEQ ID NQ:262, 389-390 and 388, SEQ ID NO:264, 393, 387 and 394, SEQ ID NO:266 and 397-399, SEQ ID NO:267, 400-401 and 394, SEQ ID NO:268, 400-401 and 394, and SEQ ID NO:269, 397, 387 and 394; further preferably contains the framework regions of the light chain variable domain comprising the amino acid sequence of one of the following: SEQ ID NO:232, 356-357 and 353, SEQ ID NO:235, 354, 360 and 353, SEQ ID NO:237, 361, 359 and 362, SEQ ID NO:251 and 374-376, SEQ ID NO:255, 371, 381 and 380, SEQ ID NO:263, 389 and 391-392, and SEQ ID NO:265, 395-396 and 394. Such preferred framework region sequence of light chain variable region may be combined with CDR regions of preferred light chain, or of other light chain, and the preferred heavy chain variable region sequence or with other heavy chain variable region sequence, provided that the antibody so produced binds to human VEGF with desired affinity.

In one embodiment, the invention provides an anti-VEGF antibody that preferably contains the CDR1 regions of the heavy chain variable domain comprising the amino acid sequence of one of the following: $GX_1X_2X_3X_4X_5X_6GX_7N$, wherein the position designated as "X" could be amino acids listed below:

$X_1$: Y, or F
$X_2$: D, N, T, S, or A
$X_3$: F, or L
$X_4$: T, D, S, Y, A, or N
$X_5$: H, N, or S
$X_6$: Y, or F
$X_7$: M, L, I, or V.

Further preferably the CDR1 region of the heavy chain variable domain comprises the amino acid sequence of one of the following: SEQ ID NO:111, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, and SEQ ID NO:135. Such preferred CDR1 sequence of heavy chain variable domain may be combined with other regions of preferred heavy chain or of other heavy chain, and the preferred light chain variable region sequence or with other light chain variable region sequence, provided that the antibody so produced binds human VEGF.

In one embodiment, the invention provides an anti-VEGF antibody that preferably contains CDR2 of the heavy chain variable domain comprising the amino acid sequence of one of the following: $WX_1NTX_2X_3GEX_4TYX_5X_6X_7FX_8R$ (SEQ ID NO: 341), wherein the position designated as "X" could be amino acids listed below:

$X_1$: I, or V
$X_2$: Y, or N
$X_3$: T, or N
$X_4$: P, T, or S
$X_5$: A, or V
$X_6$: A, Q, P, H, D, or E
$X_7$: D, or E
$X_8$: K, or T

Further preferably CDR2 of the heavy chain variable domain comprise the amino acid sequence of one of the following: SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:155, and SEQ ID NO:156. Such preferred CDR2 sequence of heavy chain variable domain may be combined with other regions of preferred heavy chain or of other heavy chain, and the preferred light chain variable region sequence or with other light chain variable region sequence, provided that the antibody so produced binds to human VEGF with desired affinity.

In one embodiment, the invention provides an anti-VEGF antibody that contains CDR3 of the heavy chain variable domain comprising the amino acid sequence: $KYPX_1YYGX_2SHWYFDV$ (SEQ ID NO: 342), wherein the position designated as "X" could be amino acids listed below:
$X_1$: Y, or H, and $X_2$: R.

Preferably, the anti-VEGF antibody has CDR3 of the heavy chain variable domain comprising the amino acid sequence of one of SEQ ID NOs:311-337, and the following sequences:

```
CAHSRHYYGSSPQYFDV
CAKYGYYYGSSHWYFDV
CAKYPHYYGASHWYFDV
CAKYPHYYGGCHWYFDV
CAKYPHYYGGSHWYFDV
CAKYPHYYGGYNQYFDV
CAKYPHYYGRSHWYFDV
CAKYPHYYGRSQWYLDV
CAKYPHYYSRTCQYFDV
```

-continued
```
CAKYPHYYSSSHWYFDV
CAKYPYFYGSSHWYFDV
CAKYPYYHGSSHWYFDV
CAKYPYYNGSSHWYFDV
CAKYPYYNSTSHWYFDV
CAKYPYYSGTSHWYFDV
CAKYPYYSGTSHWYFDY
CAKYPYYYGRSHWYFDV
CAKYPYYYGSSHWYFDV
CAKYPYYYGSSSWYFDV
CAKYPYYYSTSHWYFDV
CAKYRDFNGSSHWYFDV
CAKYSYYYGSSHWYFDV
CARARHYYGSSHCYFDL
CARDSHYYGSSHQYFDL
CAKYPHYYGTSHWYFDV
CAKYPHYYGSSHWYFDV
CAKYPYYYGTSHWYFDV.
```

Such preferred CDR3 sequence of heavy chain variable domain may be combined with other regions of preferred heavy chain or of other heavy chain, and the preferred light chain variable region sequences or with other light chain variable domain sequences, provided that the antibody so produced binds to human VEGF with desired affinity.

In one embodiment, the invention provides an anti-VEGF antibody that preferably contains the framework region of the heavy chain variable domain comprising the amino acid sequences of one of the following: $X_1VQLVX_2SGGGX_3VQPGGX_4LRLX_5CAX_6S$ (SEQ ID NO: 343)/CDR1/$WX_7RQAPGKGLEWVG$ (SEQ ID NO: 344)/CDR2/$RX_8TX_9SX_{10}DX_{11}SKX_{12}X_{13}X_{14}YLQX_{15}NSLRAEDTAVYYCA$ (SEQ ID NO: 345)/CDR3/$WX_{16}QGTLVTVSS$ (SEQ ID NO: 346), wherein the position designated as "X" could be amino acids listed below:

$X_1$: E, or Q
$X_2$: Q, or E
$X_3$: V, or L
$X_4$: S, or T
$X_5$: S, T, or R
$X_6$: A, or V
$X_7$: I, or V
$X_8$: F, or V
$X_9$: F, or I
$X_{10}$: L, or R
$X_{11}$: T, or N
$X_{12}$: S, or N
$X_{13}$: T, Q, or K
$X_{14}$: A, or V
$X_{15}$: M, or L
$X_{16}$: G, or A.

In one embodiment, the invention provides an anti-VEGF antibody that preferably contains a light chain variable domain and a heavy chain variable domain comprising the amino acid sequences of one of the following $V_L$ and $V_H$ pairs:

SEQ ID NO:1 and SEQ ID NO:70; SEQ ID NO:1 and SEQ ID NO:67; SEQ ID NO:1 and SEQ ID NO:75; SEQ ID NO:1 and SEQ ID NO:83; SEQ ID NO:14 and SEQ ID NO:55; SEQ ID NO:1 and SEQ ID NO:101; SEQ ID NO:1 and SEQ ID NO:100; SEQ ID NO:14 and SEQ ID NO:102; SEQ ID NO:1 and SEQ ID NO:103; SEQ ID NO:1 and SEQ ID NO:104; SEQ ID NO:1 and SEQ ID NO:105; SEQ ID NO:36 and SEQ ID NO:100; SEQ ID NO:26 and SEQ ID NO:100; SEQ ID NO:28 and SEQ ID NO:100; SEQ ID NO:37 and SEQ ID NO:100; SEQ ID NO:44 and SEQ ID NO:100; SEQ ID NO:54 and SEQ ID NO:100; SEQ ID NO:47 and SEQ ID NO:100, further preferably SEQ ID NO:28 and SEQ ID NO:61; SEQ ID NO:28 and SEQ ID NO:62; SEQ ID NO:28 and SEQ ID NO:63; SEQ ID NO:28 and SEQ ID NO:64; SEQ ID NO:28 and SEQ ID NO:68; SEQ ID NO:28 and SEQ ID NO:85; SEQ ID NO:28 and SEQ ID NO:86; SEQ ID NO:28 and SEQ ID NO:87; SEQ ID NO:28 and SEQ ID NO:88; SEQ ID NO:28 and SEQ ID NO:89; SEQ ID NO:28 and SEQ ID NO:90; SEQ ID NO:28 and SEQ ID NO:91; SEQ ID NO:28 and SEQ ID NO:92; SEQ ID NO:28 and SEQ ID NO:93; SEQ ID NO:28 and SEQ ID NO:94; SEQ ID NO:28 and SEQ ID NO:95; SEQ ID NO:28 and SEQ ID NO:96; SEQ ID NO:28 and SEQ ID NO:97; SEQ ID NO:28 and SEQ ID NO:98; SEQ ID NO:28 and SEQ ID NO:99; SEQ ID NO:28 and SEQ ID NO:106; SEQ ID NO:28 and SEQ ID NO:107; SEQ ID NO:28 and SEQ ID NO:108; SEQ ID NO:28 and SEQ ID NO:109; and SEQ ID NO:28 and SEQ ID NO:110.

The antibodies resulted from combination of the full-length $V_H$ and $V_L$, $V_H$/CDR, $V_H$/FR, $V_L$/CDR, $V_L$/FR (e.g., the hit variants provided in FIGS. 1A and 1B and amino acid sequences shown in FIGS. 1C and 1D) disclosed in the present invention are within the scope of the present invention; and such combination does not include the anti-VEGF antibodies disclosed in U.S. patent application Ser. No. 09/056,160, publication No: 2002/0032315.

2. Methodology for Designing and Constructing Humanized or Fully Human Anti-VEGF Antibodies The antibodies of the present invention are designed using innovative methods involving construction and selection of protein libraries in silico and in vitro. The following describes some aspects of the methodology. More detailed description of the methodology appears in U.S. patent application Ser. Nos. 10/443,134, 10/153,159, 10/153,176, 10/125,687, and 60/284,407, which are incorporated herein by reference in their entirety.

According to the present invention, an innovative methodology is provided for efficiently generating and screening protein libraries for optimized proteins with desirable biological functions, such as improved binding affinity towards biologically and therapeutically important target molecules. The methodology is used to optimize proteins by generating novel variants of a protein with enhanced properties. In particular, this methodology is used to design libraries for humanization of non-human antibodies and to optimize the affinity and other attributes of antibodies. Novel variants of amino acids and nucleic acids of antibodies are generated with human or human-like sequences while their binding affinity, stability, and expression efficiency are improved significantly.

The inventive process is carried out computationally in a high throughput manner by mining the ever-expanding databases of protein sequences of all organisms, especially human and by relating their specific sequences or their variants with functional enhancement such as binding affinity and stability that are tested experimentally. By using the inventive methodology, an expanded and yet functionally biased library of proteins such as antibodies can be constructed based on computational evaluation of extremely diverse protein sequences and functionally relevant structures in silico and subsequently tested by experimental screening and selection in vitro or in vivo.

In one aspect of the invention, a method is provided for designing and selecting protein(s) with desirable function(s). The method is preferably implemented in a computer through in silico selection of protein sequences based on the amino acid sequence of a target structural/functional motif or domain in a lead protein, herein after referred to as the "lead sequence". The lead sequence is employed to search databases of protein sequences. The choice of the database depends on the specific functional requirement of the designed motifs. For example, if the lead protein is an enzyme and the target motif includes the active site of the enzyme, databases of proteins/peptides of a particular origin, organism, species or combinations thereof, may be queried using various search criteria to yield a hit list of sequences each of which can substitute the target motif in the lead protein. A similar approach may be used for designing other motifs or domains of the lead protein. The designed sequences for each individual motif/domain may be combined to generate a library of designed proteins. In addition, to reduce immunogenicity of the designed proteins for human applications such as therapeutics or diagnosis, databases of proteins of human origin or humanized proteins are preferably searched to yield the hit list of sequences, especially for motifs derived from sites of the lead protein that serves as the scaffolding of the lead proteins such as the frameworks of an antibody. The library of designed proteins can be tested experimentally to yield proteins with improved biological function(s) over the lead protein.

In a particular aspect of the invention, the inventive methodology is implemented in designing antibodies that are diverse in sequence and yet functionally related to each other. Based on the designed antibody sequences, a library of antibodies can be constructed to include diverse sequences in the complementary determining regions (CDRs) and/or humanized frameworks (FRs) of a non-human antibody in a high throughput manner. This library of antibodies can be screened against a wide variety of target molecules for novel or improved functions.

In yet another aspect of the invention, a method is provided for in silico selection of antibody sequences based on the amino acid sequence of a region in a lead antibody, herein after referred to as the "lead sequence". The lead sequence is employed to search databases of protein sequences. The choice of the database depends on the specific functional requirement of the designed motifs. For example: in order to design the framework regions of variable chains for therapeutic application, collections of protein sequences that are evolutionarily related such as fully human immunoglobulin sequences and human germline immunoglobulin sequences should be used except for a few structurally critical sites. This would reduce the immunogenic response by preserving the origin of the sequences by introducing as few foreign mutants as possible in this highly conserved region (for framework regions). On the other hand, diverse sequence databases such as immunoglobulin sequences of various species or even unrelated sequence in genbank can be used to design the CDRs in order to improve binding affinity with antigens in this highly variable region. By using the method, a library of diverse antibody sequences can be constructed and screened experimentally in vitro or in vivo for antibody mutants with improved or desired function(s).

In one embodiment, the method comprises the steps of: providing an amino acid sequence of the variable region of the heavy chain ($V_H$) or light chain ($V_L$) of a lead antibody; identifying the amino acid sequences in the CDRs of the lead antibody; selecting one of the CDRs in the $V_H$ or $V_L$ region of the lead antibody; providing an amino acid sequence that comprises at least 3 consecutive amino acid residues in the selected CDR, the selected amino acid sequence being a lead sequence; comparing the lead sequence with a plurality of tester protein sequences; and selecting from the plurality of tester protein sequences at least two peptide segments that have at least 15% sequence identity with the lead sequence, the selected peptide segments forming a hit library.

The method may further comprise the step of: constructing a nucleic acid library comprising DNA segments encoding the amino acid sequences of the hit library.

Optionally, the method may further comprise the steps of: building an amino acid positional variant profile of the hit library; converting amino acid positional variant profile of the hit library into a nucleic acid positional variant profile by back-translating the amino acid positional variants into their corresponding genetic codons; and constructing a degenerate nucleic acid library of DNA segments by combinatorially combining the nucleic acid positional variants.

Optionally, the genetic codons may be the ones that are preferred for expression in bacteria. Optionally, genetic codons may be the ones that can reduce the size chosen such that the diversity of the degenerate nucleic acid library of DNA segments is within the experimentally coverable diversity without undue experimental efforts, for example, to be below $1 \times 10^7$, and preferably below $1 \times 10^6$.

In another embodiment, the method comprises the steps of: providing an amino acid sequence of the variable region of the heavy chain ($V_H$) or light chain ($V_L$) of a lead antibody; identifying the amino acid sequences in the CDRs and FRs of the lead antibody; selecting one of the CDRs in the $V_H$ or $V_L$ region of the lead antibody; providing a first amino acid sequence that comprises at least 3 consecutive amino acid residues in the selected CDR, the selected amino acid sequence being a CDR lead sequence; comparing the CDR lead sequence with a plurality of CDR tester protein sequences; selecting from the plurality of CDR tester protein sequences at least two peptide segments that have at least 15% sequence identity with the CDR lead sequence, the selected peptide segments forming a CDR hit library; selecting one of the FRs in the $V_H$ or $V_L$ region of the lead antibody; providing a second amino acid sequence that comprises at least 3 consecutive amino acid residues in the selected FR, the selected amino acid sequence being a FR lead sequence; comparing the FR lead sequence with a plurality of FR tester protein sequences; and selecting from the plurality of FR tester protein sequences at least two peptide segments that have at least 15% sequence identity with the FR lead sequence, the selected peptide segments forming a FR hit library; and combining the CDR hit library and the FR hit library to form a hit library.

According to the method, the plurality of CDR tester protein sequences may comprise amino acid sequences of human or non-human antibodies.

Also according to the method, the plurality of FR tester protein sequences may comprise amino acid sequences of human origins, preferably human or humanized antibodies (e.g., antibodies with at least 50% human sequence, preferably at least 70% human sequence, more preferably at least 90% human sequence, and most preferably at least 95% human sequence in $V_H$ or $V_L$), more preferably fully human antibodies, and most preferably human germline antibodies.

Also according to the method, at least one of the plurality of CDR tester protein sequences is different from the plurality of FR tester protein sequences.

Also according to the method, the plurality of CDR tester protein sequences are human or non-human antibody sequences and the plurality of FR tester protein sequences are human antibody sequences, preferably human germline antibody sequences.

The method may further comprise the step of: constructing a nucleic acid library comprising DNA segments encoding the amino acid sequences of the hit library.

Optionally, the method may further comprise the steps of: building an amino acid positional variant profile of the CDR hit library; converting the amino acid positional variant profile of the CDR hit library into a first nucleic acid positional variant profile by back-translating the amino acid positional variants into their corresponding genetic codons; and constructing a degenerate CDR nucleic acid library of DNA segments by combinatorially combining the nucleic acid positional variants.

Optionally, the genetic codons may be the ones that are preferred for expression in bacteria. Optionally, genetic codons may be the ones that can reduce the size chosen such that the diversity of the degenerate nucleic acid library of DNA segments is within the experimentally coverable diversity without undue experimental efforts, such as diversity below $1 \times 10^7$, preferably below $1 \times 10^6$.

In yet another embodiment, the method comprises the steps of: providing an amino acid sequence of the variable region of the heavy chain ($V_H$) or light chain ($V_L$) of a lead antibody; identifying the amino acid sequences in the FRs of the lead antibody; selecting one of the FRs in the $V_H$ or $V_L$ region of the lead antibody; providing a first amino acid sequence that comprises at least 3 consecutive amino acid residues in the selected FR, the selected amino acid sequence being a first FR lead sequence; comparing the first lead FR sequence with a plurality of FR tester protein sequences; and selecting from the plurality of FR tester protein sequences at least two peptide segments that have at least 15% sequence identity with the first FR lead sequence, the selected peptide segments forming a first FR hit library.

The method may further comprise the steps of: providing a second amino acid sequence that comprises at least 3 consecutive amino acid residues in a FR that is different from the selected FR, the selected amino acid sequence being a second FR lead sequence; comparing the second FR lead sequence with the plurality of FR tester protein sequences; and selecting from the plurality of FR tester protein sequences at least two peptide segments that have at least 15% sequence identity with the second FR lead sequence, the selected peptide segments forming a second FR hit library; and combining the first FR hit library and the second FR hit library to form a hit library.

According to the method, the lead CDR sequence may comprise at least 5 consecutive amino acid residues in the selected CDR. The selected CDR may be selected from the group consisting of $V_H$ CDR1, $V_H$ CDR2, $V_H$ CDR3, $V_L$ CDR1, $V_L$ CDR2, and $V_L$ CDR3 of the lead antibody.

Also according to the method, the lead FR sequence may comprise at least 5 consecutive amino acid residues in the selected FR. The selected FR may be selected from the group consisting of $V_H$ FR1, $V_H$ FR2, $V_H$ FR3, $V_H$ FR4, $V_L$ FR1, $V_L$ FR2, $V_L$ FR3 and $V_L$ FR4 of the lead antibody.

The method may further comprise the step of: constructing a nucleic acid or degenerate nucleic acid library comprising DNA segments encoding the amino acid sequences of the hit library.

In another aspect of the invention, a method is provided for in silico selection of antibody sequences based on the amino acid sequence of a region in a lead antibody, i.e., the "lead sequence", and its 3D structure. The structure of the lead sequence is employed to search databases of protein structures for segments having similar 3D structures. These segments are aligned to yield a sequence profile, herein after referred to as the "lead sequence profile". The lead sequence profile is employed to search databases of protein sequences for remote homologues of the lead sequence having low sequence identity and yet structurally similar. By using the method, a library of diverse antibody sequences can be constructed and screened experimentally in vitro or in vivo for antibody mutants with improved or desired function(s).

In one embodiment, the method comprises the steps of: providing an amino acid sequence of the variable region of the heavy chain ($V_H$) or light chain ($V_L$) of a lead antibody; identifying the amino acid sequences in the CDRs of the lead antibody; selecting one of the CDRs in the $V_H$ or $V_L$ region of the lead antibody; providing an amino acid sequence that comprises at least 3 consecutive amino acid residues in the selected CDR, the selected amino acid sequence being a lead sequence; providing a three-dimensional structure of the lead sequence; building a lead sequence profile based on the structure of the lead sequence; comparing the lead sequence profile with a plurality of tester protein sequences; and selecting from the plurality of tester protein sequences at least two peptide segments that have at least 10% sequence identity with lead sequence, the selected peptide segments forming a hit library.

According to the method, the three-dimensional structure of the lead sequence may be a structure derived from X-crystallography, nuclear magnetic resonance (NMR) spectroscopy or theoretical structural modeling.

According to the method, the step of building a lead sequence profile may include: comparing the structure of the lead sequence with the structures of a plurality of tester protein segments; determining the root mean square difference of the main chain conformations of the lead sequence and the tester protein segments; selecting the tester protein segments with root mean square difference of the main chain conformations less than 5 Å, preferably less than 4 Å, more preferably less than 3 Å, and most preferably less than 2 Å; and aligning the amino acid sequences of the selected tester protein segments with the lead sequence to build the lead sequence profile.

Optionally, the structures of the plurality of tester protein segments are retrieved from the protein data bank.

Optionally, the step of building a lead sequence profile may include: comparing the structure of the lead sequence with the structures of a plurality of tester protein segments; determining the Z-score of the main chain conformations of the lead sequence and the tester protein segments; selecting the segments of the tester protein segments with the Z-score higher than 2, preferably higher than 3, more preferably higher than 4, and most preferably higher than 5; and aligning the amino acid sequences of the selected tester protein segments with the lead sequence to build the lead sequence profile.

Optionally, the step of building a lead sequence profile may be implemented by an algorithm selected from the group consisting of CE, MAPS, Monte Carlo and 3D clustering algorithms.

The method may further comprise the step of: constructing a nucleic acid library comprising DNA segments encoding the amino acid sequences of the hit library.

Optionally, the method may further comprise the steps of: building an amino acid positional variant profile of the hit library; converting amino acid positional variant profile of the hit library into a nucleic acid positional variant profile by back-translating the amino acid positional variants into their corresponding trinucleotide codons; and constructing a degenerate nucleic acid library of DNA segments by combinatorially combining the nucleic acid positional variants.

In yet another aspect of the invention, a method is provided for in silico selection of antibody sequences based on a 3D structure of a lead antibody. A lead sequence or sequence profile from a specific region of the lead antibody to be employed to search databases of protein sequences for remote homologues of the lead sequence having low sequence identity and yet structurally similar. These remote homologues form a hit library. The sequences in the hit library are subjected to evaluation for their structural compatibility with a 3D structure of the lead antibody, hereinafter referred to as the "lead structural template". Sequences in the hit library that are structurally compatible with the lead structural template are selected and screened experimentally in vitro or in vivo for antibody mutants with improved or desired function(s).

In one embodiment, the method comprises the steps of: providing an amino acid sequence of the variable region of the heavy chain ($V_H$) or light chain ($V_L$) of a lead antibody, the lead antibody having a known three dimensional structure which is defined as a lead structural template; identifying the amino acid sequences in the CDRs of the lead antibody; selecting one of the CDRs in the $V_H$ or $V_L$ region of the lead antibody; providing an amino acid sequence that comprises at least 3 consecutive amino acid residues in the selected CDR, the selected amino acid sequence being a lead sequence; comparing the lead sequence profile with a plurality of tester protein sequences; selecting from the plurality of tester protein sequences at least two peptide segments that have at least 10% sequence identity with lead sequence, the selected peptide segments forming a hit library; determining if a member of the hit library is structurally compatible with the lead structural template using a scoring function; and selecting the members of the hit library that score equal to or better than or equal to the lead sequence.

According to the method, the scoring function is an energy scoring function selected from the group consisting of electrostatic interactions, van der Waals interactions, electrostatic solvation energy, solvent-accessible surface solvation energy, and conformational entropy.

Optionally, the scoring function is one incorporating a forcefield selected from the group consisting of the Amber forcefield, Charmm forcefield, the Discover cvff forcefields, the ECEPP forcefields, the GROMOS forcefields, the OPLS forcefields, the MMFF94 forcefield, the Tripos forcefield, the MM3 forcefield, the Dreiding forcefield, and UNRES forcefield, and other knowledge-based statistical forcefield (mean field) and structure-based thermodynamic potential functions.

Also according to the method, the step of selecting the members of the hit library includes selecting the members of the hit library that have a lower or equal total energy than that of the lead sequence calculated based on a formula of $$\Delta E_{total} = E_{vdw} + E_{bond} + E_{angle} + E_{electrostatics} + E_{solvation}$$

Also according to the method, the step of selecting the members of the hit library includes selecting the members of the hit library that have a lower binding free energy than that of the lead sequence calculated as the difference between the bound and unbound states using a refined scoring function $$\Delta G_b = \Delta G_{MM} + \Delta G_{sol} - T\Delta S_{ss}$$

where $$\Delta G_{MM} = \Delta G_{ele} + \Delta G_{vdw} \quad (1)$$

$$\Delta G_{sol} = \Delta G_{ele\text{-}sol} + \Delta G_{ASA} \quad (2)$$

The method may further comprise the step of: constructing a nucleic acid library comprising DNA segments encoding the amino acid sequences of the hit library.

Optionally, the method may further comprise the steps of: building an amino acid positional variant profile of the hit library; converting amino acid positional variant profile of the hit library into a nucleic acid positional variant profile by back-translating the amino acid positional variants into their corresponding trinucleotide codons; and constructing a degenerate nucleic acid library of DNA segments by combinatorially combining the nucleic acid positional variants.

In yet another aspect of the invention, a method is provided for in silico selection of antibody sequences based on a 3D structure or structure ensemble of a lead antibody, or a structure ensemble of multiple antibodies, hereinafter collectively referred to as the lead structural template. A lead sequence or sequence profile from a specific region of the lead antibody to be employed to search databases of protein sequences for remote homologues of the lead sequence having low sequence identity and yet structurally similar. These remote homologues form a hit library. An amino acid positional variant profile (AA-PVP) of the hit library is built based on frequency of amino acid variant appearing at each position of the lead sequence. Based on the AA-PVP, a hit variant library is constructed by combinatorially combining the amino acid variant at each position of the lead sequence with or without cutoff of low frequency variants. The sequences in the hit variant library are subjected to evaluation for their structural compatibility with the lead structural template. Sequences in the hit library that are structurally compatible with the lead structural template are selected and screened experimentally in vitro or in vivo for antibody mutants with improved or desired function(s).

In one embodiment, the method comprises the steps of: providing an amino acid sequence of the variable region of the heavy chain ($V_H$) or light chain ($V_L$) of a lead antibody, the lead antibody having a known three dimensional structure which is defined as a lead structural template; identifying the amino acid sequences in the CDRs of the lead antibody; selecting one of the CDRs in the $V_H$ or $V_L$ region of the lead antibody; providing an amino acid sequence that comprises at least 3 consecutive amino acid residues in the selected CDR, the selected amino acid sequence being a lead sequence; comparing the lead sequence with a plurality of tester protein sequences; selecting from the plurality of tester protein sequences at least two peptide segments that have at least 10% sequence identity with lead sequence, the selected peptide segments forming a hit library; building an amino acid positional variant profile of the hit library based on frequency of amino acid variant appearing at each position of the lead sequence; combining the amino acid variants in the hit library to produce a combination of hit variants which form a hit variant library; determining if a member of the hit variant library is structurally compatible with the lead structural template using a scoring function; and selecting the members of the hit variant library that score equal to or better than the lead sequence.

According to the method, the step of combining the amino acid variants in the hit library includes: selecting the amino acid variants with frequency of appearance higher than 2%, preferably 5%, more preferably 8% times, and most preferably 10% of the amino acid occurrence frequency for the cutoff and then include some of the amino acids from the lead sequence if they are missed after cutoff; and combining the selected amino acid variants in the hit library to produce a combination of hit variants which form a hit variant library.

According to the method, the scoring function is an energy scoring function selected from the group consisting of electrostatic interactions, van der Waals interactions, electrostatic solvation energy, solvent-accessible surface solvation energy, and conformational entropy.

Optionally, the scoring function is one incorporating a forcefield selected from the group consisting of the Amber forcefield, Charmm forcefield, the Discover cvff forcefields, the ECEPP forcefields, the GROMOS forcefields, the OPLS forcefields, the MMFF94 forcefield, the Tripos forcefield, the MM3 forcefield, the Dreiding forcefield, and UNRES forcefield, and other knowledge-based statistical forcefield (mean field) and structure-based thermodynamic potential functions.

The method may further comprise the step of: constructing a nucleic acid library comprising DNA segments encoding the amino acid sequences of the selected members of the hit variant library.

Optionally, the method may further comprise the steps of: partitioning theparsing the selected members of hit variant library into at least two sub-hit variant libraries; selecting a sub-hit variant library; building an amino acid positional variant profile of the selected sub-hit variant library; converting the amino acid positional variant profile of the selected sub-hit variant library into a nucleic acid positional variant profile by back-translating the amino acid positional variants into their corresponding trinucleotide codons; and constructing a degenerate nucleic acid library of DNA segments by combinatorially combining the nucleic acid positional variants.

The step of parsing the hit variant library may include: randomly selecting 10-30 members of the hit variant library that score equal to or better than the lead sequence, the selected members forming a sub-variant library.

Optionally, the step of parsing the hit variant library may include: building an amino acid positional variant profile of the hit variant library, resulting a hit variant profile; parsing the hit variant profile into segments of sub-variant profile based on the contact maps of the C$\alpha$, or C$\beta$ or heavy atoms of the structure or structure ensembles of a lead sequence within certain distance cutoff (8A to 4.5 A). A structural model or lead structural template within a distance of 8 Å, preferably within 6 Å, more preferably within 5 Å, and most preferably within 4.5 Å.

In another embodiment, the method comprises the steps of: providing an amino acid sequence of the variable region of the heavy chain ($V_H$) or light chain ($V_L$) of a lead antibody, the lead antibody having a known three dimensional structure; providing 3D structures of one or more antibodies with different sequences in $V_H$ or $V_L$ region than that of the lead antibody; forming a structure ensemble by combining the structures of the lead antibody and the one or more antibodies; the structure ensemble being defined as a lead structural template; identifying the amino acid sequences in the CDRs of the lead antibody; selecting one of the CDRs in the $V_H$ or $V_L$ region of the lead antibody; providing an amino acid sequence that comprises at least 3 consecutive amino acid residues in the selected CDR, the selected amino acid sequence being a lead sequence; comparing the lead sequence with a plurality of tester protein sequences; selecting from the plurality of tester protein sequences at least two peptide segments that have at least 10% sequence identity with lead sequence, the selected peptide segments forming a hit library; building an amino acid positional variant profile of the hit library based on frequency of amino acid variant appearing at each position of the lead sequence; combining the amino acid variants in the hit library to produce a combination of hit variants which form a hit variant library; determining if a member of the hit variant library is structurally compatible with the lead structural template using a scoring function; and selecting the members of the hit variant library that score equal to or better than the lead sequence.

In a particular embodiment, the method comprises the steps of: a) providing an amino acid sequence of the variable region of the heavy chain ($V_H$) or light chain ($V_L$) of a lead antibody, the lead antibody having a known three dimensional structure; b) identifying the amino acid sequences in the CDRs of the lead antibody; c) selecting one of the CDRs in the $V_H$ or $V_L$ region of the lead antibody; d) providing an amino acid sequence that comprises at least 3 consecutive amino acid residues in the selected CDR, the selected amino acid sequence being defined as a lead sequence; e) comparing the lead sequence with a plurality of tester protein sequences; f) selecting from the plurality of tester protein sequences at least two peptide segments that have at least 10% sequence identity with lead sequence, the selected peptide segments forming a hit library; g) building an amino acid positional variant profile of the hit library based on frequency of amino acid variant appearing at each position of the lead sequence; h) combining the amino acid variants in the hit library to produce a combination of hit variants which form a hit variant library; I) determining if a member of the hit variant library is structurally compatible with the lead structural template using a scoring function; j) selecting the members of the hit variant library that score equal to or better than the lead sequence; k) constructing a degenerate nucleic acid library comprising DNA segments encoding the amino acid sequences of the selected members of the hit variant library; l) determining the diversity of the nucleic acid library, if the diversity is higher than $1 \times 10^6$, repeating steps j) through l) until the diversity of the diversity of the nucleic acid library is equal to or lower than $1 \times 10^6$; m) introducing the DNA segments in the degenerate nucleic acid library into cells of a host organism; n) expressing the DNA segments in the host cells such that recombinant antibodies containing the amino acid sequences of the hit library are produced in the cells of the host organism; o) selecting the recombinant antibody that binds to a target antigen with affinity higher than $10^6 \, M^{-1}$; and p) repeating steps e) through o) if no recombinant antibody is found to bind to the target antigen with affinity higher than $10^6 \, M^1$.

In another particular embodiment, the method comprises the steps of: a) providing an amino acid sequence of the variable region of the heavy chain ($V_H$) or light chain ($V_L$) of a lead antibody, the lead antibody having a known three dimensional structure which is defined as a lead structural template; b) identifying the amino acid sequences in the CDRs of the lead antibody; c) selecting one of the CDRs in the $V_H$ or $V_L$ region of the lead antibody; d) providing an amino acid sequence that comprises at least 3 consecutive amino acid residues in the selected CDR, the selected amino acid sequence being defined as a lead sequence; e) mutating the lead sequence by substituting one or more of the amino acid residues of the lead sequence with one or more different amino acid residues, resulting in a lead sequence mutant library; f) determining if a member of the lead sequence mutant library is structurally compatible with the lead structural template using a first scoring function; g) selecting the lead sequence mutants that score equal to or better than the lead sequence; h) comparing the lead sequence with a plurality of tester protein sequences; I) selecting from the plurality of tester protein sequences at least two peptide segments that have at least 10% sequence identity with lead sequence, the selected peptide segments forming a hit library; j) building an amino acid positional variant profile of the hit library based on frequency of amino acid variant appearing at each position of the lead sequence; k) combining the amino acid variants in the hit library to produce a combination of hit variants; l) combining the selected lead sequence mutants with the combination of hit variants to produce a hit variant library; m) determining if a member of the hit variant library is structurally compatible with the lead structural template using a second scoring function; n) selecting the members of the hit variant library that score equal to or better than the lead sequence; o) constructing a degenerate nucleic acid library comprising DNA segments encoding the amino acid sequences of the selected members of the hit variant library; p) determining the diversity of the nucleic acid library, and if the diversity is higher than $1 \times 10^6$, repeating steps n) through p) until the diversity of the diversity of the nucleic acid library is equal to or lower than $1 \times 10^6$; q) introducing the DNA segments in the degenerate nucleic acid library into cells of a host organism; r) expressing the DNA segments in the host cells such that recombinant antibodies containing the amino acid sequences of the hit library are produced in the cells of the host organism; s) selecting the recombinant antibody that binds to a target antigen with affinity higher than $10^6 \, M^{-1}$; and t) repeating steps e) through s) if no recombinant antibody is found to bind to the target antigen with affinity higher than $10^6 \, M^{-1}$.

In yet another aspect of the present invention, a computer-implemented method is provided for constructing a library of mutant antibodies based on a lead antibody.

In one embodiment, the method comprises: taking as an input an amino acid sequence that comprises at least 3 consecutive amino acid residues in a CDR region of the lead antibody, the amino acid sequence being a lead sequence; employing a computer executable logic to compare the lead sequence with a plurality of tester protein sequences; selecting from the plurality of tester protein sequences at least two peptide segments that have at least 15% sequence identity with lead sequence; and generating as an output the selected peptide segments which form a hit library.

According to any of the above methods, the length of the lead sequence is preferably between 5-100 aa, more preferably between 6-80 aa, and most preferably between 8-50 aa.

According to any of the above methods, the step of identifying the amino sequences in the CDRs is carried out by using Kabat criteria or Chothia criteria.

Also according to any of the above methods, the lead sequence may comprise an amino acid sequence from a particular region within the $V_H$ or $V_L$ of the lead antibody, CDR1, CDR2 or CDR3, or from a combination of the CDR and FRs, such as CDR1-FR2, FR2-CDR2-FR3, and the full-length $V_H$ or $V_L$ sequence. The lead sequence preferably comprises at least 6 consecutive amino acid residues in the selected CDR, more preferably at least 7 consecutive amino acid residues in the selected CDR, and most preferably all of the amino acid residues in the selected CDR.

Also according to any of the above methods, the lead sequence may further comprise at least one of the amino acid residues immediately adjacent to the selected CDR.

Also according to any of the above methods, the lead sequence may further comprise at least one of the FRs flanking the selected CDR.

Also according to any of the above methods, the lead sequence may further comprise one or more CDRs or FRs adjacent the C-terminus or N-terminus of the selected CDR.

Also according to any of the above methods, the lead structural template may be a 3D structure of a fully assembled lead antibody, or a heavy chain or light chain variable region of the lead antibody (e.g., CDR, FR and a combination thereof).

Also according to any of the above methods, the plurality of tester protein sequences includes preferably antibody sequences, more preferably human antibody sequences, and most preferably human germline antibody sequences (V-database), especially for the framework regions.

Also according to any of the above methods, the plurality of tester protein sequences is retrieved from genbank of the NIH or Swiss-Prot database or the Kabat database for CDRs of antibodies.

Also according to any of the above methods, the step of comparing the lead sequence with the plurality of tester protein sequences is implemented by an algorithm selected from the group consisting of BLAST, PSI-BLAST, profile HMM, and COBLATH.

Also according to any of the above methods, the sequence identity of the selected peptide segments in the hit library with the lead sequence is preferably at least 25%, preferably at least 35%, and most preferably at least 45%.

According to any of the above method, the method further comprises the following steps: introducing the DNA segments in the nucleic acid or degenerate nucleic acid library into cells of a host organism; expressing the DNA segments in the host cells such that recombinant antibodies containing the amino acid sequences of the hit library encoded by the nucleic acid or degenerate nucleic acid library are produced in the cells of the host organism; and selecting the recombinant antibody that binds to a target antigen with affinity higher than $10^6$ M$^{-1}$, optionally $10^7$ M$^{-1}$, optionally $10^8$ M$^1$, optionally $10^9$ M$^{-1}$, optionally $2 \times 10^9$ M$^{-1}$, optionally $5 \times 10^9$ M$^{-1}$, optionally $1 \times 10^{10}$ M$^{-1}$, optionally $5 \times 10^{10}$ M$^{-1}$, and optionally $1 \times 10^{11}$ M$^{-1}$.

The recombinant antibodies may be fully assembled antibodies, Fab fragments, Fv fragments, or single chain antibodies.

The host organism includes any organism or its cell line that is capable of expressing transferred foreign genetic sequence, including but not limited to bacteria, yeast, plant, insect, and mammals.

The recombinant antibodies may be fully assembled antibodies, Fab fragments, Fv fragments, or single chain antibodies. For example, the recombinant antibodies may be expressed in bacterial cells and displayed on the surface of phage particles. The recombinant antibodies displayed on phage particles may be a double-chain heterodimer formed between $V_H$ and $V_L$. The heterodimerization of $V_H$ and $V_L$ chains may be facilitated by a heterodimer formed between two non-antibody polypeptide chains fused to the $V_H$ and $V_L$ chains, respectively. For example, these two non-antibody polypeptide may be derived from a heterodimeric receptors GABAB R1 (GR1) and R2 (GR2), respectively.

Alternatively, the recombinant antibodies displayed on phage particles may be a single-chain antibody containing $V_H$ and $V_L$ linked by a peptide linker. The display of the single chain antibody on the surface of phage particles may be facilitated by a heterodimer formed between a fusion of the single chain antibody with GR1 and a fusion of phage pIII capsid protein with GR2.

The target antigen to be screened against includes small molecules and macromolecules such as proteins, peptides, nucleic acids and polycarbohydrates.

Any of the above methods may further comprise the following steps: introducing the DNA segments in the nucleic acid or degenerate nucleic acid library into cells of a host organism; expressing the DNA segments in the host cells such that recombinant antibodies containing the amino acid sequences of the hit library are produced in the cells of the host organism; and selecting the recombinant antibody that binds to a target antigen with affinity higher than $10^6$ M$^{-1}$.

The binding affinity of the selected recombinant antibody to the target antigen is optionally higher than $10^7$ M$^{-1}$, optionally higher than $10^8$ M$^{-1}$, optionally higher than $1 \times 10^9$ M$^{-1}$, optionally higher than $2 \times 10^9$ M$^{-1}$, optionally higher than $5 \times 10^9$ M$^{-1}$, optionally higher than $8 \times 10^9$ M$^{-1}$, optionally higher than $1 \times 10^{10}$ M$^{-1}$, optionally higher than $2 \times 10^{10}$ M$^{-1}$, optionally higher than $5 \times 10^{10}$ M$^1$, optionally higher than $8 \times 10^{10}$ M$^{-1}$, or optionally higher than $1 \times 10^{11}$ M$^{-1}$.

The binding affinity of the selected antibody to its antigen may vary, depending the form of antibody being tested. The selected antibody being tested may be in the form of a single-chain antibody (scFv) comprising $V_H$ and $V_L$ designed by using the methodology of the present invention. Optionally, the selected antibody being tested may be in the form of a Fab comprising $V_H$ and $V_L$ designed by using the methodology of the present invention. Presumably due to its higher conformational flexibility and instability, the binding affinity of the selected antibody in the form of scFv may be 1-2 magnitude lower than that in the form of Fab. Accordingly, for a selected antibody in the form of scFv, the dissociation constant is preferably lower than $10^6$ M$^{-1}$, optionally higher than $10^7$ M$^{-1}$, optionally higher than $1 \times 10^8$ M$^{-1}$, optionally higher than $2 \times 10^8$ M$^{-1}$, optionally higher than $5 \times 10^8$ M$^{-1}$, optionally higher than $8 \times 10^8$ M$^{-1}$, optionally higher than $1 \times 10^9$ M$^{-1}$, optionally higher than $2 \times 10^9$ M$^{-1}$, optionally higher than $5 \times 10^9$ M$^{-1}$, optionally higher than $8 \times 10^9$ M$^{-1}$, optionally higher than $1 \times 10^{10}$ M$^{-1}$, optionally higher than $5 \times 10^{10}$ M$^{-1}$, or optionally higher than $1 \times 10^{11}$ M$^{-1}$.

The binding affinity of the selected recombinant antibody to the target antigen may also be represented by the dissociation constant $K_d$ measured in a kinetic study of the binding interaction between the antibody and the target antigen at a certain temperature (e.g., 4° C., 25° C., 35° C., 37° C., or 42° C.), for example, by using an instrument such as a BIAcore biosensor (see EXAMPLE). Generally, the lower $K_d$ measured, the higher affinity the antibody; and the higher temperature of measurement, the higher $K_d$ measured for the same antibody.

The $K_d$ of a selected antibody is optionally lower than 100 nM, optionally lower than 10 nM, optionally lower than 8 nM, optionally lower than 8 nM, optionally lower than 5 nM, optionally lower than 1 nM, optionally lower than 0.8 nM, optionally lower than 0.5 nM, optionally lower than 0.2 nM, optionally lower than 0.11 nM, optionally lower than 0.08 nM, optionally lower than 0.05 nM, optionally lower than 0.01 nM, or optionally lower than 0.005 nM, in the form of scFv, Fab, or other form of antibody measured at a temperature of about 4° C., 25° C., 35° C., 37° C. or 42° C.

According to any of the above embodiments, the designed proteins (e.g. antibodies) may be synthesized, or expressed in cells of any organism, including but not limited to bacteria, yeast, plant, insect, and mammal. Particular types of cells include, but are not limited to, *Drosophila melanogaster* cells, *Saccharomyces cerevisiae* and other yeasts, *E. coli, Bacillus subtilis*, SF9 cells, C129 cells, 293 cells, Neurospora, BHK, CHO, COS, and HeLa cells, fibroblasts, Schwanoma cell lines, immortalized mammalian myeloid and lymphoid cell lines, Jurkat cells, mast cells and other endocrine and exocrine cells, and neuronal cells. Examples of mammalian cells include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells, osteoclasts, chondrocytes and other connective tissue cells, keratinocytes, melanocytes, liver cells, kidney cells, and adipocytes.

Preferably, the designed protein is purified or isolated after expression according to methods known to those skilled in the art. Examples of purification methods include electrophoretic, molecular, immunological and chromatographic techniques, including ion exchange, hydrophobic, affinity, and reverse-phase HPLC chromatography, and chromatofocusing. The degree of purification necessary will vary depending on the use of the designed protein. In some instances no purification will be necessary.

Also according to any of the embodiments described above, the designed proteins can be screened for a desired function, preferably a biological function such as their binding to a known binding partner, physiological activity, stability profile (pH, thermal, buffer conditions), substrate specificity, immunogenicity, toxicity, etc.

In the screening using a cell-based assay, the designed protein may be selected based on an altered phenotype of the cell, preferably in some detectable and/or measurable way. Examples of phenotypic changes include, but are not limited to, gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e. half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptability, latency, adhesion, and uptake of viruses and bacterial pathogens.

According to any of the above embodiment, the designed proteins (e.g. antibodies) may be synthesized, or expressed as fusion proteins with a tag protein or peptide. The tag protein or peptide may be used to identify, isolate, signal, stabilize, increase flexibility of, increase degradation of, increase secretion, translocation or intracellular retention or enhance expression of the designed proteins.

The invention further provides: isolated nucleic acid encoding the antibody; a vector comprising that nucleic acid, optionally operably linked to control sequences recognized by a host cell transformed with the vector; a host cell comprising that vector; a process for producing the antibody comprising culturing the host cell so that the nucleic acid is expressed and, optionally, recovering the antibody from the host cell culture.

3. Method of Using the Antibodies of the Present Invention

The antibodies designed by using the inventive methods may be used for diagnosing or therapeutic treatment of various diseases, including but not limited to, cancer, autoimmune diseases such as multiple sclerosis, rheumatoid arthritis, systemic lupus erythematosus, Type I diabetes, and myasthenia gravis, graft-versus-host disease, cardiovascular diseases, viral infection such as HIV, hepatitis viruses, and herpes simplex virus, bacterial infection, allergy, Type II diabetes, hematological disorders such as anemia.

The antibodies can also be used as conjugates that are linked with diagnostic or therapeutic moieties, or in combination with chemotherapeutic or biological agents.

The antibodies of the invention may be used as affinity purification agents. In this process, the antibodies are immobilized on a solid phase such a Sephadex resin or filter paper, using methods well known in the art. The immobilized antibody is contacted with a sample containing the VEGF protein (or fragment thereof) to be purified, and thereafter the support is washed with a suitable solvent that will remove substantially all the material in the sample except the VEGF protein, which is bound to the immobilized antibody. Finally, the support is washed with another suitable solvent, such as glycine buffer, pH 5.0, that will release the VEGF protein from the antibody.

Anti-VEGF antibodies may also be useful in diagnostic assays for VEGF protein, e.g., detecting its expression in specific cells, tissues, or serum. Such diagnostic methods may be useful in cancer diagnosis.

For diagnostic applications, the antibody may be labeled with a detectable moiety. For example, the antibody can be labeled with a radioisotope, such as $^{35}$S, $^{14}$C, $^{125}$I, $^{3}$H, and $^{131}$I, using the techniques described in Current Protocols in Immunology, Volumes 1 and 2, Coligen et al., Ed. Wiley-Interscience, New York, N.Y., Pubs. (1991) for example and radioactivity can be measured using scintillation counting.

The antibody may also be conjugated with a fluorescent label such as rare earth chelates (e.g., europium chelates), fluorescein and its derivatives, rhodamine and its derivatives, dansyl, Lissamine, phycoerythrin and Texas Red. The fluorescent labels can be conjugated to the antibody using the techniques disclosed in Current Protocols in Immunology, supra, for example. Fluorescence can be quantified using a fluorimeter.

The antibody can be labeled with various enzyme-substrate labels such as those disclosed in U.S. Pat. No. 4,275,149. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate.

In one diagnostic application, the invention provides a method for determining the presence of VEGF protein comprising exposing a sample suspected of containing the VEGF protein to the anti-VEGF antibody and determining binding of the antibody to the sample. For this use, the invention provides a kit comprising the antibody and instructions for using the antibody to detect the VEGF protein.

The antibodies of the present invention can also be formulated for delivery via a wide variety of routes of administration. Therapeutic formulations of the antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. For example, the antibodies may be administered or coadministered orally, topically, parenterally, intraperitoneally, intravenously, intraarterially, transdermally, sublingually, intramuscularly, rectally, transbuccally, intranasally, via inhalation, vaginally, intraoccularly, via local delivery (for example by a catheter or a stent), subcutaneously, intraadiposally, intraarticularly, or intrathecally.

Depending on the type and severity of the disease, about 1 ug/kg to about 50 mg/kg (e.g., 0.1-20 mg/kg, 0.5-15 mg/Kg, and 1-10 mg/kg) of antibody is an initial candidate dosage for administration to the patient, whether, for example, by one or more separate administrations, or by continuous infusion. A typical daily or weekly dosage might range from about 1 ug/kg to about 20 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic tumor imaging.

The anti-VEGF antibodies of the present invention may be used to treat a wide variety of indications for anti-VEGF antibodies have therapeutic activity. Such indications include, but are not limited to, restenosis (e.g. coronary, carotid, and cerebral lesions), benign tumors, a various types of cancers such as primary tumors and tumor metastasis, abnormal stimulation of endothelial cells (atherosclerosis), insults to body tissue due to surgery, abnormal wound healing, abnormal angiogenesis, diseases that produce fibrosis of tissue, muscular degeneration, repetitive motion disorders, disorders of tissues that are not highly vascularized, and proliferative responses associated with organ transplants.

Examples of benign tumors include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

Specific types of cancers include, but are not limited to, leukemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Diseases associated with abnormal angiogenesis include, but are not limited to, rheumatoid arthritis, ischemic-reperfusion related brain edema and injury, cortical ischemia, ovarian hyperplasia and hypervascularity, (polycystic ovary syndrom), endometriosis, psoriasis, diabetic retinopahy, and other ocular angiogenic diseases such as retinopathy of prematurity (retrolental fibroplastic), macular degeneration, corneal graft rejection, neuroscular glaucoma and Oster Webber syndrome. In a particular embodiment, the anti-VEGF antibodies of the present invention can be used for treating age-related macular degeneration (AMD).

Examples of retinal/choroidal neovascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disese, systemic lupus erythematosis, retinopathy of prematurity, Eales disease, diabetic retinopahy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the ankle) and diseases caused by the abnormal proliferation of fibrovascular or fibrous tissue including all forms of proliferative vitreoretinopathy.

Examples of corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

The anti-VEGF antibodies of the present invention may be used in combination with an anti-angiogenesis agent for the treatment of diseases associated with abnormal angiogenesis.

Examples of anti-angiogenesis agents include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,l-3,4-dehydroproline, thiaproline], α,α-dipyridyl, β-aminopropionitrile fumarate, 4-propyl-5-(4-pyridinyl)-2(3h)-oxazolone; methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), beta.-1-anticollagenase-serum, □2-antiplasmin, bisantrene, lobenzarit disodium, n-(2-carboxyphenyl-4-chloroanthronilic acid disodium or "CCA", thalidomide; angostatic steroid, cargboxynaminolmidazole; metalloproteinase inhibitors such as BB94. Other anti-angiogenesis agents include antibodies, such as monoclonal antibodies against these angiogenic growth factors: bFGF, aFGF, FGF-5, VEGF isoforms, VEGF-C, HGF/SF and Ang-1/Ang-2.

The anti-VEGF antibodies of the present invention, preferably those having therapeutic synergistic effects with the anti-VEGF antibodies, may be employed in combination with the anti-VEGF antibodies to further enhance the therapeutic effects of these two types of drug. Examples of the therapeutic agent include, but are not limited to, alkylating agents, antibiotic agents, antimetabolic agents, hormonal agents, plant-derived agents, and biologic agents.

Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin).

Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin.

Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, imatinib mesylate (or GLEEVAC®), and gemcitabine. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), camptothecin compounds (e.g., 20(S) camptothecin, topotecan, rubitecan, and irinotecan), taxanes (e.g., paclitaxel and docetaxel).

Examples of biologic agents include, but are not limited to, immuno-modulating proteins such as cytokines, monoclonal antibodies against tumor antigens, tumor suppressor genes, and cancer vaccines. Examples of interleukins that may be used in conjunction with the antibody of the present invention include, but are not limited to, interleukin 2 (IL-2), and interleukin 4 (IL-4), interleukin 12 (IL-12). Examples of interferons that may be used in conjunction with the antibody of the present invention include, but are not limited to, interferon a, interferon b (fibroblast interferon) and interferon g (fibroblast interferon). Examples of such cytokines include, but are not limited to erythropoietin (epoietin a), granulocyte-CSF (filgrastin), and granulocyte, macrophage-CSF (sargramostim). Other immuno-modulating agents other than cytokines include, but are not limited to bacillus Calmette-Guerin, levamisole, and octreotide.

The anti-VEGF antibodies of the present invention may also be combined with a tumor necrosis factor (TNF) or its mutein in the treatment of the above diseases or conditions. The administration of anti-VEGF antibody and TNF is repeated until the desired clinical effect is achieved. In instances where solid tumors are found in the limbs or in other locations susceptible to isolation from the general circulation, the antibody and/or TNF may be administered to the isolated tumor or organ. In other embodiments, a FGF or platelet-derived growth factor (PDGF) antagonist, such as an anti-FGF or an anti-PDGF neutralizing antibody, is administered to the patient in conjunction with the anti-VEGF antibody. Treatment with anti-VEGF antibodies optimally may be suspended during periods of wound healing or desirable neovascularization.

Example of monoclonal antibodies against tumor antigens that can be used in conjunction with the anti-VEGF antibodies of the present invention include, but are not limited to, HERCEPTIN® (Trastruzumab), RITUXAN® (Rituximab), MYLOTARG® (gemtuzumab ozogamicin), CAMPATH® (alemtuzumab), ZEVALIN® (ibritumomab yiuxetan), PAN-OREX® (edrecolomab), BEXXAR® (tositumomab), ERBITUX® (cetuximab), and AVASTIN® (bevacizumab).

Examples of the tumor suppressor genes include, but are not limited to, DPC-4, NF-1, NF-2, RB, p53, WT1, BRCA1 and BRCA2.

Example of cancer vaccines include, but are not limited to gangliosides (GM2), prostate specific antigen (PSA), □-fetoprotein (AFP), carcinoembryonic antigen (CEA) (produced by colon cancers and other adenocarcinomas, e.g. breast, lung, gastric, and pancreas cancer s), melanoma associated antigens (MART-1, gp100, MAGE 1,3 tyrosinase), papillomavirus E6 and E7 fragments, whole cells or portions/lysates of antologous tumor cells and allogeneic tumor cells.

An adjuvant may be used to augment the immune response to TAAs. Examples of adjuvants include, but are not limited to, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

EXAMPLES

1. In Silico Design of Anti-VEGF Antibodies for Humanization and Affinity Maturation The methodology provided in the present invention was used to design libraries for humanization of non-human antibodies and to optimize the affinity and other attributes of antibodies. Novel variants of amino acids and nucleic acids of antibodies were generated with human or human like sequences while their binding affinity, stability, expression are improved significantly.

The inventive process was carried out computationally in a high throughput manner by mining the ever-expanding databases of protein sequences of all organisms, especially human and by relating their specific sequences or their variants with functional enhancement such as binding affinity and stability that are tested experimentally. By using the inventive methodology, an expanded and yet functionally biased library of antibodies were constructed based on computational evaluation of extremely diverse protein sequences and functionally relevant structures in silico and subsequently tested by experimental screening and selection in vitro or in vivo.

In general, the method was implemented in a computer through in silico selection of protein sequences based on the amino acid sequence of a target structural/functional motif or domain in a lead protein, herein after referred to as the "lead sequence". The lead sequence was employed to search databases of protein sequences. The choice of the database depends on the specific functional requirement of the designed motifs. For example, if the lead protein is an enzyme and the target motif includes the active site of the enzyme, databases of proteins/peptides of a particular origin, organism, species or combinations thereof, may be queried using various search criteria to yield a hit list of sequences each of which can substitute the target motif in the lead protein. A similar approach may be used for designing other motifs or domains of the lead protein. The designed sequences for each individual motif/domain may be combined to generate a library of designed proteins. In addition, to reduce immunogenicity of the designed proteins for human applications such as therapeutics or diagnosis, databases of proteins of human origin or humanized proteins are preferably searched to yield the hit list of sequences, especially for motifs derived from sites of the lead protein that serves as the scaffolding of the lead proteins such as the frameworks of an antibody. The library of designed proteins can be tested experimentally to yield proteins with improved biological function(s) over the lead protein.

In this example, the inventive methodology was implemented in designing anti-VEGF antibodies that are diverse in sequence and yet functionally related to each other. Based on the designed antibody sequences, a library of antibodies were constructed to include diverse sequences in the complementary determining regions (CDRs) and/or humanized frameworks (FRs) of a non-human antibody in a high throughput manner. This library of antibodies were screened against human VEGF for improved function such as binding affinity and pharmacokinetic property.

In designing the anti-VEGF antibodies, in silico selection of antibody sequences was based on the amino acid sequence of a region or motif in a lead anti-VEGF antibody, herein after referred to as the "lead sequence". The lead sequence was employed to search databases of protein sequences. The choice of the database depends on the specific functional requirement of the designed motifs. For example: in order to design the framework regions of variable chains for therapeutic application, collections of protein sequences that are evolutionarily related such as fully human immunoglobulin sequences and human germline immunoglobulin sequences would be used except for a few structurally critical sites. This would reduce the immunogenic response by preserving the origin of the sequences by introducing as few foreign mutants as possible in this highly conserved region (for framework regions). On the other hand, diverse sequence databases such as immunoglobulin sequences of various species or even unrelated sequence in genbank can be used to design the CDRs in order to improve binding affinity with antigens in this highly variable region. By using the method, a library of diverse antibody sequences were constructed and screened experimentally in vitro and/or in vivo for antibody mutants with improved or desired function(s).

1) Anti-VEGF Antibody Libraries Designed in Silico for Affinity Maturation

The amino acid sequence of the variable heavy chain regions of a murine anti-VEGF antibody and the segments for frameworks and CDRs (underlined and annotated) is:

(SEQ ID NO: 283)
EIQLVQSGPELKQPGETVRISCKAS<u>GYTFTNYGMN</u>(VH/CDR1)WVKQAP

GKGLKWMG<u>WINTYTGEPTYAADFKR</u>(VH/CDR2)RFTFSLETSASTAYLQ

ISNLKNDDTATYFCA<u>KYPHYYGSSHWYFDV</u>(VH/CDR3)WGAGTTVTVSS

This V$_H$ sequence therein after referred to as the "parental anti-VEGF antibody". The frameworks and CDRs are designated according to the Kabat criteria (Kabat E A, Redi-Miller M, Perry H M, Gottesman K S (1987) Sequences of Proteins of Immunological Interest 4$^{th}$ edit, National Institutes of Health, Bethesda, Md.).

The CDR and framework regions of the antibody were targeted using a modular in silico evolutionary design approach as described in more detail in U.S. patent application Ser. Nos. 10/443,134, 10/153,159, 10/153,176, 10/125,687, and 60/284,407, which are incorporated herein by reference in their entirety. Using murine anti-VEGF antibody as the lead protein and its V$_H$ CDR3 as the lead sequence, digital libraries of V$_H$ CDR3 were constructed by following the procedure.

The lead sequence includes V$_H$ CDR3 of the parental anti-VEGF antibody and a few amino acid residues from the adjacent framework regions CAK <u>YPHYYGSSHWYFDV</u>WG (SEQ ID NO: 348) A hit library was constructed by searching and selecting hit amino acid sequences to V$_H$ CDR3 from a sequence database. Variant profile was built to list all variants at each position based on the hit library and filtered with certain cutoff value to reduce of the size of the resulting hit variant library within computational or experimental limit. Variant profiles were also built in order to facilitate i) the sampling of the sequence space that covers the preferred region in the fitness landscape; ii) the partitioning and synthesis of degenerate nucleic acid libraries that target the preferred peptide ensemble sequences; iii) the experimental screening of the antibody libraries for the desired function; and iv) the analysis of experimental results with feedback for further design and optimization.

The lead structural templates were obtained from the available X-ray structures of the complexes formed between VEGF and anti-VEGF antibodies. The complex structure of VEGF and parental anti-VEGF antibody is designated as 1BJ1, and that formed between VEGF and matured anti-VEGF antibody 1CZ8. The results from 1CZ8 structural template were similar to those from 1BJ1 in the relative ranking order of the scanned sequences. Structural models of anti-VEGF antibodies can be also used.

The lead sequence for V$_H$ CDR3 is taken from the parental anti-VEGF antibody according to Kabat classification with amino acid residues CAK and WG from the adjacent framework regions flanking the V$_H$ CDR3 sequence at N- and C-terminus, respectively. Only V$_H$ CDR3 sequence of the parental antibody was used to build the HMM for searching the protein databases.

The HMM built using the single lead sequence or sequences of the structural ensembles was calibrated and used to search the Kabat database (Johnson, G and Wu, TT (2001) Nucleic Acids Research, 29, 205-206). All sequence hits that are above expectation value or E-value are listed and aligned using HAMMER 2.1.1 package. After removing the redundant sequences from the hit list, the remaining hit sequences for the lead HMM form the hit library.

The variant profile at each position was used to build the AA-PVP table (amino acid positional variant profile), which gives the number of occurrence of each amino acid residue at each position.

The variant profile can filtered to remove variants that occur at or less than the certain cutoff frequency and/or in combination with variant reprofiling using structure-based scoring. The variant profile from the sequence pool provides informative data to identify the positions in the lead sequence that can be either varied or fixed. The sites can be divided into three categories: i) Structurally conserved sites remain conserved over evolution. The high frequency residues can be used to maintain the scaffold of the target motif at these positions; ii) variable functional hot spots should be targeted with focused mutagenesis; iii) combination of both i) and ii) to stabilize the target scaffold while simultaneously providing variability in the functional hot spots.

A set of the amino acids from the functional variants should be included at the functional hot spots according to their frequencies in the variant profile because they are evolutionarily selected or optimized. Furthermore, the variants at each position can be filtered or prioritized to include other potentially beneficial mutants or exclude potentially undesirable mutants to meet the computational and experimental constraints.

Although the variant profile is informative on the preferred amino acid residues at each position and specific mutants in a preferred order, unmodified, it embodies an enormous number of recombinants. Some filtering using frequency cutoff can reduce the combinatorial sequences that need to be evaluated by computational screening or targeted directly by experimental libraries.

A structure-based scoring was applied to screen the hit library and its combinatorial sequences that form a hit variant library. Side chains of $V_H$ CDR3 of the parental anti-VEGF antibody were substituted by rotamers of corresponding amino acid variants from the hit variant library at each residue position. The conformations of rotamers were built and optimized by using the program SCWRL® (version 2.1) using backbone-dependent rotamer library (Bower M J, Cohen F E, Dunbrack R L (1997) JMB 267, 1268-82).

The scoring was done by searching the optimal rotamers and minimizing the energy by 100-200 steps using the Amber94 force field in CONGEN [Bruccoleri and Karplus (1987) Biopolymers 26:137-168] in the presence and absence of the structure of the antigen VEGF. The energy scores of an anti-VEGF variant library based on the calculated scores with and/without VEGF antigen indicate there are a large number of sequences for various variant libraries with higher scores than the parental sequences.

A refined custom scoring function that includes sidechain entropy, nonpolar solvation energy and electrostatic solvation energy can be used to gauge the simple functions used for scoring. Three energy terms were calculated: sidechain entropy, nonpolar solvation energy and electrostatic solvation energy and the backbone entropy for loops as well.

The nonelectrostatic solvation energy is made proportional to the molecular surface, as calculated by the GEPOL93 algorithm, with the scaling constant of 70 cal/mol/$A^2$ (Tunon I, Silla E, Pascual-Ahuir J L (1992) Prot Eng 5, 715-716) using GEPOL (Pascual-Ahuir J L, Silla E (1993) J Comput Chem 11, 1047-1060) command as implemented in CONGEN.

The electrostatic solvation energy is calculated using the finite-difference PB (FDPB) method as implemented in UHBD program (Davis M E, Madura J D, Luty B A, McCammon J A (1991) Comput Phys Commun 62, 187-197). The focusing method is used for the region surrounding the mutation. An automated protocol generates three grids: coarse, fine, and focus grids. The grid units are 1.5, 0.5, and 0.25 angstroms, respectively. The focusing grid is a cubic grid that spans the Cartesian volume occupied by the mutated residues. The fine grid is a cubic grid that spans the entire volume of the protein or the complex. The coarse grid is a cubic grid that is set to approximately twice the size of the fine grid in each axis and covers approximately 8 times the volume of the fine grid. The coarse grid serves to account for the long-range solvent effects and sets the boundary conditions for the fine grid. Similarly, the fine grid accounts for the electrostatic contributions of the protein interior and sets the boundary condition for the focus grid. The focus grid accounts for finer details of the localized effects due to the mutation. The dielectric constants for the protein interior and exterior are set to 4 and 78, respectively. Temperature is set to 300 Kelvin and ionic strength is set to 150 mM. Maximum iteration is set to 200. The calculations are repeated with a uniform dielectric so that both the interior and exterior dielectrics are set to 4 and the difference between the two energies is computed. The latter calculations represent the energies due to bringing the charges onto the grids.

The custom scoring function or the molecular mechanics energy using Amber94 forcefield in CONGEN plus the solvation terms from PB in UHBD used here is similar to MM-PBSA or MM-GBSA. The energy function shows better agreement with experimental data (Sharp K A. (1998) Proteins 33, 39-48; Novotny J, Bruccoleri R E, Davis M, Sharp K A (1997) J Mol Biol 268, 401-411), especially when structure ensembles by molecular dynamics calculations are used to provide more accurate methods to score sequence and its variants based on the ensemble averages of the energy functions (Kollman P A, Massova I, Reyes C, Kuhn B, Huo S H, Chong L T, Lee M, Lee T S, Duan Y, Wang W, Donini O, Cieplak P, Srinivasan P, Case D A, and Cheatham T E (2000) Acc. Chem Res. 33, 889-897).

The variant profile from the hit variant library as described above was filtered in order to reduce the potential library size while maintaining most of the preferred residues. A strategy that selects top sequences based on favorable score and/or the presence of residues likely to participate in favorable interactions was employed to identify a cluster or clusters of amino acid sequences for the nucleic acid library design. As described above, a cluster of computationally screened sequences for $V_H$ CDR3, CDR2 and CDR1, respectively, was chosen for further experimental test in vitro.

The hit variant library constructed above was targeted with a single degenerate nucleic acid library. The nucleic acid sequence profile was built using the optimal codons for specific organism that are combined with minimal sizes. A degenerate nucleic acid library was synthesized by incorporating a mixture of bases into each degenerate position. As a result of the combinatorial effect of the synthesis, this degenerate nucleic acid library encodes an expanded amino acid library.

Variants at each position for $V_H$ and $V_L$ are shown in the $V_H$ and $V_L$ amino acid position variant profile, respectively. Detailed results for $V_H$ and/or $V_L$ CDR3, CDR2, and CDR1, FR123 were summarized in anti-VEGF $V_H$ and $V_L$ Tables. These experiments demonstrated that by using the methods of the present invention, antibodies could be selected, not only with diverse sequences and phylogenic distances, but also with improved binding affinity to bind to the target VEGF antigen.

FIG. 1A is an amino acid positional variant profile (AA-PVP) for $V_L$ of anti-VEGF antibodies designed using the methodology described above. The AA-PVP of the $V_L$ chain uses the humanized $V_L$ (SEQ ID NO:1) by Baca et al. (1997) J Biol Chem 272: 10678-10684 as a reference sequence. The dot indicates the same amino acid as reference. CDRs are indicated in bold letters underlined.

FIG. 1B is an amino acid positional variant profile (AA-PVP) for $V_H$ of anti-VEGF antibodies designed using the methodology described above. The AA-PVP of the $V_H$ chain uses the humanized $V_H$ (SEQ ID NO:55) by Baca et al. (1997), supra as a reference sequence. The dot indicates the same amino acid as reference. CDRs are indicated in bold letters underlined.

The antibody libraries that were designed in silico, based on a lead sequence of the parental anti-VEGF antibody by using the methods described above were tested for their ability to bind to the antigen, VEGF, by using a novel phage display system.

2) Generation of Anti-VEGF Antibody Libraries for Framework Optimization

A murine monoclonal antibody was found to block VEGF-dependent cell proliferation and slow the tumor growth in vivo (Kim K J, Li B, Winer J, Armanini M, Gillett N, Phillips H S, Ferrara N (1993) Nature 362, 841-844). This murine antibody was humanized (Presta L G, Chen H, O'Connor S J, Chisholm V, Meng Y G, Krummen L, Winkler M, Ferrara N (1997) Cancer Res. 57, 4593-4599; Baca M, Presta L G, O'Connor S J, Wells J A (1997) J Biol Chem 272, 10678-10684) using random mutagenesis at some key framework positions following grafting of antigen-binding loops. Typically, after rounds of site-directed mutagenesis and selection, humanized antibodies are generated by replacing a human or concensus human framework with non-human amino acids from the parental non-human antibody at certain pre-determined key positions. These humanized antibodies will usually bind to its cognate antigen of its parental antibody with the reduced affinity relative its parental antibody (about 6-fold weaker for humanized anti-VEGF relative its parental murine antibody, see Baca M, Presta L G, O'Connor S J, Wells J A (1997) J Biol Chem 272, 10678-10684, and 2-fold weaker for another version of the humanized anti-VEGF, see Presta L G, Chen H, O'Connor S J, Chisholm V, Meng Y G, Krummen L, Winkler M, Ferrara N (1997) Cancer Res. 57, 4593-4599; Baca M, Presta L G, O'Connor S J, Wells J A (1997) J Biol Chem 272, 10678-10684). This loss of binding affinity would be recovered by using affinity maturation in CDRs (Chen Y, Wiesmann C, Fuh G, Li B, Christinger H W, McKay P, de Vos A M, Lowman H B (1999) J. Mol Biol 293, 865-881).

Using present inventive methods described, we have discovered several humanized frameworks that are several-folder higher in binding affinity (3.3-fold for hAB2,4-fold for hAB3 and 2-fold for hAB4) upon framework optimization than the reported humanized anti-VEGF antibody sequence (see hAB1 in FIG. 2 for the humanized anti-VEGF antibody framework reported in the literature (Presta L G, Chen H, O'Connor S J, Chisholm V, Meng Y G, Krummen L, Winkler M, Ferrara N (1997) Cancer Res. 57, 4593-4599). Because the reported humanized anti-VEGF antibody is ~2 times weaker than its corresponding murine antibody, our humanized antibodies (hAB2 and hAB3) should have ~2-fold higher binding affinity upon humanization than the corresponding murine antibody. Also, we can achieve such improvement by either increasing the on-rate ($K_{on}$) or decreasing the off-rate ($K_{off}$) or both of the humanized antibodies relative to the reported humanized antibody (hAB1) (see FIG. 2).

The amino acid sequence of the framework fr123 region of the murine anti-VEGF antibody is:

(SEQ ID NO: 292)
EIQLVQSGPELKQPGETVRISCKASWVKQAPGKGLKWMGRFTFSLETSAS

TAYLQISNLKNDDTATYFCA.

This sequence is therein after referred to as fr123 of "murine anti-VEGF antibody", see Presta L G, Chen H, O'Connor S J, Chisholm V, Meng Y G, Krummen L, Winkler M, Ferrara N (1997) Cancer Res. 57, 4593-4599). The relatively constant framework 4 can be designed if desired using the same approach. The framework and CDRs are designated according to the Kabat criteria (Kabat E A, Redi-Miller M, Perry H M, Gottesman K S (1987) Sequences of Proteins of Immunological Interest 4[th] edit, National Institutes of Health, Bethesda, Md.), although other classification can be used also. Also, separate segment of framework FR1 or FR2 or FR3 and FR4 can be designed individually and pasted together if desired. The combination of CDRs and FRs can be designed simultaneously by designing each segment or combinations of segments used the approach described here. The CDRs are the same as in SEQ283 from the murine anti-VEGF or those designed using the approach described here. However, different CDRs can be also designed and used in combination with the designed FR123 libraries. The variant profiles for the hit library are generated using the human $V_H$ germline sequences based on the lead sequence of $V_H$ FR123 of the murine anti-VEGF antibody and are filtered by using certain cutoff values. The variant at each position can be ranked based on its structural compatibility with the antibody structure using total energy or other scoring terms. Some reference amino acids are found to be favorable at certain positions based on their total energy or specific packing, although their occurrence frequency is very low. The variant profiles for the hit library can be generated and refined using the Kabat-derived human $V_H$ sequences based on the lead sequence of $V_H$ FR123 of the murine anti-VEGF antibody. The filtered variant profile can be further screened computationally to reflect the ranking order of the structural compatibility if only the antibody structure is used. Although the human vs non-human sequences differ in many positions across the entire chain for $V_H$, the amino acid libraries used in other humanization approach are focused on randomization at a few positions flanking grafted CDRs, whereas in a preferred embodiment, the humanization library targets various positions across both VH and VL chains with a few mutants at those positions for the starting anti-VEGF antibody.

In a preferred embodiment, each motif such as frameworks FR1, FR2, FR3 and FR4 or its combination such as FR123 of the antibody can be targeted using a modular in silico evolutionary design approach. It has been understood that there are only a limited number of conformations (called canonical structures) for each motif or its combination. These structural features of an antibody provide an excellent system for testing the evolutionary sequence design by using structured motifs at various regions of an antibody based on the extensive analysis of antibody structures. These structure and sequence conservation are observed across different species. In fact, the scaffolding of antibodies, or the immunoglobin fold, is one of the most abundant structure observed in nature and is highly conserved among various antibodies and related molecules.

In a preferred embodiment, the method can be also used to design antibody framework using sequence-based approach or structure ensembles that contain the induced structure changes in CDRs. Using murine anti-VEGF antibody framework as the lead protein and its $V_H$ FR123 as the lead sequence, digital libraries of $V_H$ FR123 were constructed.

In a preferred embodiment, a hit library was constructed by searching and selecting hit amino acid sequences using $V_H$ FR123 as the lead sequence. Variant profile was built to list all variants at each position based on the hit library and filtered with certain cutoff value to reduce of the size of the resulting hit variant library within computational or experimental limit. Variant profiles were also built in order to facilitate i) the sampling of the sequence space that covers the preferred region in the fitness landscape; ii) the partitioning and synthesis of degenerate nucleic acid libraries that target the preferred peptide ensemble sequences; iii) the experimental screening of the antibody libraries for the desired function; and iv) the analysis of experimental results with feedback for further design and optimization.

The lead structural templates were obtained from the available X-ray structures of the complexes formed between VEGF and anti-VEGF antibodies. The complex structure of VEGF and parental anti-VEGF antibody is designated as 1BJ1, and that formed between VEGF and matured anti-VEGF antibody 1CZ8. The results from 1CZ8 structural template were similar to those from 1BJ1 in the relative ranking order of the scanned sequences. The modeled structure or structure ensemble or ensemble average can be also used for screening sequences. The lead sequence for VH FR123 (SEQ283) is taken from the murine anti-VEGF antibody according to Kabat classification. The HMM built using the single lead sequence was calibrated and used to search human heavy chain germline sequence database and/or human sequence database (including human germlines and humanized sequences) derived from Kabat database (Johnson, G and Wu, TT (2001) Nucleic Acids Research, 29, 205-206). All sequence hits that are above expectation value or B-value are listed and aligned using HAMMER 2.1.1 package. After removing the redundant sequences from the hit list, the remaining hit sequences for the lead HMM form the hit library. The sequence identities of the hit sequences from the human VH germline ranges from 40 to 68% of the lead sequence, whereas the corresponding sequence identities of the hit sequences from human immunoglobin sequences derived from Kabat database (the database are parsed to fr123 fragment in order to increase the sensitivity of the search and their relative ranking) (other database would be used if the contain the immunoglobin sequences of human origins) ranging from ~30 to 75%. The evolutionary distances between the hits can be analysed by using the program TreeView 1.6.5.

The AA-PVP tables give the number of occurrence of each amino acid residue at each position. There are some differences between the hit sequences from the human VH germlines and those from Kabat-derived human $V_H$ sequences: amino acids of non-human origins resulting from amino acids that are structurally important to stabilize the scaffold of the target antibodies etc. This filtered variant profile can be further screened computationally to reflect the ranking order of the structural compatibility if only the antibody structure is used. In short, using different database of human origin for framework optimization would provide diverse but powerful choices of amino acids for framework optimization including humanization with improved binding affinity and stability. With the increase in our knowledge in developing therapeutic antibodies, more and more antibody sequence data will be accumulated and guide our design using present invention. No prior assumption is needed to assume the key positions and amino acids associated with those positions. Because this information is revealed automatically using present inventive method, it will become better defined with increase in their occurrence in database as more data are accumulated. Variants can be re-profiled or prioritized to include other potentially beneficial mutants using structure-based criteria. The structure-based energy scoring provides another way to re-profile the occurrence of variants at each position for the hit variant library which was originally built based on profiling of sequences selected from protein databases. Some filtering using frequency cutoff can reduce the combinatorial sequences that need to be evaluated by computational screening or targeted directly by experimental libraries. Even with the cutoff applied to the variant profile, there is still a large number of combinatorial sequences that needs to be scored and evaluated in the final sequences for experimental screening.

A structure-based scoring is applied to screen the hit library and its combinatorial sequences that form a hit variant library. Side chains of $V_H$ FR123 of the anti-VEGF antibody in 1CZ8 or 1BJ1 were substituted by rotamers of corresponding amino acid variants from the hit variant library at each residue position by using the program SCWRL® (version 2.1) using backbone-dependent rotamer library (Bower M J, Cohen F E, Dunbrack R L (1997) JMB 267, 1268-82). The scoring was done using energetic terms or their combination with a scaling factor for each term after the structure is optimized using the optimal rotamers and energy minimization using the Amber94 force field in CONGEN [Bruccoleri and Karplus (1987) Biopolymers 26:137-168] in the presence and absence of the structure of the antigen VEGF.

The designed framework VH fr123 have good structural compatibility with the structure relative to the murine reference. The human-like features of the framework optimization as defined partly by its database were also gauged using the phylogenetic distance analysis of the designed sequences with those from human germlines or humanized frameworks.

The variant profile from the hit variant library as described above was filtered in order to reduce the potential library size while maintaining most of the preferred residues obtained from a hit variant library after eliminating amino acids with occurrences lower than the cutoff value and/or by screening sequences based on their compatibility with the structural scaffolding.

The hit variant library constructed above was targeted with a degenerate oligonucleotides. The degenerate nucleic acid library constructed above was cloned into a phage display system and the phage-displayed antibodies (ccFv) were selected based on their binding to immobilized VEGF coated onto 96-well plates. The library was installed into a phage display vector pABMD12 in which the $V_H$ of anti-VEGF was replaced by the library. As a result, $V_L$ and a variety of $V_H$ generated from the library would pair to form a functional ccFv of anti-VEGF. The phage display library was then used for further panning against immobilized VEGF protein antigen.

In order to generate a library that can cover such a wide range of scattered distribution of degenerative positions, multiple overlapping degenerative DNA oligonucleotides were synthesized with degenerative positions at the sites where the library was designed. The assembly process consisted of two PCR reactions, assembly PCR, and amplification PCR. The assembly oligos were designed with 35-40mers and overlapped by 15-20 bases with melting temperature of about 60° C. by average. One additional pair of amplification oligo primers (Amp93 and Amp94) was created for final amplification of the designed products. Accordingly, the assembly PCR includes: equal amount of the assembly oligo primers in a final total concentration of 8 uM, dNTP of 0.8 uM, 1×pfu buffer (Strategene), and 2.5 units of pfu turbo (Strategene). The thermal cycle was performed as follows: 94° C.×45", 58° C.×45", 72° C.×45" for 30 cycles and a final extension of 10 minutes at 72° C. The PCR product mix was diluted 10 folds and used as the template for the amplification PCR in which all reagents were remained the same except for addition of the amplification primers at the final concentration of 1 uM. The thermal cycle was performed as follows: 94° C.×45", 60° C.×45", 72° C.×45" for 30 cycles and a final extension of 20 minutes at 72° C. The final product (the $V_H$ library) was purified, digested with HindIII and StyI, and finally subcloned into vector pABMD12 to replace the original murine $V_H$. The library was used to electrically transform TG1 competent cells, which were in turn amplified and rescued by helper phage KO7 (Amersham) before production of phages of the library at 30° C. overnight according to standard procedure.

To screen the library constructed described in the above example, purified homodimeric VEGF protein (Calbiochem) was diluted in designated concentration in coating buffer (0.05 M $NaHCO_3$, pH 9.6) and immobilized on Maxisorb wells (Nunc) at 4° C. overnight. The coated wells were then blocked in 5% milk at 37° C. for 1 hr before phage library diluted in PBS was applied in the wells for incubation at 37° C. for 2 hrs. The incubation mix also routinely contained 2% milk to minimize nonspecific binding. At the end of the incubation, the wells were washed and the phages bound were subsequently eluted by 1.4% triethylamine before infecting TG1 cells followed by rescue by KO7 helper phage for amplification. To amplify the phages, infected and rescued TG1 cells were then grown at 30° C. overnight in the presence of carbenicilline and kanamycin before phage library was harvested. The phages amplified were used as the input library for the next round of panning. Meanwhile, individual clones from $5^{th}$ panning and on were randomly sampled for phage ELISA, in which specific binding to immobilized VEGF would be confirmed, and demonstrated 100% positives from the 5$^{th}$ to 7$^{th}$ pannings. Finally, isolated clones grown on plates of 2xYT/carbenicilline (100 ug/ml)/kanamycin (70 ug/ml) were sampled for sequencing beginning from the 5$^{th}$ panning (P5) to define the hit positions and hit sequences against the design.

FIG. 1C shows amino acid sequences of full length $V_L$ (as compared with that of the humanized $V_L$ (SEQ ID NO:1) as in Baca et al. (1997) J Biol Chem 272:10678-10684, and mouse anti-VEGF monoclonal antibody (SEQ ID NO:284) as in Kim et al. (1993) Nature 362:841-844, $V_L$/CDR, and $V_L$/FR of selected anti-VEGF antibodies.

FIG. 1D shows amino acid sequences of full length $V_H$ (as compared with that of the humanized $V_H$ (SEQ ID NO:55) as in Baca et al. (1997) J Biol Chem 272:10678-10684, that of affinity-matured $V_H$ (SEQ ID NO:56) as in Chen et al. (1999) J. Mol. Biol. 293:865-881), and that of mouse anti-VEGF monoclonal antibody (SEQ ID NO:283) as in as in Kim et al. (1993) Nature 362:841-844, $V_L$/CDR), $V_H$/CDR, and $V_H$/FR of selected anti-VEGF antibodies.

For the purpose of direct comparison with anti-VEGF antibodies generated by others, the humanized $V_L$ (SEQ ID NO:1.) disclosed in the present invention is the same as the $V_L$ of antibody Y0317 described in Chen et al. (1999) J. Mol. Biol. 293:865-881; and $V_H$ (SEQ ID NO:55) disclosed in the present invention is the same as the $V_L$ of antibody Y0192 described in Chen et al. (1999), supra. The humanized and affinity matured $V_H$ (SEQ ID NO:56) disclosed in the present invention is the same as the $V_H$ of antibody Y0317 described in Chen et al. (1999), supra.

The selected optimized $V_H$ frameworks also cluster together with the humanized $V_H$ sequence, very close in phylogenetic distance to the human germline $V_H3$ family, while the murine $V_H$ framework is very distant from the optimized $V_H$ frameworks and human germlines. The phylogenetic analysis of the hit sequences against the entire human immunoglubin repertoire of $V_H$ suggests that they are indeed most closely related to human germline family III.

This supports the conclusion that the present inventive method in designing optimized frameworks with fully human or human-like sequences of the optimized antibodies, depending on the fine balance between human-like and compatibility with structure template or templates from ensemble structure or structure average.

Using our inventive methods described, we have discovered numerous heavy chain (e.g., SEQ ID NO:70, SEQ ID NO:67 and SEQ ID NO:75) humanized frameworks with higher binding affinity upon framework optimization than the parental or reference anti-VEGF antibody sequence (SEQ ID NO:55). This improvement comes mainly from a larger increase in the on-rate ($K_{on}$) and small decrease in the off-rate ($K_{off}$) by framework humanization alone. FIG. 2A shows the affinity data of 5 antibodies, parental antibody (hAB1) and the optimized frameworks (hAB2, hAB3, hAB5) of anti-VEGF antibody selected from designer libraries using BIAcore biosensor. The measurement was performed by measuring the change of SPR units (y-axis) vs time (x-axis) when a purified antibody binds its antigen (VEGF) immobilized on the CM5 biochip at 25° C. Two humanized frameworks hAB2 and hAB3 are ~4-folder higher in binding affinity (in single chain format) upon framework optimization than the parental/reference anti-VEGF antibody sequence reported in the literature (Presta L G, Chen H, O'Connor S J, Chisholm V, Meng Y G, Krummen L, Winkler M, Ferrara N (1997) Cancer Res. 57, 4593-4599), these two humanized antibodies should have ~2-fold higher binding affinity upon humanization than the corresponding murine antibody.

2. Selection of Candidate Antibodies 1) ccFv-a Heterodimeric Coiled-Coil Stabilized Antibody The present invention provides a new strategy to stabilize $V_H$ and $V_L$ heterodimer. A unique heterodimerization sequence pair was designed and used to create a Fab-like, functional artificial Fv fragment ccFv (US200030027247A1). This sequence pair specifically forms a coiled-coil structure and mediates the functional heterodimerization of GABA$_B$-R1 and GABA$_B$-R2 receptors. Each of the heterodimeric sequence pair was derived from the coiled coil domains of heterodimeric receptors GABAB R1 and R2, respectively. For the purpose of engineering a heterodimer of $V_H$ and $V_L$ of an antibody, the pair of sequences GR1 and GR2, are fused to the carboxy-terminus of $V_H$ and $V_L$ fragment, respectively. Thus, the functional pairing of $V_H$ and $V_L$, ccFv (coiled coil Fv), is mediated by specific heterodimerization of GR1 and GR2. Recombinant ccFv antibody fragments were expressed with a molecular weight 35 kDa.

$V_H$ and $V_L$ sequences of an anti-VEGF antibody was cloned into a vector that expressed two fusion proteins: $V_H$-GR1 and $V_L$-GR2-pIII fusions. The expressed $V_H$-GR1 and $V_L$-GR2-pIII fusions are secreted into periplasmic space, where they heterodimerize to form a stable ccFv antibody via the coiled-coil domain. To display ccFv antibodies on the surface of filamentous bacteriophage, the vector above was transformed into bacterial TG1 cells, which were further superinfected with KO7 helper phage.

2) Adaptor-Mediated Phage Display System

In the conventional phage display system, a protein of interest is fused to a phage capsid protein such as pIII in order to be displayed on the surface of phage. This fusion protein will be assembled into phage particles with the wild-type phage proteins provided by a helper phage such as KO7. A new phage display system named adaptor-directed display system as described in US20030104355A1 was used for displaying various antibody fragments on the surface of phage. In general, an antibody fragment such as single chain variable fragment is carried to the surface of the phage particle by a pair of adaptors that specifically form a heterodimer, one being fused with the displayed protein in an expression vector and the other being fused with a phage capsid protein in a helper vector. Particularly, each of the heterodimeric sequence pair, GR1 and GR2, was derived from the coiled coil domains of heterodimeric receptors GABA$_B$ R1 and R2, respectively. For the purpose of displaying an antibody fragment, the sequences GR1 was fused to the carboxy-terminus of an antibody fragment in an prokaryotic expression vector, whereas GR2 was fused to the amino terminus of the capsid protein III of bacterophage genome. The heterodimer is formed via a sequence pair specifically forms a coiled-coil structure and mediates the functional display of the antibody fragment upon rescue of the E. coli carrying the expression vector by the helper phage.

3) Preparation of Candidate Antibody Libraries

DNA of libraries of candidate antibodies was prepared based on PCR assembly using standard PCR procedure. The DNA was then restriction digested, purified, and ligated into an appropriate vector as described above. After ligation, DNA was transformed into TG1 cells. Phages were prepared from TG1 cells by a helper phage infection. The infected TG1 cells were grown in 2xYT/Amp/Kan at 30° C. overnight. The phagemid particles were precipitated by PEG/NaCl from culture supernatants, and resuspended in PBS.

4) Selection of Candidate Antibody Libraries

The phage libraries of the candidate antibodies were used for library selection against immobilized VEGF. Purified recombinant human VEGF165 was purchased from Calbiochem (cat. No: 80054-994). The glycosylated, disulfide-linked homodimer of a 165 amino acid residue variant of human VEGF has an apparent molecular weight of 42 kD (Burke et al. Biochem. Biophys. Res. Commun. 207:348 (1995); Neufeld et al. Prog. Growth Factor Res. 5: 89 (1994); Leung et al. Science 246:1306 (1989)). In general, after incubation period of binding, unbound phages were washed away and bound phages were eluted and amplified for the next round of panning. Similar procedures used in general for phage display have been illustrated in the past (Barbas et al., Phage display: a laboratory manual, Cold Spring Harbor Laboratory Press, 2001).

For example, an aliquot of 100 ul of 2 ug/ml purified human recombinant VEGF165 was first immobilized onto each well of a 96-well plate. After blocking with 5% milk in PBS, an aliquot of the library phages in 2% milk/PBS was added into the well and incubated. The phage containing solution was then discarded, and the wells were washed. Bound phages were finally eluted with 100 mM triethylamine, and were added to TG1 culture for infection. The phages prepared from infected TG1 cells were consequently used for the next round of panning. Positive clones were then confirmed by ELISA against VEGF antigen protein, in which the phages bound to the immobilized antigen were detected by incubation with HRP-conjugated anti-M13 antibody against phage coat protein pVIII. The substrate ABTS [2,2'Azino-bis(3-ethylbenzthiazoline-6-sulfonic acid)] was used for measurement of HRP activity. DNAs of those clones that were positively confirmed were sequenced. DNA sequences sampled were then translated to amino acid sequences. Selected sequences were combined to generate new variants. Selected variants were expressed to produce soluble antibody fragments for affinity evaluation.

3. Amplification of $V_k$ and $V_l$ from Human PBLs

The total RNA was extracted from human peripheral blood lymphocytes (PBLs), and was used as a template for first-strand cDNA synthesis by using olig-dT primer and reverse transcriptase in a standard procedure (first strain cDNA synthesis kit was purchased Roche Applied Science). The antibody light-chain variable genes were amplified from the single stranded cDNA by PCR. The PCR primers were designed and synthesized based on Kaba V-gene database (table 1). In order to amplify all 6 subfamily of $V_k$ genes, 6 degenerate primers targeted the 5' end of the 40 germline human $V_k$ genes and 3 degenerate primers targeted the 3' end of the 5 human Jk segment genes were used. For the PCR amplification of all 10 subfamily of Vl genes, 8 degenerate primers targeted the 5' end of the 31 germline human Vl genes and 2 degenerate primers target to the 3' end of the 4 Jl segment genes were used. The PCR amplified Vk and Vl genes were further cloned into a phagemid vector carried a humanized anti-VEGF antibody VH to generate phage display library.

TABLE 1

Primers for Vk and Vl amplification

| | | SEQ ID NO: |
|---|---|---|
| Vk | ATTAATGGATCCGMCATCCRGWTGACCCAGTCTCC | 421 |
| | ATTAATGGATCCGATRTTGTGATGACYCAGWCTCC | 422 |

TABLE 1-continued

Primers for Vk and Vl amplification

| | | SEQ ID NO: |
|---|---|---|
| | ATTAATGGATCCGAAATWGTGWTGACRCAGTCTCC | 423 |
| | ATTAATGGATCCGACATCGTGATGACCCAGTCTCC | 424 |
| | ATTAATGGATCCGAAACGACACTCACGCAGTCTCC | 425 |
| | ATTAATGGATCCGAAATTGTGCTGACTCAGTCTCC | 426 |
| Vl | ATTAATGGATCCCAGTCTGTGYTGACKCAGCC | 427 |
| | ATTAATGGATCCCAGTCTGCCCTGACTCAGCC | 428 |
| | ATTAATGGATCCTCCTATGAGCTGACWCAGCyAC | 429 |
| | ATTAATGGATCCTCTTCTGAGCTGACTCAGGAC | 430 |
| | ATTAATGGATCCCTGCCTGTGCTGACTCAGCC | 431 |
| | ATTAATGGATCCCAGCYTGTGCTGACTCAATC | 432 |
| | ATTAATGGATCCCAGSCTGTGCTGACTCAGCC | 433 |
| | ATTAATGGATCCAATTTTATGCTGACTCAGCCC | 434 |
| | ATTAATGGATCCCAGRCTGTGGTGACYCAGGAG | 435 |
| | ATTAATGGATCCCAGGCAGGGCTGACTCAGCC | 436 |
| Jk | TTAATTGCGGCCGCTTTGATYTCCASCTTGGTCCC | 437 |
| | TTAATTGCGGCCGCTTTGATATCCACTTTGGTCCC | 438 |
| | TTAATTGCGGCCGCTTTAATCTCCAGTCGTGTCCC | 439 |
| Jl | TTAATTGCGGCCGCTAGGACGGTSASCTTGG | 440 |
| | TTAATTGCGGCCGCGAGGACGGTCAGCTGGG | 441 |

4. Expression of Soluble Antibody Fragments

Soluble antibody fragments in the format of single chain variable fragment (scFv) can be generated in prokaryotic (*E. coli*) and eukaryotic (yeast) expression systems for the purpose of biophysical analysis. Construction of scFv includes a VH fragment and a VL fragment connected by a linker of $(G_4S)_3$ (SEQ ID NO: 442) as described in previous studies ((Barbas et al., Phage display: a laboratory manual, Cold Spring Harbor Laboratory Press, 2001). Expression vector used for prokaryotic expression is illustrated in FIG. 7. Competent bacterial cells, e.g., BL21, were prepared and transformed with a vector that carries the antibody fragment according to methods known in the art (Sambrook, Fritsch and Maniatis, Molecular Cloning: A Laboratory Manual, 2nd Ed., Cold Spring Harbor Press, Cold Spring Harbor, N.Y., (1989); Antibodies: A Laboratory Manual, Cold Spring Harbor Laboratory, 1988). The transformed cells are cultured under conditions suitable for protein expression. Such conditions are well known to artisans in the field and hence are not detailed herein. The expressed antibodies are harvested using conventional methods known in the art and used for further analysis. Expression in yeast was performed using Pichia expression kit purchased from Invitrogen and according to manufacturer's instruction. All antibodies were tagged with a HA-His6 tag (SEQ ID NO: 443) at C-terminus, and purified by NTA and Superdex 75 columns. In order to determine the purity and expression yield of antibody fragments, 20 ul of purified proteins are analyzed by SDS-PAGE gel, and visualized by staining with Coomassie Brilliant Blue R-250.

5. Affinity Analysis of Selected Antibody Fragments

BIAcore Biosensor Assay was used to determine antibody affinity. VEGF protein (purchased from Calbiochem) was coupled to a CM-5 biosensor ship by amine coupling. After immobilization, CM-5 chips with 200 to 1000 response unites of VEGF were kept at 4° C. before use. All experiments were performed at 25° C. or 35° C. Each sample in PBS buffer was injected over VEGF surface at a flow rate of 20 ul/min using Biacore 1000 (Biacore AB, Sweden), and bound antibodies were removed from chip by 10 ul of glycine-HCl, PH 1.5 at the end of each cycle. Each sensorgram was recorded and normalized to a PBS base line. To determine the antibody affinity including association and dissociation rate constants, the sensorgrams were analyzed by binding curve fitting to 1:1 Langmuir binding model using BIAevalvation version 3 software.

6. Evaluation of Stability of Antibody Fragments

In order to evaluate stability of the defined antibody fragments, soluble antibodies in PBS were incubated in 4° C., 37° C., and 42° C., respectively. The antibody concentration was 0.5 uM or 1 uM. After indicated times of incubation, antibody solutions were set at 25° C. for 1 hr, then directly injected over VEGF surface in Biacore 1000. The antibody binding RU was recorded, and used for stability analysis.

```

The invention claimed is:

1. A monoclonal antibody that specifically binds to a human VEGF and has a VL and VH pair selected from the group consisting of: SEQ ID NO:28 and 88; SEQ ID NO:28 and 90; SEQ ID NO:28 and 91; SEQ ID NO:28 and 106; SEQ ID NO:28 and 107; SEQ ID NO:28 and 108; and SEQ ID NO:28 and 109.

2. A monoclonal antibody that specifically binds to human VEGF and has a VL and VH pair selected from the group consisting of: SEQ ID NO:26 and 88; SEQ ID NOs:26 and 90; SEQ ID NOs:26 and 91; SEQ ID NOs:26 and 106; SEQ ID NOs:26 and 107; SEQ ID NOs:26 and 108; SEQ ID NOs:26 and 109; SEQ ID NOs:28 and 88; SEQ ID NOs:28 and 90; SEQ ID NOs:28 and 91; SEQ ID NOs:28 and 106; SEQ ID NOs:28 and 107; SEQ ID NOs:28 and 108; SEQ ID NOs:28 and 109; SEQ ID NOs:36 and 88; SEQ ID NOs:36 and 90; SEQ ID NOs:36 and 91; SEQ ID NOs:36 and 106; SEQ ID NOs:36 and 107; SEQ ID NOs:36 and 108; and SEQ ID NOs:36 and 109.

3. The monoclonal antibody of claim 2, wherein the antibody is a scFv.

4. The monoclonal antibody of claim 2, wherein the antibody is a Fab.

5. A monoclonal antibody that specifically binds to human VEGF and has a VL and VH pair selected from the group consisting of: SEQ ID NOs:26 and 106; SEQ ID NOs:28 and 106; and SEQ ID NOs:36 and 106.

6. A monoclonal antibody that specifically binds to human VEGF and has a VL and VH pair consisting of SEQ ID NOs:28 and 106.

7. A monoclonal antibody that specifically binds to human VEGF and has a VL domain consisting of SEQ ID NO:28 in combination with a VH domain selected from SEQ ID NO:106, SEQ ID NO:107, SEQ ID NO:108, SEQ ID NO:109, SEQ ID NO:88, SEQ ID NO:90, and SEQ ID NO:91.

8. The monoclonal antibody of claim 6, wherein the antibody is a scFv.

9. The monoclonal antibody of claim 6, wherein the antibody is a Fab.

* * * * *

                        SEQUENCE LISTING

<160> NUMBER OF SEQ ID NOS: 443

<210> SEQ ID NO 1
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Glu Leu Thr Gln Ser Pro Ser Ser Leu Ser Val Ser Ala Gly
1               5                   10                  15

Asp Arg Val Thr Ile Ser Cys Ser Ala Ser Gln Asp Ile Ser Asn Tyr
            20                  25                  30

Leu Asn Trp Tyr Gln Gln Lys Pro Gly Lys Ala Pro Arg Val Leu Ile
        35                  40                  45

Tyr Phe Thr Ser Ser Leu His Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Val Ala Val Tyr Tyr Cys Gln Gln Tyr Ser Thr Val Pro Trp
                85                  90                  95
Thr Phe Gly Gln Gly Thr Lys Val Glu Ile Lys
            100                 105

<210> SEQ ID NO 3
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Glu Leu Thr Gln Ser Pro Ser Ser Leu Ser Val Thr Pro Gly
1               5                   10                  15
Glu Arg Ala Thr Ile Thr Cys Ser Ala Ser Gln Asp Ile Ser Asn Tyr
                20                  25                  30
Leu Asn Trp Tyr Gln Gln Lys Pro Gly Lys Ala Pro Gln Val Leu Ile
            35                  40                  45
Tyr Phe Thr Ser Ser Leu His Ser Gly Val Pro Asp Arg Phe Ser Gly
        50                  55                  60
Ser Gly Ser Gly Thr Asp Phe Thr Leu Thr Ile Ser Ser Leu Gln Ala
65                  70                  75                  80
Glu Asp Phe Ala Ile Tyr Tyr Cys Gln Gln Tyr Ser Thr Val Pro Trp
                85                  90                  95
Thr Phe Gly Gln Gly Thr Lys Val Glu Ile Lys
            100                 105

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Glu Leu Thr Gln Ser Pro Ser Ser Leu Ser Val Thr Pro Gly
1               5                   10                  15
Glu Arg Ala Thr Ile Thr Cys Ser Ala Ser Gln Asp Ile Ser Asn Tyr
                20                  25                  30
Leu Asn Trp Tyr Gln Gln Lys Pro Gly Gln Ala Pro Gln Leu Leu Ile
            35                  40                  45
Tyr Phe Thr Ser Ser Leu His Ser Gly Val Pro Asp Arg Phe Ser Gly
        50                  55                  60
Ser Gly Ser Gly Thr Asp Phe Thr Leu Thr Ile Ser Arg Leu Gln Ala
65                  70                  75                  80
Glu Asp Val Ala Val Tyr Tyr Cys Gln Gln Tyr Ser Thr Val Pro Trp
                85                  90                  95
Thr Phe Gly Gln Gly Thr Lys Val Glu Ile Lys
            100                 105

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 5

```
Asp Ile Glu Met Thr Gln Ser Pro Ser Ser Leu Ser Ala Ser Leu Gly
1               5                   10                  15

Glu Arg Val Thr Ile Ser Cys Ser Ala Ser Gln Asp Ile Ser Asn Tyr
            20                  25                  30

Leu Asn Trp Tyr Gln Gln Lys Pro Gly Lys Ala Pro His Leu Leu Ile
        35                  40                  45

Tyr Phe Thr Ser Ser Leu His Ser Gly Val Pro Tyr Arg Phe Ser Gly
    50                  55                  60

Ser Gly Ser Gly Thr Asp Phe Thr Leu Thr Ile Ser Ser Leu Gln Ala
65                  70                  75                  80

Glu Asp Phe Ala Ala Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Asp Ile Val Met Thr Gln Ser Pro Ser Ser Leu Ser Ala Thr Pro Gly
1               5                   10                  15

Glu Arg Val Thr Ile Thr Cys Ser Ala Ser Gln Asp Ile Ser Asn Tyr
            20                  25                  30

Leu Asn Trp Tyr Gln Gln Lys Pro Gly Gln Ala Pro Arg Val Leu Ile
        35                  40                  45

Tyr Phe Thr Ser Ser Leu His Ser Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Val Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Asp Ile Val Met Thr Gln Ser Pro Ser Ser Leu Ser Ala Thr Pro Gly
1               5                   10                  15

Glu Arg Val Thr Ile Ser Cys Ser Ala Ser Gln Asp Ile Ser Asn Tyr
            20                  25                  30

Leu Asn Trp Tyr Gln Gln Lys Pro Gly Lys Ala Pro Ser Leu Leu Val
        35                  40                  45

Tyr Phe Thr Ser Ser Leu His Ser Gly Val Pro Ser Arg Phe Ser Gly
    50                  55                  60
```

```
Ser Gly Ser Gly Thr Asp Phe Thr Leu Thr Ile Ser Arg Leu Gln Ala
 65                  70                  75                  80

Glu Asp Phe Ala Ile Tyr Tyr Cys Gln Gln Tyr Ser Thr Val Pro Trp
                 85                  90                  95

Thr Phe Gly Gln Gly Thr Lys Val Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Val Leu Thr Gln Ser Pro Ser Ser Leu Ser Ala Thr Pro Gly
1               5                   10                  15

Asp Arg Val Thr Ile Ser Cys Ser Ala Ser Gln Asp Ile Ser Asn Tyr
                20                  25                  30

Leu Asn Trp Tyr Gln Gln Lys Pro Gly Gln Ala Pro Gln Leu Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Ala
 65                  70                  75                  80

Glu Asp Val Ala Thr Tyr Tyr Cys Gln Gln Tyr Ser Thr Val Pro Trp
                 85                  90                  95

Thr Phe Gly Gln Gly Thr Lys Val Glu Ile Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Val Leu Thr Gln Ser Pro Ser Ser Leu Ser Ala Thr Pro Gly
1               5                   10                  15

Glu Arg Ala Thr Ile Thr Cys Ser Ala Ser Gln Asp Ile Ser Asn Tyr
                20                  25                  30

Leu Asn Trp Tyr Gln Gln Lys Pro Gly Lys Ala Pro His Leu Leu Ile
            35                  40                  45

Tyr Phe Thr Ser Ser Leu His Ser Gly Val Pro Tyr Arg Phe Ser Gly
        50                  55                  60

Ser Gly Ser Gly Thr Asp Phe Thr Leu Thr Ile Ser Ser Leu Gln Ala
 65                  70                  75                  80

Glu Asp Phe Ala Ile Tyr Tyr Cys Gln Gln Tyr Ser Thr Val Pro Trp
                 85                  90                  95

Thr Phe Gly Gln Gly Thr Lys Val Glu Ile Lys
            100                 105

<210> SEQ ID NO 10
<211> LENGTH: 107
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 10

```
Asp Ile Glu Met Thr Gln Ser Pro Ser Ser Leu Ser Ala Thr Pro Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Arg Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Arg Leu Gln Pro
65                  70                  75                  80

Glu Asp Val Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Asp Ile Glu Met Thr Gln Ser Pro Ser Ser Leu Ser Val Thr Pro Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro His Leu Leu Ile
        35                  40                  45

Tyr Phe Thr Ser Ser Leu His Ser Gly Val Pro Asp Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Asp Ile Glu Leu Thr Gln Ser Pro Ser Ser Leu Ser Ala Thr Leu Gly
1               5                   10                  15

Glu Arg Val Thr Ile Ser Cys Ser Ala Ser Gln Asp Ile Ser Asn Tyr
            20                  25                  30

Leu Asn Trp Tyr Gln Gln Lys Pro Gly Lys Ala Pro His Val Leu Ile
        35                  40                  45
```

```
Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Arg Leu Gln Ala
 65                  70                  75                  80

Glu Asp Val Ala Thr Tyr Tyr Cys Gln Gln Tyr Ser Thr Val Pro Trp
                85                  90                  95

Thr Phe Gly Gln Gly Thr Lys Val Glu Ile Lys
            100                 105

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Glu Met Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Gln Ala Pro Arg Val Leu Ile
            35                  40                  45

Tyr Phe Thr Ser Ser Leu His Ser Gly Val Pro Asp Arg Phe Ser Gly
        50                  55                  60

Ser Gly Ser Gly Thr Asp Phe Thr Leu Thr Ile Ser Ser Leu Gln Ala
 65                  70                  75                  80

Glu Asp Phe Ala Val Tyr Tyr Cys Gln Gln Tyr Ser Thr Val Pro Trp
                85                  90                  95

Thr Phe Gly Gln Gly Thr Lys Val Glu Ile Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Leu Thr Gln Ser Pro Ser Ser Leu Ser Ala Ser Ala Gly
 1               5                  10                  15

Asp Arg Val Thr Ile Ser Cys Ser Ala Ser Gln Asp Ile Ser Asn Tyr
                20                  25                  30

Leu Asn Trp Tyr Gln Gln Lys Pro Gly Lys Ala Pro Gln Leu Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

```
<210> SEQ ID NO 15
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Val Met Thr Gln Ser Pro Ser Ser Leu Ser Ala Ser Pro Gly
1               5                   10                  15

Glu Arg Ala Thr Ile Ser Cys Asn Ala Ser Gln Ser Ile Gly Thr Tyr
            20                  25                  30

Leu Ala Trp Tyr Gln Gln Lys Pro Gly Gln Ala Pro Gln Val Leu Ile
        35                  40                  45

Tyr Gly Ala Ser Asn Leu Ala Ser Gly Val Pro Gly Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Asn Ser Lys Pro Trp
                85                  90                  95

Thr Phe Gly Gly Gly Thr Lys Val Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Val Met Thr Gln Ser Pro Ser Ser Leu Ser Ala Ser Pro Gly
1               5                   10                  15

Glu Arg Ala Thr Ile Ser Cys Arg Ala Ser Gln Ser Ile Ser Ser Tyr
            20                  25                  30

Leu Ala Trp Tyr Gln Gln Lys Pro Gly Gln Ala Pro Gln Val Leu Ile
        35                  40                  45

Tyr Gly Ala Ser Asn Leu Ala Ser Gly Val Pro Asn Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Ser Pro Trp
                85                  90                  95

Thr Phe Gly Gly Gly Thr Lys Val Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Val Met Thr Gln Ser Pro Ser Ser Leu Ser Ala Ser Pro Gly
1               5                   10                  15

Glu Arg Ala Thr Ile Thr Cys His Ala Ser Gln Ser Ile Gly Thr Tyr
            20                  25                  30
```

-continued

Leu Ala Trp Tyr Gln Gln Lys Pro Gly Gln Ala Pro His Val Leu Ile
        35                  40                  45

Tyr Gly Ala Ser Asn Leu Ala Ser Gly Val Pro Asn Arg Phe Ser Gly
    50                  55                  60

Ser Arg Ser Gly Thr Asp Phe Thr Leu Thr Ile Ser Ser Leu Gln Pro
65                  70                  75                  80

Asp Asp Phe Ala Val Tyr Tyr Cys Gln Gln Tyr Asn Ser Thr Pro Trp
                85                  90                  95

Thr Phe Gly Gly Gly Thr Lys Val Glu Ile Lys
            100                 105

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Val Met Thr Gln Ser Pro Ser Ser Leu Ser Ala Ser Pro Gly
1               5                   10                  15

Glu Arg Ala Thr Ile Thr Cys His Ala Ser Gln Ser Ile Ser Thr Tyr
            20                  25                  30

Leu Ala Trp Tyr Gln Gln Lys Pro Gly Gln Ala Pro Gln Val Leu Ile
        35                  40                  45

Tyr Asp Ala Ser Asn Leu Ala Ser Gly Val Pro Gly Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Asn Ser Ala Pro Trp
                85                  90                  95

Thr Phe Gly Gly Gly Thr Lys Val Glu Ile Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Val Met Thr Gln Ser Pro Ser Ser Leu Ser Ala Ser Pro Gly
1               5                   10                  15

Glu Arg Ala Thr Ile Thr Cys Lys Ala Ser Gln Ser Ile Gly Thr Tyr
            20                  25                  30

Leu Ala Trp Tyr Gln Gln Lys Pro Gly Gln Ala Pro Arg Val Leu Ile
        35                  40                  45

Tyr Asp Ala Ser Asn Leu Ala Ser Gly Val Pro Asn Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Thr Pro Tyr
                85                  90                  95

Thr Phe Gly Gly Gly Thr Lys Val Glu Ile Lys
            100                 105

```
<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Lys Met Thr Gln Ser Pro Ser Ser Leu Ser Ala Ser Pro Gly
1               5                   10                  15

Glu Arg Ala Thr Ile Ser Cys Lys Ala Ser Gln Ser Ile Gly Ser Tyr
            20                  25                  30

Leu Ala Trp Tyr Gln Gln Lys Pro Gly Gln Ala Pro Ser Val Leu Ile
        35                  40                  45

Tyr Ala Ala Ser Asn Leu Ala Ser Gly Val Pro Asn Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Tyr Ser Gly Pro Trp
                85                  90                  95

Thr Phe Gly Gly Gly Thr Lys Val Glu Ile Lys
            100                 105

<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Lys Met Thr Gln Ser Pro Ser Ser Leu Ser Ala Ser Pro Gly
1               5                   10                  15

Glu Arg Ala Thr Ile Thr Cys Asn Ala Ser Gln Ser Ile Ser Thr Tyr
            20                  25                  30

Leu Ala Trp Tyr Gln Gln Lys Pro Gly Gln Ala Pro Lys Val Leu Ile
        35                  40                  45

Tyr Gly Ala Ser Asn Leu Ala Ser Gly Val Pro Asn Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Asn Ser Ala Pro Trp
                85                  90                  95

Thr Phe Gly Gly Gly Thr Lys Val Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Val Met Thr Gln Ser Pro Ser Thr Leu Ser Ala Ser Pro Gly
1               5                   10                  15

Glu Arg Ala Thr Ile Ser Cys Lys Ala Ser Gln Ser Ile Gly Ser Tyr
            20                  25                  30
```

```
Leu Ala Trp Tyr Gln Gln Lys Pro Gly Gln Ala Pro Arg Val Leu Ile
            35                  40                  45

Tyr Ser Ala Ser Asn Leu Ala Ser Gly Val Pro Ser Arg Phe Ser Gly
         50                  55                  60

Ser Arg Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Asn Ser Thr Pro Trp
                85                  90                  95

Thr Phe Gly Gly Gly Thr Lys Val Glu Ile Lys
            100                 105
```

<210> SEQ ID NO 23
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Asp Ile Val Met Thr Gln Ser Pro Ser Thr Leu Ser Ala Ser Pro Gly
1               5                   10                  15

Glu Arg Ala Thr Ile Ser Cys Lys Ala Ser Gln Ser Ile Gly Thr Tyr
            20                  25                  30

Leu Ala Trp Tyr Gln Gln Lys Pro Gly Gln Ala Pro Arg Val Leu Ile
            35                  40                  45

Tyr Asp Ala Ser Asn Leu Ala Ser Gly Val Pro Asn Arg Phe Ser Gly
         50                  55                  60

Ser Arg Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Tyr Ser Thr Pro Trp
                85                  90                  95

Thr Phe Gly Gly Gly Thr Lys Val Ala Ile Lys
            100                 105
```

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Asp Ile Val Met Thr Gln Ser Pro Ser Thr Leu Ser Ala Ser Pro Gly
1               5                   10                  15

Glu Arg Ala Thr Ile Ser Cys Lys Ala Ser Gln Ser Ile Gly Thr Tyr
            20                  25                  30

Leu Ala Trp Tyr Gln Gln Lys Pro Gly Gln Ala Pro Arg Val Leu Ile
            35                  40                  45

Tyr Ser Ala Ser Asn Leu Ala Ser Gly Val Pro Asn Arg Phe Ser Gly
         50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Thr Pro Trp
                85                  90                  95

Thr Phe Gly Gly Gly Thr Lys Val Glu Ile Lys
            100                 105
```

```
<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Val Met Thr Gln Ser Pro Ser Thr Leu Ser Ala Ser Pro Gly
1               5                   10                  15

Glu Arg Ala Thr Ile Thr Cys His Ala Ser Gln Ser Ile Ser Ser Tyr
            20                  25                  30

Leu Ala Trp Tyr Gln Gln Lys Pro Gly Gln Ala Pro Asn Val Leu Ile
        35                  40                  45

Tyr Gly Ala Ser Asn Leu Ala Ser Gly Val Pro Asp Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Asn Ser Thr Pro Trp
                85                  90                  95

Thr Phe Gly Gly Gly Thr Lys Val Glu Ile Lys
            100                 105

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Val Met Thr Gln Ser Pro Ser Thr Leu Ser Ala Ser Pro Gly
1               5                   10                  15

Glu Arg Ala Thr Ile Thr Cys His Ala Ser Gln Ser Ile Ser Thr Tyr
            20                  25                  30

Leu Ala Trp Tyr Gln Gln Lys Pro Gly Gln Ala Pro Arg Val Leu Ile
        35                  40                  45

Tyr Gly Ala Ser Asn Leu Ala Ser Gly Val Pro Asn Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Asn Ser Ala Pro Trp
                85                  90                  95

Thr Phe Gly Gly Gly Thr Lys Val Glu Ile Lys
            100                 105

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Val Met Thr Gln Ser Pro Ser Thr Leu Ser Ala Ser Pro Gly
1               5                   10                  15

Glu Arg Ala Thr Ile Thr Cys Lys Ala Ser Gln Ser Ile Ser Thr Tyr
            20                  25                  30
```

```
Leu Ala Trp Tyr Gln Gln Lys Pro Gly Gln Ala Pro Gln Val Leu Ile
            35                  40                  45

Tyr Asp Ala Ser Asn Leu Ala Ser Gly Val Pro Asn Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Asn Ser Ala Pro Trp
                85                  90                  95

Thr Phe Gly Gly Gly Thr Lys Val Glu Ile Lys
            100                 105

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Val Met Thr Gln Ser Pro Ser Thr Leu Ser Ala Ser Pro Gly
1               5                   10                  15

Glu Arg Ala Thr Ile Thr Cys Asn Ala Ser Gln Ser Ile Gly Ser Tyr
            20                  25                  30

Leu Ala Trp Tyr Gln Gln Lys Pro Gly Gln Ala Pro Lys Val Leu Ile
            35                  40                  45

Tyr Gly Ala Ser Asn Leu Ala Ser Gly Val Pro Ser Arg Phe Ser Gly
 50                  55                  60

Ser Arg Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Asn Ser Thr Pro Trp
                85                  90                  95

Thr Phe Gly Gly Gly Thr Lys Leu Glu Ile Lys
            100                 105

<210> SEQ ID NO 29
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Val Met Thr Gln Ser Pro Ser Thr Leu Ser Ala Ser Pro Gly
1               5                   10                  15

Glu Arg Ala Thr Ile Thr Cys Asn Ala Ser Gln Ser Ile Gly Thr Tyr
            20                  25                  30

Leu Ala Trp Tyr Gln Gln Lys Pro Gly Gln Ala Pro Asn Leu Leu Ile
            35                  40                  45

Tyr Asp Ala Ser Asn Leu Ala Ser Gly Val Pro Gly Arg Phe Ser Gly
 50                  55                  60

Ser Arg Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Thr Pro Trp
                85                  90                  95

Thr Phe Gly Gly Gly Thr Lys Val Glu Ile Lys
            100                 105
```

```
<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Val Met Thr Gln Ser Pro Ser Thr Leu Ser Ala Ser Pro Gly
1               5                   10                  15

Glu Arg Ala Thr Ile Thr Cys Asn Ala Ser Gln Ser Ile Gly Thr Tyr
            20                  25                  30

Leu Ala Trp Tyr Gln Gln Lys Pro Gly Gln Ala Pro Asn Val Leu Ile
        35                  40                  45

Tyr Asp Ala Ser Asn Leu Ala Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Tyr Ser Ala Pro Trp
                85                  90                  95

Thr Phe Gly Gly Gly Thr Lys Val Glu Ile Lys
            100                 105

<210> SEQ ID NO 31
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Val Met Thr Gln Ser Pro Ser Thr Leu Ser Ala Ser Pro Gly
1               5                   10                  15

Glu Arg Ala Thr Ile Thr Cys Asn Ala Ser Gln Ser Ile Ser Thr Tyr
            20                  25                  30

Leu Ala Trp Tyr Gln Gln Lys Pro Gly Gln Ala Pro Arg Val Leu Ile
        35                  40                  45

Tyr Gly Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Asn Ser Thr Pro Trp
                85                  90                  95

Thr Phe Gly Gly Gly Thr Lys Val Glu Ile Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Val Met Thr Gln Ser Pro Ser Thr Leu Ser Ala Ser Pro Gly
1               5                   10                  15

Glu Arg Ala Thr Ile Thr Cys Gln Ala Ser Gln Ser Ile Ser Thr Tyr
            20                  25                  30
```

```
Leu Ala Trp Tyr Gln Gln Lys Pro Gly Gln Ala Pro Lys Val Leu Ile
            35                  40                  45

Tyr Asp Ala Ser Asn Leu Ala Ser Gly Val Pro Gly Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Tyr Asn Ser Thr Pro Trp
                 85                  90                  95

Thr Phe Gly Gly Gly Thr Lys Val Glu Ile Lys
                100                 105
```

<210> SEQ ID NO 33
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Asp Ile Val Met Thr Gln Ser Pro Ser Thr Leu Ser Ala Ser Pro Gly
 1               5                  10                  15

Glu Arg Ala Thr Ile Thr Cys Arg Ala Ser Gln Ser Ile Ser Thr Tyr
                 20                  25                  30

Leu Ala Trp Tyr Gln Gln Lys Pro Gly Gln Ala Pro Arg Leu Leu Ile
            35                  40                  45

Tyr Ser Ala Ser Asn Leu Ala Ser Gly Val Pro Asn Arg Phe Ser Gly
         50                  55                  60

Ser Arg Ser Gly Thr Asp Phe Thr Leu Thr Ile Ser Ser Leu Gln Pro
 65                  70                  75                  80

Glu Asp Phe Ala Val Tyr Tyr Cys Gln Gln Tyr Tyr Ser Thr Pro Trp
                 85                  90                  95

Thr Phe Gly Gly Gly Thr Lys Val Glu Ile Lys
                100                 105
```

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Asp Ile Val Met Thr Gln Ser Pro Ser Thr Leu Ser Ala Ser Pro Gly
 1               5                  10                  15

Glu Arg Ala Thr Ile Thr Cys Ser Ala Ser Gln Ser Ile Gly Thr Tyr
                 20                  25                  30

Leu Ala Trp Tyr Gln Gln Lys Pro Gly Gln Ala Pro Ser Val Leu Ile
            35                  40                  45

Tyr Gly Ala Ser Asn Leu Ala Ser Gly Val Pro Gly Arg Phe Ser Gly
         50                  55                  60

Ser Gly Ser Gly Thr Asp Phe Thr Leu Thr Ile Ser Ser Leu Gln Ala
 65                  70                  75                  80

Glu Asp Phe Ala Val Tyr Tyr Cys Gln Gln Tyr Asn Ser Ala Pro Trp
                 85                  90                  95

Thr Phe Gly Gly Gly Thr Lys Val Glu Ile Lys
                100                 105
```

<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Val Met Thr Gln Ser Pro Ser Thr Leu Ser Ala Ser Pro Gly
1               5                   10                  15

Glu Arg Ala Thr Ile Thr Cys Ser Ala Ser Gln Ser Ile Ser Thr Tyr
            20                  25                  30

Leu Ala Trp Tyr Gln Gln Lys Pro Gly Gln Ala Pro Gln Val Leu Ile
        35                  40                  45

Tyr Ala Ala Ser Asn Leu Ala Ser Gly Val Pro Asn Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Tyr Ser Thr Pro Trp
                85                  90                  95

Thr Phe Gly Gly Gly Thr Lys Val Glu Ile Lys
            100                 105

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ala Ile Arg Met Thr Gln Ser Pro Ser Ser Val Ser Ala Ser Val Gly
1               5                   10                  15

Asp Thr Val Thr Ile Ala Cys Arg Ala Ser Gln Ala Ile Arg Asn Asp
            20                  25                  30

Leu Thr Trp Tyr Gln Gln Lys Pro Gly Thr Ala Pro Lys Leu Leu Ile
        35                  40                  45

Tyr Gly Ala Thr Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Thr Thr Pro Trp
                85                  90                  95

Thr Phe Gly Gln Gly Thr Lys Val Asp Ile Lys
            100                 105

<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Val Met Thr Gln Thr Pro Ser Ser Leu Ser Ala Ser Val Gly
1               5                   10                  15

Asp Thr Val Thr Ile Thr Cys Arg Ala Ser Arg Asp Ile Arg Asn Asp
            20                  25                  30

Leu Ala Trp Tyr Gln Gln Lys Pro Gly Lys Ala Pro Glu Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Asp Ile Lys
            100                 105

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Ile Val Leu Thr Gln Ser Pro Ser Ser Leu Ser Ala Ser Ile Gly
1               5                   10                  15

Asp Arg Val Ala Ile Thr Cys Arg Ala Ser Arg Asp Ile Thr Thr Asp
            20                  25                  30

Leu Ala Trp Tyr Gln Gln Ile Pro Gly Lys Ala Pro Lys Leu Leu Ile
            35                  40                  45

Tyr Ala Ala Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Ala Tyr Tyr Cys Gln Gln Ser Tyr Ser Thr Pro Trp
                85                  90                  95

Thr Phe Gly Gln Gly Thr Lys Val Asp Ile Lys
            100                 105

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Ile Val Leu Thr Gln Ser Pro Ser Ser Leu Ser Ala Ser Val Gly
1               5                   10                  15

Asp Arg Ile Thr Ile Thr Cys Arg Ala Ser Arg Asp Ile Arg Asp Asp
            20                  25                  30

Leu Ala Trp Tyr Gln Gln Lys Pro Gly Lys Ala Pro Lys Val Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys
            100                 105

```
<210> SEQ ID NO 40
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Ile Asn Trp Tyr Gln Gln Lys Pro Gly Lys Ala Pro Lys Leu Leu Ile
        35                  40                  45

Tyr Ala Ala Ser Ser Leu Gln Ser Gly Val Thr Ser Arg Phe Ser Gly
    50                  55                  60

Ser Gly Ser Gly Thr Asp Phe Thr Leu Thr Ile Arg Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Ile Val Met Thr Gln Ser Pro Ser Ser Leu Ser Ala Ser Val Gly
1               5                   10                  15

Asp Arg Val Thr Ile Thr Cys Arg Ala Ser Gln Ala Ile Tyr Asp Tyr
            20                  25                  30

Leu Ala Trp Tyr Gln Gln Lys Pro Gly Lys Ala Pro Asn Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Asp Ile Lys
            100                 105

<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Ile Val Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Lys Asp
            20                  25                  30
```

```
Leu Ala Trp Tyr Gln Gln Lys Pro Gly Ile Ala Pro Lys Val Leu Ile
            35                  40                  45

Tyr Ala Ala Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Pro Pro Trp
                 85                  90                  95

Thr Phe Gly Gln Gly Thr Lys Leu Glu Ile Lys
                100                 105

<210> SEQ ID NO 43
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Ile Val Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Thr Tyr
                 20                  25                  30

Ile Asn Trp Tyr Gln Gln Lys Pro Gly Lys Ala Pro Lys Leu Leu Ile
            35                  40                  45

Tyr Ala Ala Ser Ser Leu Gln Ser Gly Val Thr Ser Arg Phe Ser Gly
         50                  55                  60

Ser Gly Ser Gly Thr Asp Phe Thr Leu Thr Ile Arg Ser Leu Gln Pro
 65                  70                  75                  80

Glu Asp Phe Ala Thr Tyr Tyr Cys Gln Gln Ser Tyr Ser Thr Pro Trp
                 85                  90                  95

Thr Phe Gly Gln Gly Thr Lys Val Glu Ile Lys
                100                 105

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Met Thr Gln Ser Pro Ser Ser Leu Ser Ala Ser Val Gly
  1               5                  10                  15

Asp Thr Val Thr Ile Ala Cys Arg Ala Ser Arg Asp Ile Arg Asn Asp
                 20                  25                  30

Leu Ala Trp Tyr Gln Gln Lys Pro Gly Lys Ala Pro Lys Leu Leu Ile
            35                  40                  45

Tyr Ala Ala Ser Arg Leu Gln Ser Gly Val Pro Ser Arg Phe Ser Gly
         50                  55                  60

Thr Gly Ser Gly Thr Asp Phe Ala Leu Thr Ile Ser Ser Leu Gln Pro
 65                  70                  75                  80

Glu Asp Ser Ala Ser Tyr Tyr Cys Gln Gln Ser Tyr Thr Ile Pro Trp
                 85                  90                  95

Thr Phe Gly Gln Gly Thr Lys Leu Glu Ile Lys
                100                 105
```

```
<210> SEQ ID NO 45
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Thr Thr Leu Thr Gln Ser Pro Ser Ser Leu Ser Ala Ser Val Gly
1               5                   10                  15

Asp Thr Ile Thr Ile Ser Cys Arg Ser Ser Gln Pro Ile Thr Asn Asp
            20                  25                  30

Leu Ala Trp Tyr Gln Gln Lys Pro Gly Lys Ala Pro Asn Leu Leu Ile
        35                  40                  45

Tyr Ala Ala Ser Arg Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 46
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Leu Pro Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Leu Ser
    50                  55                  60

Gly Ser Lys Ser Gly Thr Ser Ala Ser Leu Ala Ile Ser Gly Leu Leu
65                  70                  75                  80

Ser Glu Asp Glu Ala Asp Tyr Tyr Cys Ala Ser Trp Asp Asp Ser Leu
                85                  90                  95

Thr Gly Tyr Val Phe Gly Thr Gly Thr Gln Leu Thr Val Leu
            100                 105                 110

<210> SEQ ID NO 47
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Leu Pro Val Leu Thr Gln Pro Pro Ser Ala Ser Gly Thr Pro Gly Gln
1               5                   10                  15

Arg Val Thr Ile Ser Cys Ser Gly Ser Tyr Ser Asn Ile Gly Ser Asn
            20                  25                  30
```

Ala Val Asn Trp Tyr Gln Gln Leu Pro Gly Ala Ala Pro Lys Val Leu
         35                  40                  45

Met Tyr Thr Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Asn Gly Tyr Val Phe Gly Thr Gly Thr Lys Leu Thr Val Leu
                100                 105                 110

<210> SEQ ID NO 48
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asn Phe Met Leu Thr Gln Pro Pro Ser Thr Ser Gly Thr Pro Gly Gln
 1               5                  10                  15

Arg Val Thr Ile Ser Cys Ser Gly Ser Thr Ser Asn Ile Gly Ser Asn
                 20                  25                  30

Ser Val Thr Trp Tyr Gln Gln Leu Pro Gly Thr Ala Pro Lys Val Leu
         35                  40                  45

Met Tyr Thr Asn Asn Gln Arg Pro Ser Gly Val Pro Glu Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Tyr Val Phe Gly Thr Gly Thr Lys Leu Thr Val Leu
                100                 105                 110

<210> SEQ ID NO 49
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Ala Val Leu Thr Gln Pro Pro Ser Ala Ser Gly Thr Pro Gly Gln
 1               5                  10                  15

Ser Val Thr Ile Ser Cys Ser Gly Thr Thr Ser Asn Ile Gly Ser Asn
                 20                  25                  30

Ser Val Asn Trp Tyr Gln Gln Leu Pro Gly Thr Ala Pro Lys Val Leu
         35                  40                  45

Ile Tyr Gly Asn Asp Gln Arg Pro Ser Gly Val Pro Asp Arg Phe Ser
 50                  55                  60

Gly Ser Arg Ser Ala Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Ser Gly Tyr Val Phe Gly Ala Gly Thr Gln Leu Thr Val Leu
                100                 105                 110

```
<210> SEQ ID NO 50
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Pro Val Leu Thr Gln Pro Pro Ser Ala Ser Ala Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Val Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Leu Thr Val Leu
            100                 105                 110

<210> SEQ ID NO 51
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Pro Val Leu Thr Gln Pro Pro Ser Ala Ser Gly Thr Pro Gly Gln
1               5                   10                  15

Arg Val Thr Ile Ser Cys Ser Gly Ser Ser Asn Val Gly Arg Asn
            20                  25                  30

Thr Val Asn Trp Tyr Gln Gln Phe Pro Gly Thr Ala Pro Lys Phe Leu
        35                  40                  45

Met Tyr Gly Asn Asp Glu Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Tyr Val Phe Gly Thr Gly Thr Gln Leu Thr Val Leu
            100                 105                 110

<210> SEQ ID NO 52
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Pro Val Leu Thr Gln Pro Pro Ser Thr Ser Gly Thr Pro Gly Gln
1               5                   10                  15

Arg Val Thr Ile Ser Cys Ser Gly Ser Ser Ser Asn Ile Gly Ser Asn
            20                  25                  30
```

```
Ser Val Thr Trp Tyr Gln Gln Leu Pro Gly Thr Ala Pro Lys Val Leu
            35                  40                  45

Met Tyr Thr Asn Asn Gln Arg Pro Ser Gly Val Pro Glu Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Ser Gly Tyr Val Phe Gly Thr Gly Thr Lys Leu Thr Val Leu
                100                 105                 110

<210> SEQ ID NO 53
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Ser Val Leu Thr Gln Pro Pro Ser Ala Ser Gly Thr Pro Gly Gln
 1               5                  10                  15

Arg Val Thr Ile Ser Cys Ser Gly Ser Asn Ser Asn Ile Gly Ser Asn
             20                  25                  30

Asn Val Tyr Trp Tyr Gln Gln Phe Pro Gly Thr Ala Pro Lys Val Leu
            35                  40                  45

Ile Tyr Gly Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Gly Ala Trp Asp Asp Ser Leu
                 85                  90                  95

Asn Gly Tyr Val Phe Gly Thr Gly Thr Lys Leu Thr Val Leu
                100                 105                 110

<210> SEQ ID NO 54
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Ser Ala Leu Thr Gln Pro Pro Ser Val Ser Gly Ala Pro Gly Gln
 1               5                  10                  15

Arg Val Thr Ile Ser Cys Thr Gly Arg Ser Ser Asn Ile Gly Ala Gly
             20                  25                  30

His Asp Val His Trp Tyr Gln Gln Leu Pro Gly Thr Ala Pro Lys Leu
            35                  40                  45

Leu Ile Tyr Ala Asn Asp Gln Arg Pro Ser Gly Val Pro Asp Arg Phe
 50                  55                  60

Ser Asp Ser Lys Ser Gly Thr Ser Ala Ser Leu Gly Ile Ser Gly Leu
 65                  70                  75                  80

Arg Ser Glu Asp Glu Ala Asp Tyr Phe Cys Ala Thr Trp Asp Asp Ser
                 85                  90                  95

Leu His Gly Tyr Val Phe Gly Thr Gly Thr Lys Val Thr Val Leu
                100                 105                 110
```

<210> SEQ ID NO 55
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 56
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120

<210> SEQ ID NO 57
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Gly Gln Leu Val Gln Ser Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 58
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Val Gln Leu Val Glu Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Ile Ser Leu Asp Asn Ser Lys Ser Gln Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Ala Gln Gly Thr Leu Val Thr Val Ser Ser
        115                 120

<210> SEQ ID NO 59
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Gln Ser Gly Gly Gly Leu Val Gln Pro Gly Gly
1               5                   10                  15

Thr Leu Arg Leu Ser Cys Ala Ala Ser Gly Tyr Thr Phe Thr Asn Tyr
            20                  25                  30

```
Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Asn Thr Ala Tyr
 65                 70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
            115                 120
```

<210> SEQ ID NO 60
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Glu Val Gln Leu Val Gln Ser Gly Gly Gly Val Val Gln Pro Gly Gly
 1               5                  10                  15

Ser Leu Arg Leu Arg Cys Ala Ala Ser Gly Tyr Thr Phe Thr Asn Tyr
                20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Phe Ser Leu Asp Thr Ser Lys Ser Thr Ala Tyr
 65                 70                  75                  80

Leu Gln Leu Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
            115                 120
```

<210> SEQ ID NO 61
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

```
Glu Val Gln Leu Val Gln Ser Gly Gly Gly Val Val Gln Pro Gly Gly
 1               5                  10                  15

Ser Leu Arg Leu Ser Cys Ala Ala Ser Gly Phe Asp Phe Thr Asn Tyr
                20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Phe Ser Leu Asp Thr Ser Lys Ser Thr Ala Tyr
 65                 70                  75                  80
```

-continued

```
Leu Gln Leu Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 62
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Ala Leu Asp His Phe
            20                  25                  30

Gly Leu Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 63
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asp Phe Tyr Asn Tyr
            20                  25                  30

Gly Ile Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala His Glu Phe
    50                  55                  60

Thr Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120
```

```
<210> SEQ ID NO 64
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Ser Leu Asp His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 65
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Asn Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 66
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 66

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Ile Ser Leu Asp Asn Ser Lys Ser Thr Val Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 67
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 68
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Phe Ser Leu Asn Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 69
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
                20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Asn Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 70
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
                20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

```
Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 71
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Gln Ser Gly Gly Gly Val Val Gln Pro Gly Gly
1               5                   10                  15

Ser Leu Arg Leu Thr Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Asn Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Arg Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 72
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Gln Ser Gly Gly Gly Val Val Gln Pro Gly Gly
1               5                   10                  15

Ser Leu Arg Leu Thr Cys Ala Val Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Ile Ser Arg Asp Thr Ser Lys Asn Gln Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120
```

```
<210> SEQ ID NO 73
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Gln Ser Gly Gly Gly Val Val Gln Pro Gly Gly
1               5                   10                  15

Thr Leu Arg Leu Ser Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 74
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Gln Ser Gly Gly Gly Val Val Gln Pro Gly Gly
1               5                   10                  15

Thr Leu Arg Leu Thr Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 75
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 75

Glu Val Gln Leu Val Gln Ser Gly Gly Gly Val Val Gln Pro Gly Gly
1               5                   10                  15

Thr Leu Arg Leu Thr Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 76
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Gln Ser Gly Gly Gly Val Val Gln Pro Gly Gly
1               5                   10                  15

Thr Leu Arg Leu Thr Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Ile Ser Leu Asp Thr Ser Lys Ser Thr Val Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 77
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Val Glu Ser Gly Gly Gly Leu Val Gln Pro Gly Gly
1               5                   10                  15

Ser Leu Arg Leu Thr Cys Ala Ala Ser Gly Tyr Thr Phe Thr Asn Tyr
            20                  25                  30

```
Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Lys Ala Tyr
65                  70                  75                  80

Leu Gln Leu Asn Ser Leu Arg Ala Glu Asp Thr Ala Val Tyr Tyr Cys
                85                  90                  95

Ala Arg Tyr Pro His Tyr Tyr Gly Ser Ser His Trp Tyr Phe Asp Val
            100                 105                 110

Trp Gly Gln Gly Thr Leu Val Thr Val Ser Ser
        115                 120
```

<210> SEQ ID NO 78
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Gln Val Gln Leu Val Gln Ser Gly Gly Gly Leu Val Gln Pro Gly Gly
1               5                   10                  15

Thr Leu Arg Leu Thr Cys Ala Val Ser Gly Tyr Thr Phe Thr Asn Tyr
                20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Ala Pro Thr Tyr Ala Ala Asp Phe
    50                  55                  60

Lys Arg Arg Leu Thr Phe Ser Leu Asp Asn Ser Lys Asn Pro Pro Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120
```

<210> SEQ ID NO 79
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

```
Gln Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
                20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Phe Ser Leu Asp Asn Ser Lys Ser Thr Val Tyr
65                  70                  75                  80
```

```
Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 80
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Ile Ser Leu Asp Thr Ser Lys Asn Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 81
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Gln Ser Gly Gly Gly Val Val Gln Pro Gly Gly
1               5                   10                  15

Ser Leu Arg Leu Thr Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Ile Ser Leu Asp Thr Ser Lys Ser Gln Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120
```

```
<210> SEQ ID NO 82
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82
```

Gln Val Gln Leu Val Gln Ser Gly Gly Gly Val Val Gln Pro Gly Gly
1               5                   10                  15

Ser Leu Arg Leu Thr Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Ile Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

```
<210> SEQ ID NO 83
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83
```

Gln Val Gln Leu Val Gln Ser Gly Gly Gly Val Val Gln Pro Gly Gly
1               5                   10                  15

Ser Leu Arg Leu Thr Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Ile Ser Leu Asp Thr Ser Lys Ser Gln Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

```
<210> SEQ ID NO 84
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 84

Gln Val Gln Leu Val Gln Ser Gly Gly Val Val Gln Pro Gly Gly
1               5                   10                  15

Thr Leu Arg Leu Thr Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 85
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Gln Ser Gly Gly Val Val Gln Pro Gly Gly Ser
1               5                   10                  15

Leu Arg Leu Ser Cys Ala Ala Ser Gly Tyr Thr Phe Thr His Tyr Gly
            20                  25                  30

Leu Asn Trp Leu Arg Gln Ala Pro Gly Lys Gly Pro Glu Trp Val Gly
        35                  40                  45

Trp Val Asn Thr Tyr Thr Gly Glu Thr Thr Tyr Ala Asp Glu Phe Lys
    50                  55                  60

Arg Arg Val Thr Phe Ser Leu Asp Thr Ser Lys Ser Thr Ala Tyr Leu
65                  70                  75                  80

Gln Leu Asn Ser Leu Arg Ala Glu Asp Thr Ala Val Tyr Tyr Cys Ala
                85                  90                  95

Lys Tyr Pro Tyr Tyr Gly Arg Ser His Trp Tyr Phe Asp Val Trp
            100                 105                 110

Gly Gln Gly Thr Leu Val Thr Val Ser Ser
        115                 120

<210> SEQ ID NO 86
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Val Gln Leu Val Gln Ser Gly Gly Gly Val Val Gln Pro Gly Gly
1               5                   10                  15

Ser Leu Arg Leu Ser Cys Ala Ala Ser Gly Phe Asn Phe Thr His Tyr
            20                  25                  30
```

```
Gly Ile Asn Trp Ile Arg Gln Ala Pro Gly Lys Gly Pro Glu Trp Val
        35                  40                  45

Gly Trp Ile Asn Thr Asn Asn Gly Glu Pro Thr Tyr Ala Gln Asp Phe
     50                  55                  60

Lys Arg Arg Val Thr Phe Ser Leu Asp Thr Ser Lys Ser Thr Ala Tyr
 65                  70                  75                  80

Leu Gln Leu Asn Ser Leu Arg Ala Glu Asp Thr Ala Val Tyr Tyr Cys
                 85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120
```

<210> SEQ ID NO 87
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Glu Val Gln Leu Val Gln Ser Gly Gly Gly Val Val Gln Pro Gly Gly
  1               5                  10                  15

Ser Leu Arg Leu Ser Cys Ala Ala Ser Gly Tyr Asp Phe Ala His Tyr
                 20                  25                  30

Gly Leu Asn Trp Ile Arg Gln Ala Pro Gly Lys Gly Leu Glu Trp Val
        35                  40                  45

Gly Trp Val Asn Thr Tyr Thr Gly Glu Ser Thr Tyr Val Pro Glu Phe
     50                  55                  60

Lys Arg Arg Val Thr Phe Ser Leu Asp Thr Ser Lys Ser Thr Ala Tyr
 65                  70                  75                  80

Leu Gln Leu Asn Ser Leu Arg Ala Glu Asp Thr Ala Val Tyr Tyr Cys
                 85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120
```

<210> SEQ ID NO 88
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Glu Val Gln Leu Val Gln Ser Gly Gly Gly Val Val Gln Pro Gly Gly
  1               5                  10                  15

Ser Leu Arg Leu Ser Cys Ala Ala Ser Gly Tyr Asp Phe Ala His Tyr
                 20                  25                  30

Gly Val Asn Trp Leu Arg Gln Ala Pro Gly Lys Gly Leu Glu Trp Val
        35                  40                  45

Gly Trp Ile Asn Thr Tyr Thr Gly Glu Thr Tyr Ala His Asp Phe
     50                  55                  60

Lys Arg Arg Val Thr Phe Ser Leu Asp Thr Ser Lys Ser Thr Ala Tyr
 65                  70                  75                  80
```

```
Leu Gln Leu Asn Ser Leu Arg Ala Glu Asp Thr Ala Val Tyr Tyr Cys
            85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
            115                 120

<210> SEQ ID NO 89
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asp Phe Ala Ser Phe
            20                  25                  30

Gly Ile Asn Trp Ile Arg Gln Ala Pro Gly Lys Gly Leu Glu Trp Val
            35                  40                  45

Gly Trp Ile Asn Thr Tyr Thr Gly Glu Ser Thr Tyr Ala Gln Asp Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
            85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
            115                 120

<210> SEQ ID NO 90
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asp Phe Asp His Phe
            20                  25                  30

Gly Ile Asn Trp Ile Arg Gln Ala Pro Gly Lys Gly Pro Glu Trp Val
            35                  40                  45

Gly Trp Ile Asn Thr Tyr Thr Gly Glu Pro Thr Tyr Val Asp Glu Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
            85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
            115                 120
```

```
<210> SEQ ID NO 91
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asp Phe Asn Asn Tyr
            20                  25                  30

Gly Met Asn Trp Ile Arg Gln Ala Pro Gly Lys Gly Pro Glu Trp Val
        35                  40                  45

Gly Trp Ile Asn Thr Tyr Asn Gly Glu Pro Thr Tyr Ala Pro Asp Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120

<210> SEQ ID NO 92
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asp Phe Ser His Phe
            20                  25                  30

Gly Ile Asn Trp Ile Arg Gln Ala Pro Gly Lys Gly Leu Glu Trp Val
        35                  40                  45

Gly Trp Ile Asn Thr Tyr Thr Gly Glu Thr Thr Tyr Ala His Asp Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120

<210> SEQ ID NO 93
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 93

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asp Phe Ser His Phe
            20                  25                  30

Gly Ile Asn Trp Val Arg Gln Ala Pro Gly Lys Gly Pro Glu Trp Val
        35                  40                  45

Gly Trp Ile Asn Thr Tyr Thr Gly Glu Thr Thr Tyr Val Pro Glu Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro Tyr Tyr Tyr Gly Arg Ser His Trp Tyr Phe Asp Val
            100                 105                 110

Trp Gly Gln Gly Thr Leu Val Thr Val Ser Ser
        115                 120

<210> SEQ ID NO 94
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asp Phe Ser Asn Tyr
            20                  25                  30

Gly Leu Asn Trp Val Arg Gln Ala Pro Gly Lys Gly Pro Glu Trp Val
        35                  40                  45

Gly Trp Ile Asn Thr Tyr Thr Gly Glu Pro Thr Tyr Ala Glu Glu Phe
    50                  55                  60

Thr Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro Tyr Tyr Tyr Gly Arg Ser His Trp Tyr Phe Asp Val
            100                 105                 110

Trp Gly Gln Gly Thr Leu Val Thr Val Ser Ser
        115                 120

<210> SEQ ID NO 95
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asp Phe Thr His Tyr
            20                  25                  30
```

```
Gly Leu Asn Trp Ile Arg Gln Ala Pro Gly Lys Gly Pro Glu Trp Val
        35                  40                  45

Gly Trp Ile Asn Thr Tyr Thr Gly Glu Thr Thr Tyr Ala His Glu Phe
    50                  55                  60

Thr Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
                100                 105                 110

Trp Gly Gln Gly Thr Leu Val Thr Val Ser Ser
        115                 120
```

<210> SEQ ID NO 96
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

```
Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asn Phe Tyr His Tyr
                20                  25                  30

Gly Val Asn Trp Val Arg Gln Ala Pro Gly Lys Gly Pro Glu Trp Val
        35                  40                  45

Gly Trp Val Asn Thr Tyr Thr Gly Glu Thr Thr Tyr Ala Gln Glu Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
                100                 105                 110

Trp Gly Gln Gly Thr Leu Val Thr Val Ser Ser
        115                 120
```

<210> SEQ ID NO 97
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asn Phe Tyr Ser Tyr
                20                  25                  30

Gly Leu Asn Trp Val Arg Gln Ala Pro Gly Lys Gly Pro Glu Trp Val
        35                  40                  45

Gly Trp Ile Asn Thr Tyr Thr Gly Glu Pro Thr Tyr Ala Gln Glu Phe
    50                  55                  60

Lys Arg Arg Val Thr Phe Ser Leu Asp Thr Ser Lys Ser Thr Ala Tyr
65                  70                  75                  80
```

```
Leu Gln Leu Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120

<210> SEQ ID NO 98
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Ser Phe Asp His Tyr
            20                  25                  30

Gly Leu Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Asp Glu Phe
    50                  55                  60

Thr Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120

<210> SEQ ID NO 99
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Thr Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120
```

```
<210> SEQ ID NO 100
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Ile Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120

<210> SEQ ID NO 101
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120

<210> SEQ ID NO 102
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 102

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Arg Ser His Trp Tyr Phe Asp Val
            100                 105                 110

Trp Gly Gln Gly Thr Leu Val Thr Val Ser Ser
        115                 120

<210> SEQ ID NO 103
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120

<210> SEQ ID NO 104
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30
```

```
Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Arg Ser His Trp Tyr Phe Asp Val
            100                 105                 110

Trp Gly Gln Gly Thr Leu Val Thr Val Ser Ser
        115                 120
```

<210> SEQ ID NO 105
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Arg Ser His Trp Tyr Phe Asp Val
            100                 105                 110

Trp Gly Gln Gly Thr Leu Val Thr Val Ser Ser
        115                 120
```

<210> SEQ ID NO 106
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asp Phe Thr His Phe
            20                  25                  30

Gly Leu Asn Trp Ile Arg Gln Ala Pro Gly Lys Gly Pro Glu Trp Val
        35                  40                  45

Gly Trp Ile Asn Thr Tyr Thr Gly Glu Pro Thr Tyr Ala Gln Asp Phe
    50                  55                  60

Lys Arg Arg Val Thr Phe Ser Leu Asp Thr Ser Lys Ser Thr Ala Tyr
65                  70                  75                  80
```

Leu Gln Leu Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120

<210> SEQ ID NO 107
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asp Leu Ser His Tyr
            20                  25                  30

Gly Leu Asn Trp Ile Arg Gln Ala Pro Gly Lys Gly Pro Glu Trp Val
        35                  40                  45

Gly Trp Ile Asn Thr Tyr Thr Gly Glu Pro Thr Tyr Ala Pro Asp Phe
    50                  55                  60

Thr Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120

<210> SEQ ID NO 108
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asn Phe Ser His Phe
            20                  25                  30

Gly Leu Asn Trp Leu Arg Gln Ala Pro Gly Lys Gly Leu Glu Trp Val
        35                  40                  45

Gly Trp Ile Asn Thr Tyr Asn Gly Glu Thr Thr Tyr Ala Pro Asp Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120

```
<210> SEQ ID NO 109
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asn Phe Ser His Phe
            20                  25                  30

Gly Leu Asn Trp Leu Arg Gln Ala Pro Gly Lys Gly Pro Glu Trp Val
        35                  40                  45

Gly Trp Ile Asn Thr Tyr Thr Gly Glu Pro Thr Tyr Ala Pro Glu Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120

<210> SEQ ID NO 110
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Val Gln Leu Val Gln Ser Gly Gly Gly Val Val Gln Pro Gly Gly
1               5                   10                  15

Ser Leu Arg Leu Ser Cys Ala Ala Ser Gly Tyr Asp Phe Thr His Phe
            20                  25                  30

Gly Leu Asn Trp Val Arg Gln Ala Pro Gly Lys Gly Leu Glu Trp Val
        35                  40                  45

Gly Trp Val Asn Thr Tyr Thr Gly Glu Thr Thr Tyr Ala His Glu Phe
    50                  55                  60

Lys Arg Arg Val Thr Phe Ser Leu Asp Thr Ser Lys Ser Thr Ala Tyr
65                  70                  75                  80

Leu Gln Leu Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 111

Gly Phe Asp Phe Thr Asn Tyr Gly Met Asn
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Tyr Thr Phe Thr Asn Tyr Gly Met Asn
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Tyr Ser Leu Asp His Tyr Gly Met Asn
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Tyr Ala Leu Asp His Phe Gly Leu Asn
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Tyr Asp Phe Tyr Asn Tyr Gly Ile Asn
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Tyr Thr Phe Thr Asn Tyr Gly Met Asn
1               5                   10
```

```
<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Tyr Ser Phe Asp His Tyr Gly Leu Asn
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Tyr Asp Phe Ser Asn Tyr Gly Leu Asn
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Tyr Asp Phe Ser His Phe Gly Ile Asn
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Tyr Asp Phe Ala His Tyr Gly Val Asn
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Tyr Asp Phe Asp His Phe Gly Ile Asn
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 122

Gly Tyr Asp Phe Asn Asn Tyr Gly Met Asn
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Tyr Asp Phe Ala Ser Phe Gly Ile Asn
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Phe Asn Phe Thr His Tyr Gly Ile Asn
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Tyr Asp Phe Ala His Tyr Gly Leu Asn
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Tyr Asn Phe Tyr His Tyr Gly Val Asn
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Tyr Asp Phe Thr His Tyr Gly Leu Asn
1               5                   10
```

```
<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Tyr Asn Phe Tyr Ser Tyr Gly Leu Asn
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Tyr Asp Phe Ser His Phe Gly Ile Asn
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Tyr Thr Phe Thr His Tyr Gly Leu Asn
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Tyr Asp Phe Thr His Phe Gly Leu Asn
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Tyr Asp Leu Ser His Tyr Gly Leu Asn
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 133

Gly Tyr Asn Phe Ser His Phe Gly Leu Asn
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Tyr Asn Phe Ser His Phe Gly Leu Asn
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Tyr Asp Phe Thr His Phe Gly Leu Asn
1               5                   10

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Trp Ile Asn Thr Tyr Thr Gly Glu Pro Thr Tyr Ala His Glu Phe Thr
1               5                   10                  15

Arg

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Trp Ile Asn Thr Tyr Thr Gly Glu Pro Thr Tyr Ala Ala Asp Phe Thr
1               5                   10                  15

Arg

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 138

Trp Ile Asn Thr Tyr Thr Gly Glu Pro Thr Tyr Ala Asp Glu Phe Thr
1               5                   10                  15

Arg

<210> SEQ ID NO 139
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Trp Ile Asn Thr Tyr Thr Gly Glu Pro Thr Tyr Ala Glu Glu Phe Thr
1               5                   10                  15

Arg

<210> SEQ ID NO 140
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Trp Ile Asn Thr Tyr Thr Gly Glu Thr Thr Tyr Val Pro Glu Phe Lys
1               5                   10                  15

Arg

<210> SEQ ID NO 141
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Trp Ile Asn Thr Tyr Thr Gly Glu Thr Thr Tyr Ala His Asp Phe Lys
1               5                   10                  15

Arg

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Trp Ile Asn Thr Tyr Thr Gly Glu Pro Thr Tyr Val Asp Glu Phe Lys
1               5                   10                  15

Arg

<210> SEQ ID NO 143
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 143

Trp Ile Asn Thr Tyr Asn Gly Glu Pro Thr Tyr Ala Pro Asp Phe Lys
1               5                   10                  15
Arg

<210> SEQ ID NO 144
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Trp Ile Asn Thr Tyr Thr Gly Glu Ser Thr Tyr Ala Gln Asp Phe Lys
1               5                   10                  15
Arg

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Trp Ile Asn Thr Asn Asn Gly Glu Pro Thr Tyr Ala Gln Asp Phe Lys
1               5                   10                  15
Arg

<210> SEQ ID NO 146
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Trp Val Asn Thr Tyr Thr Gly Glu Ser Thr Tyr Val Pro Glu Phe Lys
1               5                   10                  15
Arg

<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Trp Val Asn Thr Tyr Thr Gly Glu Thr Thr Tyr Ala Gln Glu Phe Lys
1               5                   10                  15
Arg

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 148

Trp Ile Asn Thr Tyr Thr Gly Glu Thr Thr Tyr Ala His Glu Phe Thr
1               5                   10                  15

Arg

<210> SEQ ID NO 149
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Trp Ile Asn Thr Tyr Thr Gly Glu Pro Thr Tyr Ala Gln Glu Phe Lys
1               5                   10                  15

Arg

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Trp Ile Asn Thr Tyr Thr Gly Glu Thr Thr Tyr Ala His Asp Phe Lys
1               5                   10                  15

Arg

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Trp Val Asn Thr Tyr Thr Gly Glu Thr Thr Tyr Ala Asp Glu Phe Lys
1               5                   10                  15

Arg

<210> SEQ ID NO 152
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Trp Ile Asn Thr Tyr Thr Gly Glu Pro Thr Tyr Ala Gln Asp Phe Lys
1               5                   10                  15

Arg

<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 153

Trp Ile Asn Thr Tyr Thr Gly Glu Pro Thr Tyr Ala Pro Asp Phe Thr
1               5                   10                  15

Arg

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Trp Ile Asn Thr Tyr Asn Gly Glu Thr Thr Tyr Ala Pro Asp Phe Lys
1               5                   10                  15

Arg

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Trp Ile Asn Thr Tyr Thr Gly Glu Pro Thr Tyr Ala Pro Glu Phe Lys
1               5                   10                  15

Arg

<210> SEQ ID NO 156
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Trp Val Asn Thr Tyr Thr Gly Glu Thr Thr Tyr Ala His Glu Phe Lys
1               5                   10                  15

Arg

<210> SEQ ID NO 157
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Glu Val Gln Leu Val Gln Ser Gly Gly Gly Val Val Gln Pro Gly Gly
1               5                   10                  15

Ser Leu Arg Leu Ser Cys Ala Ala Ser
            20                  25

<210> SEQ ID NO 158
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 158

Glu Val Gln Leu Val Gln Ser Gly Gly Gly Val Val Gln Pro Gly Gly
1               5                   10                  15

Ser Leu Arg Leu Ser Cys Ala Ala Ser
            20                  25

<210> SEQ ID NO 159
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Glu Val Gln Leu Val Gln Ser Gly Gly Gly Val Val Gln Pro Gly Gly
1               5                   10                  15

Ser Leu Arg Leu Ser Cys Ala Ala Ser
            20                  25

<210> SEQ ID NO 160
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Glu Val Gln Leu Val Gln Ser Gly Gly Gly Val Val Gln Pro Gly Gly
1               5                   10                  15

Ser Leu Arg Leu Thr Cys Ala Val Ser
            20                  25

<210> SEQ ID NO 161
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Glu Val Gln Leu Val Gln Ser Gly Gly Gly Val Val Gln Pro Gly Gly
1               5                   10                  15

Ser Leu Arg Leu Ser Cys Ala Ala Ser
            20                  25

<210> SEQ ID NO 162
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gln Val Gln Leu Val Gln Ser Gly Gly Gly Val Val Gln Pro Gly Gly
1               5                   10                  15

Ser Leu Arg Leu Thr Cys Ala Ala Ser
            20                  25
```

```
<210> SEQ ID NO 163
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Glu Val Gln Leu Val Gln Ser Gly Gly Gly Val Val Gln Pro Gly Gly
1               5                   10                  15

Thr Leu Arg Leu Thr Cys Ala Ala Ser
            20                  25

<210> SEQ ID NO 164
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Asn Ala Ser Gln Ser Ile Gly Thr Tyr Leu Ala
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Lys Ala Ser Gln Ser Ile Gly Thr Tyr Leu Ala
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

His Ala Ser Gln Ser Ile Ser Ser Tyr Leu Ala
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ser Ala Ser Gln Ser Ile Ser Thr Tyr Leu Ala
1               5                   10

<210> SEQ ID NO 168
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 168

Arg Ala Ser Gln Ser Ile Ser Thr Tyr Leu Ala
1               5                   10

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Lys Ala Ser Gln Ser Ile Gly Ser Tyr Leu Ala
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

His Ala Ser Gln Ser Ile Ser Thr Tyr Leu Ala
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Arg Ala Ser Gln Ser Ile Ser Ser Tyr Leu Ala
1               5                   10

<210> SEQ ID NO 172
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Asn Ala Ser Gln Ser Ile Gly Ser Tyr Leu Ala
1               5                   10

<210> SEQ ID NO 173
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Ala Ser Gln Ser Ile Gly Thr Tyr Leu Ala
1               5                   10
```

```
<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Lys Ala Ser Gln Ser Ile Ser Thr Tyr Leu Ala
1               5                   10

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asn Ala Ser Gln Ser Ile Ser Thr Tyr Leu Ala
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

His Ala Ser Gln Ser Ile Gly Thr Tyr Leu Ala
1               5                   10

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gln Ala Ser Gln Ser Ile Ser Thr Tyr Leu Ala
1               5                   10

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Arg Ala Ser Gln Ser Ile Ser Thr Tyr Ile Asn
1               5                   10

<210> SEQ ID NO 179
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 179

Arg Ala Ser Arg Asp Ile Arg Asn Asp Leu Ala
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Arg Ala Ser Arg Asp Ile Thr Thr Asp Leu Ala
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Arg Ala Ser Gln Asp Ile Arg Lys Asp Leu Ala
1               5                   10

<210> SEQ ID NO 182
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Arg Ala Ser Gln Ala Ile Arg Asn Asp Leu Thr
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Arg Ala Ser Gln Ala Ile Tyr Asp Tyr Leu Ala
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Arg Ser Ser Gln Pro Ile Thr Asn Asp Leu Ala
1               5                   10
```

-continued

<210> SEQ ID NO 185
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Arg Ala Ser Arg Asp Ile Arg Asp Asp Leu Ala
1               5                   10

<210> SEQ ID NO 186
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ser Gly Ser Ser Ser Asn Val Gly Arg Asn Thr Val Asn
1               5                   10

<210> SEQ ID NO 187
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Gly Ser Thr Ser Asn Ile Gly Ser Asn Pro Val Asn
1               5                   10

<210> SEQ ID NO 188
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Thr Gly Arg Ser Ser Asn Ile Gly Ala Gly His Asp Val His
1               5                   10

<210> SEQ ID NO 189
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ser Gly Ser Asn Ser Asn Ile Gly Ser Asn Asn Val Tyr
1               5                   10

<210> SEQ ID NO 190
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ser Gly Ser Tyr Ser Asn Ile Gly Ser Asn Ala Val Asn
1               5                   10

<210> SEQ ID NO 191
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Gly Thr Thr Ser Asn Ile Gly Ser Asn Ser Val Asn
1               5                   10

<210> SEQ ID NO 192
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ser Gly Ser Ser Ser Asn Ile Gly Ser Asn Ser Val Thr
1               5                   10

<210> SEQ ID NO 193
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Gly Ser Thr Ser Asn Ile Gly Ser Asn Ser Val Thr
1               5                   10

<210> SEQ ID NO 194
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Gly Ser Ser Ser Asn Ile Gly Ser Asn Pro Val Asn
1               5                   10

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Ala Ser Asn Leu Ala Ser
1               5

```
<210> SEQ ID NO 196
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Asp Ala Ser Asn Leu Ala Ser
1               5

<210> SEQ ID NO 197
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ser Ala Ser Asn Leu Ala Ser
1               5

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ala Ala Ser Ser Leu Gln Ser
1               5

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ala Ala Ser Arg Leu Gln Ser
1               5

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ala Ala Ser Thr Leu Gln Ser
1               5

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 201

Gly Ala Thr Thr Leu Gln Ser
1               5

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ala Ala Ser Arg Leu Gln Gly
1               5

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Asn Asp Glu Arg Pro Ser
1               5

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ala Ala Ser Asn Leu Ala Ser
1               5

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ala Asn Asp Gln Arg Pro Ser
1               5

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Asn Asn Gln Arg Pro Ser
1               5
```

```
<210> SEQ ID NO 207
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Thr Asn Asn Gln Arg Pro Ser
1               5

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Asn Asp Gln Arg Pro Ser
1               5

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Asn Asn Gln Arg Pro Ser
1               5

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gln Gln Tyr Asn Ser Lys Pro Trp Thr
1               5

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gln Gln Tyr Ser Ser Thr Pro Tyr Thr
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 212

Gln Gln Tyr Asn Ser Thr Pro Trp Thr
1               5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gln Gln Tyr Tyr Ser Thr Pro Trp Thr
1               5

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gln Gln Tyr Asn Ser Ala Pro Trp Thr
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gln Gln Tyr Ser Ser Ser Pro Trp Thr
1               5

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Gln Gln Tyr Tyr Ser Gly Pro Trp Thr
1               5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Gln Gln Tyr Ser Ser Thr Pro Trp Thr
1               5
```

```
<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gln Gln Tyr Tyr Ser Ala Pro Trp Thr
1               5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gln Gln Ser Tyr Ser Thr Pro Trp Thr
1               5

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gln Gln Ser Tyr Ser Pro Pro Trp Thr
1               5

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gln Gln Ser Tyr Thr Ile Pro Trp Thr
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gln Gln Ser Ser Thr Thr Pro Trp Thr
1               5

<210> SEQ ID NO 223
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 223

Ala Thr Trp Asp Asp Ser Leu Asn Gly Tyr Val
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ala Ser Trp Asp Asp Ser Leu Thr Gly Tyr Val
1               5                   10

<210> SEQ ID NO 225
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ala Thr Trp Asp Asp Ser Leu His Gly Tyr Val
1               5                   10

<210> SEQ ID NO 226
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Ala Trp Asp Asp Ser Leu Asn Gly Tyr Val
1               5                   10

<210> SEQ ID NO 227
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ala Ala Trp Asp Asp Ser Leu Asn Gly Tyr Val
1               5                   10

<210> SEQ ID NO 228
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Ala Trp Asp Asp Ser Leu Ser Gly Tyr Val
1               5                   10
```

<210> SEQ ID NO 229
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Asp Ile Val Met Thr Gln Ser Pro Ser Ser Leu Ser Ala Ser Pro Gly
1               5                   10                  15

Glu Arg Ala Thr Ile Ser Cys
            20

<210> SEQ ID NO 230
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Asp Ile Val Met Thr Gln Ser Pro Ser Ser Leu Ser Ala Ser Pro Gly
1               5                   10                  15

Glu Arg Ala Thr Ile Thr Cys
            20

<210> SEQ ID NO 231
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Asp Ile Val Met Thr Gln Ser Pro Ser Thr Leu Ser Ala Ser Pro Gly
1               5                   10                  15

Glu Arg Ala Thr Ile Thr Cys
            20

<210> SEQ ID NO 232
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Asp Ile Val Met Thr Gln Ser Pro Ser Thr Leu Ser Ala Ser Pro Gly
1               5                   10                  15

Glu Arg Ala Thr Ile Thr Cys
            20

<210> SEQ ID NO 233
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 233

Asp Ile Val Met Thr Gln Ser Pro Ser Thr Leu Ser Ala Ser Pro Gly
1               5                   10                  15

Glu Arg Ala Thr Ile Thr Cys
            20

<210> SEQ ID NO 234
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Asp Ile Val Met Thr Gln Ser Pro Ser Thr Leu Ser Ala Ser Pro Gly
1               5                   10                  15

Glu Arg Ala Thr Ile Ser Cys
            20

<210> SEQ ID NO 235
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Asp Ile Val Met Thr Gln Ser Pro Ser Thr Leu Ser Ala Ser Pro Gly
1               5                   10                  15

Glu Arg Ala Thr Ile Thr Cys
            20

<210> SEQ ID NO 236
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Asp Ile Val Met Thr Gln Ser Pro Ser Ser Leu Ser Ala Ser Pro Gly
1               5                   10                  15

Glu Arg Ala Thr Ile Ser Cys
            20

<210> SEQ ID NO 237
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Asp Ile Val Met Thr Gln Ser Pro Ser Thr Leu Ser Ala Ser Pro Gly
1               5                   10                  15

Glu Arg Ala Thr Ile Thr Cys
            20
```

<210> SEQ ID NO 238
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Asp Ile Lys Met Thr Gln Ser Pro Ser Ser Leu Ser Ala Ser Pro Gly
1               5                   10                  15

Glu Arg Ala Thr Ile Ser Cys
            20

<210> SEQ ID NO 239
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Asp Ile Val Met Thr Gln Ser Pro Ser Thr Leu Ser Ala Ser Pro Gly
1               5                   10                  15

Glu Arg Ala Thr Ile Thr Cys
            20

<210> SEQ ID NO 240
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Asp Ile Val Met Thr Gln Ser Pro Ser Ser Leu Ser Ala Ser Pro Gly
1               5                   10                  15

Glu Arg Ala Thr Ile Thr Cys
            20

<210> SEQ ID NO 241
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Asp Ile Val Met Thr Gln Ser Pro Ser Thr Leu Ser Ala Ser Pro Gly
1               5                   10                  15

Glu Arg Ala Thr Ile Thr Cys
            20

<210> SEQ ID NO 242
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 242

Asp Ile Val Met Thr Gln Ser Pro Ser Thr Leu Ser Ala Ser Pro Gly
1               5                   10                  15

Glu Arg Ala Thr Ile Ser Cys
            20

<210> SEQ ID NO 243
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Asp Ile Val Met Thr Gln Ser Pro Ser Thr Leu Ser Ala Ser Pro Gly
1               5                   10                  15

Glu Arg Ala Thr Ile Thr Cys
            20

<210> SEQ ID NO 244
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Asp Ile Val Met Thr Gln Ser Pro Ser Thr Leu Ser Ala Ser Pro Gly
1               5                   10                  15

Glu Arg Ala Thr Ile Thr Cys
            20

<210> SEQ ID NO 245
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Asp Ile Val Met Thr Gln Ser Pro Ser Ser Leu Ser Ala Ser Pro Gly
1               5                   10                  15

Glu Arg Ala Thr Ile Thr Cys
            20

<210> SEQ ID NO 246
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Asp Ile Val Met Thr Gln Ser Pro Ser Thr Leu Ser Ala Ser Pro Gly
1               5                   10                  15

Glu Arg Ala Thr Ile Ser Cys
            20
```

```
<210> SEQ ID NO 247
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Asp Ile Val Met Thr Gln Ser Pro Ser Thr Leu Ser Ala Ser Pro Gly
1               5                   10                  15

Glu Arg Ala Thr Ile Thr Cys
            20

<210> SEQ ID NO 248
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Asp Ile Val Met Thr Gln Ser Pro Ser Thr Leu Ser Ala Ser Pro Gly
1               5                   10                  15

Glu Arg Ala Thr Ile Thr Cys
            20

<210> SEQ ID NO 249
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Asp Ile Lys Met Thr Gln Ser Pro Ser Ser Leu Ser Ala Ser Pro Gly
1               5                   10                  15

Glu Arg Ala Thr Ile Thr Cys
            20

<210> SEQ ID NO 250
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Glu Ile Val Met Thr Gln Ser Pro Ser Ser Leu Ser Ala Ser Val Gly
1               5                   10                  15

Asp Arg Val Thr Ile Thr Cys
            20

<210> SEQ ID NO 251
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 251

Asp Ile Val Met Thr Gln Thr Pro Ser Ser Leu Ser Ala Ser Val Gly
1               5                  10                  15

Asp Thr Val Thr Ile Thr Cys
            20

<210> SEQ ID NO 252
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Glu Ile Val Leu Thr Gln Ser Pro Ser Ser Leu Ser Ala Ser Ile Gly
1               5                  10                  15

Asp Arg Val Ala Ile Thr Cys
            20

<210> SEQ ID NO 253
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Glu Ile Val Leu Thr Gln Ser Pro Ser Ser Leu Ser Ala Ser Val Gly
1               5                  10                  15

Asp Arg Val Thr Ile Thr Cys
            20

<210> SEQ ID NO 254
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Glu Ile Val Met Thr Gln Ser Pro Ser Ser Leu Ser Ala Ser Val Gly
1               5                  10                  15

Asp Arg Val Thr Ile Thr Cys
            20

<210> SEQ ID NO 255
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Glu Ile Val Met Thr Gln Ser Pro Ser Ser Leu Ser Ala Ser Val Gly
1               5                  10                  15

Asp Thr Val Thr Ile Ala Cys
            20
```

```
<210> SEQ ID NO 256
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ala Ile Arg Met Thr Gln Ser Pro Ser Ser Val Ser Ala Ser Val Gly
 1               5                  10                  15

Asp Thr Val Thr Ile Ala Cys
            20

<210> SEQ ID NO 257
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Glu Ile Val Met Thr Gln Ser Pro Ser Ser Leu Ser Ala Ser Val Gly
 1               5                  10                  15

Asp Arg Val Thr Ile Thr Cys
            20

<210> SEQ ID NO 258
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Glu Thr Thr Leu Thr Gln Ser Pro Ser Ser Leu Ser Ala Ser Val Gly
 1               5                  10                  15

Asp Thr Ile Thr Ile Ser Cys
            20

<210> SEQ ID NO 259
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Glu Ile Val Leu Thr Gln Ser Pro Ser Ser Leu Ser Ala Ser Val Gly
 1               5                  10                  15

Asp Arg Ile Thr Ile Thr Cys
            20

<210> SEQ ID NO 260
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 260

Asp Ile Gln Leu Thr Gln Ser Pro Ser Ser Leu Ser Ala Ser Ala Gly
1               5                   10                  15

Asp Arg Val Thr Ile Ser Cys
            20

<210> SEQ ID NO 261
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gln Pro Val Leu Thr Gln Pro Pro Ser Ala Ser Gly Thr Pro Gly Gln
1               5                   10                  15

Arg Val Thr Ile Ser Cys
            20

<210> SEQ ID NO 262
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Leu Pro Val Leu Thr Gln Pro Pro Ser Ala Ser Gly Thr Pro Gly Gln
1               5                   10                  15

Arg Val Thr Ile Ser Cys
            20

<210> SEQ ID NO 263
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Gln Ser Ala Leu Thr Gln Pro Pro Ser Val Ser Gly Ala Pro Gly Gln
1               5                   10                  15

Arg Val Thr Ile Ser Cys
            20

<210> SEQ ID NO 264
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gln Ser Val Leu Thr Gln Pro Pro Ser Ala Ser Gly Thr Pro Gly Gln
1               5                   10                  15

Arg Val Thr Ile Ser Cys
            20
```

```
<210> SEQ ID NO 265
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Leu Pro Val Leu Thr Gln Pro Pro Ser Ala Ser Gly Thr Pro Gly Gln
1               5                   10                  15

Arg Val Thr Ile Ser Cys
            20

<210> SEQ ID NO 266
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gln Ala Val Leu Thr Gln Pro Pro Ser Ala Ser Gly Thr Pro Gly Gln
1               5                   10                  15

Ser Val Thr Ile Ser Cys
            20

<210> SEQ ID NO 267
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gln Pro Val Leu Thr Gln Pro Pro Ser Thr Ser Gly Thr Pro Gly Gln
1               5                   10                  15

Arg Val Thr Ile Ser Cys
            20

<210> SEQ ID NO 268
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Asn Phe Met Leu Thr Gln Pro Pro Ser Thr Ser Gly Thr Pro Gly Gln
1               5                   10                  15

Arg Val Thr Ile Ser Cys
            20

<210> SEQ ID NO 269
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 269

Gln Pro Val Leu Thr Gln Pro Pro Ser Ala Ser Ala Thr Pro Gly Gln
1               5                   10                  15

Arg Val Thr Ile Ser Cys
            20

<210> SEQ ID NO 270
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Glu Val Gln Leu Val Glu Ser Gly Gly Gly Val Val Gln Pro Gly Gly
1               5                   10                  15

Ser Leu Arg Leu Ser Cys Ala Ala Ser
            20                  25

<210> SEQ ID NO 271
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Glu Val Gln Leu Val Gln Ser Gly Gly Gly Leu Val Gln Pro Gly Gly
1               5                   10                  15

Thr Leu Arg Leu Ser Cys Ala Ala Ser
            20                  25

<210> SEQ ID NO 272
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Glu Val Gln Leu Val Gln Ser Gly Gly Gly Val Val Gln Pro Gly Gly
1               5                   10                  15

Ser Leu Arg Leu Arg Cys Ala Ala Ser
            20                  25

<210> SEQ ID NO 273
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Glu Val Gln Leu Val Gln Ser Gly Gly Gly Val Val Gln Pro Gly Gly
1               5                   10                  15

Ser Leu Arg Leu Ser Cys Ala Ala Ser
            20                  25
```

<210> SEQ ID NO 274
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 274

Glu Val Gln Leu Val Gln Ser Gly Gly Gly Val Val Gln Pro Gly Gly
1               5                   10                  15

Thr Leu Arg Leu Ser Cys Ala Ala Ser
            20                  25

<210> SEQ ID NO 275
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 275

Glu Val Gln Leu Val Gln Ser Gly Gly Gly Val Val Gln Pro Gly Gly
1               5                   10                  15

Thr Leu Arg Leu Thr Cys Ala Ala Ser
            20                  25

<210> SEQ ID NO 276
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 276

Glu Val Gln Leu Val Gln Ser Gly Gly Gly Val Val Gln Pro Gly Gly
1               5                   10                  15

Thr Leu Arg Leu Thr Cys Ala Ala Ser
            20                  25

<210> SEQ ID NO 277
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 277

Gln Val Gln Leu Val Glu Ser Gly Gly Gly Leu Val Gln Pro Gly Gly
1               5                   10                  15

Ser Leu Arg Leu Thr Cys Ala Ala Ser
            20                  25

<210> SEQ ID NO 278
<211> LENGTH: 25
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 278

Gln Val Gln Leu Val Gln Ser Gly Gly Gly Val Val Gln Pro Gly Gly
1               5                   10                  15

Ser Leu Arg Leu Ser Cys Ala Ala Ser
            20                  25

<210> SEQ ID NO 279
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gln Val Gln Leu Val Gln Ser Gly Gly Gly Val Val Gln Pro Gly Gly
1               5                   10                  15

Ser Leu Arg Leu Ser Cys Ala Ala Ser
            20                  25

<210> SEQ ID NO 280
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gln Val Gln Leu Val Gln Ser Gly Gly Gly Val Val Gln Pro Gly Gly
1               5                   10                  15

Ser Leu Arg Leu Thr Cys Ala Ala Ser
            20                  25

<210> SEQ ID NO 281
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gln Val Gln Leu Val Gln Ser Gly Gly Gly Val Val Gln Pro Gly Gly
1               5                   10                  15

Ser Leu Arg Leu Thr Cys Ala Ala Ser
            20                  25

<210> SEQ ID NO 282
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gln Val Gln Leu Val Gln Ser Gly Gly Gly Val Val Gln Pro Gly Gly
1               5                   10                  15

Thr Leu Arg Leu Thr Cys Ala Ala Ser
            20                  25
```

<210> SEQ ID NO 283
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 283

Glu Ile Gln Leu Val Gln Ser Gly Pro Glu Leu Lys Gln Pro Gly Glu
1               5                   10                  15

Thr Val Arg Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Glu Thr Ser Ala Ser Thr Ala Tyr
65                  70                  75                  80

Leu Gln Ile Ser Asn Leu Lys Asn Asp Asp Thr Ala Thr Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Thr Thr Val Thr Val Ser Ser
        115                 120

<210> SEQ ID NO 284
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 284

Asp Ile Gln Met Thr Gln Thr Thr Ser Ser Leu Ser Ala Ser Leu Gly
1               5                   10                  15

Asp Arg Val Ile Ile Ser Cys Ser Ala Ser Gln Asp Ile Ser Asn Tyr
            20                  25                  30

Leu Asn Trp Tyr Gln Gln Lys Pro Asp Gly Thr Val Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Thr Val Pro Trp
                85                  90                  95

Thr Phe Gly Gly Gly Thr Lys Leu Glu Ile Lys
            100                 105

<210> SEQ ID NO 285
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 285

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala His Ser Arg His Tyr Tyr Gly Ser Ser Pro Gln Tyr Phe Asp Val
            100                 105                 110

Trp Gly Gln Gly Thr Leu Val Thr Val Ser Ser
        115                 120

<210> SEQ ID NO 286
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Gly Tyr Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 287
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

```
Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ala Ser His Trp Tyr Phe Asp Val
            100                 105                 110

Trp Gly Gln Gly Thr Leu Val Thr Val Ser Ser
        115                 120
```

<210> SEQ ID NO 288
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Gly Cys His Trp Tyr Phe Asp Val
            100                 105                 110

Trp Gly Gln Gly Thr Leu Val Thr Val Ser Ser
        115                 120
```

<210> SEQ ID NO 289
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80
```

```
Leu Gln Met Asn Ser Leu Arg Ala Glu Asp Thr Ala Val Tyr Tyr Cys
                85                  90                  95

Ala Lys Tyr Pro His Tyr Tyr Gly Gly Ser His Trp Tyr Phe Asp Val
            100                 105                 110

Trp Gly Gln Gly Thr Leu Val Thr Val Ser Ser
        115                 120

<210> SEQ ID NO 290
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Gly Tyr Asn Gln Tyr Phe Asp Val
            100                 105                 110

Trp Gly Gln Gly Thr Leu Val Thr Val Ser Ser
        115                 120

<210> SEQ ID NO 291
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Arg Ser His Trp Tyr Phe Asp Val
            100                 105                 110

Trp Gly Gln Gly Thr Leu Val Thr Val Ser Ser
        115                 120
```

```
<210> SEQ ID NO 292
<211> LENGTH: 70
<212> TYPE: PRT
<213> ORGANISM: Mus sp.

<400> SEQUENCE: 292

Glu Ile Gln Leu Val Gln Ser Gly Pro Glu Leu Lys Gln Pro Gly Glu
1               5                   10                  15

Thr Val Arg Ile Ser Cys Lys Ala Ser Trp Val Lys Gln Ala Pro Gly
            20                  25                  30

Lys Gly Leu Lys Trp Met Gly Arg Phe Thr Phe Ser Leu Glu Thr Ser
        35                  40                  45

Ala Ser Thr Ala Tyr Leu Gln Ile Ser Asn Leu Lys Asn Asp Asp Thr
    50                  55                  60

Ala Thr Tyr Phe Cys Ala
65                  70

<210> SEQ ID NO 293
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Arg Ser Gln Trp Tyr Leu Asp Val
            100                 105                 110

Trp Gly Gln Gly Thr Leu Val Thr Val Ser Ser
        115                 120

<210> SEQ ID NO 294
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60
```

```
Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Ser Arg Thr Cys Gln Tyr Phe Asp Val
            100                 105                 110

Trp Gly Gln Gly Thr Leu Val Thr Val Ser Ser
        115                 120
```

<210> SEQ ID NO 295
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Tyr Thr Phe Thr Asn Tyr
             20                  25                  30

Gly Met Asn Trp Val Arg Gln Ala Pro Gly Lys Gly Leu Glu Trp Val
         35                  40                  45

Gly Trp Ile Asn Thr Tyr Thr Gly Glu Pro Thr Tyr Ala Ala Asp Phe
     50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Ser Ser His Trp Tyr Phe Asp Val
            100                 105                 110

Trp Gly Gln Gly Thr Leu Val Thr Val Ser Ser
        115                 120
```

<210> SEQ ID NO 296
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Tyr Thr Phe Thr Asn Tyr
             20                  25                  30

Gly Met Asn Trp Val Arg Gln Ala Pro Gly Lys Gly Leu Glu Trp Val
         35                  40                  45

Gly Trp Ile Asn Thr Tyr Thr Gly Glu Pro Thr Tyr Ala Ala Asp Phe
     50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95
```

```
Ala Lys Tyr Pro Tyr Phe Tyr Gly Ser Ser His Trp Tyr Phe Asp Val
                100                 105                 110

Trp Gly Gln Gly Thr Leu Val Thr Val Ser Ser
        115                 120

<210> SEQ ID NO 297
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr His Gly Ser Ser His Trp Tyr Phe Asp Val
                100                 105                 110

Trp Gly Gln Gly Thr Leu Val Thr Val Ser Ser
        115                 120

<210> SEQ ID NO 298
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Asn Gly Ser Ser His Trp Tyr Phe Asp Val
                100                 105                 110

Trp Gly Gln Gly Thr Leu Val Thr Val Ser Ser
        115                 120
```

```
<210> SEQ ID NO 299
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Asn Ser Thr Ser His Trp Tyr Phe Asp Val
            100                 105                 110

Trp Gly Gln Gly Thr Leu Val Thr Val Ser Ser
        115                 120

<210> SEQ ID NO 300
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Ser Gly Thr Ser His Trp Tyr Phe Asp Val
            100                 105                 110

Trp Gly Gln Gly Thr Leu Val Thr Val Ser Ser
        115                 120

<210> SEQ ID NO 301
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 301

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Ser Gly Thr Ser His Trp Tyr Phe Asp Tyr
            100                 105                 110

Trp Gly Gln Gly Thr Leu Val Thr Val Ser Ser
        115                 120

<210> SEQ ID NO 302
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Arg Ser His Trp Tyr Phe Asp Val
            100                 105                 110

Trp Gly Gln Gly Thr Leu Val Thr Val Ser Ser
        115                 120

<210> SEQ ID NO 303
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30
```

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

Ala Lys Tyr Pro Tyr Tyr Tyr Gly Ser Ser His Trp Tyr Phe Asp Val
                100                 105                 110

Trp Gly Gln Gly Thr Leu Val Thr Val Ser Ser
        115                 120

<210> SEQ ID NO 304
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

Ala Lys Tyr Pro Tyr Tyr Tyr Gly Ser Ser Ser Trp Tyr Phe Asp Val
                100                 105                 110

Trp Gly Gln Gly Thr Leu Val Thr Val Ser Ser
        115                 120

<210> SEQ ID NO 305
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Ser Thr Ser His Trp Tyr Phe Asp Val
            100                 105                 110

Trp Gly Gln Gly Thr Leu Val Thr Val Ser Ser
        115                 120

<210> SEQ ID NO 306
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Arg Asp Phe Asn Gly Ser Ser His Trp Tyr Phe Asp Val
            100                 105                 110

Trp Gly Gln Gly Thr Leu Val Thr Val Ser Ser
        115                 120

<210> SEQ ID NO 307
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Ser Tyr Tyr Gly Ser Ser His Trp Tyr Phe Asp Val
            100                 105                 110

Trp Gly Gln Gly Thr Leu Val Thr Val Ser Ser
        115                 120

```
<210> SEQ ID NO 308
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Arg His Tyr Tyr Gly Ser Ser His Cys Tyr Phe Asp Leu
            100                 105                 110

Trp Gly Gln Gly Thr Leu Val Thr Val Ser Ser
        115                 120

<210> SEQ ID NO 309
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Ser His Tyr Tyr Gly Ser Ser His Gln Tyr Phe Asp Leu
            100                 105                 110

Trp Gly Gln Gly Thr Leu Val Thr Val Ser Ser
        115                 120

<210> SEQ ID NO 310
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 310

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Thr Ser His Trp Tyr Phe Asp Val
            100                 105                 110

Trp Gly Gln Gly Thr Leu Val Thr Val Ser Ser
        115                 120

<210> SEQ ID NO 311
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Cys Ala His Ser Arg His Tyr Tyr Gly Ser Ser Pro Gln Tyr Phe Asp
1               5                   10                  15

Val

<210> SEQ ID NO 312
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Cys Ala Lys Tyr Gly Tyr Tyr Gly Ser Ser His Trp Tyr Phe Asp
1               5                   10                  15

Val

<210> SEQ ID NO 313
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Cys Ala Lys Tyr Pro His Tyr Tyr Gly Ala Ser His Trp Tyr Phe Asp
1               5                   10                  15

Val

<210> SEQ ID NO 314
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 314

Cys Ala Lys Tyr Pro His Tyr Tyr Gly Gly Cys His Trp Tyr Phe Asp
1               5                   10                  15

Val

<210> SEQ ID NO 315
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Cys Ala Lys Tyr Pro His Tyr Tyr Gly Gly Ser His Trp Tyr Phe Asp
1               5                   10                  15

Val

<210> SEQ ID NO 316
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Cys Ala Lys Tyr Pro His Tyr Tyr Gly Gly Tyr Asn Gln Tyr Phe Asp
1               5                   10                  15

Val

<210> SEQ ID NO 317
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Cys Ala Lys Tyr Pro His Tyr Tyr Gly Arg Ser His Trp Tyr Phe Asp
1               5                   10                  15

Val

<210> SEQ ID NO 318
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Cys Ala Lys Tyr Pro His Tyr Tyr Gly Arg Ser Gln Trp Tyr Leu Asp
1               5                   10                  15

Val
```

```
<210> SEQ ID NO 319
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Cys Ala Lys Tyr Pro His Tyr Tyr Ser Arg Thr Cys Gln Tyr Phe Asp
1               5                   10                  15

Val

<210> SEQ ID NO 320
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Cys Ala Lys Tyr Pro His Tyr Tyr Ser Ser Ser His Trp Tyr Phe Asp
1               5                   10                  15

Val

<210> SEQ ID NO 321
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Cys Ala Lys Tyr Pro Tyr Phe Tyr Gly Ser Ser His Trp Tyr Phe Asp
1               5                   10                  15

Val

<210> SEQ ID NO 322
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Cys Ala Lys Tyr Pro Tyr Tyr His Gly Ser Ser His Trp Tyr Phe Asp
1               5                   10                  15

Val

<210> SEQ ID NO 323
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Cys Ala Lys Tyr Pro Tyr Tyr Asn Gly Ser Ser His Trp Tyr Phe Asp
1               5                   10                  15

Val
```

```
<210> SEQ ID NO 324
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Cys Ala Lys Tyr Pro Tyr Tyr Asn Ser Thr Ser His Trp Tyr Phe Asp
1               5                   10                  15

Val

<210> SEQ ID NO 325
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Cys Ala Lys Tyr Pro Tyr Tyr Ser Gly Thr Ser His Trp Tyr Phe Asp
1               5                   10                  15

Val

<210> SEQ ID NO 326
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Cys Ala Lys Tyr Pro Tyr Tyr Ser Gly Thr Ser His Trp Tyr Phe Asp
1               5                   10                  15

Tyr

<210> SEQ ID NO 327
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Cys Ala Lys Tyr Pro Tyr Tyr Tyr Gly Arg Ser His Trp Tyr Phe Asp
1               5                   10                  15

Val

<210> SEQ ID NO 328
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Cys Ala Lys Tyr Pro Tyr Tyr Tyr Gly Ser Ser His Trp Tyr Phe Asp
1               5                   10                  15

Val
```

```
<210> SEQ ID NO 329
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Cys Ala Lys Tyr Pro Tyr Tyr Tyr Gly Ser Ser Ser Trp Tyr Phe Asp
1               5                   10                  15

Val

<210> SEQ ID NO 330
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Cys Ala Lys Tyr Pro Tyr Tyr Tyr Ser Thr Ser His Trp Tyr Phe Asp
1               5                   10                  15

Val

<210> SEQ ID NO 331
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Cys Ala Lys Tyr Arg Asp Phe Asn Gly Ser Ser His Trp Tyr Phe Asp
1               5                   10                  15

Val

<210> SEQ ID NO 332
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Cys Ala Lys Tyr Ser Tyr Tyr Tyr Gly Ser Ser His Trp Tyr Phe Asp
1               5                   10                  15

Val

<210> SEQ ID NO 333
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Cys Ala Arg Ala Arg His Tyr Tyr Gly Ser Ser His Cys Tyr Phe Asp
1               5                   10                  15

Leu
```

<210> SEQ ID NO 334
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Cys Ala Arg Asp Ser His Tyr Tyr Gly Ser Ser His Gln Tyr Phe Asp
1               5                   10                  15

Leu

<210> SEQ ID NO 335
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Cys Ala Lys Tyr Pro His Tyr Tyr Gly Thr Ser His Trp Tyr Phe Asp
1               5                   10                  15

Val

<210> SEQ ID NO 336
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Cys Ala Lys Tyr Pro His Tyr Tyr Gly Ser Ser His Trp Tyr Phe Asp
1               5                   10                  15

Val

<210> SEQ ID NO 337
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Cys Ala Lys Tyr Pro Tyr Tyr Tyr Gly Thr Ser His Trp Tyr Phe Asp
1               5                   10                  15

Val

<210> SEQ ID NO 338
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Asp, Glu or Ala
<220> FEATURE:
<221> NAME/KEY: MOD_RES
<222> LOCATION: (2)..(2)
<223> OTHER INFORMATION: Ile or Thr -continued

```
<220> FEATURE:
<221> NAME/KEY: MOD_RES
<222> LOCATION: (3)..(3)
<223> OTHER INFORMATION: Val, Glu, Lys, Arg, Gln or Thr
<220> FEATURE:
<221> NAME/KEY: MOD_RES
<222> LOCATION: (4)..(4)
<223> OTHER INFORMATION: Met or Leu
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (10)..(10)
<223> OTHER INFORMATION: Ser or Thr
<220> FEATURE:
<221> NAME/KEY: MOD_RES
<222> LOCATION: (11)..(11)
<223> OTHER INFORMATION: Leu or Val
<220> FEATURE:
<221> NAME/KEY: MOD_RES
<222> LOCATION: (13)..(13)
<223> OTHER INFORMATION: Ala or Val
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (15)..(15)
<223> OTHER INFORMATION: Pro, Val, Leu, Ala or Ile
<220> FEATURE:
<221> NAME/KEY: MOD_RES
<222> LOCATION: (17)..(17)
<223> OTHER INFORMATION: Glu or Asp
<220> FEATURE:
<221> NAME/KEY: MOD_RES
<222> LOCATION: (18)..(18)
<223> OTHER INFORMATION: Arg or Thr
<220> FEATURE:
<221> NAME/KEY: MOD_RES
<222> LOCATION: (19)..(19)
<223> OTHER INFORMATION: Ala, Val or Ile
<220> FEATURE:
<221> NAME/KEY: MOD_RES
<222> LOCATION: (20)..(20)
<223> OTHER INFORMATION: Thr or Ala
<220> FEATURE:
<221> NAME/KEY: MOD_RES
<222> LOCATION: (22)..(22)
<223> OTHER INFORMATION: Thr, Ser or Ala
<220> FEATURE:
<221> NAME/KEY: MOD_RES
<222> LOCATION: (24)..(24)
<223> OTHER INFORMATION: Ser, Arg, Asn, Lys, His or Gln
<220> FEATURE:
<221> NAME/KEY: MOD_RES
<222> LOCATION: (25)..(25)
<223> OTHER INFORMATION: Ala or Ser
<220> FEATURE:
<221> NAME/KEY: MOD_RES
<222> LOCATION: (27)..(27)
<223> OTHER INFORMATION: Gln or Arg
<220> FEATURE:
<221> NAME/KEY: MOD_RES
<222> LOCATION: (28)..(28)
<223> OTHER INFORMATION: Ser, Asp, Ala or Pro
<220> FEATURE:
<221> NAME/KEY: MOD_RES
<222> LOCATION: (30)..(30)
<223> OTHER INFORMATION: Ser, Gly, Arg, Thr or Tyr
<220> FEATURE:
<221> NAME/KEY: MOD_RES
<222> LOCATION: (31)..(31)
<223> OTHER INFORMATION: Thr, Asn, Ser, Asp or Lys
```

```
<220> FEATURE:
<221> NAME/KEY: MOD_RES
<222> LOCATION: (32)..(32)
<223> OTHER INFORMATION: Tyr or Asp
<220> FEATURE:
<221> NAME/KEY: MOD_RES
<222> LOCATION: (33)..(33)
<223> OTHER INFORMATION: Leu or Ile
<220> FEATURE:
<221> NAME/KEY: MOD_RES
<222> LOCATION: (34)..(34)
<223> OTHER INFORMATION: Ala, Asn or Thr
<220> FEATURE:
<221> NAME/KEY: MOD_RES
<222> LOCATION: (39)..(39)
<223> OTHER INFORMATION: Lys or Ile
<220> FEATURE:
<221> NAME/KEY: MOD_RES
<222> LOCATION: (42)..(42)
<223> OTHER INFORMATION: Gln, Lys, Thr or Ile
<220> FEATURE:
<221> NAME/KEY: MOD_RES
<222> LOCATION: (45)..(45)
<223> OTHER INFORMATION: Arg, Lys, Gln, Asn, His, Ser or Glu
<220> FEATURE:
<221> NAME/KEY: MOD_RES
<222> LOCATION: (46)..(46)
<223> OTHER INFORMATION: Val or Leu
<220> FEATURE:
<221> NAME/KEY: MOD_RES
<222> LOCATION: (48)..(48)
<223> OTHER INFORMATION: Ile or Val
<220> FEATURE:
<221> NAME/KEY: MOD_RES
<222> LOCATION: (50)..(50)
<223> OTHER INFORMATION: Phe, Ala, Gly, Asp or Ser
<220> FEATURE:
<221> NAME/KEY: MOD_RES
<222> LOCATION: (51)..(51)
<223> OTHER INFORMATION: Ala or Thr
<220> FEATURE:
<221> NAME/KEY: MOD_RES
<222> LOCATION: (52)..(52)
<223> OTHER INFORMATION: Ser or Thr
<220> FEATURE:
<221> NAME/KEY: MOD_RES
<222> LOCATION: (53)..(53)
<223> OTHER INFORMATION: Asn, Ser, Arg or Thr
<220> FEATURE:
<221> NAME/KEY: MOD_RES
<222> LOCATION: (55)..(55)
<223> OTHER INFORMATION: Ala, His or Gln
<220> FEATURE:
<221> NAME/KEY: MOD_RES
<222> LOCATION: (56)..(56)
<223> OTHER INFORMATION: Ser or Gly
<220> FEATURE:
<221> NAME/KEY: MOD_RES
<222> LOCATION: (59)..(59)
<223> OTHER INFORMATION: Pro or Thr
<220> FEATURE:
<221> NAME/KEY: MOD_RES
<222> LOCATION: (60)..(60)
<223> OTHER INFORMATION: Ser, Asn, Asp, Gly or Tyr
<220> FEATURE:
<221> NAME/KEY: MOD_RES
<222> LOCATION: (65)..(65)
<223> OTHER INFORMATION: Ser or Thr
<220> FEATURE:
<221> NAME/KEY: MOD_RES
<222> LOCATION: (66)..(66)
<223> OTHER INFORMATION: Gly or Arg
<220> FEATURE:
<221> NAME/KEY: MOD_RES
<222> LOCATION: (72)..(72)
<223> OTHER INFORMATION: Thr or Ala
```

```
<220> FEATURE:
<221> NAME/KEY: MOD_RES
<222> LOCATION: (76)..(77)
<223> OTHER INFORMATION: Ser or Arg
<220> FEATURE:
<221> NAME/KEY: MOD_RES
<222> LOCATION: (80)..(80)
<223> OTHER INFORMATION: Pro or Ala
<220> FEATURE:
<221> NAME/KEY: MOD_RES
<222> LOCATION: (81)..(81)
<223> OTHER INFORMATION: Glu or Asp
<220> FEATURE:
<221> NAME/KEY: MOD_RES
<222> LOCATION: (83)..(83)
<223> OTHER INFORMATION: Phe, Val or Ser
<220> FEATURE:
<221> NAME/KEY: MOD_RES
<222> LOCATION: (85)..(85)
<223> OTHER INFORMATION: Val, Thr, Ile, Ala or Ser
<220> FEATURE:
<221> NAME/KEY: MOD_RES
<222> LOCATION: (91)..(91)
<223> OTHER INFORMATION: Tyr or Ser
<220> FEATURE:
<221> NAME/KEY: MOD_RES
<222> LOCATION: (92)..(92)
<223> OTHER INFORMATION: Ser, Tyr or Asn
<220> FEATURE:
<221> NAME/KEY: MOD_RES
<222> LOCATION: (93)..(93)
<223> OTHER INFORMATION: Ser or Thr
<220> FEATURE:
<221> NAME/KEY: MOD_RES
<222> LOCATION: (94)..(94)
<223> OTHER INFORMATION: Thr, Val, Ala, Pro, Lys, Gly, Ser or Ile
<220> FEATURE:
<221> NAME/KEY: MOD_RES
<222> LOCATION: (96)..(96)
<223> OTHER INFORMATION: Trp or Tyr
<220> FEATURE:
<221> NAME/KEY: MOD_RES
<222> LOCATION: (100)..(100)
<223> OTHER INFORMATION: Gln or Gly
<220> FEATURE:
<221> NAME/KEY: MOD_RES
<222> LOCATION: (104)..(104)
<223> OTHER INFORMATION: Val or Leu
<220> FEATURE:
<221> NAME/KEY: MOD_RES
<222> LOCATION: (105)..(105)
<223> OTHER INFORMATION: Glu, Asp or Ala

<400> SEQUENCE: 338

Xaa Xaa Xaa Xaa Thr Gln Xaa Pro Ser Xaa Xaa Ser Xaa Xaa Xaa Gly
1               5                   10                  15

Xaa Xaa Xaa Xaa Ile Xaa Cys Xaa Xaa Ser Xaa Xaa Ile Xaa Xaa Xaa
                20                  25                  30

Xaa Xaa Trp Tyr Gln Gln Xaa Pro Gly Xaa Ala Pro Xaa Xaa Leu Xaa
            35                  40                  45

Tyr Xaa Xaa Xaa Xaa Leu Xaa Xaa Gly Val Xaa Xaa Arg Phe Ser Gly
    50                  55                  60

Xaa Xaa Ser Gly Thr Asp Phe Xaa Leu Thr Ile Xaa Xaa Leu Gln Xaa
65                  70                  75                  80

Xaa Asp Xaa Ala Xaa Tyr Tyr Cys Gln Gln Xaa Xaa Xaa Xaa Pro Xaa
                85                  90                  95

Thr Phe Gly Xaa Gly Thr Lys Xaa Xaa Ile Lys
                100                 105
```

```
<210> SEQ ID NO 339
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln, Leu or Asn
<220> FEATURE:
<221> NAME/KEY: MOD_RES
<222> LOCATION: (2)..(2)
<223> OTHER INFORMATION: Pro, Ala, Phe or Ser
<220> FEATURE:
<221> NAME/KEY: MOD_RES
<222> LOCATION: (3)..(3)
<223> OTHER INFORMATION: Val or Met
<220> FEATURE:
<221> NAME/KEY: MOD_RES
<222> LOCATION: (10)..(10)
<223> OTHER INFORMATION: Ala or Thr
<220> FEATURE:
<221> NAME/KEY: MOD_RES
<222> LOCATION: (12)..(12)
<223> OTHER INFORMATION: Gly or Ala
<220> FEATURE:
<221> NAME/KEY: MOD_RES
<222> LOCATION: (17)..(17)
<223> OTHER INFORMATION: Arg or Ser
<220> FEATURE:
<221> NAME/KEY: MOD_RES
<222> LOCATION: (25)..(25)
<223> OTHER INFORMATION: Ser or Thr
<220> FEATURE:
<221> NAME/KEY: MOD_RES
<222> LOCATION: (26)..(26)
<223> OTHER INFORMATION: Ser, Thr, Tyr or Asn
<220> FEATURE:
<221> NAME/KEY: MOD_RES
<222> LOCATION: (29)..(29)
<223> OTHER INFORMATION: Ile or Val
<220> FEATURE:
<221> NAME/KEY: MOD_RES
<222> LOCATION: (31)..(31)
<223> OTHER INFORMATION: Ser or Arg
<220> FEATURE:
<221> NAME/KEY: MOD_RES
<222> LOCATION: (33)..(33)
<223> OTHER INFORMATION: Ser, Pro, Asn, Ala or Thr
<220> FEATURE:
<221> NAME/KEY: MOD_RES
<222> LOCATION: (35)..(35)
<223> OTHER INFORMATION: Asn, Thr or Tyr
<220> FEATURE:
<221> NAME/KEY: MOD_RES
<222> LOCATION: (40)..(40)
<223> OTHER INFORMATION: Leu or Phe
<220> FEATURE:
<221> NAME/KEY: MOD_RES
<222> LOCATION: (43)..(43)
<223> OTHER INFORMATION: Thr or Ala
<220> FEATURE:
<221> NAME/KEY: MOD_RES
<222> LOCATION: (47)..(47)
<223> OTHER INFORMATION: Val, Leu or Phe
<220> FEATURE:
<221> NAME/KEY: MOD_RES
<222> LOCATION: (49)..(49)
<223> OTHER INFORMATION: Met or Ile
<220> FEATURE:
<221> NAME/KEY: MOD_RES
<222> LOCATION: (51)..(51)
<223> OTHER INFORMATION: Gly, Thr or Ser
<220> FEATURE:
<221> NAME/KEY: MOD_RES
<222> LOCATION: (53)..(53)
<223> OTHER INFORMATION: Asn or Asp
```

```
<220> FEATURE:
<221> NAME/KEY: MOD_RES
<222> LOCATION: (54)..(54)
<223> OTHER INFORMATION: Gln or Glu
<220> FEATURE:
<221> NAME/KEY: MOD_RES
<222> LOCATION: (61)..(61)
<223> OTHER INFORMATION: Asp or Glu
<220> FEATURE:
<221> NAME/KEY: MOD_RES
<222> LOCATION: (63)..(63)
<223> OTHER INFORMATION: Phe or Leu
<220> FEATURE:
<221> NAME/KEY: MOD_RES
<222> LOCATION: (67)..(67)
<223> OTHER INFORMATION: Lys or Arg
<220> FEATURE:
<221> NAME/KEY: MOD_RES
<222> LOCATION: (69)..(69)
<223> OTHER INFORMATION: Gly or Ala
<220> FEATURE:
<221> NAME/KEY: MOD_RES
<222> LOCATION: (80)..(80)
<223> OTHER INFORMATION: Gln, Leu or Arg
<220> FEATURE:
<221> NAME/KEY: MOD_RES
<222> LOCATION: (90)..(90)
<223> OTHER INFORMATION: Ala or Gly
<220> FEATURE:
<221> NAME/KEY: MOD_RES
<222> LOCATION: (91)..(91)
<223> OTHER INFORMATION: Ala, Ser or Thr
<220> FEATURE:
<221> NAME/KEY: MOD_RES
<222> LOCATION: (97)..(97)
<223> OTHER INFORMATION: Asn, Ser or Thr
<220> FEATURE:
<221> NAME/KEY: MOD_RES
<222> LOCATION: (103)..(103)
<223> OTHER INFORMATION: Thr or Ala
<220> FEATURE:
<221> NAME/KEY: MOD_RES
<222> LOCATION: (106)..(106)
<223> OTHER INFORMATION: Lys or Gln

<400> SEQUENCE: 339

Xaa Xaa Xaa Leu Thr Gln Pro Pro Ser Xaa Ser Xaa Thr Pro Gly Gln
1               5                   10                  15

Xaa Val Thr Ile Ser Cys Ser Gly Xaa Xaa Ser Asn Xaa Gly Xaa Asn
            20                  25                  30

Xaa Val Xaa Trp Tyr Gln Gln Xaa Pro Gly Xaa Ala Pro Lys Xaa Leu
        35                  40                  45

Xaa Tyr Xaa Asn Xaa Xaa Arg Pro Ser Gly Val Pro Xaa Arg Xaa Ser
    50                  55                  60

Gly Ser Xaa Ser Xaa Thr Ser Ala Ser Leu Ala Ile Ser Gly Leu Xaa
65                  70                  75                  80

Ser Glu Asp Glu Ala Asp Tyr Tyr Cys Xaa Xaa Trp Asp Asp Ser Leu
                85                  90                  95

Xaa Gly Tyr Val Phe Gly Xaa Gly Thr Xaa Leu Thr Val Leu
            100                 105                 110

<210> SEQ ID NO 340
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (1)..(1)
<223> OTHER INFORMATION: Glu or Gln
<220> FEATURE:
<221> NAME/KEY: MOD_RES
<222> LOCATION: (2)..(2)
<223> OTHER INFORMATION: Val or Gly
<220> FEATURE:
<221> NAME/KEY: MOD_RES
<222> LOCATION: (6)..(6)
<223> OTHER INFORMATION: Gln or Glu
<220> FEATURE:
<221> NAME/KEY: MOD_RES
<222> LOCATION: (11)..(11)
<223> OTHER INFORMATION: Val or Leu
<220> FEATURE:
<221> NAME/KEY: MOD_RES
<222> LOCATION: (17)..(17)
<223> OTHER INFORMATION: Ser or Thr
<220> FEATURE:
<221> NAME/KEY: MOD_RES
<222> LOCATION: (21)..(21)
<223> OTHER INFORMATION: Ser, Thr or Arg
<220> FEATURE:
<221> NAME/KEY: MOD_RES
<222> LOCATION: (24)..(24)
<223> OTHER INFORMATION: Ala or Val
<220> FEATURE:
<221> NAME/KEY: MOD_RES
<222> LOCATION: (27)..(27)
<223> OTHER INFORMATION: Tyr or Phe
<220> FEATURE:
<221> NAME/KEY: MOD_RES
<222> LOCATION: (28)..(28)
<223> OTHER INFORMATION: Thr, Asp, Asn, Ser or Ala
<220> FEATURE:
<221> NAME/KEY: MOD_RES
<222> LOCATION: (29)..(29)
<223> OTHER INFORMATION: Phe or Leu
<220> FEATURE:
<221> NAME/KEY: MOD_RES
<222> LOCATION: (30)..(30)
<223> OTHER INFORMATION: Thr, Asp, Tyr, Ala, Ser or Asn
<220> FEATURE:
<221> NAME/KEY: MOD_RES
<222> LOCATION: (31)..(31)
<223> OTHER INFORMATION: Asn, His or Ser
<220> FEATURE:
<221> NAME/KEY: MOD_RES
<222> LOCATION: (32)..(32)
<223> OTHER INFORMATION: Tyr or Phe
<220> FEATURE:
<221> NAME/KEY: MOD_RES
<222> LOCATION: (34)..(34)
<223> OTHER INFORMATION: Met, Leu, Ile or Val
<220> FEATURE:
<221> NAME/KEY: MOD_RES
<222> LOCATION: (37)..(37)
<223> OTHER INFORMATION: Ile, Val or Leu
<220> FEATURE:
<221> NAME/KEY: MOD_RES
<222> LOCATION: (45)..(45)
<223> OTHER INFORMATION: Leu or Pro
<220> FEATURE:
<221> NAME/KEY: MOD_RES
<222> LOCATION: (51)..(51)
<223> OTHER INFORMATION: Ile or Val
<220> FEATURE:
<221> NAME/KEY: MOD_RES
<222> LOCATION: (54)..(54)
<223> OTHER INFORMATION: Tyr or Asn
<220> FEATURE:
<221> NAME/KEY: MOD_RES
<222> LOCATION: (55)..(55)
<223> OTHER INFORMATION: Thr or Asn
```

```
<220> FEATURE:
<221> NAME/KEY: MOD_RES
<222> LOCATION: (57)..(57)
<223> OTHER INFORMATION: Glu or Ala
<220> FEATURE:
<221> NAME/KEY: MOD_RES
<222> LOCATION: (58)..(58)
<223> OTHER INFORMATION: Pro, Thr or Ser
<220> FEATURE:
<221> NAME/KEY: MOD_RES
<222> LOCATION: (61)..(61)
<223> OTHER INFORMATION: Ala or Val
<220> FEATURE:
<221> NAME/KEY: MOD_RES
<222> LOCATION: (62)..(62)
<223> OTHER INFORMATION: Ala, His, Gln, Pro, Asp or Glu
<220> FEATURE:
<221> NAME/KEY: MOD_RES
<222> LOCATION: (63)..(63)
<223> OTHER INFORMATION: Asp or Glu
<220> FEATURE:
<221> NAME/KEY: MOD_RES
<222> LOCATION: (65)..(65)
<223> OTHER INFORMATION: Lys or Thr
<220> FEATURE:
<221> NAME/KEY: MOD_RES
<222> LOCATION: (68)..(68)
<223> OTHER INFORMATION: Val, Phe or Leu
<220> FEATURE:
<221> NAME/KEY: MOD_RES
<222> LOCATION: (70)..(70)
<223> OTHER INFORMATION: Phe or Ile
<220> FEATURE:
<221> NAME/KEY: MOD_RES
<222> LOCATION: (72)..(72)
<223> OTHER INFORMATION: Leu or Arg
<220> FEATURE:
<221> NAME/KEY: MOD_RES
<222> LOCATION: (73)..(73)
<223> OTHER INFORMATION: Asp or Asn
<220> FEATURE:
<221> NAME/KEY: MOD_RES
<222> LOCATION: (74)..(74)
<223> OTHER INFORMATION: Thr or Asn
<220> FEATURE:
<221> NAME/KEY: MOD_RES
<222> LOCATION: (77)..(77)
<223> OTHER INFORMATION: Ser or Asn
<220> FEATURE:
<221> NAME/KEY: MOD_RES
<222> LOCATION: (78)..(78)
<223> OTHER INFORMATION: Thr, Gln, Pro or Lys
<220> FEATURE:
<221> NAME/KEY: MOD_RES
<222> LOCATION: (79)..(79)
<223> OTHER INFORMATION: Ala, Val or Pro
<220> FEATURE:
<221> NAME/KEY: MOD_RES
<222> LOCATION: (83)..(83)
<223> OTHER INFORMATION: Leu or Met
<220> FEATURE:
<221> NAME/KEY: MOD_RES
<222> LOCATION: (98)..(98)
<223> OTHER INFORMATION: Lys or Arg
<220> FEATURE:
<221> NAME/KEY: MOD_RES
<222> LOCATION: (101)..(101)
<223> OTHER INFORMATION: His or Tyr
<220> FEATURE:
<221> NAME/KEY: MOD_RES
<222> LOCATION: (105)..(105)
<223> OTHER INFORMATION: Ser, Arg or Thr
<220> FEATURE:
<221> NAME/KEY: MOD_RES
<222> LOCATION: (114)..(114)
<223> OTHER INFORMATION: Gly or Ala
```

```
<400> SEQUENCE: 340

Xaa Xaa Gln Leu Val Xaa Ser Gly Gly Gly Xaa Val Gln Pro Gly Gly
1               5                   10                  15

Xaa Leu Arg Leu Xaa Cys Ala Xaa Ser Gly Xaa Xaa Xaa Xaa Xaa Xaa
            20                  25                  30

Gly Xaa Asn Trp Xaa Arg Gln Ala Pro Gly Lys Gly Xaa Glu Trp Val
        35                  40                  45

Gly Trp Xaa Asn Thr Xaa Xaa Gly Xaa Xaa Thr Tyr Xaa Xaa Xaa Phe
    50                  55                  60

Xaa Arg Arg Xaa Thr Xaa Ser Xaa Xaa Ser Lys Xaa Xaa Xaa Xaa Tyr
65                  70                  75                  80

Leu Gln Xaa Asn Ser Leu Arg Ala Glu Asp Thr Ala Val Tyr Tyr Cys
            85                  90                  95

Ala Xaa Tyr Pro Xaa Tyr Tyr Gly Xaa Ser His Trp Tyr Phe Asp Val
            100                 105                 110

Trp Xaa Gln Gly Thr Leu Val Thr Val
        115                 120

<210> SEQ ID NO 341
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Val
<220> FEATURE:
<221> NAME/KEY: MOD_RES
<222> LOCATION: (5)..(5)
<223> OTHER INFORMATION: Tyr or Asn
<220> FEATURE:
<221> NAME/KEY: MOD_RES
<222> LOCATION: (6)..(6)
<223> OTHER INFORMATION: Thr or Asn
<220> FEATURE:
<221> NAME/KEY: MOD_RES
<222> LOCATION: (9)..(9)
<223> OTHER INFORMATION: Pro, Thr or Ser
<220> FEATURE:
<221> NAME/KEY: MOD_RES
<222> LOCATION: (12)..(12)
<223> OTHER INFORMATION: Ala or Val
<220> FEATURE:
<221> NAME/KEY: MOD_RES
<222> LOCATION: (13)..(13)
<223> OTHER INFORMATION: Ala, Gln, Pro, His, Asp or Glu
<220> FEATURE:
<221> NAME/KEY: MOD_RES
<222> LOCATION: (14)..(14)
<223> OTHER INFORMATION: Asp or Glu
<220> FEATURE:
<221> NAME/KEY: MOD_RES
<222> LOCATION: (16)..(16)
<223> OTHER INFORMATION: Lys or Thr

<400> SEQUENCE: 341

Trp Xaa Asn Thr Xaa Xaa Gly Glu Xaa Thr Tyr Xaa Xaa Xaa Phe Xaa
1               5                   10                  15
Arg

<210> SEQ ID NO 342
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Tyr or His

<400> SEQUENCE: 342

Lys Tyr Pro Xaa Tyr Tyr Gly Arg Ser His Trp Tyr Phe Asp Val
1               5                   10                  15

<210> SEQ ID NO 343
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Gln
<220> FEATURE:
<221> NAME/KEY: MOD_RES
<222> LOCATION: (6)..(6)
<223> OTHER INFORMATION: Gln or Glu
<220> FEATURE:
<221> NAME/KEY: MOD_RES
<222> LOCATION: (11)..(11)
<223> OTHER INFORMATION: Val or Leu
<220> FEATURE:
<221> NAME/KEY: MOD_RES
<222> LOCATION: (17)..(17)
<223> OTHER INFORMATION: Ser or Thr
<220> FEATURE:
<221> NAME/KEY: MOD_RES
<222> LOCATION: (21)..(21)
<223> OTHER INFORMATION: Ser, Thr or Arg
<220> FEATURE:
<221> NAME/KEY: MOD_RES
<222> LOCATION: (24)..(24)
<223> OTHER INFORMATION: Ala or Val

<400> SEQUENCE: 343

Xaa Val Gln Leu Val Xaa Ser Gly Gly Gly Xaa Val Gln Pro Gly Gly
1               5                   10                  15

Xaa Leu Arg Leu Xaa Cys Ala Xaa Ser
            20                  25

<210> SEQ ID NO 344
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Val

<400> SEQUENCE: 344

Trp Xaa Arg Gln Ala Pro Gly Lys Gly Leu Glu Trp Val Gly
1               5                   10

<210> SEQ ID NO 345
<211> LENGTH: 31
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Phe or Val
<220> FEATURE:
<221> NAME/KEY: MOD_RES
<222> LOCATION: (4)..(4)
<223> OTHER INFORMATION: Phe or Ile
<220> FEATURE:
<221> NAME/KEY: MOD_RES
<222> LOCATION: (6)..(6)
<223> OTHER INFORMATION: Leu or Arg
<220> FEATURE:
<221> NAME/KEY: MOD_RES
<222> LOCATION: (8)..(8)
<223> OTHER INFORMATION: Thr or Asn
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (12)..(12)
<223> OTHER INFORMATION: Thr, Gln or Lys
<220> FEATURE:
<221> NAME/KEY: MOD_RES
<222> LOCATION: (13)..(13)
<223> OTHER INFORMATION: Ala or Val
<220> FEATURE:
<221> NAME/KEY: MOD_RES
<222> LOCATION: (17)..(17)
<223> OTHER INFORMATION: Met or Leu

<400> SEQUENCE: 345

Arg Xaa Thr Xaa Ser Xaa Asp Xaa Ser Lys Xaa Xaa Xaa Tyr Leu Gln
1               5                   10                  15

Xaa Asn Ser Leu Arg Ala Glu Asp Thr Ala Val Tyr Tyr Cys Ala
            20                  25                  30

<210> SEQ ID NO 346
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly or Ala

<400> SEQUENCE: 346

Trp Xaa Gln Gly Thr Leu Val Thr Val Ser Ser
1               5                   10

<210> SEQ ID NO 347
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Gln
<220> FEATURE:
<221> NAME/KEY: MOD_RES
<222> LOCATION: (2)..(2)
<223> OTHER INFORMATION: Val or Gly
```

```
<220> FEATURE:
<221> NAME/KEY: MOD_RES
<222> LOCATION: (6)..(6)
<223> OTHER INFORMATION: Gln or Glu
<220> FEATURE:
<221> NAME/KEY: MOD_RES
<222> LOCATION: (11)..(11)
<223> OTHER INFORMATION: Val or Leu
<220> FEATURE:
<221> NAME/KEY: MOD_RES
<222> LOCATION: (17)..(17)
<223> OTHER INFORMATION: Ser or Thr
<220> FEATURE:
<221> NAME/KEY: MOD_RES
<222> LOCATION: (21)..(21)
<223> OTHER INFORMATION: Ser, Thr or Arg
<220> FEATURE:
<221> NAME/KEY: MOD_RES
<222> LOCATION: (24)..(24)
<223> OTHER INFORMATION: Ala or Val
<220> FEATURE:
<221> NAME/KEY: MOD_RES
<222> LOCATION: (27)..(27)
<223> OTHER INFORMATION: Tyr or Phe
<220> FEATURE:
<221> NAME/KEY: MOD_RES
<222> LOCATION: (28)..(28)
<223> OTHER INFORMATION: Thr, Asp, Asn, Ser or Ala
<220> FEATURE:
<221> NAME/KEY: MOD_RES
<222> LOCATION: (29)..(29)
<223> OTHER INFORMATION: Phe or Leu
<220> FEATURE:
<221> NAME/KEY: MOD_RES
<222> LOCATION: (30)..(30)
<223> OTHER INFORMATION: Thr, Asp, Tyr, Ala, Ser or Asn
<220> FEATURE:
<221> NAME/KEY: MOD_RES
<222> LOCATION: (31)..(31)
<223> OTHER INFORMATION: Asn, His or Ser
<220> FEATURE:
<221> NAME/KEY: MOD_RES
<222> LOCATION: (32)..(32)
<223> OTHER INFORMATION: Tyr or Phe
<220> FEATURE:
<221> NAME/KEY: MOD_RES
<222> LOCATION: (34)..(34)
<223> OTHER INFORMATION: Met, Leu, Ile or Val
<220> FEATURE:
<221> NAME/KEY: MOD_RES
<222> LOCATION: (37)..(37)
<223> OTHER INFORMATION: Ile, Val or Leu
<220> FEATURE:
<221> NAME/KEY: MOD_RES
<222> LOCATION: (45)..(45)
<223> OTHER INFORMATION: Leu or Pro
<220> FEATURE:
<221> NAME/KEY: MOD_RES
<222> LOCATION: (51)..(51)
<223> OTHER INFORMATION: Ile or Val
<220> FEATURE:
<221> NAME/KEY: MOD_RES
<222> LOCATION: (54)..(54)
<223> OTHER INFORMATION: Tyr or Asn
<220> FEATURE:
<221> NAME/KEY: MOD_RES
<222> LOCATION: (55)..(55)
<223> OTHER INFORMATION: Thr or Asn
<220> FEATURE:
<221> NAME/KEY: MOD_RES
<222> LOCATION: (57)..(57)
<223> OTHER INFORMATION: Glu or Ala
<220> FEATURE:
<221> NAME/KEY: MOD_RES
<222> LOCATION: (58)..(58)
<223> OTHER INFORMATION: Pro, Thr or Ser
```

```
<220> FEATURE:
<221> NAME/KEY: MOD_RES
<222> LOCATION: (61)..(61)
<223> OTHER INFORMATION: Ala or Val
<220> FEATURE:
<221> NAME/KEY: MOD_RES
<222> LOCATION: (62)..(62)
<223> OTHER INFORMATION: Ala, His, Gln, Pro, Asp or Glu
<220> FEATURE:
<221> NAME/KEY: MOD_RES
<222> LOCATION: (63)..(63)
<223> OTHER INFORMATION: Asp or Glu
<220> FEATURE:
<221> NAME/KEY: MOD_RES
<222> LOCATION: (65)..(65)
<223> OTHER INFORMATION: Lys or Thr
<220> FEATURE:
<221> NAME/KEY: MOD_RES
<222> LOCATION: (68)..(68)
<223> OTHER INFORMATION: Val, Phe or Leu
<220> FEATURE:
<221> NAME/KEY: MOD_RES
<222> LOCATION: (70)..(70)
<223> OTHER INFORMATION: Phe or Ile
<220> FEATURE:
<221> NAME/KEY: MOD_RES
<222> LOCATION: (72)..(72)
<223> OTHER INFORMATION: Leu or Arg
<220> FEATURE:
<221> NAME/KEY: MOD_RES
<222> LOCATION: (73)..(73)
<223> OTHER INFORMATION: Asp or Asn
<220> FEATURE:
<221> NAME/KEY: MOD_RES
<222> LOCATION: (74)..(74)
<223> OTHER INFORMATION: Thr or Asn
<220> FEATURE:
<221> NAME/KEY: MOD_RES
<222> LOCATION: (77)..(77)
<223> OTHER INFORMATION: Ser or Asn
<220> FEATURE:
<221> NAME/KEY: MOD_RES
<222> LOCATION: (78)..(78)
<223> OTHER INFORMATION: Thr, Gln, Pro or Lys
<220> FEATURE:
<221> NAME/KEY: MOD_RES
<222> LOCATION: (79)..(79)
<223> OTHER INFORMATION: Ala, Val or Pro
<220> FEATURE:
<221> NAME/KEY: MOD_RES
<222> LOCATION: (83)..(83)
<223> OTHER INFORMATION: Leu or Met
<220> FEATURE:
<221> NAME/KEY: MOD_RES
<222> LOCATION: (98)..(98)
<223> OTHER INFORMATION: Lys, Arg or His
<220> FEATURE:
<221> NAME/KEY: MOD_RES
<222> LOCATION: (99)..(99)
<223> OTHER INFORMATION: Tyr, Ala, Asp or Ser
<220> FEATURE:
<221> NAME/KEY: MOD_RES
<222> LOCATION: (100)..(100)
<223> OTHER INFORMATION: Pro, Arg, Ser or Gly
<220> FEATURE:
<221> NAME/KEY: MOD_RES
<222> LOCATION: (101)..(101)
<223> OTHER INFORMATION: Tyr, His or Asp
<220> FEATURE:
<221> NAME/KEY: MOD_RES
<222> LOCATION: (102)..(102)
<223> OTHER INFORMATION: Tyr or Phe
<220> FEATURE:
<221> NAME/KEY: MOD_RES
<222> LOCATION: (103)..(103)
<223> OTHER INFORMATION: Tyr, Asn, Ser or His
```

```
<220> FEATURE:
<221> NAME/KEY: MOD_RES
<222> LOCATION: (104)..(104)
<223> OTHER INFORMATION: Gly or Ser
<220> FEATURE:
<221> NAME/KEY: MOD_RES
<222> LOCATION: (105)..(105)
<223> OTHER INFORMATION: Ser, Thr, Arg, Gly or Ala
<220> FEATURE:
<221> NAME/KEY: MOD_RES
<222> LOCATION: (106)..(106)
<223> OTHER INFORMATION: Ser, Tyr, Cys or Thr
<220> FEATURE:
<221> NAME/KEY: MOD_RES
<222> LOCATION: (107)..(107)
<223> OTHER INFORMATION: His, Pro, Cys, Asn, Gln or Ser
<220> FEATURE:
<221> NAME/KEY: MOD_RES
<222> LOCATION: (108)..(108)
<223> OTHER INFORMATION: Trp, Gln or Cys
<220> FEATURE:
<221> NAME/KEY: MOD_RES
<222> LOCATION: (110)..(110)
<223> OTHER INFORMATION: Phe or Leu
<220> FEATURE:
<221> NAME/KEY: MOD_RES
<222> LOCATION: (112)..(112)
<223> OTHER INFORMATION: Val, Leu or Tyr
<220> FEATURE:
<221> NAME/KEY: MOD_RES
<222> LOCATION: (114)..(114)
<223> OTHER INFORMATION: Gly or Ala

<400> SEQUENCE: 347

Xaa Xaa Gln Leu Val Xaa Ser Gly Gly Gly Xaa Val Gln Pro Gly Gly
1               5                   10                  15

Xaa Leu Arg Leu Xaa Cys Ala Xaa Ser Gly Xaa Xaa Xaa Xaa Xaa Xaa
            20                  25                  30

Gly Xaa Asn Trp Xaa Arg Gln Ala Pro Gly Lys Gly Xaa Glu Trp Val
        35                  40                  45

Gly Trp Xaa Asn Thr Xaa Xaa Gly Xaa Xaa Thr Tyr Xaa Xaa Xaa Phe
    50                  55                  60

Xaa Arg Arg Xaa Thr Xaa Ser Xaa Xaa Xaa Ser Lys Xaa Xaa Xaa Tyr
65                  70                  75                  80

Leu Gln Xaa Asn Ser Leu Arg Ala Glu Asp Thr Ala Val Tyr Tyr Cys
                85                  90                  95

Ala Xaa Xaa Xaa Xaa Xaa Xaa Xaa Xaa Xaa Xaa Tyr Xaa Asp Xaa
            100                 105                 110

Trp Xaa Gln Gly Thr Leu Val Thr Val
        115                 120

<210> SEQ ID NO 348
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Cys Ala Lys Tyr Pro His Tyr Tyr Gly Ser Ser His Trp Tyr Phe Asp
1               5                   10                  15

Val Trp Gly
```

```
<210> SEQ ID NO 349
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Gln, Val, Glu or Leu
<220> FEATURE:
<221> NAME/KEY: MOD_RES
<222> LOCATION: (4)..(4)
<223> OTHER INFORMATION: Met or Leu
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (8)..(8)
<223> OTHER INFORMATION: Pro, His or Thr
<220> FEATURE:
<221> NAME/KEY: MOD_RES
<222> LOCATION: (9)..(9)
<223> OTHER INFORMATION: Ser or Lys
<220> FEATURE:
<221> NAME/KEY: MOD_RES
<222> LOCATION: (10)..(10)
<223> OTHER INFORMATION: Ser or Thr
<220> FEATURE:
<221> NAME/KEY: MOD_RES
<222> LOCATION: (11)..(11)
<223> OTHER INFORMATION: Leu or Met
<220> FEATURE:
<221> NAME/KEY: MOD_RES
<222> LOCATION: (13)..(13)
<223> OTHER INFORMATION: Ala, Thr or Val
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (15)..(15)
<223> OTHER INFORMATION: Val, Ala, Leu or Pro
<220> FEATURE:
<221> NAME/KEY: MOD_RES
<222> LOCATION: (17)..(17)
<223> OTHER INFORMATION: Asp or Glu
<220> FEATURE:
<221> NAME/KEY: MOD_RES
<222> LOCATION: (19)..(19)
<223> OTHER INFORMATION: Val or Ala
<220> FEATURE:
<221> NAME/KEY: MOD_RES
<222> LOCATION: (20)..(20)
<223> OTHER INFORMATION: Thr, Ser or Ile
<220> FEATURE:
<221> NAME/KEY: MOD_RES
<222> LOCATION: (22)..(22)
<223> OTHER INFORMATION: Thr or Ser
<220> FEATURE:
<221> NAME/KEY: MOD_RES
<222> LOCATION: (24)..(24)
<223> OTHER INFORMATION: Ser, Arg, His, Lys, Asn or Gln
<220> FEATURE:
<221> NAME/KEY: MOD_RES
<222> LOCATION: (29)..(29)
<223> OTHER INFORMATION: Ile or Val
<220> FEATURE:
<221> NAME/KEY: MOD_RES
<222> LOCATION: (30)..(30)
<223> OTHER INFORMATION: Ser or Gly
<220> FEATURE:
<221> NAME/KEY: MOD_RES
<222> LOCATION: (31)..(31)
<223> OTHER INFORMATION: Asn, Ser or Thr
```

```
<220> FEATURE:
<221> NAME/KEY: MOD_RES
<222> LOCATION: (32)..(32)
<223> OTHER INFORMATION: Tyr or Ala
<220> FEATURE:
<221> NAME/KEY: MOD_RES
<222> LOCATION: (33)..(33)
<223> OTHER INFORMATION: Leu or Val
<220> FEATURE:
<221> NAME/KEY: MOD_RES
<222> LOCATION: (34)..(34)
<223> OTHER INFORMATION: Asn or Ala
<220> FEATURE:
<221> NAME/KEY: MOD_RES
<222> LOCATION: (41)..(41)
<223> OTHER INFORMATION: Gly or Asp
<220> FEATURE:
<221> NAME/KEY: MOD_RES
<222> LOCATION: (42)..(42)
<223> OTHER INFORMATION: Lys, His or Gln
<220> FEATURE:
<221> NAME/KEY: MOD_RES
<222> LOCATION: (43)..(43)
<223> OTHER INFORMATION: Ala, Ser or Thr
<220> FEATURE:
<221> NAME/KEY: MOD_RES
<222> LOCATION: (44)..(44)
<223> OTHER INFORMATION: Pro or Val
<220> FEATURE:
<221> NAME/KEY: MOD_RES
<222> LOCATION: (45)..(45)
<223> OTHER INFORMATION: Lys, Arg, His, Asn, Gln or Ser
<220> FEATURE:
<221> NAME/KEY: MOD_RES
<222> LOCATION: (46)..(46)
<223> OTHER INFORMATION: Val or Leu
<220> FEATURE:
<221> NAME/KEY: MOD_RES
<222> LOCATION: (50)..(50)
<223> OTHER INFORMATION: Phe, Ala, Cys, Asp, Gly, Ser or Tyr
<220> FEATURE:
<221> NAME/KEY: MOD_RES
<222> LOCATION: (51)..(51)
<223> OTHER INFORMATION: Thr or Ala
<220> FEATURE:
<221> NAME/KEY: MOD_RES
<222> LOCATION: (53)..(53)
<223> OTHER INFORMATION: Ser or Phe
<220> FEATURE:
<221> NAME/KEY: MOD_RES
<222> LOCATION: (54)..(54)
<223> OTHER INFORMATION: Leu or Arg
<220> FEATURE:
<221> NAME/KEY: MOD_RES
<222> LOCATION: (55)..(55)
<223> OTHER INFORMATION: His or Tyr
<220> FEATURE:
<221> NAME/KEY: MOD_RES
<222> LOCATION: (56)..(56)
<223> OTHER INFORMATION: Ser or Thr
<220> FEATURE:
<221> NAME/KEY: MOD_RES
<222> LOCATION: (60)..(60)
<223> OTHER INFORMATION: Ser, Asp, Ala, Gly, Tyr or Asn
<220> FEATURE:
<221> NAME/KEY: MOD_RES
<222> LOCATION: (63)..(63)
<223> OTHER INFORMATION: Ser or Thr
<220> FEATURE:
<221> NAME/KEY: MOD_RES
<222> LOCATION: (65)..(65)
<223> OTHER INFORMATION: Ser or Asn
<220> FEATURE:
<221> NAME/KEY: MOD_RES
<222> LOCATION: (66)..(66)
<223> OTHER INFORMATION: Gly or Arg
```

```
<220> FEATURE:
<221> NAME/KEY: MOD_RES
<222> LOCATION: (71)..(71)
<223> OTHER INFORMATION: Phe or Tyr
<220> FEATURE:
<221> NAME/KEY: MOD_RES
<222> LOCATION: (72)..(72)
<223> OTHER INFORMATION: Thr or Ser
<220> FEATURE:
<221> NAME/KEY: MOD_RES
<222> LOCATION: (73)..(73)
<223> OTHER INFORMATION: Leu or Phe
<220> FEATURE:
<221> NAME/KEY: MOD_RES
<222> LOCATION: (77)..(77)
<223> OTHER INFORMATION: Ser or Arg
<220> FEATURE:
<221> NAME/KEY: MOD_RES
<222> LOCATION: (78)..(78)
<223> OTHER INFORMATION: Leu or Val
<220> FEATURE:
<221> NAME/KEY: MOD_RES
<222> LOCATION: (79)..(79)
<223> OTHER INFORMATION: Gln or Glu
<220> FEATURE:
<221> NAME/KEY: MOD_RES
<222> LOCATION: (80)..(80)
<223> OTHER INFORMATION: Pro or Ala
<220> FEATURE:
<221> NAME/KEY: MOD_RES
<222> LOCATION: (83)..(83)
<223> OTHER INFORMATION: Phe, Leu or Val
<220> FEATURE:
<221> NAME/KEY: MOD_RES
<222> LOCATION: (85)..(85)
<223> OTHER INFORMATION: Thr, Val, Ala or Ile
<220> FEATURE:
<221> NAME/KEY: MOD_RES
<222> LOCATION: (91)..(91)
<223> OTHER INFORMATION: Tyr or His
<220> FEATURE:
<221> NAME/KEY: MOD_RES
<222> LOCATION: (92)..(92)
<223> OTHER INFORMATION: Ser, Cys, Asn or Tyr
<220> FEATURE:
<221> NAME/KEY: MOD_RES
<222> LOCATION: (94)..(94)
<223> OTHER INFORMATION: Val, Ser, Ala, Gly, Thr, Cys, Asp, Glu, Lys,
      Asn, Gln, Arg, Trp or Tyr
<220> FEATURE:
<221> NAME/KEY: MOD_RES
<222> LOCATION: (96)..(96)
<223> OTHER INFORMATION: Trp, Cys, Phe, Leu, Gln or Tyr

<400> SEQUENCE: 349

Asp Ile Xaa Xaa Thr Gln Xaa Xaa Xaa Xaa Ser Xaa Xaa Xaa Gly
1               5                   10                  15

Xaa Arg Xaa Xaa Ile Xaa Cys Xaa Ala Ser Gln Asp Xaa Xaa Xaa
                20                  25                  30

Xaa Xaa Trp Tyr Gln Gln Lys Pro Xaa Xaa Xaa Xaa Xaa Leu Ile
            35                  40                  45

Tyr Xaa Xaa Ser Xaa Xaa Xaa Xaa Gly Val Pro Xaa Arg Phe Xaa Gly
    50                  55                  60

Xaa Xaa Ser Gly Thr Asp Xaa Xaa Xaa Thr Ile Ser Xaa Xaa Xaa Xaa
65                  70                  75                  80

Glu Asp Xaa Ala Xaa Tyr Tyr Cys Gln Gln Xaa Xaa Thr Xaa Pro Xaa
                85                  90                  95

Thr
```

```
<210> SEQ ID NO 350
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Gln
<220> FEATURE:
<221> NAME/KEY: MOD_RES
<222> LOCATION: (6)..(6)
<223> OTHER INFORMATION: Glu or Gln
<220> FEATURE:
<221> NAME/KEY: MOD_RES
<222> LOCATION: (11)..(11)
<223> OTHER INFORMATION: Leu or Val
<220> FEATURE:
<221> NAME/KEY: MOD_RES
<222> LOCATION: (17)..(17)
<223> OTHER INFORMATION: Ser or Thr
<220> FEATURE:
<221> NAME/KEY: MOD_RES
<222> LOCATION: (21)..(21)
<223> OTHER INFORMATION: Ser or Thr
<220> FEATURE:
<221> NAME/KEY: MOD_RES
<222> LOCATION: (24)..(24)
<223> OTHER INFORMATION: Ala or Val
<220> FEATURE:
<221> NAME/KEY: MOD_RES
<222> LOCATION: (27)..(27)
<223> OTHER INFORMATION: Tyr or Phe
<220> FEATURE:
<221> NAME/KEY: MOD_RES
<222> LOCATION: (28)..(28)
<223> OTHER INFORMATION: Thr, Ala, Asp, Asn, Ser or Tyr
<220> FEATURE:
<221> NAME/KEY: MOD_RES
<222> LOCATION: (29)..(29)
<223> OTHER INFORMATION: Phe or Leu
<220> FEATURE:
<221> NAME/KEY: MOD_RES
<222> LOCATION: (30)..(30)
<223> OTHER INFORMATION: Thr, Ala, Asp, Asn, Ser or Tyr
<220> FEATURE:
<221> NAME/KEY: MOD_RES
<222> LOCATION: (31)..(31)
<223> OTHER INFORMATION: Asn, His, Arg or Ser
<220> FEATURE:
<221> NAME/KEY: MOD_RES
<222> LOCATION: (32)..(32)
<223> OTHER INFORMATION: Tyr or Phe
<220> FEATURE:
<221> NAME/KEY: MOD_RES
<222> LOCATION: (33)..(33)
<223> OTHER INFORMATION: Gly, Ala, Ser or Thr
<220> FEATURE:
<221> NAME/KEY: MOD_RES
<222> LOCATION: (34)..(34)
<223> OTHER INFORMATION: Met, Leu, Val or Ile
<220> FEATURE:
<221> NAME/KEY: MOD_RES
<222> LOCATION: (37)..(37)
<223> OTHER INFORMATION: Val, Ile, Ala, Leu, Pro or Thr
<220> FEATURE:
<221> NAME/KEY: MOD_RES
<222> LOCATION: (45)..(45)
<223> OTHER INFORMATION: Leu or Pro
<220> FEATURE:
<221> NAME/KEY: MOD_RES
<222> LOCATION: (51)..(51)
<223> OTHER INFORMATION: Ile or Val
<220> FEATURE:
<221> NAME/KEY: MOD_RES
<222> LOCATION: (54)..(54)
<223> OTHER INFORMATION: Tyr or Asn
```

-continued

```
<220> FEATURE:
<221> NAME/KEY: MOD_RES
<222> LOCATION: (55)..(55)
<223> OTHER INFORMATION: Thr or Asn
<220> FEATURE:
<221> NAME/KEY: MOD_RES
<222> LOCATION: (58)..(58)
<223> OTHER INFORMATION: Pro, Ser or Thr
<220> FEATURE:
<221> NAME/KEY: MOD_RES
<222> LOCATION: (61)..(61)
<223> OTHER INFORMATION: Ala or Val
<220> FEATURE:
<221> NAME/KEY: MOD_RES
<222> LOCATION: (62)..(62)
<223> OTHER INFORMATION: Ala, Pro, Asp, Glu, His or Gln
<220> FEATURE:
<221> NAME/KEY: MOD_RES
<222> LOCATION: (63)..(63)
<223> OTHER INFORMATION: Asp or Glu
<220> FEATURE:
<221> NAME/KEY: MOD_RES
<222> LOCATION: (65)..(65)
<223> OTHER INFORMATION: Lys or Thr
<220> FEATURE:
<221> NAME/KEY: MOD_RES
<222> LOCATION: (68)..(68)
<223> OTHER INFORMATION: Phe, Val or Leu
<220> FEATURE:
<221> NAME/KEY: MOD_RES
<222> LOCATION: (70)..(70)
<223> OTHER INFORMATION: Phe or Ile
<220> FEATURE:
<221> NAME/KEY: MOD_RES
<222> LOCATION: (72)..(72)
<223> OTHER INFORMATION: Leu or Arg
<220> FEATURE:
<221> NAME/KEY: MOD_RES
<222> LOCATION: (74)..(74)
<223> OTHER INFORMATION: Thr or Asn
<220> FEATURE:
<221> NAME/KEY: MOD_RES
<222> LOCATION: (77)..(77)
<223> OTHER INFORMATION: Ser or Asn
<220> FEATURE:
<221> NAME/KEY: MOD_RES
<222> LOCATION: (78)..(78)
<223> OTHER INFORMATION: Thr, Lys, Pro or Gln
<220> FEATURE:
<221> NAME/KEY: MOD_RES
<222> LOCATION: (79)..(79)
<223> OTHER INFORMATION: Ala, Leu, Pro or Val
<220> FEATURE:
<221> NAME/KEY: MOD_RES
<222> LOCATION: (83)..(83)
<223> OTHER INFORMATION: Met or Leu
<220> FEATURE:
<221> NAME/KEY: MOD_RES
<222> LOCATION: (98)..(98)
<223> OTHER INFORMATION: Lys, Arg, His, Asn, Gln or Ser
<220> FEATURE:
<221> NAME/KEY: MOD_RES
<222> LOCATION: (99)..(99)
<223> OTHER INFORMATION: Tyr, Ser, Ala, Gly, Thr, Cys, Asp, Arg, Glu,
     Asn, Gln, Lys, Trp, Pro or His
<220> FEATURE:
<221> NAME/KEY: MOD_RES
<222> LOCATION: (100)..(100)
<223> OTHER INFORMATION: Pro, Ser, Arg, Ala, Gly, Thr, Cys, Asp, His,
     Asn, Gln, Tyr, Glu, Lys or Trp
<220> FEATURE:
<221> NAME/KEY: MOD_RES
<222> LOCATION: (101)..(101)
<223> OTHER INFORMATION: His, Tyr, Cys, Asp, Gly or Arg
<220> FEATURE:
<221> NAME/KEY: MOD_RES
<222> LOCATION: (102)..(102)
<223> OTHER INFORMATION: Tyr, Val, Asp, Glu, Phe or Leu
```

```
<220> FEATURE:
<221> NAME/KEY: MOD_RES
<222> LOCATION: (103)..(103)
<223> OTHER INFORMATION: Tyr, Cys, Asp, Gly, Asn or Ser
<220> FEATURE:
<221> NAME/KEY: MOD_RES
<222> LOCATION: (104)..(104)
<223> OTHER INFORMATION: Gly or Ser
<220> FEATURE:
<221> NAME/KEY: MOD_RES
<222> LOCATION: (105)..(105)
<223> OTHER INFORMATION: Ser, Thr, Ala, Gly, Pro or Arg
<220> FEATURE:
<221> NAME/KEY: MOD_RES
<222> LOCATION: (106)..(106)
<223> OTHER INFORMATION: Ser, Asn, Thr, Ala, Gly, Cys, Asp, Tyr, Glu,
      Lys, Gln, Arg, or Trp
<220> FEATURE:
<221> NAME/KEY: MOD_RES
<222> LOCATION: (107)..(107)
<223> OTHER INFORMATION: His, Cys, Asn, Arg, Ser or Tyr
<220> FEATURE:
<221> NAME/KEY: MOD_RES
<222> LOCATION: (108)..(108)
<223> OTHER INFORMATION: Trp, Cys, Gln or Tyr
<220> FEATURE:
<221> NAME/KEY: MOD_RES
<222> LOCATION: (112)..(112)
<223> OTHER INFORMATION: Val, Tyr or Leu

<400> SEQUENCE: 350

Xaa Val Gln Leu Val Xaa Ser Gly Gly Gly Xaa Val Gln Pro Gly Gly
1               5                   10                  15

Xaa Leu Arg Leu Xaa Cys Ala Xaa Ser Gly Xaa Xaa Xaa Xaa Xaa
            20                  25                  30

Xaa Xaa Asn Trp Xaa Arg Gln Ala Pro Gly Lys Gly Xaa Glu Trp Val
        35                  40                  45

Gly Trp Xaa Asn Thr Xaa Xaa Gly Glu Xaa Thr Tyr Xaa Xaa Xaa Phe
    50                  55                  60

Xaa Arg Arg Xaa Thr Xaa Ser Xaa Asp Xaa Ser Lys Xaa Xaa Xaa Tyr
65                  70                  75                  80

Leu Gln Xaa Asn Ser Leu Arg Ala Glu Asp Thr Ala Val Tyr Tyr Cys
                85                  90                  95

Ala Xaa Xaa Xaa Xaa Xaa Xaa Xaa Xaa Xaa Xaa Tyr Phe Asp Xaa
            100                 105                 110

Trp Gly

<210> SEQ ID NO 351
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Trp Tyr Gln Gln Lys Pro Gly Gln Ala Pro Gln Val Leu Ile Tyr
1               5                   10                  15

<210> SEQ ID NO 352
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 352

Gly Val Pro Gly Arg Phe Ser Gly Ser Gly Ser Gly Thr Asp Phe Thr
1               5                   10                  15

Leu Thr Ile Ser Ser Leu Gln Pro Glu Asp Phe Ala Val Tyr Tyr Cys
            20                  25                  30

<210> SEQ ID NO 353
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Phe Gly Gly Gly Thr Lys Val Glu Ile Lys
1               5                   10

<210> SEQ ID NO 354
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Trp Tyr Gln Gln Lys Pro Gly Gln Ala Pro Arg Val Leu Ile Tyr
1               5                   10                  15

<210> SEQ ID NO 355
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Gly Val Pro Asn Arg Phe Ser Gly Ser Arg Ser Gly Thr Asp Phe Thr
1               5                   10                  15

Leu Thr Ile Ser Ser Leu Gln Pro Glu Asp Phe Ala Val Tyr Tyr Cys
            20                  25                  30

<210> SEQ ID NO 356
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Trp Tyr Gln Gln Lys Pro Gly Gln Ala Pro Asn Val Leu Ile Tyr
1               5                   10                  15

<210> SEQ ID NO 357
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 357

Gly Val Pro Asp Arg Phe Ser Gly Ser Arg Ser Gly Thr Asp Phe Thr
1               5                   10                  15

Leu Thr Ile Ser Ser Leu Gln Pro Glu Asp Phe Ala Val Tyr Tyr Cys
            20                  25                  30

<210> SEQ ID NO 358
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Trp Tyr Gln Gln Lys Pro Gly Gln Ala Pro Arg Leu Leu Ile Tyr
1               5                   10                  15

<210> SEQ ID NO 359
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Gly Val Pro Ser Arg Phe Ser Gly Ser Arg Ser Gly Thr Asp Phe Thr
1               5                   10                  15

Leu Thr Ile Ser Ser Leu Gln Pro Glu Asp Phe Ala Val Tyr Tyr Cys
            20                  25                  30

<210> SEQ ID NO 360
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Gly Val Pro Asn Arg Phe Ser Gly Ser Gly Ser Gly Thr Asp Phe Thr
1               5                   10                  15

Leu Thr Ile Ser Ser Leu Gln Pro Glu Asp Phe Ala Val Tyr Tyr Cys
            20                  25                  30

<210> SEQ ID NO 361
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Trp Tyr Gln Gln Lys Pro Gly Gln Ala Pro Lys Val Leu Ile Tyr
1               5                   10                  15

<210> SEQ ID NO 362
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 362

Phe Gly Gly Gly Thr Lys Leu Glu Ile Lys
1               5                   10

<210> SEQ ID NO 363
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Trp Tyr Gln Gln Lys Pro Gly Gln Ala Pro Ser Val Leu Ile Tyr
1               5                   10                  15

<210> SEQ ID NO 364
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Gly Val Pro Gly Arg Phe Ser Gly Ser Gly Ser Gly Thr Asp Phe Thr
1               5                   10                  15

Leu Thr Ile Ser Ser Leu Gln Ala Glu Asp Phe Ala Val Tyr Tyr Cys
            20                  25                  30

<210> SEQ ID NO 365
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Val Tyr Tyr Cys
            20                  25                  30

<210> SEQ ID NO 366
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Trp Tyr Gln Gln Lys Pro Gly Gln Ala Pro Asn Leu Leu Ile Tyr
1               5                   10                  15

<210> SEQ ID NO 367
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 367

Gly Val Pro Gly Arg Phe Ser Gly Ser Arg Ser Gly Thr Asp Phe Thr
1               5                   10                  15

Leu Thr Ile Ser Ser Leu Gln Pro Glu Asp Phe Ala Val Tyr Tyr Cys
            20                  25                  30

<210> SEQ ID NO 368
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Trp Tyr Gln Gln Lys Pro Gly Gln Ala Pro His Val Leu Ile Tyr
1               5                   10                  15

<210> SEQ ID NO 369
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Gly Val Pro Asn Arg Phe Ser Gly Ser Arg Ser Gly Thr Asp Phe Thr
1               5                   10                  15

Leu Thr Ile Ser Ser Leu Gln Pro Asp Asp Phe Ala Val Tyr Tyr Cys
            20                  25                  30

<210> SEQ ID NO 370
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Phe Gly Gly Gly Thr Lys Val Ala Ile Lys
1               5                   10

<210> SEQ ID NO 371
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Trp Tyr Gln Gln Lys Pro Gly Lys Ala Pro Lys Leu Leu Ile Tyr
1               5                   10                  15

<210> SEQ ID NO 372
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 372

Gly Val Thr Ser Arg Phe Ser Gly Ser Gly Ser Gly Thr Asp Phe Thr
1               5                   10                  15

Leu Thr Ile Arg Ser Leu Gln Pro Glu Asp Phe Ala Thr Tyr Tyr Cys
            20                  25                  30

<210> SEQ ID NO 373
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Phe Gly Gln Gly Thr Lys Val Glu Ile Lys
1               5                   10

<210> SEQ ID NO 374
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Trp Tyr Gln Gln Lys Pro Gly Lys Ala Pro Glu Leu Leu Ile Tyr
1               5                   10                  15

<210> SEQ ID NO 375
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 376
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Phe Gly Gln Gly Thr Lys Val Asp Ile Lys
1               5                   10

<210> SEQ ID NO 377
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 377

Trp Tyr Gln Gln Ile Pro Gly Lys Ala Pro Lys Leu Leu Ile Tyr
1               5                   10                  15

<210> SEQ ID NO 378
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Ala Tyr Tyr Cys
            20                  25                  30

<210> SEQ ID NO 379
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Trp Tyr Gln Gln Lys Pro Gly Ile Ala Pro Lys Val Leu Ile Tyr
1               5                   10                  15

<210> SEQ ID NO 380
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Phe Gly Gln Gly Thr Lys Leu Glu Ile Lys
1               5                   10

<210> SEQ ID NO 381
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381

Gly Val Pro Ser Arg Phe Ser Gly Thr Gly Ser Gly Thr Asp Phe Ala
1               5                   10                  15

Leu Thr Ile Ser Ser Leu Gln Pro Glu Asp Ser Ala Ser Tyr Tyr Cys
            20                  25                  30

<210> SEQ ID NO 382
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 382

Trp Tyr Gln Gln Lys Pro Gly Thr Ala Pro Lys Leu Leu Ile Tyr
1               5                   10                  15

<210> SEQ ID NO 383
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Trp Tyr Gln Gln Lys Pro Gly Lys Ala Pro Asn Leu Leu Ile Tyr
1               5                   10                  15

<210> SEQ ID NO 384
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Trp Tyr Gln Gln Lys Pro Gly Lys Ala Pro Lys Val Leu Ile Tyr
1               5                   10                  15

<210> SEQ ID NO 385
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Trp Tyr Gln Gln Lys Pro Gly Lys Ala Pro Gln Leu Leu Ile Tyr
1               5                   10                  15

<210> SEQ ID NO 386
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Trp Tyr Gln Gln Phe Pro Gly Thr Ala Pro Lys Phe Leu Met Tyr
1               5                   10                  15

<210> SEQ ID NO 387
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 387

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
                20                  25                  30

```
<210> SEQ ID NO 388
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Phe Gly Thr Gly Thr Gln Leu Thr Val Leu
1               5                   10

<210> SEQ ID NO 389
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Trp Tyr Gln Gln Leu Pro Gly Thr Ala Pro Lys Leu Leu Ile Tyr
1               5                   10                  15

<210> SEQ ID NO 390
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 390

Gly Val Pro Asp Arg Leu Ser Gly Ser Lys Ser Gly Thr Ser Ala Ser
1               5                   10                  15

Leu Ala Ile Ser Gly Leu Leu Ser Glu Asp Glu Ala Asp Tyr Tyr Cys
            20                  25                  30

<210> SEQ ID NO 391
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 391

Gly Val Pro Asp Arg Phe Ser Asp Ser Lys Ser Gly Thr Ser Ala Ser
1               5                   10                  15

Leu Gly Ile Ser Gly Leu Arg Ser Glu Asp Glu Ala Asp Tyr Phe Cys
            20                  25                  30

<210> SEQ ID NO 392
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Phe Gly Thr Gly Thr Lys Val Thr Val Leu
1               5                   10
```

```
<210> SEQ ID NO 393
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Trp Tyr Gln Gln Phe Pro Gly Thr Ala Pro Lys Val Leu Ile Tyr
1               5                   10                  15

<210> SEQ ID NO 394
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Phe Gly Thr Gly Thr Lys Leu Thr Val Leu
1               5                   10

<210> SEQ ID NO 395
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Trp Tyr Gln Gln Leu Pro Gly Ala Ala Pro Lys Val Leu Met Tyr
1               5                   10                  15

<210> SEQ ID NO 396
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 397
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Trp Tyr Gln Gln Leu Pro Gly Thr Ala Pro Lys Val Leu Ile Tyr
1               5                   10                  15

<210> SEQ ID NO 398
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 398

Gly Val Pro Asp Arg Phe Ser Gly Ser Arg Ser Ala Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 399
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Phe Gly Ala Gly Thr Gln Leu Thr Val Leu
1               5                   10

<210> SEQ ID NO 400
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Trp Tyr Gln Gln Leu Pro Gly Thr Ala Pro Lys Val Leu Met Tyr
1               5                   10                  15

<210> SEQ ID NO 401
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

Gly Val Pro Glu Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 402
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Trp Val Arg Gln Ala Pro Gly Lys Gly Leu Glu Trp Val Gly
1               5                   10

<210> SEQ ID NO 403
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 403

Arg Phe Thr Phe Ser Leu Asp Thr Ser Lys Ser Thr Ala Tyr Leu Gln
1               5                   10                  15

Met Asn Ser Leu Arg Ala Glu Asp Thr Ala Val Tyr Tyr Cys Ala
            20                  25                  30

<210> SEQ ID NO 404
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Trp Gly Gln Gly Thr Leu Val Thr Val Ser Ser
1               5                   10

<210> SEQ ID NO 405
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 405

Arg Phe Thr Phe Ser Leu Asp Thr Ser Lys Asn Thr Ala Tyr Leu Gln
1               5                   10                  15

Leu Asn Ser Leu Arg Ala Glu Asp Thr Ala Val Tyr Tyr Cys Ala
            20                  25                  30

<210> SEQ ID NO 406
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Trp Ile Arg Gln Ala Pro Gly Lys Gly Leu Glu Trp Val Gly
1               5                   10

<210> SEQ ID NO 407
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

Arg Phe Thr Ile Ser Leu Asp Asn Ser Lys Ser Thr Val Tyr Leu Gln
1               5                   10                  15

Met Asn Ser Leu Arg Ala Glu Asp Thr Ala Val Tyr Tyr Cys Ala
            20                  25                  30

<210> SEQ ID NO 408
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 408

Arg Phe Thr Ile Ser Arg Asp Thr Ser Lys Asn Gln Ala Tyr Leu Gln
1               5                   10                  15

Met Asn Ser Leu Arg Ala Glu Asp Thr Ala Val Tyr Tyr Cys Ala
            20                  25                  30

<210> SEQ ID NO 409
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

Arg Val Thr Phe Ser Leu Asp Thr Ser Lys Ser Thr Ala Tyr Leu Gln
1               5                   10                  15

Leu Asn Ser Leu Arg Ala Glu Asp Thr Ala Val Tyr Tyr Cys Ala
            20                  25                  30

<210> SEQ ID NO 410
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410

Arg Phe Thr Ile Ser Leu Asp Thr Ser Lys Ser Gln Ala Tyr Leu Gln
1               5                   10                  15

Met Asn Ser Leu Arg Ala Glu Asp Thr Ala Val Tyr Tyr Cys Ala
            20                  25                  30

<210> SEQ ID NO 411
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

Arg Val Thr Phe Ser Leu Asp Thr Ser Lys Ser Thr Ala Tyr Leu Gln
1               5                   10                  15

Met Asn Ser Leu Arg Ala Glu Asp Thr Ala Val Tyr Tyr Cys Ala
            20                  25                  30

<210> SEQ ID NO 412
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Arg Phe Thr Ile Ser Leu Asp Asn Ser Lys Ser Gln Ala Tyr Leu Gln
1               5                   10                  15

Met Asn Ser Leu Arg Ala Glu Asp Thr Ala Val Tyr Tyr Cys Ala
            20                  25                  30
```

<210> SEQ ID NO 413
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Trp Ala Gln Gly Thr Leu Val Thr Val Ser Ser
1               5                   10

<210> SEQ ID NO 414
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 414

Arg Phe Thr Phe Ser Leu Asp Thr Ser Lys Asn Thr Ala Tyr Leu Gln
1               5                   10                  15

Met Asn Ser Leu Arg Ala Glu Asp Thr Ala Val Tyr Tyr Cys Ala
            20                  25                  30

<210> SEQ ID NO 415
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Arg Val Thr Ile Ser Leu Asp Thr Ser Lys Ser Thr Val Tyr Leu Gln
1               5                   10                  15

Met Asn Ser Leu Arg Ala Glu Asp Thr Ala Val Tyr Tyr Cys Ala
            20                  25                  30

<210> SEQ ID NO 416
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 416

Arg Phe Thr Phe Ser Leu Asp Thr Ser Lys Ser Lys Ala Tyr Leu Gln
1               5                   10                  15

Leu Asn Ser Leu Arg Ala Glu Asp Thr Ala Val Tyr Tyr Cys Ala
            20                  25                  30

<210> SEQ ID NO 417
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 417

Arg Val Thr Phe Ser Leu Asp Asn Ser Lys Ser Thr Val Tyr Leu Gln
1               5                   10                  15

Met Asn Ser Leu Arg Ala Glu Asp Thr Ala Val Tyr Tyr Cys Ala
            20                  25                  30

<210> SEQ ID NO 418
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Arg Phe Thr Ile Ser Leu Asp Thr Ser Lys Asn Thr Ala Tyr Leu Gln
1               5                   10                  15

Leu Asn Ser Leu Arg Ala Glu Asp Thr Ala Val Tyr Tyr Cys Ala
            20                  25                  30

<210> SEQ ID NO 419
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Arg Val Thr Ile Ser Leu Asp Thr Ser Lys Ser Gln Ala Tyr Leu Gln
1               5                   10                  15

Met Asn Ser Leu Arg Ala Glu Asp Thr Ala Val Tyr Tyr Cys Ala
            20                  25                  30

<210> SEQ ID NO 420
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Arg Val Thr Ile Ser Leu Asp Thr Ser Lys Ser Thr Ala Tyr Leu Gln
1               5                   10                  15

Leu Asn Ser Leu Arg Ala Glu Asp Thr Ala Val Tyr Tyr Cys Ala
            20                  25                  30

<210> SEQ ID NO 421
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
attaatggat ccgmcatccr gwtgacccag tctcc                              35

<210> SEQ ID NO 422
<211> LENGTH: 35
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 422
attaatggat ccgatrttgt gatgacycag wctcc                               35

<210> SEQ ID NO 423
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
attaatggat ccgaaatwgt gwtgacrcag tctcc                               35

<210> SEQ ID NO 424
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
attaatggat ccgacatcgt gatgacccag tctcc                               35

<210> SEQ ID NO 425
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 425
attaatggat ccgaaacgac actcacgcag tctcc                               35

<210> SEQ ID NO 426
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 426
attaatggat ccgaaattgt gctgactcag tctcc                               35

<210> SEQ ID NO 427
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 427
attaatggat cccagtctgt gytgackcag cc                                  32

<210> SEQ ID NO 428
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 428
attaatggat cccagtctgc cctgactcag cc                                    32

<210> SEQ ID NO 429
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 429
attaatggat cctcctatga gctgacwcag cyac                                  34

<210> SEQ ID NO 430
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 430
attaatggat cctcttctga gctgactcag gac                                   33

<210> SEQ ID NO 431
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 431
attaatggat ccctgcctgt gctgactcag cc                                    32

<210> SEQ ID NO 432
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 432
attaatggat cccagcytgt gctgactcaa tc                                    32

<210> SEQ ID NO 433
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 433
attaatggat cccagsctgt gctgactcag cc                                    32

<210> SEQ ID NO 434
<211> LENGTH: 33
<212> TYPE: DNA
<213> ORGANISM: Artificial Sequence
```

-continued

<220> FEATURE:
<223> OTHER INFORMATION: Description of Artificial Sequence: Synthetic
      primer

<400> SEQUENCE: 434
attaatggat ccaattttat gctgactcag ccc                                33

<210> SEQ ID NO 435
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 435
attaatggat cccagrctgt ggtgacycag gag                                33

<210> SEQ ID NO 436
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 436
attaatggat cccaggcagg gctgactcag cc                                 32

<210> SEQ ID NO 437
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 437
ttaattgcgg ccgctttgat ytccascttg gtccc                              35

<210> SEQ ID NO 438
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
ttaattgcgg ccgctttgat atccactttg gtccc                              35

<210> SEQ ID NO 439
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439
ttaattgcgg ccgctttaat ctccagtcgt gtccc                              35

<210> SEQ ID NO 440
<211> LENGTH: 31
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 440
ttaattgcgg ccgctaggac ggtsascttg g                                31

<210> SEQ ID NO 441
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441
ttaattgcgg ccgcgaggac ggtcagctgg g                                31

<210> SEQ ID NO 442
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Gly Gly Gly Gly Ser Gly Gly Gly Gly Ser Gly Gly Gly Gly Ser
1               5                  10                  15

<210> SEQ ID NO 443
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 443

His His His His His His
1               5
```